US012630538B2

(12) United States Patent
Vandyck et al.

(10) Patent No.: US 12,630,538 B2
(45) Date of Patent: May 19, 2026

(54) ANTI-VIRAL COMPOUNDS

(71) Applicants: Aligos Therapeutics, Inc., South San Francisco, CA (US); Katholieke Universiteit Leuven, Leuven (BE)

(72) Inventors: Koen Vandyck, Paal (BE); Dorothée Alice Marie-Eve Bardiot, Leuven (BE); Pierre Jean-Marie Bernard Raboisson, Wavre (BE); Leonid Beigelman, San Mateo, CA (US); Antitsa Dimitrova Stoycheva, Half Moon Bay, CA (US); Sandro Boland, Leuven (BE); Arnaud Didier Marie Marchand, Leuven (BE)

(73) Assignees: Aligos Therapeutics, Inc., South San Francisco, CA (US); Katholieke Universiteit Leuven, Leuven (BE)

( * ) Notice: Subject to any disclaimer, the term of this patent is extended or adjusted under 35 U.S.C. 154(b) by 303 days.

(21) Appl. No.: 18/347,099

(22) Filed: Jul. 5, 2023

(65) Prior Publication Data

US 2024/0018126 A1 Jan. 18, 2024

Related U.S. Application Data

(60) Provisional application No. 63/367,788, filed on Jul. 6, 2022.

(51) Int. Cl.
*C07D 403/12* (2006.01)
*A61P 31/14* (2006.01)

(52) U.S. Cl.
CPC ............ *C07D 403/12* (2013.01); *A61P 31/14* (2018.01)

(58) Field of Classification Search
CPC .................................................... C07D 403/12
See application file for complete search history.

(56) References Cited

U.S. PATENT DOCUMENTS 4,388,305 A 6/1983 Trouet et al.
4,639,456 A 1/1987 Trouet et al.
4,970,297 A 11/1990 Castelhano et al.
5,147,865 A 9/1992 Habich et al.
5,364,931 A 11/1994 Haebich et al.
5,510,333 A 4/1996 Angelastro et al.
5,514,694 A 5/1996 Powers et al.
5,741,812 A 4/1998 Burk et al.
5,756,528 A 5/1998 Anthony et al.
5,847,135 A 12/1998 Bemis et al.
5,856,309 A 1/1999 Konetschny-Rapp et al.
5,874,424 A 2/1999 Batchelor et al.
5,955,616 A 9/1999 Ohtani et al.
6,159,984 A 12/2000 Guzi et al.
6,162,791 A 12/2000 Karimian et al.
6,174,887 B1 1/2001 Haruta et al.
9,603,864 B2 3/2017 Blatt et al.
11,124,497 B1 9/2021 Arnold et al.
11,174,231 B1 11/2021 Arnold et al.
11,851,422 B2 12/2023 Vandyck et al.
11,952,365 B2 4/2024 Vandyck et al.
12,065,428 B2 8/2024 Bardiot et al.
12,252,481 B2 3/2025 Vandyck et al.
2003/0153788 A1 8/2003 Kobayashi et al.
2003/0216325 A1 11/2003 Saksena et al.
2004/0110945 A1 6/2004 Nakayama et al.
2004/0171489 A1 9/2004 Hacker et al.
2006/0111303 A1 5/2006 Hatayama et al.
2007/0032433 A1 2/2007 Saksena et al.
2007/0208001 A1 9/2007 Zhou et al.
2007/0238769 A1 10/2007 Ochi et al.
2012/0329704 A1 12/2012 Ruijter et al.
2013/0109661 A1 5/2013 Hermann et al.
2013/0164694 A1 6/2013 Wang et al.
2013/0178478 A1 7/2013 Hermann et al.
2014/0194386 A1 7/2014 Burns et al.
2014/0374657 A1 12/2014 Matsuyama et al.
2017/0324007 A1 11/2017 Pentlehmer
2021/0355111 A1 11/2021 Arnold et al.
2022/0009903 A1 1/2022 Vandyck et al.
2022/0033383 A1 2/2022 Panarese et al.
2022/0259145 A1 8/2022 Liu et al.
2022/0396550 A1 12/2022 Ghosh et al.
2022/0402905 A1 12/2022 Soliman et al.
2022/0411401 A1 12/2022 Ghosh et al.

(Continued)

FOREIGN PATENT DOCUMENTS

AU 2002318741 3/2003
CA 2851462 7/2004

(Continued)

OTHER PUBLICATIONS

Abdelnabi et al., "Comparing infectivity and virulence of emerging SARS-CoV-2 variants in Syrian hamsters" EBioMedicine (2021) Jun. 68:103403. doi: 10.1016/j.ebiom.2021.103403.
Ahmad et al., "Exploring the Binding Mechanism of PF-07321332 SARS-CoV-2 Protease Inhibitor through Molecular Dynamics and Binding Free Energy Simulations" Int. J. Mol. Sci. (2021) 22(17):91242.
Alugubelli et al., "A systemic exploration of beceprevir-based main protease inhibitos as SARS-CoV-2 antivirals" European J. of Med. Chem. (2022) 240:114596.
Arakawa et al., "Synthetic Study of Optically Active 3-Azabicyclo[3.3.0]octane-2,6,8-tricarboxylic Acid" Chemical & Pharmaceutical Bulletin (2003) 51(8), 1015-1020.

(Continued)

*Primary Examiner* — Matthew P Coughlin
(74) *Attorney, Agent, or Firm* — Knobbe, Martens, Olson & Bear, LLP

(57) ABSTRACT

Provided herein are compounds of Formula (I), or pharmaceutically acceptable salts thereof, pharmaceutical compositions that include a compound described herein (including pharmaceutically acceptable salts of a compound described herein) and methods of synthesizing the same. Also provided herein are methods of treating diseases and/or conditions with a compound of Formula (I), or a pharmaceutically acceptable salt thereof.

21 Claims, No Drawings

(56) References Cited

U.S. PATENT DOCUMENTS

| | | | |
|---|---|---|---|
| 2023/0002413 | A1 | 1/2023 | Wu et al. |
| 2023/0024012 | A1 | 1/2023 | Chattrejee et al. |
| 2023/0031213 | A1 | 2/2023 | Wu et al. |
| 2023/0065527 | A1 | 3/2023 | Wu et al. |
| 2023/0093249 | A1 | 3/2023 | Vandyck et al. |
| 2023/0140238 | A1 | 5/2023 | Bardiot et al. |
| 2023/0192713 | A1 | 6/2023 | Wu et al. |
| 2023/0212116 | A1 | 7/2023 | Liu et al. |
| 2024/0018126 | A1 | 1/2024 | Vandyck et al. |
| 2024/0109871 | A1 | 4/2024 | Vandyck et al. |
| 2024/0124395 | A1 | 4/2024 | Ghosh et al. |
| 2024/0182444 | A1 | 6/2024 | Bardiot et al. |
| 2024/0199647 | A1 | 6/2024 | Bardiot et al. |
| 2024/0228460 | A1 | 7/2024 | Rolfe et al. |
| 2024/0239772 | A1 | 7/2024 | Stauffer et al. |
| 2024/0239807 | A1 | 7/2024 | Ammann et al. |
| 2025/0042915 | A1 | 2/2025 | Ammann et al. |

FOREIGN PATENT DOCUMENTS

| | | | |
|---|---|---|---|
| CA | 3230859 | | 3/2023 |
| CA | 3201360 | | 6/2023 |
| CL | 199902360 | | 9/2000 |
| CL | 200101723 | | 5/2002 |
| CN | 103254129 | | 8/2013 |
| CN | 103288832 | | 9/2013 |
| CN | 107540726 | | 1/2018 |
| CN | 113444144 | | 9/2021 |
| CN | 114149415 | | 3/2022 |
| CN | 114426568 | | 5/2022 |
| CN | 115433256 | A | 12/2022 |
| CN | 115490681 | A | 12/2022 |
| CN | 115594734 | A | 1/2023 |
| CN | 115894504 | A | 4/2023 |
| CN | 116969957 | A | 10/2023 |
| DE | 4016994 | | 11/1991 |
| EP | 0393445 | | 10/1990 |
| EP | 0402646 | | 12/1990 |
| EP | 472077 | | 2/1992 |
| EP | 472078 | | 2/1992 |
| EP | 520336 | | 12/1992 |
| EP | 525420 | | 2/1993 |
| EP | 0530537 | | 3/1993 |
| EP | 0641800 | | 3/1995 |
| EP | 0644198 | | 3/1995 |
| EP | 1881001 | | 3/1995 |
| EP | 0805147 | | 11/1997 |
| EP | 1217000 | | 6/2002 |
| EP | 1760076 | | 3/2007 |
| EP | 1881002 | | 1/2008 |
| EP | 2270025 | | 1/2011 |
| EP | 3835296 | A1 | 6/2021 |
| EP | 4159211 | A1 | 4/2023 |
| EP | 4357342 | A1 | 4/2024 |
| EP | 4368610 | A1 | 5/2024 |
| IN | 2006 | | 1/2008 |
| JP | 63144084 | | 6/1988 |
| JP | 06192199 | | 7/1994 |
| JP | 04334357 | | 11/1995 |
| JP | 07309866 | A | 11/1995 |
| JP | 09124571 | | 5/1997 |
| JP | 2002145848 | | 5/2002 |
| JP | 2005336172 | | 12/2005 |
| JP | 2006232707 | | 9/2006 |
| JP | 2013032343 | | 2/2013 |
| JP | 2015174929 | | 10/2015 |
| JP | 7055528 | B1 | 4/2022 |
| WO | WO 89/04833 | | 6/1989 |
| WO | WO 92/00954 | | 1/1992 |
| WO | WO 92/07869 | | 5/1992 |
| WO | WO 92/20357 | | 11/1992 |
| WO | WO 93/02057 | | 2/1993 |
| WO | WO 93/12796 | | 7/1993 |
| WO | WO 93/17003 | | 9/1993 |
| WO | WO 94/00421 | | 1/1994 |
| WO | WO 94/11339 | | 5/1994 |
| WO | WO 95/07294 | | 3/1995 |
| WO | WO 95/09858 | | 4/1995 |
| WO | WO 95/12611 | | 5/1995 |
| WO | WO 95/35308 | | 12/1995 |
| WO | WO 96/16981 | | 6/1996 |
| WO | WO 96/20725 | | 7/1996 |
| WO | WO 96/20949 | | 7/1996 |
| WO | WO 96/39137 | | 12/1996 |
| WO | WO 96/40732 | | 12/1996 |
| WO | WO 97/05135 | | 2/1997 |
| WO | WO 97/08133 | | 3/1997 |
| WO | WO 97/22619 | | 6/1997 |
| WO | WO 97/31939 | | 9/1997 |
| WO | WO 98/01133 | | 1/1998 |
| WO | WO 98/53814 | | 12/1998 |
| WO | WO 98/53817 | | 12/1998 |
| WO | WO 98/57945 | | 12/1998 |
| WO | WO 99/67230 | | 12/1999 |
| WO | WO 2000/016627 | | 3/2000 |
| WO | WO 2000/023454 | | 4/2000 |
| WO | WO 2000/051974 | | 9/2000 |
| WO | WO 2000/055125 | | 9/2000 |
| WO | WO 2000/071572 | | 11/2000 |
| WO | WO 2001/012186 | | 2/2001 |
| WO | WO 01/79167 | | 10/2001 |
| WO | WO 2002/008244 | | 1/2002 |
| WO | WO 2002/053534 | | 7/2002 |
| WO | WO 2002/085899 | | 10/2002 |
| WO | WO 2003/004468 | | 1/2003 |
| WO | WO 2003/008380 | | 1/2003 |
| WO | WO 2003/029284 | | 4/2003 |
| WO | WO 2003/035060 | | 5/2003 |
| WO | WO 2003/039529 | | 5/2003 |
| WO | WO 2003/062265 | | 7/2003 |
| WO | WO 2003/091202 | | 11/2003 |
| WO | WO 2004/032846 | | 4/2004 |
| WO | WO 2004/046107 | | 6/2004 |
| WO | WO 2004/062601 | | 7/2004 |
| WO | WO 2005/014532 | | 2/2005 |
| WO | WO 2005/061475 | | 7/2005 |
| WO | WO 2005/102381 | | 11/2005 |
| WO | WO 2006/061714 | | 6/2006 |
| WO | WO 2007/022459 | | 2/2007 |
| WO | WO 2007/067836 | | 6/2007 |
| WO | WO 2007/085895 | | 8/2007 |
| WO | WO 2007109080 | | 9/2007 |
| WO | WO 2008/074035 | | 6/2008 |
| WO | WO 2008/110008 | | 9/2008 |
| WO | WO 2008/121065 | | 10/2008 |
| WO | WO 2008/141227 | | 11/2008 |
| WO | WO 2008/154642 | | 12/2008 |
| WO | WO 2009/043889 | | 4/2009 |
| WO | WO 2009/103160 | | 8/2009 |
| WO | WO 2009/105782 | | 8/2009 |
| WO | WO 2010/077836 | | 7/2010 |
| WO | WO 2010/126881 | | 11/2010 |
| WO | WO 2010/132601 | | 11/2010 |
| WO | WO 2011/043994 | | 4/2011 |
| WO | WO 2011/047287 | | 4/2011 |
| WO | WO 2011/048390 | | 4/2011 |
| WO | WO 2011/050160 | | 4/2011 |
| WO | WO 2011/082337 | | 7/2011 |
| WO | WO 2011/094426 | | 8/2011 |
| WO | WO 2011/103932 | | 9/2011 |
| WO | WO 2011/103933 | | 9/2011 |
| WO | WO 2011/129457 | | 10/2011 |
| WO | WO 2012/020747 | | 2/2012 |
| WO | WO 2012/058645 | | 5/2012 |
| WO | WO 2012/065963 | | 5/2012 |
| WO | WO 2012/083048 | | 6/2012 |
| WO | WO 2012/122420 | | 9/2012 |
| WO | WO 2012/122422 | | 9/2012 |
| WO | WO 2012/123938 | | 9/2012 |
| WO | WO 2012/140500 | | 10/2012 |
| WO | WO 2012/163724 | | 12/2012 |
| WO | WO 2013/003720 | | 1/2013 |
| WO | WO 2013/133178 | | 9/2013 |
| WO | WO 2013/178816 | | 12/2013 |

(56) References Cited

FOREIGN PATENT DOCUMENTS

| | | |
|---|---|---|
| WO | WO 2013/188344 | 12/2013 |
| WO | WO 2014/151958 | 9/2014 |
| WO | WO 2014/154682 | 10/2014 |
| WO | WO 2014/188178 | 11/2014 |
| WO | WO 2016/075150 | 5/2016 |
| WO | WO 2016/187712 | 12/2016 |
| WO | WO 2017/091616 | 6/2017 |
| WO | WO 2017/160269 | 9/2017 |
| WO | WO 2017/197377 | 11/2017 |
| WO | WO 2018/020357 | 2/2018 |
| WO | WO 2018/042343 | 3/2018 |
| WO | WO 2018/045084 | 3/2018 |
| WO | WO 2018/064119 | 4/2018 |
| WO | WO 2018/112626 | 6/2018 |
| WO | WO 2018/152633 | 8/2018 |
| WO | WO 2018/167269 | 9/2018 |
| WO | WO 2019/190885 | 10/2019 |
| WO | WO 2019/190999 | 10/2019 |
| WO | WO 2020/006294 | 1/2020 |
| WO | WO 2020/030143 | 2/2020 |
| WO | WO 2020/123675 | 6/2020 |
| WO | WO 2020/136298 | 6/2020 |
| WO | WO 2020/160707 | 8/2020 |
| WO | WO 2020/185830 | 9/2020 |
| WO | WO 2021/146211 | 7/2021 |
| WO | WO 2021/151265 | 8/2021 |
| WO | WO 2021/151387 | 8/2021 |
| WO | WO 2021/207632 | 10/2021 |
| WO | WO 2021/221043 | 11/2021 |
| WO | WO 2021/226546 | 11/2021 |
| WO | WO 2021/231872 | 11/2021 |
| WO | WO 2021/234668 | 11/2021 |
| WO | WO 2021/236771 | 11/2021 |
| WO | WO 2021/250648 | 12/2021 |
| WO | WO 2021/252491 | 12/2021 |
| WO | WO 2021/252644 | 12/2021 |
| WO | WO 2022/020242 | 1/2022 |
| WO | WO 2022/020711 | 1/2022 |
| WO | WO 2022/040002 | 2/2022 |
| WO | WO 2022/109363 | 5/2022 |
| WO | WO 2022/119858 | 6/2022 |
| WO | WO 2022/133069 | 6/2022 |
| WO | WO 2022/187491 | 9/2022 |
| WO | WO 2022/208113 | 10/2022 |
| WO | WO 2022/208262 | 10/2022 |
| WO | WO 2022/218442 | 10/2022 |
| WO | WO 2022/266236 | 12/2022 |
| WO | WO 2022/266363 | 12/2022 |
| WO | WO 2022/266368 | 12/2022 |
| WO | WO 2023/002409 | 1/2023 |
| WO | WO 2023/003610 | 1/2023 |
| WO | WO 2023/004291 | 1/2023 |
| WO | WO 2023/283256 | 1/2023 |
| WO | WO 2023/283831 | 1/2023 |
| WO | WO 2023/286844 | 1/2023 |
| WO | WO 2023/009187 | 2/2023 |
| WO | WO 2023/011443 | 2/2023 |
| WO | WO 2023/014758 | 2/2023 |
| WO | WO 2023/023469 | 2/2023 |
| WO | WO 2023/023631 | 2/2023 |
| WO | WO 2023/030459 | 3/2023 |
| WO | WO 2023/036093 | 3/2023 |
| WO | WO 2023/036140 | 3/2023 |
| WO | WO 2023/043816 | 3/2023 |
| WO | WO 2023/044171 | 3/2023 |
| WO | WO 2023/052638 | 4/2023 |
| WO | WO 2023/088418 | 5/2023 |
| WO | WO 2023/104882 | 6/2023 |
| WO | WO 2023/107419 | 6/2023 |
| WO | WO 2023/122260 | 6/2023 |
| WO | WO 2023/125846 | 7/2023 |
| WO | WO 2023/133174 | 7/2023 |
| WO | WO 2023/137007 | 7/2023 |
| WO | WO 2023/149981 | 8/2023 |
| WO | WO 2023/149982 | 8/2023 |
| WO | WO 2023/150790 | 8/2023 |
| WO | WO 2023/160634 | 8/2023 |
| WO | WO 2023/165334 | 9/2023 |
| WO | WO 2023/165459 | 9/2023 |
| WO | WO 2023/168844 | 9/2023 |
| WO | WO 2023/169572 | 9/2023 |
| WO | WO 2023/177854 | 9/2023 |
| WO | WO 2023/180189 | 9/2023 |
| WO | WO 2023/185763 | 10/2023 |
| WO | WO 2023/194840 | 10/2023 |
| WO | WO 2023/196307 | 10/2023 |
| WO | WO 2023/235109 | 12/2023 |
| WO | WO 2023/245162 | 12/2023 |
| WO | WO 2023/245166 | 12/2023 |
| WO | WO 2024/006949 | 1/2024 |
| WO | WO 2024/008044 | 1/2024 |
| WO | WO 2024/008196 | 1/2024 |
| WO | WO 2024/010585 | 1/2024 |
| WO | WO 2024/010794 | 1/2024 |
| WO | WO 2024/031089 | 2/2024 |
| WO | WO 2024/037520 | 2/2024 |
| WO | WO 2024/059087 | 3/2024 |
| WO | WO 2024/074651 | 4/2024 |
| WO | WO 2024/076680 | 4/2024 |
| WO | WO 2024/079067 | 4/2024 |
| WO | WO 2024/081318 | 4/2024 |
| WO | WO 2024/081351 | 4/2024 |
| WO | WO 2024/086111 | 4/2024 |
| WO | WO 2024/086777 | 4/2024 |
| WO | WO 2024/089159 | 5/2024 |
| WO | WO 2024/097296 | 5/2024 |
| WO | WO 2024/102455 | 5/2024 |
| WO | WO 2024/102986 | 5/2024 |
| WO | WO 2024/102999 | 5/2024 |
| WO | WO 2024/107778 | 5/2024 |
| WO | WO 2024/107783 | 5/2024 |
| WO | WO 2024/108673 | 5/2024 |
| WO | WO 2024/112621 | 5/2024 |
| WO | WO 2024/124287 | 6/2024 |
| WO | WO 2024/130411 | 6/2024 |
| WO | WO 2024/137764 | 6/2024 |
| WO | WO 2024/151465 | 7/2024 |
| WO | WO 2024/174966 | 8/2024 |
| WO | WO 2024/183629 | 9/2024 |
| WO | WO 2024/222796 | 10/2024 |
| WO | WO 2024/222830 | 10/2024 |
| WO | WO 2024/227410 | 11/2024 |
| WO | WO 2024/229253 | 11/2024 |
| WO | WO 2024/232829 | 11/2024 |
| WO | WO 2024/237816 | 11/2024 |

OTHER PUBLICATIONS

Breuning et al, "Enantioselective synthesis of tricyclic amino acid derivatives based on a rigid 45-azatricyclo[5.2.1.0$^{2,6}$]decane skeleton" Beilstein Journal of Organic Chemistry (2009) 5(81):1-5.

CAS Reg. No. 1040187-41-4, Entry Date Aug. 11, 2008.

CAS Reg. No. 1212645-49-2, Entry Date Mar. 21, 2010.

CAS Reg. No. 1240410-37-0, Entry Date Sep. 9, 2010.

Calaza et al., "Synthesis of [c]-Fused Bicyclic Proline Analogues" Eur. J. Org. Chem. (2015), 2015(8):1633-1658.

Chia et al., "Novel Coronavirus Main Protease Di- and Tripeptide Inhibitors for Treating COVID-19" ACS Med. Chem. Lett. (2002) 13:1388-1389.

Cox et al., "Escaping form Flatland: Substituted Bridged Pyrrolidine Fragments with Inherent Three-Dimensional Character" ACS Med. Chem. Lett. (2020) 11(6):1185-1190.

De Graaff et al., "IBX-mediated oxidation of unactivated cyclic amines: application in highly diastereoselective oxidative Ugi-type and aza-Friedel-Crafts reactions" Org. Biomol. Chem. (2015) 13:10108-10112.

Eiden et al., "Synthesis of a 3-Amino-2,3-dihdropyrid-4-one and Related Heterocyclic Anaalogues as|Mechanism-Based Inhibitors of BioA, a Pyridoxal Phosphate-Dependent Enzyme" J. Org. Chem. (2017) 82(15):7806-7819.

Farmer et al., "Inhibitors of hepatitis C virus NS3•4A protease: P2 proline variants." Letters in Drug Design & Discovery (2005) 2(7):497-502.

(56) References Cited

OTHER PUBLICATIONS

Gansauer et al., "R-exo Cyclizations by Template Catalysis" Ang. Chem. Int. Ed. (2009) 48(47), 8882-8885, S8882/1-S8882/32.
Good et al., "AT-527, a Double Prodrug of a Guanosine Nucleotide Analog, Is a Potent Inhibitor of SARS-CoV-2 In Vitro and a Promising Oral Antiviral for Treatment of COVID-19" Antimicrobial Agents and Chemotherapy (2021) 65(4):e02479-20.
Gupton et al., "Application of 2-Substituted Vinamidinium Salts to the Synthesis of 2,4-Disubstituted Pyrroles" J. Org. Chem. (1990) 55(15):4735-4740.
Hartford, B., "To conquer COVID-19, create the perfect pill" Chemical & Engineering News (2021) 99(19):28-31.
Hartford, B., "Pfizer unveils its oral SARS-CoV-2 inhibitor" Chemical & Engineering News (2021), 99(13):7.
Hoffmann et al., "SARS-CoV-2 Cell Entry Depends on ACE2 and TMPRSS2 and Is Blocked by a Clinically Proven Protease Inhibitor" Cell (2020) 181:271-280.
IUPAC-IUB Commission on Biochemical Nomenclature (See, Biochem. 11:942-944 (1972).
Johnson et al., "Synthesis and Characterization of Novel Bi- and Tricyclic α-Amino Acids" Synthetic Communications (2011) 41(18):2769-2793.
Kim et al., "Broad-Spectrum Antivirals against 3C or 3C-Like Proteases of Picornavirus, Noroviruses, and Coronoviruses" Journal of Virology (2012) 86(21):11754-11762.
Liu et al., "Modular and Stereoselective Synthesis of Tetrasubstituted Helical Alkenes via a Palladium-Catalyzed Domino Reaction" Org. Lett. (2012) 14(14):3648-3651.
Liu et al., "An Improved and Enantioselective Preparation of the Telaprevir Bicyclic [3.3.0] Proline Intermediate and Reuse of Unwanted Enantiomer" Org. Process Res. Dev. (2016) 20(2):320-324.
Macchiagodena et al., "Virtual Double-System Single-Box for Absolute Dissociation Free Energy Calculations in Gromacs" J. Chem. Inf. Model (2021) 61:5320-5326.
Macchiagodena et al., "Characterization of the non-covalent interaction between the PF-07321332 inhibitor and the SARS-CoV-2 main protease" J. Mol. Graphics & Modelling (2022) 110:108042.
Mellott et al., "A cysteine protease inhibitor blocks SARS-CoV-2 infection of human and monkey cells" bioRxiv (2020) 2020.2010.2023.347534.
Moody et al., "Stereospecific synthesis of naturally-occurring 4-alkylideneglutamic acids, 4-alkylglutates and 4-alkylprolines" J. Chem. Soc., Perkin Trans. 1 (1997) 23:3519-3530.
Mulamreddy et al., "4-Vinylproline" J. Org. Chem. (2018) 83(21):13580-13586.
Ngo et al., "Insights into the Binding and Covalent Inhibition Mechanism of PF-07321332 to SARS-CoV-2 Mpro" ChemRxiv (2021) 1-10.
Owen et al., "An oral SARS-CoV $M^{pro}$ inhibitor clinical candidate for the treatment of COVID-19" Science (2021) 374(6575):1586-1593.
Pavan et al., "Supervised Molecular Dynamics (SuMD) Insights into the mechanism of action of SARS-Co-V-2 main protease inhibitor PF-07321332" Journal of Enzyme Inhibition and Medicinal Chemistry (2021) 36(1):1646-1650.
Ramos-Guzman et al., "Computational simulations on the binding and reactivity of a nitrile inhibitor of the SARS-CoV-2 main protease" Chem. Commun. (2021) 57(72):9096-9099 & Supporting Information.
Roy et al., "The Hemetsberger-Knittel Synthesis of Substituted 5-,6-, and 7-Azaindoles" Synthesis (2005) 16:2751-2757.
Rulísek et al., "An Experimental and Theoretical Study of Stereoselectivity of Furan-Maleic Anhydride and Furan-Maleimide Diels-Alder Reactions" J. Org. Chem. (2005) 70(16):6295-6302.
Shang et al., "Cell entry mechanism of SARS-CoV-2" PNAS (2020) 117:11727-11734.
Steuten et al., "Challenges for targeting SARS-CoV-2 proteases as a therapeutics strategy for COVID-19" bioRxiv (2020) 2020.2011.2021.392753.
Zhang et al, "α-Ketoamides as Broad-Spectrum Inhibitors of Coronavirus and Enterovirus Replication: Structure-Based Design, Synthesis. And Activity Assessment" J. Med. Chem. (2020) 53:4562-4578.
Zhao et al., "Crystal Structure of SARS-CoV-2 main protease in complex with protease inhibitor PF-07321332" Protein & Cell (2021) https://doi.org/10.1007/s13238-021-00883-2.
Znabet et al., "Asymmetric synthesis of synthetic alkaloids by a tandem biocatalysis/Ugi/Pictet-Spengler-type cyclization sequence" Chem. Commun. (2010) 46(41):7706-7708 & Supplemental Information.
Znabet et al., "Highly stereoselective synthesis of substituted prolyl peptides using a combination of biocatalytic desymmetrization and multicomponent reactions." Angewandte Chemie International Edition (2010) 49(31):5298-5292.
https://www.cdc.gov/coronavirus/2019-ncov/need-extra-precautions/groups-at-higher-risk.html.
International Search Report and Written Opinion mailed Aug. 28, 2023 for PCT Application No. PCT/US2023/026908, filed Jul. 5, 2023.
Balasubramaniam et al., "The Growing Synthetic Utility of the Weinreb Amide" Synthesis (2008) 23:3707-3738.
CAS Reg. No. 2321331-16-0, Entered May 30, 2019.
CAS Reg. No. 2582799-50-4, STN Entry Date Feb. 4, 2021.
CAS Reg. No. 2582799-51-5, STN Entry Date Feb. 4, 2021.
Concellon et al., "Enantiopure Preparation of the Two Enantiomers of the Pseudo-C2-Symmetric N,N-Dibenzyl-1,2:4,5-diepoxypentan-3-amine" J. Org. Chem. (2001) 66(25):8661-8665.
Corey et al, "Enantioselective Synthesis of α-Amino Nitriles from N-Benzhydryl Imines and HCN with a Chiral Bicyclic Guanidine as Catalyst" Org. Lett. (1999) 1(1):157-160.
Cowley et al., "Spirocyclic systems derived from pyroglutamic acid" Org. Biomol. Chem. (2011) 9:7042-7056.
Evans et al., "Directed Reduction of β-Hydroxy Ketones Employing Tetramethylammonium Triacetoxyborohydride" J. Am. Chem. Soc. (1988) 110(11):3560-3578.
Fukuda et al. "Construction of Tetrasubstituted Carbon by an Organocatalyst: Cyanation Reaction of Ketones and Ketimines Catalyzed by a Nucleophilic-N-Heterocyclic Carbene" Synthesis, (2006) 16:2649-2652.
Kim et al., "Direct C(sp3)-H Cyanation Enabled by a Highly Active Decatungstate Photocatalyst" Org. Lett. (2021) 23(14): 5501-5505.
Mendonca et al., "Novel route to the synthesis of peptides containing 2-amino-1'-hydroxymethyl ketones and their application as cathepsin K inhibitors" Bioorganic & Medicinal Chemistry Letters (2002) 12(20):2887-2891.
Nahm et al., "N-Methoxy-N-Methylamides as Effective Acylating Agents" Tetrahedron Lett. (1981) 22(39), 3815-3818.
Nicolaou et al, "New Synthetic Technologies for the Construction of Heterocycles and Tryptamines" J. Am. Chem. Soc. (2009) 131(10):3690-3699.
Pace et al., "Chemoselective Synthesis of N-Substituted α-Amino-α'-chloro Ketones via Chloromethylation of Glycine-Derived Weinreb Amides" Advanced Synthesis & Catalysis (2013) 355(5):919-926.
Pedregal et al., "Highly chemoselective reduction of N-Boc protected lactams" Tetrahedron Lett. (1994) 35(13):2053-2056.
Rasnick, D., "Synthesis of peptide fluoromethyl ketones and the inhibition of human cathepsin B" Anal. Biochem. (1985) 149:461-465.
Sakaine et al., "Modified Julia-Kocienski Reagents for a Stereoselective Introduction of Trisubstituted Double Bonds: A Formal Total Synthesis of Limazepine E and Barmumycin" J. Org. Chem. (2018) 83(9):5323-5330.
Shi et al., "Direct Synthesis of α-Amino Nitriles from Sulfonamides via Base-Mediated C—H Cyanation" Org. Lett. (2021) 23(10):4018-4022.
Sun et al., "Synthesis of EF24-Tripeptide Chloromethyl Ketone: A Novel Curcumin-Related Anticancer Drug Delivery System" J. Med. Chem. (2006) 49(11):3153-3158.
International Preliminary Report on Patentability issued on Dec. 18, 2024 for PCT Application No. PCT/US2023/026908, filed Jul. 5, 2023.

ANTI-VIRAL COMPOUNDS

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference in their entireties under 37 CFR 1.57, and Rules 4.18 and 20.6, including U.S. Provisional Application No. 63/367,788, filed Jul. 6, 2022.

BACKGROUND

Field

The present application relates to the fields of chemistry, biochemistry and medicine. Disclosed herein are compounds of Formula (I), or pharmaceutically acceptable salt thereof, pharmaceutical compositions that include a compound described herein (including pharmaceutically acceptable salts of a compound described herein) and methods of synthesizing the same. Also disclosed herein are methods of treating diseases and/or conditions with a compound of Formula (I), or a pharmaceutically acceptable salt thereof.

Description

A positive-sense single-stranded RNA virus ((+)ssRNA virus) is a virus that uses positive sense, single stranded, RNA as its genetic material. Positive-sense single-stranded RNA viruses can be enveloped or non-enveloped. Coronaviridae, Picornaviridae and Norviruses are each a (+)ssRNA virus. Each of the aforementioned viruses are known to infect mammals, including humans.

SUMMARY

Some embodiments disclosed herein relate to a compound of Formula (I), or a pharmaceutically acceptable salt thereof.

Some embodiments disclosed herein relate to a pharmaceutical composition that can contain an effective amount of a compound of Formula (I), or a pharmaceutically acceptable salt thereof.

Some embodiments described herein relate to a method of treating a coronavirus infection that can include administering to a subject identified as suffering from the coronavirus infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of treating a coronavirus infection.

Some embodiments disclosed herein relate to a method of inhibiting replication of a coronavirus that can include contacting a cell infected with the coronavirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of inhibiting the replication a coronavirus.

Some embodiments described herein relate to a method of treating a picornavirus infection that can include administering to a subject identified as suffering from the picornavirus infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of treating a picornavirus infection.

Some embodiments disclosed herein relate to a method of inhibiting replication of a picornavirus that can include contacting a cell infected with the picornavirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of inhibiting the replication a picornavirus.

Some embodiments described herein relate to a method of treating a norovirus infection that can include administering to a subject identified as suffering from the norovirus infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of treating a norovirus infection.

Some embodiments disclosed herein relate to a method of inhibiting replication of a norovirus that can include contacting a cell infected with the norovirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of inhibiting the replication a norovirus.

These are other embodiments are described in greater detail below.

DETAILED DESCRIPTION

Coronaviridae viruses are a family of enveloped, positive-stranded, single-stranded, spherical RNA viruses. Coronaviruses are named for the crown-like spikes on their surface. The Coronaviridae family includes two sub-families, Coronavirus and Torovirus. The Coronavirus genus has a helical nucleocapsid, and Torovirus genus has a tubular nucleocapsid. The Coronaviridae family of viruses includes Middle East respiratory syndrome coronavirus (MERS-CoV), SARS and SARS-CoV-2.

Coronavirus disease 2019 (COVID-19) (also referred to as novel coronavirus pneumonia or 2019-nCoV acute respiratory disease) is an infectious disease caused by the virus severe respiratory syndrome coronavirus 2 (SARS-CoV-2) (also referred to as novel coronavirus 2019, or 2019-nCoV). The disease was first identified in December 2019 and spread globally, causing a pandemic. Symptoms of COVID-19 include fever, cough, shortness of breath, fatigue, headache, loss of smell, nasal congestion, sore throat, coughing up sputum, pain in muscles or joints, chills, nausea, vomiting, and diarrhea. In severe cases, symptoms can include difficulty waking, confusion, blueish face or lips, coughing up blood, decreased white blood cell count, and kidney failure. Complications can include pneumonia, viral sepsis, acute respiratory distress syndrome, and kidney failure.

COVID-19 is especially threatening to public health. The virus is highly contagious, and studies currently indicate that it can be spread by asymptomatic carriers or by those who are pre-symptomatic. Likewise, the early stage of the disease is slow-progressing enough that carriers do not often realize they are infected, leading them to expose numerous others to the virus. The combination of COVID-19's ease of transmission, its high rate of hospitalization of victims, and its death rate make the virus a substantial public health risk, especially for countries without a healthcare system equipped to provide supportive care to pandemic-level numbers of patients. There is not yet a vaccine or specific antiviral treatment for COVID-19 and accordingly, there is a pressing need for treatments or cures.

SARS-CoV-2 is not the only coronavirus that causes disease. It is a β-coronavirus, a genus of coronaviruses that includes other human pathogens, including SARS-CoV (the causative agent of SARS), MERS-CoV (the causative agent of MERS), and HCoV-OC43 (a causative agent of the common cold). The infectivity of these viruses, and the severity of the diseases they cause, varies widely. β-coronavirus can also manifest as zoonotic infections, spread to and from humans and animals. Additionally, non-human species such as camels, bats, tigers, non-human primates, and rabbits can be susceptible to β-coronavirus. Accordingly, there is a pressing need for treatments or cures to multiple coronaviruses.

The present disclosure provides molecules useful against coronaviruses, and especially SARS-CoV-2, the causative agent of COVID-19 in humans. Accordingly, the present disclosure fulfills the need in the art for compounds that can be safely and effectively treat or prevent coronavirus infections in humans.

Picornaviruses are a family of positive strand RNA, nonenveloped viruses. A picornavirus has 60 identical subunits (vertices) which contain five protomers. Each protomer is made up of one copy of four proteins, named VP1, VP2, VP3 and VP4. There are several genera of picornaviruses, including, Enterovirus, Aphthovirus, Cardiovirus and Hepatovirus. Enteroviruses known to infect human include, but are not limited to, Rhinovirus A, Rhinovirus B, Rhinovirus C, Coxsackievirus A, Coxsackievirus B and Poliovirus. There is no specific treatment for a picornavirus infection.

Noroviruses are single-stranded positive-sense RNA, non-enveloped viruses belonging to the Caliciviridae family. Noroviruses are often spread by the fecal-oral route, and are a common cause of gastroenteritis. Infected subjects can experience nausea, non-bloody diarrhea, vomiting and/or abdominal pain. Those suffering from a norovirus infection can become severely dehydrated and require medical attention. As with a picornavirus infection, there is no specific treatment for a norovirus infection. Accordingly, there is a need for compounds that effectively treat or prevent a picornavirus and/or a norovirus infection.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) (such as 1, 2 or 3) individually and independently selected from deuterium, alkyl, alkenyl, alkynyl, cycloalkyl, cycloalkenyl, aryl, heteroaryl, heterocyclyl, aryl(alkyl), heteroaryl(alkyl), heterocyclyl(alkyl), hydroxy, alkoxy, acyl, cyano, halogen, thiocarbonyl, 0-carbamyl, N-carbamyl, O-thiocarbamyl, N-thiocarbamyl, C-amido, N-amido, S-sulfonamido, N-sulfonamido, C-carboxy, O-carboxy, C-amido(alkyl), isocyanato, thiocyanato, nitro, azido, silyl, sulfenyl, sulfinyl, sulfonyl, haloalkyl, haloalkoxy, trihalomethanesulfonyl, trihalomethanesulfonamido, an amino, a mono-substituted amine and a di-substituted amine.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heterocyclyl group. That is, the alkyl, alkenyl, alkynyl, ring of the cycloalkyl, ring of the cycloalkenyl, ring of the aryl, ring of the heteroaryl or ring of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. The length of an alkenyl can vary. For example, the alkenyl can be a $C_{2-4}$ alkenyl, $C_{2-6}$ alkenyl or $C_{2-8}$ alkenyl. Examples of alkenyl groups include allenyl, vinylmethyl and ethenyl. An alkenyl group may be unsubstituted or substituted.

As used herein, "alkynyl" refers to an alkyl group that contains in the straight or branched hydrocarbon chain one or more triple bonds. The length of an alkynyl can vary. For example, the alkynyl can be a $C_{2-4}$ alkynyl, $C_{2-6}$ alkynyl or $C_{2-8}$ alkynyl. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused- or spiro-fashion. Cycloalkyl groups can contain 3 to 10 atoms in the ring(s). 3 to 8 atoms in the ring(s) or 3 to 6 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused- or spiro-fashion. A cycloalkenyl can contain 3 to 10 atoms in the ring(s) or 3 to 8 atoms in the ring(s). A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic, bicyclic and tricyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" refers to a monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The number of atoms in the ring(s) of a heterocyclyl group can vary. For example, the heterocyclyl group can contain 4 to 14 atoms in the ring(s), 5 to 10 atoms in the ring(s) or 5 to 6 atoms in the ring(s). The heteroatom (s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocyclyl may be quaternized. Heterocyclyl groups may be unsubstituted or substituted. Examples of such "heterocyclyl groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and 3,4-methylenedioxyphenyl).

As used herein, "cycloalkyl(alkyl)" refers to an cycloalkyl group connected, as a substituent, via a lower alkylene group. The lower alkylene and cycloalkyl group of an cycloalkyl(alkyl) may be substituted or unsubstituted. A cycloalkyl(alkyl) group may be unsubstituted or substituted.

As used herein, "aryl(alkyl)" refer to an aryl group connected, as a substituent, via a lower alkylene group. The lower alkylene and aryl group of an aryl(alkyl) may be substituted or unsubstituted. Examples include but are not limited to benzyl, 2-phenyl(alkyl), 3-phenyl(alkyl), and naphthyl(alkyl).

As used herein, "heteroaryl(alkyl)" refer to a heteroaryl group connected, as a substituent, via a lower alkylene group. The lower alkylene and heteroaryl group of heteroaryl(alkyl) may be substituted or unsubstituted. Examples include but are not limited to 2-thienyl(alkyl), 3-thienyl(alkyl), furyl(alkyl), thienyl(alkyl), pyrrolyl(alkyl), pyridyl(alkyl), isoxazolyl(alkyl), imidazolyl(alkyl), and their benzo-fused analogs.

A "heterocyclyl(alkyl)" refer to a heterocyclic group connected, as a substituent, via a lower alkylene group. The lower alkylene and heterocyclyl of a heterocyclyl(alkyl)

may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl(methyl) and 1,3-thiazinan-4-yl(methyl).

"Lower alkylene groups" are straight-chained $—CH_2—$ tethering groups, forming bonds to connect molecular fragments via their terminal carbon atoms. Examples include but are not limited to methylene ($—CH_2—$), ethylene ($—CH_2CH_2—$), propylene ($—CH_2CH_2CH_2—$) and butylene ($—CH_2CH_2CH_2CH_2—$). A lower alkylene group can be substituted by replacing one or more hydrogen of the lower alkylene group with a substituent(s) listed under the definition of "substituted." Further, when a lower alkylene group is substituted, the lower alkylene can be substituted by replacing both hydrogens on the same carbon with a cycloalkyl group (e.g., 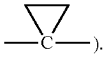 ).

As used herein, "alkoxy" refers to the formula —OR wherein R is an alkyl, an alkenyl, an alkynyl, a cycloalkyl, a cycloalkenyl, an aryl, a heteroaryl, a heterocyclyl, a cycloalkyl(alkyl), an aryl(alkyl), a heteroaryl(alkyl) or a heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzyloxy. In some instances, an alkoxy can be —OR, wherein R is an unsubstituted $C_{1-4}$ alkyl. An alkoxy may be substituted or unsubstituted.

As used herein, "acyl" refers to a hydrogen, an alkyl, an alkenyl, an alkynyl, a cycloalkyl, a cycloalkenyl, an aryl, a heteroaryl, a heterocyclyl, an aryl(alkyl), a heteroaryl(alkyl) or a heterocyclyl(alkyl) connected, as substituents, via a carbonyl group. Examples include formyl, acetyl, propanoyl, benzoyl and acryl. An acyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to a O-alkyl group and O-monocyclic cycloalkyl group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy, 2-fluoroisobutoxy, chloro-substituted cyclopropyl, fluoro-substituted cyclopropyl, chloro-substituted cyclobutyl and fluoro-substituted cyclobutyl. In some instances, a haloalkoxy can be —OR, wherein R is a $C_{1-4}$ alkyl substituted by 1, 2 or 3 halogens. A haloalkoxy may be substituted or unsubstituted.

A "sulfenyl" group refers to an "—SR" group in which R can be hydrogen, an alkyl, an alkenyl, an alkynyl, a cycloalkyl, a cycloalkenyl, an aryl, a heteroaryl, a heterocyclyl, an aryl(alkyl), a heteroaryl(alkyl) or a heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "$SO_2R$" group in which R can be the same as defined with respect to sulfenyl. A sulfonyl may be substituted or unsubstituted.

An "O-carboxy" group refers to a "RC(=O)O—" group in which R can be hydrogen, an alkyl, an alkenyl, an alkynyl, a cycloalkyl, a cycloalkenyl, an aryl, a heteroaryl, a heterocyclyl, an aryl(alkyl), a heteroaryl(alkyl) or a heterocyclyl (alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "$X_3CSO_2—$" group wherein each X is a halogen.

A "trihalomethanesulfonamido" group refers to an "$X_3CS(O)_2N(R_A)—$" group wherein each X is a halogen, and $R_A$ is hydrogen, an alkyl, an alkenyl, an alkynyl, a cycloalkyl, a cycloalkenyl, an aryl, a heteroaryl, a heterocyclyl, an aryl (alkyl), a heteroaryl(alkyl) or a heterocyclyl(alkyl).

The term "amino" as used herein refers to a $—NH_2$ group.

As used herein, the term "hydroxy" refers to a —OH group.

A "cyano" group refers to a "—CN" group.

The term "azido" as used herein refers to a $—N_3$ group.

An "isocyanato" group refers to a "—NCO" group.

A "thiocyanato" group refers to a "—SCN" group.

An "isothiocyanato" group refers to an "—NCS" group.

A "mercapto" group refers to an "—SH" group.

A "carbonyl" group refers to a —C(=O)— group.

An "S-sulfonamido" group refers to a "$—SO_2N(R_AR_B)$" group in which $R_A$ and $R_B$ can be independently hydrogen, an alkyl, an alkenyl, an alkynyl, a cycloalkyl, a cycloalkenyl, an aryl, a heteroaryl, a heterocyclyl, an aryl(alkyl), a heteroaryl(alkyl) or a heterocyclyl(alkyl). An S-sulfonamido may be substituted or unsubstituted.

An "N-sulfonamido" group refers to a "$RSO_2N(R_A)—$" group in which R and $R_A$ can be independently hydrogen, an alkyl, an alkenyl, an alkynyl, a cycloalkyl, a cycloalkenyl, an aryl, a heteroaryl, a heterocyclyl, an aryl(alkyl), a heteroaryl (alkyl) or a heterocyclyl(alkyl). An N-sulfonamido may be substituted or unsubstituted.

An "O-carbamyl" group refers to a "$—OC(=O)N(R_AR_B)$" group in which $R_A$ and $R_B$ can be independently hydrogen, an alkyl, an alkenyl, an alkynyl, a cycloalkyl, a cycloalkenyl, an aryl, a heteroaryl, a heterocyclyl, an aryl (alkyl), a heteroaryl(alkyl) or a heterocyclyl(alkyl). An O-carbamyl may be substituted or unsubstituted.

An "N-carbamyl" group refers to an "$ROC(=O)N(R_A)—$" group in which R and $R_A$ can be independently hydrogen, an alkyl, an alkenyl, an alkynyl, a cycloalkyl, a cycloalkenyl, an aryl, a heteroaryl, a heterocyclyl, an aryl (alkyl), a heteroaryl(alkyl) or a heterocyclyl(alkyl). An N-carbamyl may be substituted or unsubstituted.

An "O-thiocarbamyl" group refers to a "$—OC(=S)—N(R_AR_B)$" group in which $R_A$ and $R_B$ can be independently hydrogen, an alkyl, an alkenyl, an alkynyl, a cycloalkyl, a cycloalkenyl, an aryl, a heteroaryl, a heterocyclyl, an aryl (alkyl), a heteroaryl(alkyl) or a heterocyclyl(alkyl). An O-thiocarbamyl may be substituted or unsubstituted.

An "N-thiocarbamyl" group refers to an "$ROC(=S)N(R_A)—$" group in which R and $R_A$ can be independently hydrogen, an alkyl, an alkenyl, an alkynyl, a cycloalkyl, a cycloalkenyl, an aryl, a heteroaryl, a heterocyclyl, an aryl (alkyl), a heteroaryl(alkyl) or a heterocyclyl(alkyl). An N-thiocarbamyl may be substituted or unsubstituted.

A "C-amido" group refers to a "—C(═O)N($R_AR_B$)" group in which $R_A$ and $R_B$ can be independently hydrogen, an alkyl, an alkenyl, an alkynyl, a cycloalkyl, a cycloalkenyl, an aryl, a heteroaryl, a heterocyclyl, an aryl(alkyl), a heteroaryl(alkyl) or a heterocyclyl(alkyl). A C-amido may be substituted or unsubstituted.

An "N-amido" group refers to a "RC(═O)N($R_A$)—" group in which R and $R_A$ can be independently hydrogen, an alkyl, an alkenyl, an alkynyl, a cycloalkyl, a cycloalkenyl, an aryl, a heteroaryl, a heterocyclyl, an aryl(alkyl), a heteroaryl (alkyl) or a heterocyclyl(alkyl). An N-amido may be substituted or unsubstituted.

A "mono-substituted amine" refers to a "—NH$R_A$" in which $R_A$ can be independently an alkyl, an alkenyl, an alkynyl, a cycloalkyl, a cycloalkenyl, an aryl, a heteroaryl, a heterocyclyl, an aryl(alkyl), a heteroaryl(alkyl) or a heterocyclyl(alkyl). A mono-substituted amine may be substituted or unsubstituted. In some instances, a mono-substituted amine can be —NH$R_A$, wherein $R_A$ can be an unsubstituted $C_{1-6}$ alkyl or an unsubstituted or a substituted benzyl.

A "di-substituted amine" refers to a "—N$R_AR_B$" in which $R_A$ and $R_B$ can be independently can be independently an alkyl, an alkenyl, an alkynyl, a cycloalkyl, a cycloalkenyl, an aryl, a heteroaryl, a heterocyclyl, an aryl(alkyl), a heteroaryl (alkyl) or a heterocyclyl(alkyl). A mono-substituted amine may be substituted or unsubstituted. In some instances, a mono-substituted amine can be —N$R_AR_B$, wherein $R_A$ and $R_B$ can be independently an unsubstituted $C_{1-6}$ alkyl or an unsubstituted or a substituted benzyl.

A "ketoamide" group refers to a —C(═O)—C(═O)N ($R_AR_B$) group in which $R_A$ and $R_B$ can be independently hydrogen, an alkyl, an alkenyl, an alkynyl, a cycloalkyl, a cycloalkenyl, an aryl, a heteroaryl, a heterocyclyl, an aryl (alkyl), a heteroaryl(alkyl) or a heterocyclyl(alkyl). A ketoamide may be substituted or unsubstituted.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof. In addition, the term "comprising" is to be interpreted synonymously with the phrases "having at least" or "including at least". When used in the context of a compound or composition, the term "comprising" means that the compound or composition includes at least the recited features or components, but may also include additional features or components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality.

It is understood that, in any compound described herein having one or more chiral centers, if an absolute stereochemistry is not expressly indicated, then each center may independently be of (R)-configuration or (S)-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Where a range of values is provided, it is understood that the upper and lower limit, and each intervening value between the upper and lower limit of the range is encompassed within the embodiments.

Compounds

Some embodiments disclosed herein relate to a compound of Formula (I), or a pharmaceutically acceptable salt thereof:

(I)

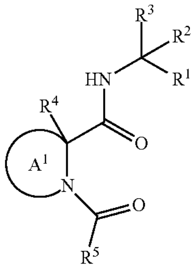

wherein: Ring $A^1$ can be

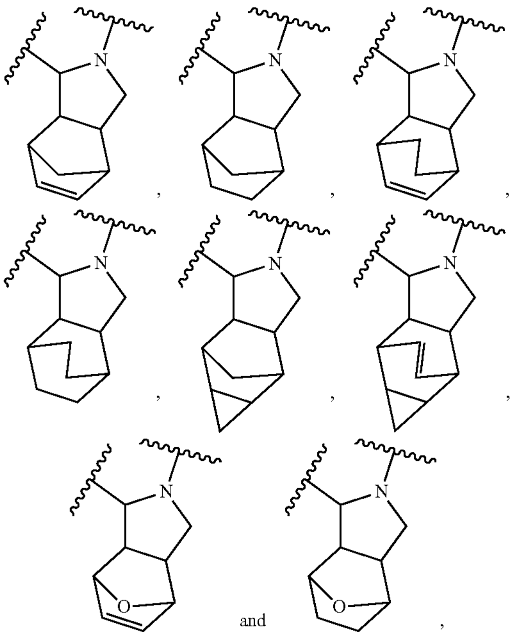

, , , , , and , and wherein Ring $A^1$ can be optionally substituted with one or more moieties independently selected from =O, =$CH_2$, deuterium, halogen, hydroxy, an unsubstituted $C_{1-4}$ alkyl, an unsubstituted $C_{1-4}$ haloalkyl, an unsubstituted $C_{2-4}$ alkenyl and an unsubstituted or a substituted $C_{3-6}$ monocyclic cycloalkyl; $R^1$ can be selected from cyano, an unsubstituted or a substituted $C_{2-5}$ alkynyl, an unsubstituted or a substituted acyl, an unsubstituted or a substituted ketoamide, —CH(OH)—(S(=O)$_2$—O—), —CH(OH)((P=O)(OR$^6$)$_2$) and —C(=O)CH$_2$—O—((P=O)(OR$^7$)$_2$); each $R^6$ and each $R^7$ can be independently hydrogen, an unsubstituted $C_{1-6}$ alkyl, an unsubstituted $C_{2-6}$ alkenyl, an unsubstituted $C_{1-6}$ haloalkyl, an unsubstituted or a substituted aryl or an unsubstituted or a substituted aryl($C_{1-4}$ alkyl); $R^2$ can be hydrogen, deuterium or halogen; $R^3$ can be an unsubstituted or a substituted monocyclic nitrogen-containing heterocyclyl ($C_{1-4}$ alkyl), an unsubstituted or a substituted bicyclic nitrogen-containing heterocyclyl($C_{1-4}$ alkyl) or an unsubstituted or a substituted monocyclic nitrogen-containing heteroaryl ($C_{1-4}$ alkyl); $R^4$ can be hydrogen, deuterium or halogen; $R^5$ can be

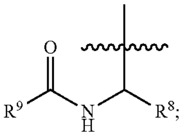

$R^8$ can be selected from an unsubstituted or a substituted $C_{2-6}$ alkyl, an unsubstituted or a substituted $C_{2-6}$ alkenyl, an unsubstituted or a substituted $C_{2-6}$ alkynyl, an unsubstituted or a substituted monocyclic $C_{3-6}$ cycloalkyl, an unsubstituted or a substituted bicyclic $C_{5-8}$ cycloalkyl, an unsubstituted or a substituted monocyclic 4- to 6-membered heterocyclyl and an unsubstituted monocyclic $C_{3-6}$ cycloalkyl ($CH_2$)—, wherein when the $C_{2-6}$ alkyl is substituted, the $C_{2-6}$ alkyl can be substituted 1, 2, 3 or 4 times with a substituent independently selected from halogen, cyano, an unsubstituted or a substituted monocyclic $C_{3-6}$ cycloalkyl, an unsubstituted $C_{1-4}$ alkoxy and an unsubstituted $C_{1-4}$ haloalkoxy, or the $C_{2-6}$ alkyl is substituted 1 to 13 times with deuterium; wherein when the $C_{2-6}$ alkenyl, the $C_{2-6}$ alkynyl, the monocyclic $C_{3-6}$ cycloalkyl, the bicyclic $C_{5-8}$ cycloalkyl and the monocyclic 4- to 6-membered heterocyclyl are substituted, the $C_{2-6}$ alkenyl, the $C_{2-6}$ alkynyl, the monocyclic $C_{3-6}$ cycloalkyl, the bicyclic $C_{5-8}$ cycloalkyl and the monocyclic 4- to 6-membered heterocyclyl can be substituted 1, 2, 3 or 4 times with a substituent independently selected from halogen, an unsubstituted $C_{1-4}$ alkyl, an unsubstituted $C_{2-4}$ alkenyl, an unsubstituted $C_{2-4}$ alkynyl, an unsubstituted $C_{1-4}$ haloalkyl, an unsubstituted or a substituted monocyclic $C_{3-6}$ cycloalkyl and an unsubstituted $C_{1-4}$ alkoxy; and $R^9$ can be an unsubstituted or a substituted alkoxy.

The substituent $R^1$ can be various moieties. In some embodiments, $R^1$ can be an unsubstituted ketoamide. In some embodiments, $R^1$ can be a substituted ketoamide. The ketoamide can have the structure —C(=O)—C(=O)NR$^{y1}$R$^{z1}$. In some embodiments, $R^1$ can be an acyl, for example, $R^1$ can be —C(=O)H, —C(=O)(an unsubstituted $C_{1-4}$ alkyl), —C(=O)(an unsubstituted to a substituted benzyl), —C(=O)(an unsubstituted to a substituted monocyclic heteroaryl) or —C(=O)(an unsubstituted to a substituted bicyclic heteroaryl). In some embodiments, $R^1$ can be a substituted acyl. The acyl for $R^1$ can have the structure —C(=O)R$^{y2}$. When the acyl is substituted, the possible groups that can be present on the acyl include hydroxy, a substituted or an unsubstituted alkoxy (such as —O-(an unsubstituted $C_{1-4}$ alkyl), —O-(an unsubstituted $C_{3-6}$ cycloalkyl), a substituted or an unsubstituted phenoxy or a substituted or an unsubstituted benzyloxy) or —O—(C=O)-(an unsubstituted $C_{1-6}$ alkyl). In some embodiments, $R^1$ can be an unsubstituted can be —C(=O)—N-sulfonamido.

$R^{y1}$, $R^{y2}$ and $R^{z1}$ can be a variety of groups. In some embodiments, $R^{y1}$, $R^{y2}$ and $R^{z1}$ can be independently selected from hydrogen, $C_{1-8}$ alkyl, $C_{2-8}$ alkenyl, $C_{2-8}$ alkynyl, $C_{3-8}$ cycloalkyl (for example, a monocyclic $C_{3-8}$ cycloalkyl), $C_{3-8}$ cycloalkenyl (such as a monocyclic $C_{3-8}$ cycloalkenyl), aryl (such as phenyl or naphthyl), heteroaryl (including a monocyclic or a bicyclic heteroaryl), heterocyclyl (for example, a monocyclic or a bicyclic heterocyclyl), aryl(alkyl) (such as benzyl), heteroaryl(alkyl) (including a monocyclic heteroaryl($CH_2$)— and a monocyclic (heteroaryl($CH_2CH_2$)—) or heterocyclyl(alkyl) (such as a monocyclic heterocyclyl($CH_2$)— and a monocyclic heterocyclyl($CH_2CH_2$)—), wherein each of the aforementioned $R^{y1}$, $R^{y2}$ and $R^{z1}$ groups can be unsubstituted or substituted. In some embodiments, $R^{y1}$, $R^{y2}$ and $R^{z1}$ can be independently selected from H, $C_{1-6}$ alkyl, an unsubstituted $C_{1-4}$ haloalkyl (including —$CF_3$, —$CCl_3$, —$CHF_2$, —$C(CH_3)F_2$, —$CHCl_2$, —$CH_2F$, —$CH(CH_3)F$, —$CH_2CF_3$, —$CH_2Cl$, —$CH_2CH_2F$, —$CH_2CH_2Cl$, —$CH_2CH_2CH_2F$ and —$CH_2CH_2CH_2Cl$), —$C_{1-4}$ alkyl(OH) (including —$CH_2OH$, —$CH_2CH_2OH$ and —$CH(CH_3)OH$), —$C_{1-4}$ alkyl($C_{1-4}$ alkoxy) (such as —$CH_2O$(an unsubstituted $C_{1-4}$ alkyl) and —$CH_2CH_2O$(an unsubstituted $C_{1-4}$ alkyl)), —$C_{1-4}$ alkyl-O-(a monocyclic $C_{3-6}$ cycloalkyl) (such as —$CH_2O$(a monocyclic $C_{3-6}$ cycloalkyl), —$CH_2CH_2O$(a monocyclic $C_{3-6}$ cycloalkyl)), —$C_{1-4}$ alkyl-O-(phenyl) (for example, —$CH_2O$(phenyl) and —$CH_2CH_2O$(phenyl)), —$C_{1-4}$ alkyl-O-(5- to 6-membered monocyclic heteroaryl) (such as —$CH_2O$ (5- to 6-membered monocyclic heteroaryl) and —$CH_2CH_2O$ (5- to 6-membered monocyclic heteroaryl)), —$C_{1-4}$ alkyl-O-(5- to 6-membered monocyclic heterocyclyl) (for example, —$CH_2O$ (5- to 6-membered monocyclic heterocyclyl) and —$CH_2CH_2O$ (5- to 6-membered monocyclic heterocyclyl)), —$C_{1-4}$ alkyl-O-(a monocyclic $C_{3-6}$ cycloalkyl($C_{1-4}$ alkyl) (such as —$C_{1-4}$ alkyl-O—$CH_2$-(monocyclic $C_{3-6}$ cycloalkyl) and —$C_{1-4}$ alkyl-O—$CH_2CH_2$-(monocyclic $C_{3-6}$ cycloalkyl)), —$C_{1-4}$ alkyl-O-(benzyl) (for example, —$CH_2O$(benzyl) and —$CH_2CH_2O$(benzyl)), —$C_{1-4}$ alkyl-O-(5- to 6-membered monocyclic heteroaryl($C_{1-4}$ alkyl), —$C_{1-4}$ alkyl-O-(5- to 6-membered monocyclic heterocyclyl($C_{1-4}$ alkyl), —$C_{1-4}$ alkyl-O(C═O) (an unsubstituted $C_{1-6}$ alkyl) (for example, —$CH_2O$(C═O) (an unsubstituted $C_{1-8}$ alkyl)), a monocyclic $C_{3-8}$ cycloalkyl (such as cyclopropyl, cyclobutyl, cyclopentyl, cyclohexyl, cycloheptyl and cyclooctyl), a monocyclic heteroaryl (such as imidazole, 1,3,4-oxadiazole and pyridinyl), a monocyclic heterocyclyl (for example, tetrahydrofuran and tetrahydropyran), a bicyclic heteroaryl (for example, benzothiazole, benzoimidazole and benzooxazole), a bicyclic heterocyclyl, a monocyclic $C_{3-6}$ cycloalkyl(alkyl), aryl(alkyl) (such as benzyl), heteroaryl(alkyl) (for example, a monocyclic heteroaryl-($CH_2$)—, such as pyridinyl-($CH_2$)—) and heterocyclyl(alkyl) (for example, a monocyclic heterocyclyl-($CH_2$)—), wherein each of the aforementioned $R^{y1}$, $R^{y2}$ and $R^{z1}$ groups can be unsubstituted or substituted.

In some embodiments, $R^1$ can be —C(═O)$R^{y2}$, wherein $R^{y2}$ can be —$C_{1-4}$ alkyl(OH) (such as —$CH_2OH$). In some embodiments, $R^1$ can be —C(═O)—C(═O)$NR^{y1}R^{z1}$; wherein $R^{y1}$ can be H; and $R^{z1}$ can be any of the moieties listed for $R^{z1}$ in the previous paragraph. In some embodiments, $R^1$ can be —C(═O)—C(═O)$NR^{y1}R^{z1}$; wherein $R^{y1}$ can be H; and $R^{z1}$ can be a monocyclic $C_{3-8}$ cycloalkyl (for example, cyclopropyl, cyclobutyl, cyclopentyl, cyclohexyl, cycloheptyl and cyclooctyl).

Prodrug-type and phosphate-containing moieties can be present at $R^1$. In some embodiments, $R^1$ can be —CH(OH)—(S(═O)$_2$—O—). In other embodiments, $R^1$ can be —CH(OH)((P═O)(OR$^6$)$_2$), wherein each $R^6$ can be independently hydrogen, an unsubstituted $C_1$-6 alkyl, an unsubstituted $C_{2-6}$ alkenyl, an unsubstituted $C_{1-6}$ haloalkyl, an unsubstituted or a substituted aryl or an unsubstituted or a substituted aryl($C_{1-4}$ alkyl). In still other embodiments, $R^1$ can be —C(═O)$CH_2$—O—((P═O)(OR$^7$)$_2$), wherein each $R^7$ can be independently hydrogen, an unsubstituted $C_{1-6}$ alkyl, an unsubstituted $C_{2-6}$ alkenyl, an unsubstituted $C_{1-6}$ haloalkyl, an unsubstituted or a substituted aryl or an unsubstituted or a substituted aryl($C_{1-4}$ alkyl). Other examples of $R^6$ and $R^7$ groups include methyl, ethyl, n-propyl, iso-propyl, n-butyl, iso-butyl, sec-butyl, tert-butyl, pentyl (straight-chained and branched), hexyl (straight-chained and branched), ethenyl, propenyl, butenyl, pentenyl, hexenyl, chloromethyl, fluoromethyl, difluoromethyl, dichloromethyl, trifluoromethyl, trichloromethyl, an unsubstituted or a substituted phenyl and an unsubstituted or a substituted benzyl.

In some embodiments, $R^1$ can be cyano. In other embodiments, $R^1$ can be an unsubstituted $C_{2-5}$ alkynyl. In still other embodiments, $R^1$ can be a substituted $C_{2-5}$ alkynyl. The $C_{2-5}$ alkynyl can have various structures. For example, the $C_{2-5}$ alkynyl can have the structure —$(CH_2)_1$—$C_{2-4}$ alkynyl or —$(CH_2)_2$—$C_{2-3}$ alkynyl.

As described herein, Ring $A^1$ can be

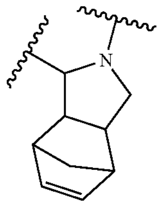

, wherein Ring $A^1$ can be optionally substituted. In some embodiments, Ring $A^1$ can be an unsubstituted

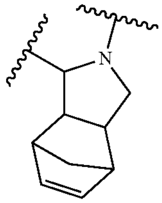

.

In other embodiments, Ring $A^1$ can be a substituted

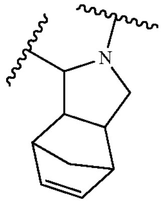

.

In still other embodiments, Ring $A^1$ can be an unsubstituted

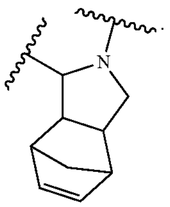

In yet still other embodiments, Ring $A^1$ can be a substituted

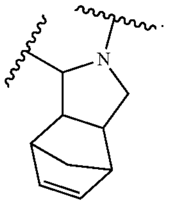 [SMILES: *C1C2C3C=CC(C3)C2CN1*]

In some embodiments, Ring $A^1$ can be an unsubstituted

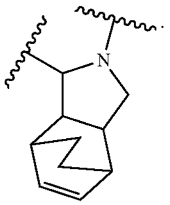 [SMILES: *C1C2C3C=CC(CC3)C2CN1*]

In other embodiments, Ring $A^1$ can be a substituted

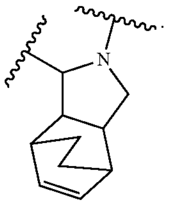 [SMILES: *C1C2C3C=CC(CC3)C2CN1*]

In still other embodiments, Ring $A^1$ can be an unsubstituted

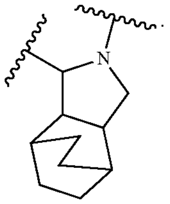 [SMILES: *C1C2C3CCC(CC3)C2CN1*]

In yet still other embodiments, Ring $A^1$ can be a substituted

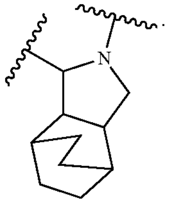 [SMILES: *C1C2C3CCC(CC3)C2CN1*]

In some embodiments, Ring $A^1$ can be an unsubstituted

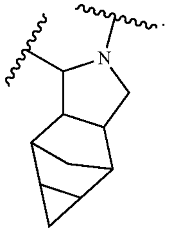 [SMILES: *C1C2C3CC(C4CC43)C2CN1*]

In other embodiments, Ring $A^1$ can be a substituted

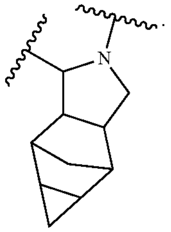 [SMILES: *C1C2C3CC(C4CC43)C2CN1*]

In still other embodiments, Ring $A^1$ can be an unsubstituted

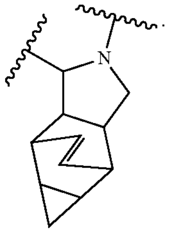 [SMILES: *C1C2C3C=CC(C4CC34)C2CN1*]

In yet still other embodiments, Ring $A^1$ can be a substituted

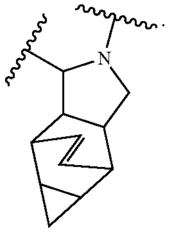 [SMILES: *C1C2C3C=CC(C4CC34)C2CN1*]

In some embodiments, Ring $A^1$ can be an unsubstituted

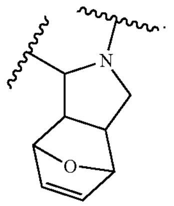 [SMILES: *C1C2C3C=CC(O3)C2CN1*]

In other embodiments, Ring $A^1$ can be a substituted

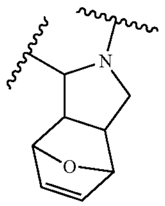 [SMILES: *C1C2C3C=CC(O3)C2CN1*]

In still other embodiments, Ring $A^1$ can be an unsubstituted

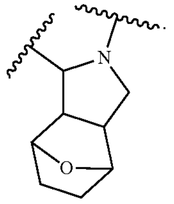 [SMILES: *C1C2C3CCC(O3)C2CN1*]

In yet still other embodiments, Ring $A^1$ can be a substituted

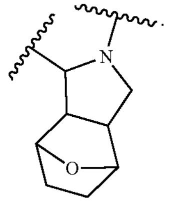 [SMILES: *C1C2C3CCC(O3)C2CN1*]

Those skilled in the art understand that the nitrogen shown in each of the ring structures for Ring $A^1$ corresponds to the ring nitrogen shown in Formula (I), and the carbon adjacent to the ring nitrogen with the

corresponds to the carbon to which $R^4$ is attached. For example, those skilled in the art understand that when Ring $A^1$ is

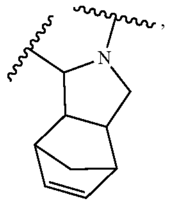 [SMILES: *C1C2C3C=CC(C3)C2CN1*]

then a compound of Formula (I), or a pharmaceutically acceptable salt thereof, can have the following structure:

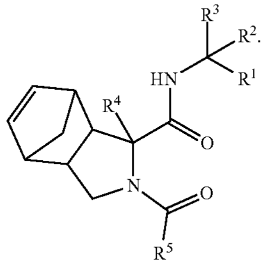

As provided herein, Ring $A^1$ can be substituted with one or more moieties independently selected from $=O$, $=CH_2$, deuterium, halogen, hydroxy, an unsubstituted $C_{1-4}$ alkyl, an unsubstituted $C_{1-4}$ haloalkyl, an unsubstituted $C_{2-4}$ alkenyl and an unsubstituted or a substituted $C_{3-6}$ monocyclic cycloalkyl. Example of suitable substituents that can be present in Ring $A^1$ include halogen (such as F or Cl), an unsubstituted $C_{1-4}$ alkyl (for example, methyl, ethyl, n-propyl, iso-propyl, n-butyl, iso-butyl, sec-butyl and tert-butyl), an unsubstituted $C_{1-4}$ haloalkyl (including $—CF_3$, $—CCl_3$, $—CHF_2$, $—C(CH_3)F_2$, $—CHCl_2$, $—CH_2F$, $—CH(CH_3)F$, $—CH_2CF_3$, $—CH_2Cl$, $—CH_2CH_2F$, $—CH_2CH_2Cl$, $—CH_2CH_2CH_2F$ and $—CH_2CH_2CH_2Cl$), an unsubstituted $C_{2-4}$ alkenyl (such as ethenyl, propenyl and butenyl) and an unsubstituted or a substituted $C_{3-6}$ monocyclic cycloalkyl (for example, cyclopropyl, cyclobutyl, cyclopentyl and cyclohexyl). When Ring $A^1$ is substituted by an unsubstituted or a substituted $C_{3-6}$ monocyclic cycloalkyl, the unsubstituted or a substituted $C_{3-6}$ monocyclic cycloalkyl can replace one hydrogen. In some embodiments, an unsubstituted or a substituted $C_{3-6}$ monocyclic cycloalkyl can replace two hydrogens of Ring $A^1$ such that the unsubstituted or a substituted $C_{3-6}$ monocyclic cycloalkyl is connected to Ring A in a spiro-fashion. Examples of an unsubstituted or a substituted $C_{3-6}$ monocyclic cycloalkyl replacing two hydrogen of Ring $A^1$ includes the following:

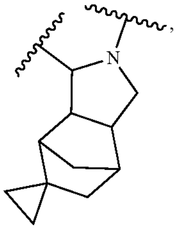

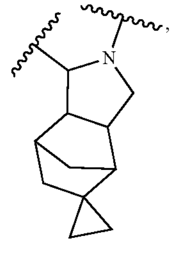

-continued
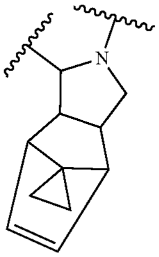 and 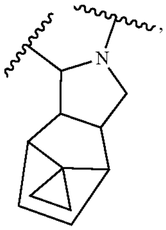,
wherein each can be unsubstituted or substituted as described herein. Examples of Ring A[1] include, but are not limited to, the following:
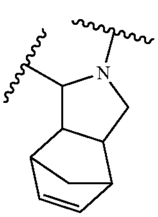, 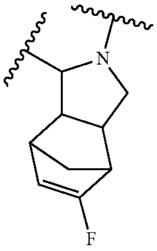, 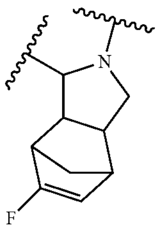,
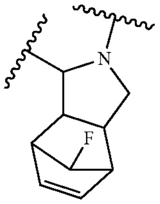, 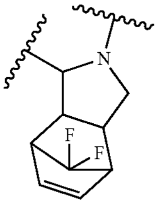, 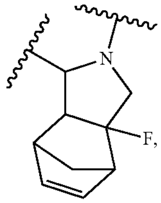
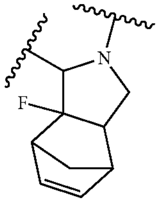, 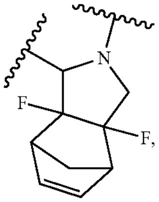, 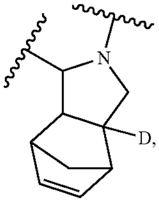
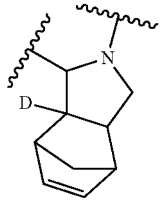, 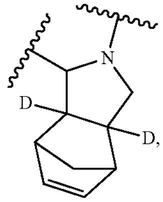, 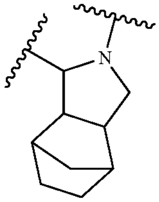
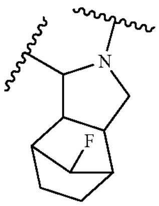, 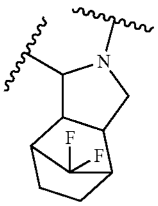, 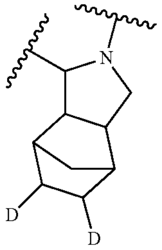,
-continued
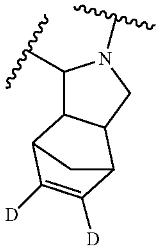, 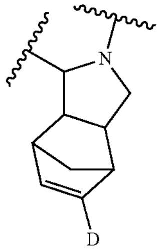, 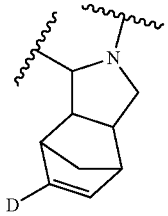,
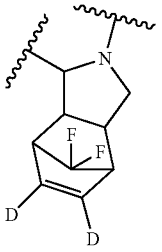, 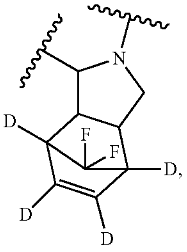 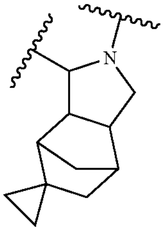,
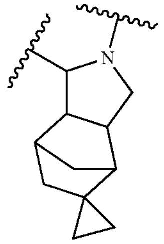, 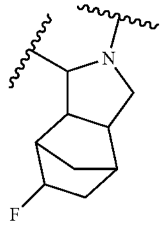, 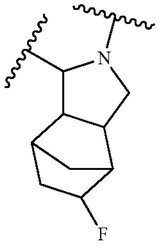,
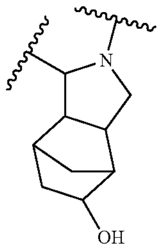, 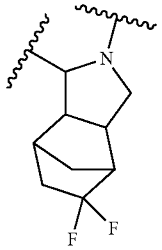,
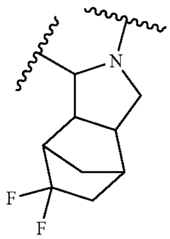, 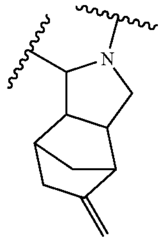, 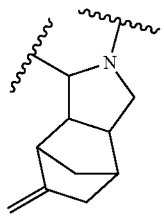,
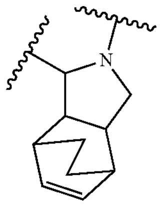, 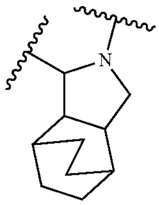, 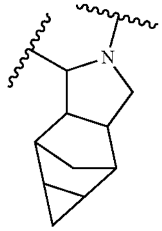, -continued

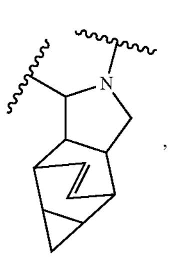 , 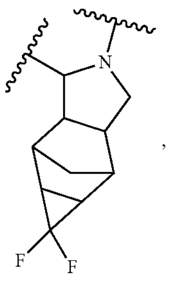 , 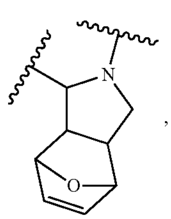 ,

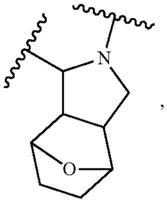 , 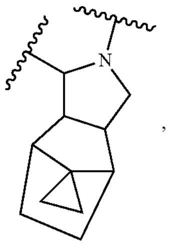 , 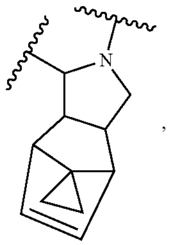 ,

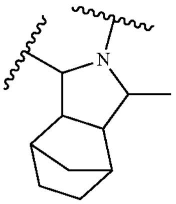 , 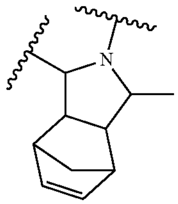 ,

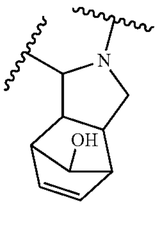 and 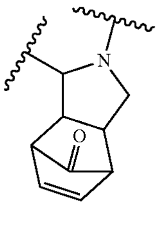 .

In some embodiments, $R^4$ can be hydrogen. In other embodiments, $R^4$ can be deuterium. In still other embodiments, $R^4$ can be halogen (such as fluoro or chloro).

As provided herein $R^3$ can be a non-hydrogen substituent selected from an unsubstituted or a substituted monocyclic nitrogen-containing heterocyclyl($C_{1-4}$ alkyl) and an unsubstituted or a substituted bicyclic nitrogen-containing heterocyclyl($C_{1-4}$ alkyl). In some embodiments, $R^3$ can be an unsubstituted monocyclic nitrogen-containing heteroaryl ($C_{1-4}$ alkyl). In other embodiments, $R^3$ can be a substituted monocyclic nitrogen-containing heteroaryl($C_{1-4}$ alkyl). In still other embodiments, $R^3$ can be an unsubstituted bicyclic nitrogen-containing heterocyclyl($C_{1-4}$ alkyl). In yet still other embodiments, $R^3$ can be a substituted bicyclic nitrogen-containing heterocyclyl($C_{1-4}$ alkyl). When $R^3$ is a bicyclic nitrogen-containing heterocyclyl($C_{1-4}$ alkyl), the two rings of the bicyclic heterocyclyl can be connected in a fused-fashion (including bridged-fashion) or a spiro-fashion. In some embodiments, $R^3$ can be an unsubstituted monocyclic nitrogen-containing heteroaryl($C_{1-4}$ alkyl). In other embodiments, $R^3$ can be a substituted monocyclic nitrogen-containing heteroaryl($C_{1-4}$ alkyl).

Those skilled in the art understand that when two rings are connected in a spiro-fashion, the two rings are connected by a single ring atom. For example, in the structure

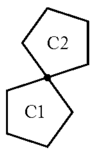

rings C1 and C2 are joined in a spiro-fashion. When two rings described herein are connected in a fused-fashion, the two rings are connected by two or more ring atoms. In some instances, the two rings can be connected by two adjacent ring atoms. As an example, rings D1 and D1 are connected in a fused-fashion by two adjacent ring atom

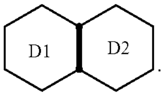 .

In some instances, two rings described herein can be connected by three or more atoms are shared between the two rings. The following structure:

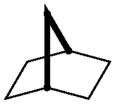

is an example of two rings being connected by three or more ring atoms. When two rings are connected by three or more ring atoms, the three or more ring atoms connecting the two rings would be referred to by those skilled in the art as "bridging" atoms. Further, those skilled in the art would understand based on the disclosure provided herein that two rings connected in a "bridged" fashion is an example of two rings connected in a fused-fashion.

The number of ring atoms for a monocyclic and a bicyclic nitrogen-containing heterocyclyl($C_{1-4}$ alkyl) can vary. Non-limiting examples include an unsubstituted or a substituted 5-membered monocyclic nitrogen-containing heterocyclyl ($C_{1-4}$ alkyl), 6-membered monocyclic nitrogen-containing heterocyclyl($C_{1-4}$ alkyl), an unsubstituted or a substituted 9-membered bicyclic nitrogen-containing heterocyclyl($C_{1-4}$ alkyl) and 10-membered bicyclic nitrogen-containing heterocyclyl($C_{1-4}$ alkyl). Examples of suitable $R^3$ groups include the following: azepan-2-one($C_{1-4}$ alkyl), imidazolidin-2-one($C_{1-4}$ alkyl), tetrahydropyrimidin-2-one($C_{1-4}$ alkyl), pyrrolidin-2-one($C_{1-4}$ alkyl), piperidin-2-one($C_{1-4}$ alkyl), pyrazolidin-3-one($C_{1-4}$ alkyl), oxazolidin-4-one($C_{1-4}$ alkyl), 1,4-oxazepan-3-one($C_{1-4}$ alkyl), morpholin-3-one ($C_{1-4}$ alkyl),

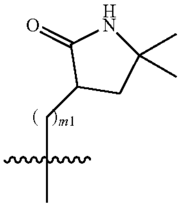 , 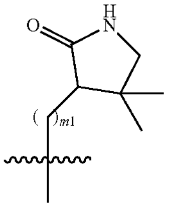 ,

-continued

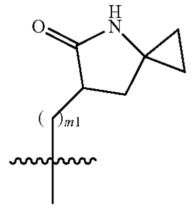,
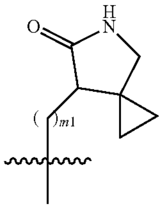,
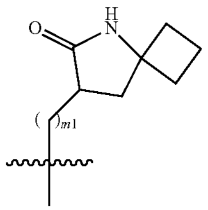,
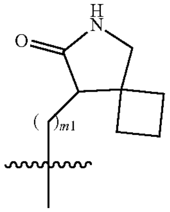,
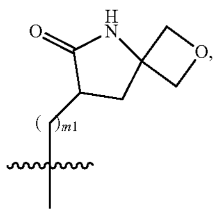
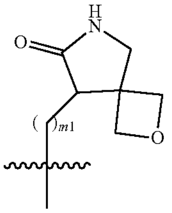,
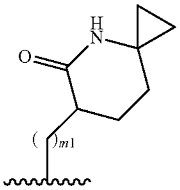,
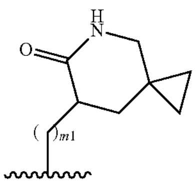,
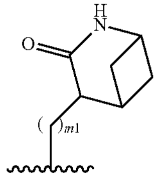,
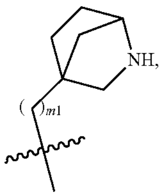
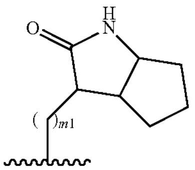,
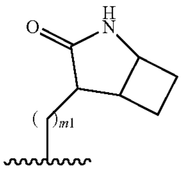,
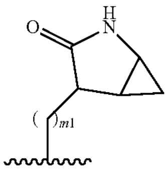,
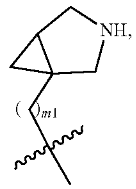
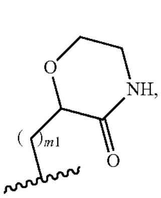
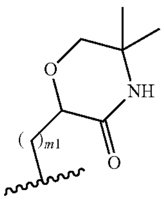
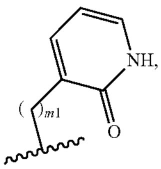
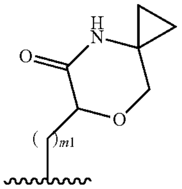,
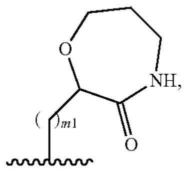

-continued

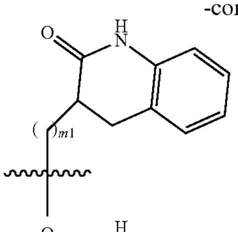,
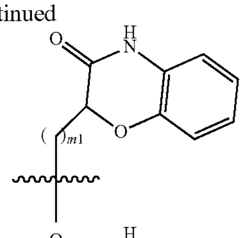,
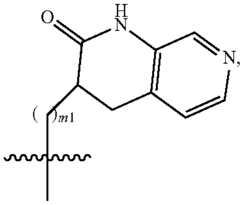
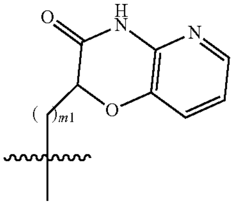,
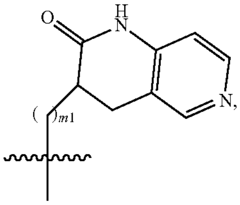
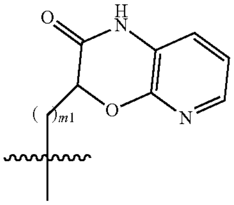,
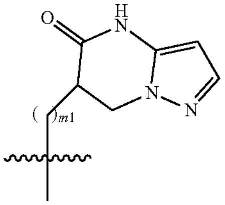,
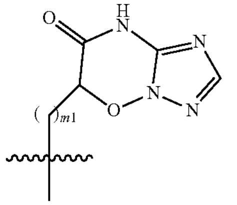 and
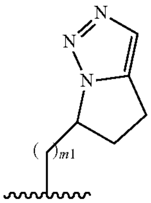, wherein each m1 can be independently 1, 2, 3 or 4, (including substituted or unsubstituted versions of the aforementioned). The $R^3$ groups provided herein can be substituted with one or more moieties independently selected from those listed for "optionally substituted." In some embodiments, a $R^3$ group provided herein can be substituted with one or more moieties selected from deuterium, halogen, hydroxy, an unsubstituted $C_{1-4}$ alkyl, an unsubstituted $C_{2-4}$ alkenyl an unsubstituted $C_{1-4}$ alkoxy, amino, -(an unsubstituted $C_{1-4}$ alkyl)-O—P—$(OH)_2$ (such as —$CH_2$—O—P—$(OH)_2$) and -(an unsubstituted $C_{1-4}$ alkyl)-O—P—(O(an unsubstituted $C_{1-4}$ alkyl))$_2$ (such as —$CH_2$—O—P—$(OCH_3)_2$).

Non-limiting examples of $R^3$ moieties include the following:

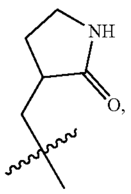
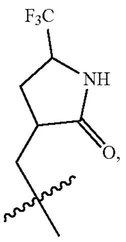
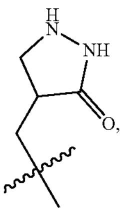

-continued
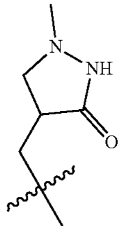 , 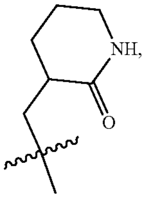
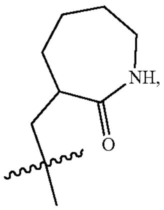 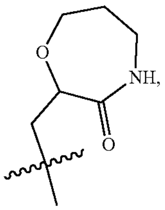
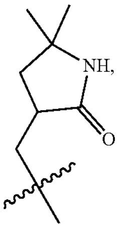 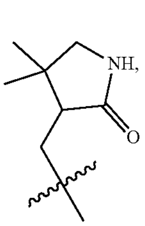 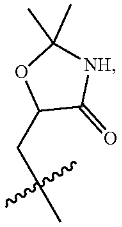
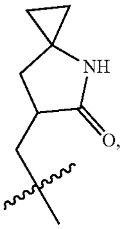 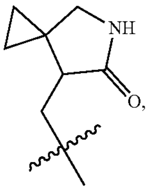 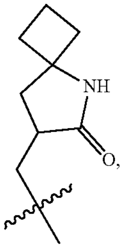
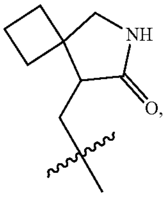 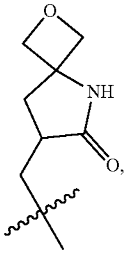 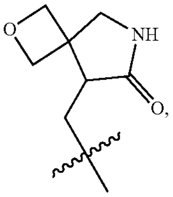
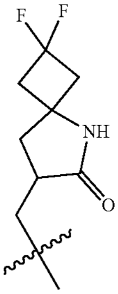 , 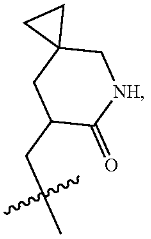 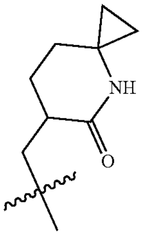 ,
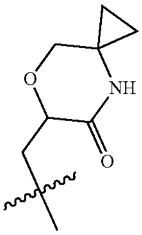 , 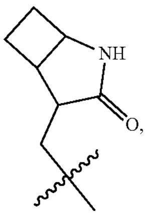 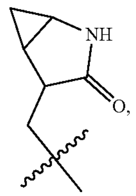
-continued
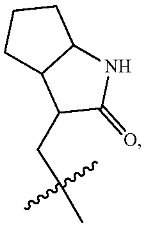 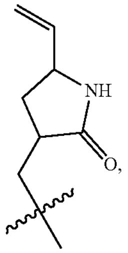 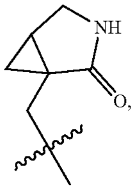
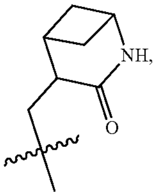 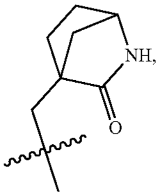 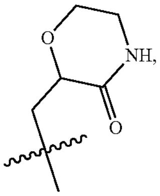
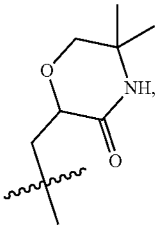 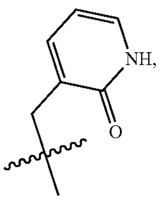
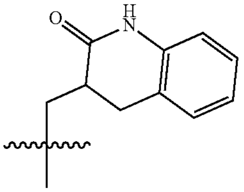 , 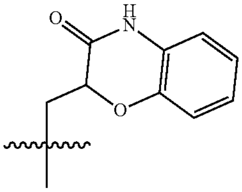 ,
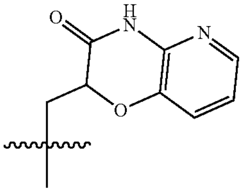 , 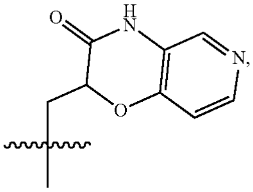
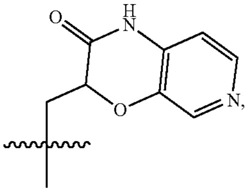 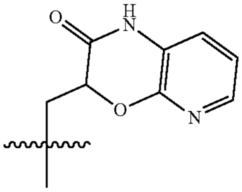 ,
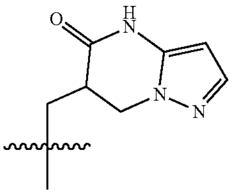 , 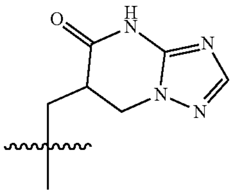 and
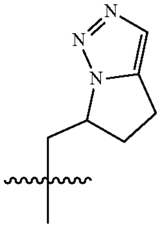 .

In some embodiments, $R^2$ can be hydrogen. In other embodiments, $R^2$ can be deuterium. In still other embodiments, $R^2$ can be halogen (for example, fluoro or chloro).

As provided herein, $R^5$ can be

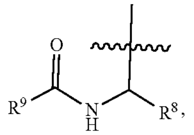

wherein $R^9$ can be an unsubstituted or a substituted alkoxy. In some embodiments, $R^9$ can be an unsubstituted alkoxy. In other embodiments, $R^9$ can be a substituted alkoxy. Various alkoxys can be present for $R^9$. For example, —O-(hydrocarbon) (such as —O—($C_{1-8}$ alkyl)), —O-(monocyclic $C_{3-8}$ cycloalkyl), —O-(bicyclic $C_{5-8}$ cycloalkyl), —O-(phenyl), —O-(bicyclic aryl), —O-(monocyclic heteroaryl), —O-(bicyclic heteroaryl), —O-(monocyclic heterocyclyl) and —O-(bicyclic heterocyclyl). A non-limiting list of examples of $C_{1-6}$ alkoxys are methoxy, ethoxy, n-propoxy, iso-propoxy, n-butoxy, iso-butoxy, sec-butoxy, tert-butoxy, pentoxy (straight-chained or branched), hexoxy (straight-chained or branched), —O-cyclopropyl, —O-cyclobutyl, —O— cyclopentyl, —O-cyclohexyl and —O-(bicyclo[1.1.1]pentyl). A variety of substituents can be present on a substituted alkoxy for $R^9$. Examples of suitable substituents are those provided for "optionally substituted." In some embodiments, 1, 2, 3 or 4 substituents can be present on a substituted alkoxy. For example, a substituted alkoxy can be substituted 1, 2, 3 or 4 times with substituents independently selected from halogen, hydroxy, an unsubstituted $C_{1-4}$ alkyl and an unsubstituted $C_{1-4}$ haloalkyl.

The $R^8$ moieties can be a substituted or an unsubstituted version of a $C_{2-6}$ alkyl, a $C_{2-6}$ alkenyl, a $C_{2-6}$ alkynyl, a monocyclic $C_{3-6}$ cycloalkyl, a bicyclic $C_{5-8}$ cycloalkyl or a monocyclic 4- to 6-membered heterocyclyl. In some embodiments, $R^8$ can be an unsubstituted $C_{2-6}$ alkyl. In other embodiments, $R^8$ can be a substituted $C_{2-6}$ alkyl. Exemplary $C_{2-6}$ alkyls include methyl, ethyl, n-propyl, isopropyl, n-butyl, isobutyl, sec-butyl, tert-butyl, pentyl (straight-chained and branched) and hexyl (straight-chained and branched). In some embodiments, $R^8$ can be an unsubstituted $C_{2-6}$ alkenyl. In other embodiments, $R^8$ can be a substituted $C_{2-6}$ alkenyl. In still other embodiments, $R^8$ can be an unsubstituted $C_{2-6}$ alkynyl. In yet still other embodiments, $R^8$ can be a substituted $C_{2-6}$ alkynyl.

Cyclic moieties, including monocyclic and bicyclic moieties, can also be present for $R^8$. In some embodiments, $R^8$ can be an unsubstituted monocyclic $C_{3-6}$ cycloalkyl. In some embodiments, $R^8$ can be a substituted monocyclic $C_{3-6}$ cycloalkyl. For example, $R^8$ can be a substituted or an unsubstituted cyclopropyl, a substituted or an unsubstituted cyclobutyl, a substituted or an unsubstituted cyclopentyl or a substituted or an unsubstituted cyclohexyl. In some embodiments, $R^8$ can be an unsubstituted bicyclic $C_{5-8}$ cycloalkyl. In other embodiments, $R^8$ can be an unsubstituted bicyclic $C_{5-8}$ cycloalkyl. The two rings of the bicyclic $C_{5-8}$ cycloalkyl can joined in a fused or a spiro-fashion. Examples of rings connected in a fused and a spiro-fashion are provided herein. In some embodiments, $R^8$ can be an unsubstituted or a substituted bicyclo[1.1.1]pentyl. In still other embodiments, $R^8$ can be an unsubstituted monocyclic 4- to 6-membered heterocyclyl. In yet still other embodiments, $R^8$ can be an unsubstituted monocyclic 4- to 6-membered heterocyclyl. The number of heteroatoms present in a monocyclic 4- to 6-membered heterocyclyl for $R^8$ can vary. Suitable heteroatoms include, but are not limited to, O (oxygen), S (sulfur) and N (nitrogen). Examples of monocyclic 4- to 6-membered heterocyclyls are oxetane, thietane, azetidine, pyrrolidine, tetrahydrofuran, tetrahydrothiophene, tetrahydropyran, tetrahydrothiopyran and piperidine (including unsubstituted or substituted versions of each of the aforementioned). In some embodiments, $R^8$ can be an unsubstituted monocyclic $C_{3-6}$ cycloalkyl($CH_2$)—. Various monocyclic $C_{3-6}$ cycloalkyl are described herein. As examples, $R^8$ can be selected from cyclopropyl($CH_2$)—, cyclobutyl($CH_2$)—, cyclopentyl($CH_2$)— and cyclohexyl($CH_2$)—.

As described herein, $R^8$ can be substituted. In some embodiments, when $R^8$ is a $C_{2-6}$ alkyl that is substituted, the $C_{2-6}$ alkyl can be substituted 1, 2, 3 or 4 times with a substituent independently selected from halogen, cyano, an unsubstituted or a substituted monocyclic $C_{3-6}$ cycloalkyl, an unsubstituted $C_{1-4}$ alkoxy and an unsubstituted $C_{1-4}$ haloalkoxy. In some embodiments, $R^8$ can be a $C_{2-6}$ alkyl that is substituted 1 to 13 times with deuterium. In some embodiments, $R^8$ can be a $C_{2-6}$ alkyl that is substituted 1 to 9 times with deuterium, 1 to 6 times with deuterium, 1 to 5 times with deuterium or 1 to 3 times with deuterium. Each halogen can be independently F (fluoro) or $C_1$ (chloro). Exemplary unsubstituted and substituted monocyclic $C_{3-6}$ cycloalkyls that can be present on a substituted $C_{2-6}$ alkyl for $R^8$ include cyclopropyl, cyclobutyl, cyclopentyl, cyclohexyl and halogen-substituted monocyclic $C_{3-6}$ cycloalkyls. Suitable unsubstituted $C_{1-4}$ alkoxys that can be substituted on a $C_{2-6}$ alkyl of $R^8$ include methoxy, ethoxy, n-propoxy, isopropoxy, n-butoxy, isobutoxy, sec-butoxy and tert-butoxy. Examples of an unsubstituted $C_{1-4}$ haloalkoxy can be substituted on a $C_{2-6}$ alkyl of $R^8$ include —$OCl_3$, —$OCF_3$, —$OCH_2C_1$, —$OCH_2F$, —$OCHCl_2$ and —$OCHF_2$. In some embodiments, when $R^8$ is a substituted $C_{2-6}$ alkenyl, a substituted $C_{2-6}$ alkynyl, a substituted monocyclic $C_{3-6}$ cycloalkyl, a substituted bicyclic $C_{5-8}$ cycloalkyl or a substituted monocyclic 4- to 6-membered heterocyclyl, each of the aforementioned can be substituted 1, 2, 3 or 4 times with a substituents independently selected from halogen, an unsubstituted $C_{1-4}$ alkyl, an unsubstituted $C_{2-4}$ alkenyl, an unsubstituted $C_{2-4}$ alkynyl, an unsubstituted $C_{1-4}$ haloalkyl, an unsubstituted or a substituted monocyclic $C_{3-6}$ cycloalkyl and an unsubstituted $C_{1-4}$ alkoxy. Examples of unsubstituted $C_1$_4 alkyls, an unsubstituted $C_{2-4}$ alkenyl and an unsubstituted $C_{2-4}$ alkynyl that can be substituted on a substituted $C_{2-6}$ alkenyl, a substituted $C_{2-6}$ alkynyl, a substituted monocyclic $C_{3-6}$ cycloalkyl, a substituted bicyclic $C_{5-8}$ cycloalkyl or a substituted monocyclic 4- to 6-membered heterocyclyl include methyl, ethyl, n-propyl, isopropyl, n-butyl, isobutyl, sec-butyl, tert-butyl, ethenyl, propenyl, butenyl, ethynyl, propynyl and butynyl. Suitable halogens and unsubstituted $C_{1-4}$ alkoxys that can be present on a substituted $C_{2-6}$ alkenyl, a substituted $C_{2-6}$ alkynyl, a substituted monocyclic $C_{3-6}$ cycloalkyl, a substituted bicyclic $C_{5-8}$ cycloalkyl or a substituted monocyclic 4- to 6-membered heterocyclyl are described herein, such as in this paragraph. Non-limiting list of unsubstituted and substituted monocyclic $C_{3-6}$ cycloalkyls include cyclopropyl, cyclobutyl, cyclopentyl, cyclohexyl and halogen-substituted monocyclic $C_{3-6}$ cycloalkyls. Examples of unsubstituted $C_{1-6}$ haloalkyls that can be present on a substituted $C_{2-6}$ alkenyl, a substituted $C_{2-6}$ alkynyl, a substituted monocyclic $C_{3-6}$ cycloalkyl, a substituted bicyclic $C_{5-8}$ cycloalkyl or a substituted monocyclic 4- to 6-membered heterocyclyl include, but are not limited to, $-CF_3$, $-CCl_3$, $-CHF_2$, $-C(CH_3)F_2$, $-CHCl_2$, $-CH_2F$, $-CH(CH_3)F$, $-CH_2CF_3$, $-CH_2C_1$, $-CH_2CH_2F$, $-CH_2CH_2Cl$, $-CH_2CH_2CH_2F$ and $-CH_2CH_2CH_2Cl$.
Exemplary $R^5$ groups include the following:
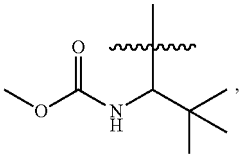,
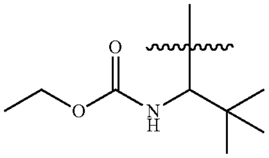,
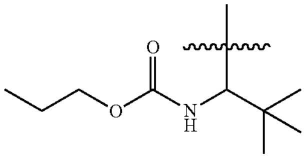,
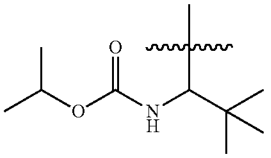,
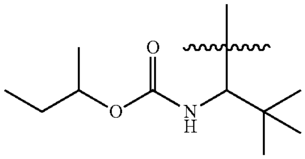,
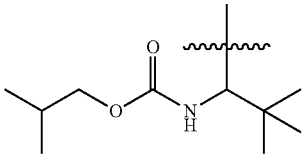,
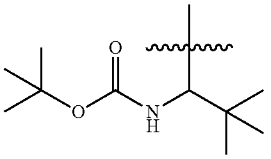,
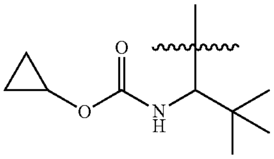,
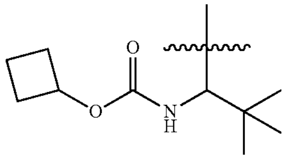,
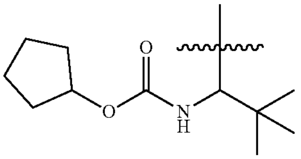,
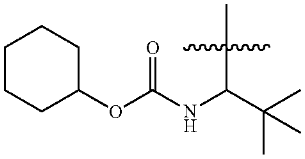,
-continued
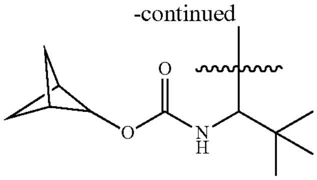
and
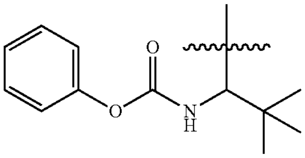.
Examples of compounds of Formula (I), include the following:
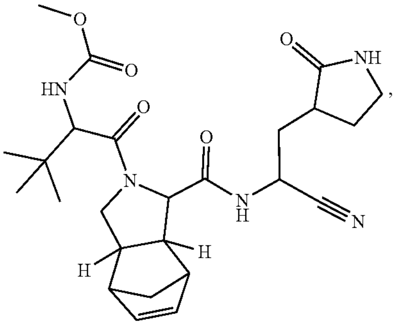,
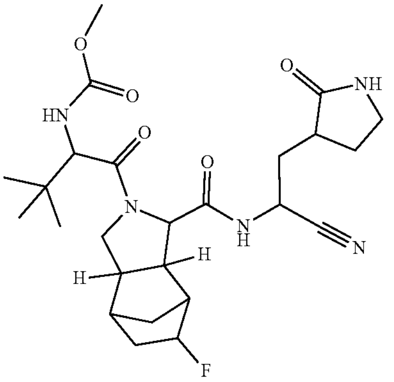
and
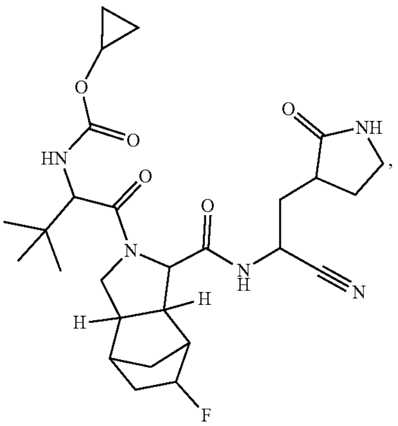,
a pharmaceutically acceptable salt of any of the foregoing.

Additional examples of compounds of Formula (I), include the following:

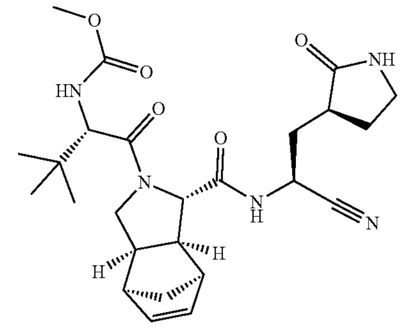

,

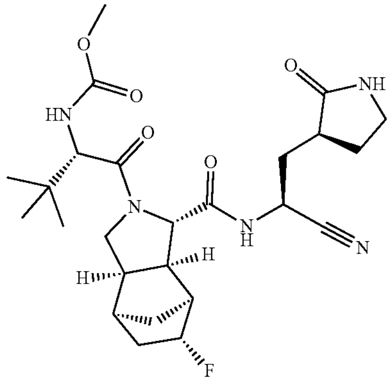

and

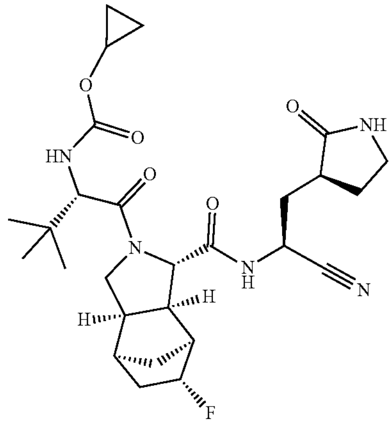

, a pharmaceutically acceptable salt of any of the foregoing.

In some embodiments, Ring $A^1$ can be

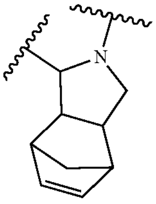

;

$R^1$ can be cyano; $R^2$ can be hydrogen; $R^3$ can be an unsubstituted or a substituted monocyclic nitrogen-containing heterocyclyl($C_{1-4}$ alkyl); and $R^4$ can be hydrogen. In some embodiments, Ring $A^1$ can be

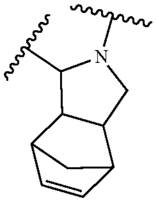

;

$R^1$ can be cyano; $R^2$ can be hydrogen; $R^3$ can be an unsubstituted or a substituted monocyclic nitrogen-containing heterocyclyl($C_{1-4}$ alkyl); $R^4$ can be hydrogen; $R^8$ can be an unsubstituted $C_{2-6}$ alkyl. In some embodiments, Ring $A^1$ can be

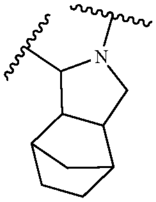

;

$R^1$ can be cyano; $R^2$ can be hydrogen; $R^3$ can be an unsubstituted or a substituted monocyclic nitrogen-containing heterocyclyl($C_{1-4}$ alkyl); and $R^4$ can be hydrogen. In some embodiments, Ring $A^1$ can be

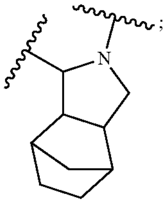 [SMILES: *C1C2C3CCC(C3)C2CN1*]

;

$R^1$ can be cyano; $R^2$ can be hydrogen; $R^3$ can be an unsubstituted or a substituted monocyclic nitrogen-containing heterocyclyl($C_{1-4}$ alkyl); $R^4$ can be hydrogen; and

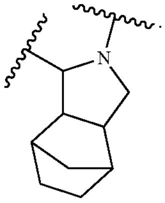 [SMILES: *C1C2C3CCC(C3)C2CN1*]

.

$R^8$ can be an unsubstituted $C_{2-6}$ alkyl. In some embodiments, Ring $A^1$ cannot be. In some embodiments, Ring $A^1$ cannot be

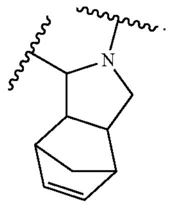 [SMILES: *C1C2C3C=CC(C3)C2CN1*]

Synthesis

Compounds of Formula (I) along with those described herein may be prepared in various ways. General synthetic routes for preparing compounds of Formula (I) are shown and described herein along with some examples of starting materials used to synthesize compounds described herein. Additionally, for the purpose of the general synthetic routes, the structures depicted are appropriately protected, as known by one skilled in the art and the generic structures are meant to include these protecting groups. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Scheme A

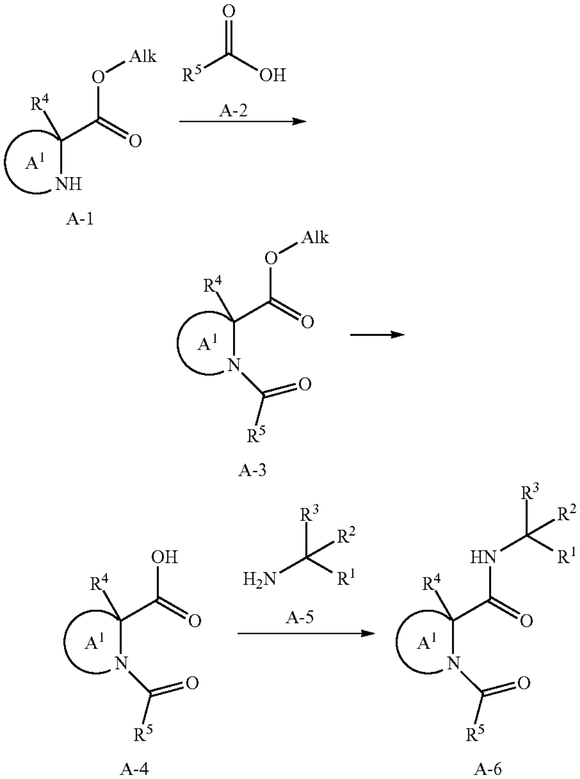

Scheme A describes the synthesis of compounds of general Formula (A-6). An amino ester of general Formula (A-1) (Alk represents alkyl) with an acid of general Formula (A-2), either by activating the carboxylic acid by converting it to an acid chloride, followed by reaction with the amino acid in the presence of a base, or by activation of the acid with a coupling reagent (such as HATU) followed by coupling with the amino ester in the presence of a base (such as DIPEA), resulting in a compound of general Formula (A-3). The ester functionality of general Formula (A-3) can be hydrolyzed, for example, under basic conditions of —OAlk is —OMe, using LiOH in MeOH, providing in a compound of general Formula (A-4). Further coupling of the carboxylic acid of general Formula (A-4) with an amine of general Formula (A-5) can provide a compound of general Formula (A-6). For the purpose of the generic synthesis, $R^1$ may be a latent functionality, converted to a functionality as described herein for $R^1$.

Scheme A1

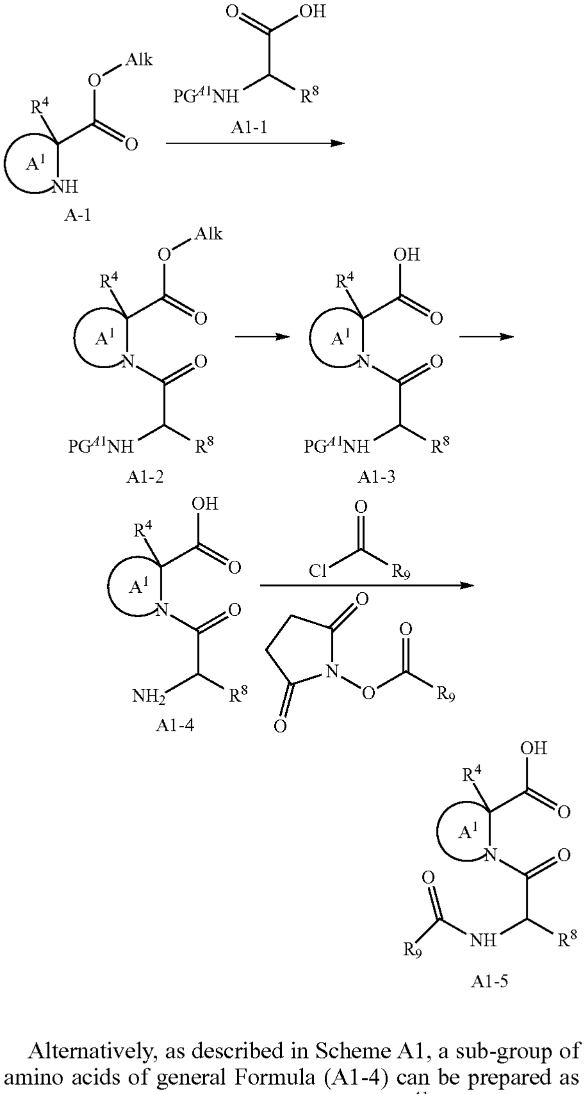

Alternatively, as described in Scheme A1, a sub-group of amino acids of general Formula (A1-4) can be prepared as described in Scheme A1. A protected ($PG^{A1}$) amino acid of general Formula (A1-1) can be coupled with an aminoester of general Formula (A-1) under known amide formation conditions, for example, HATU and $iPr_2NEt$. The ester of a compound of Formula (A1-2) can be deprotected, for example, by using LiOH in $THF/H_2O$, resulting in the acid of general Formula (A1-3). The protecting group $PG^{A1}$ can be removed, for example, by treatment with TFA in case $PG^{A1}$ being Boc, resulting in a compound of general Formula (A1-4). This compound can be converted to a compound of general Formula (A1-5), for example, by treatment with an alkyl chloroformate (such as methyl chloroformate) in the presence of abase (for example, triethylamine), or a (2,5-dioxopyrrolidin-1-yl) carbonate derivative (for example, cyclopropyl (2,5-dioxopyrrolidin-1-yl) carbonate) in the presence of a base (such as triethylamine).

General methodology for the synthesis of amino acids of general Formula (A1-1), or precursors that could be converted to an amino acid of general Formula (A1-1) by one skilled in the art, are described in the literature, and include the following examples:

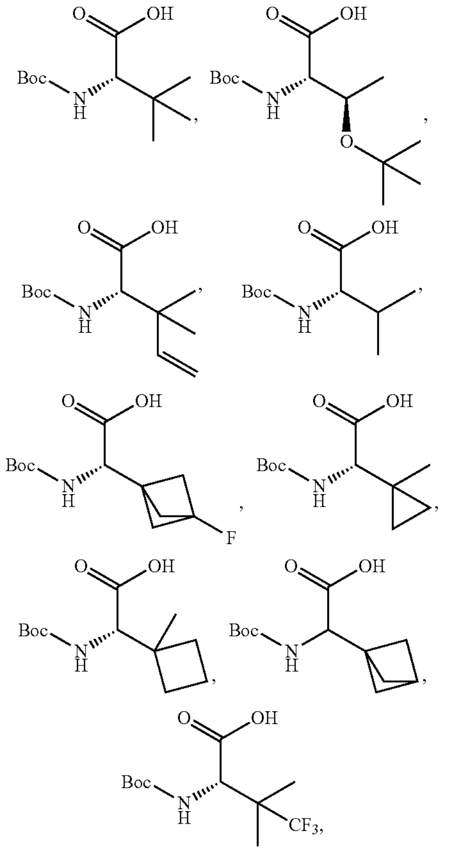

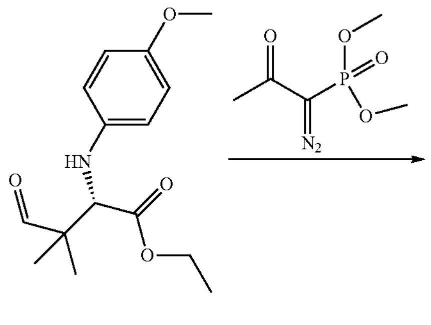

-continued

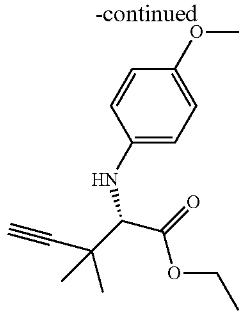

and

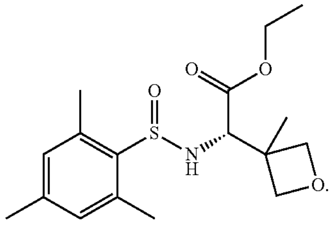

Scheme B

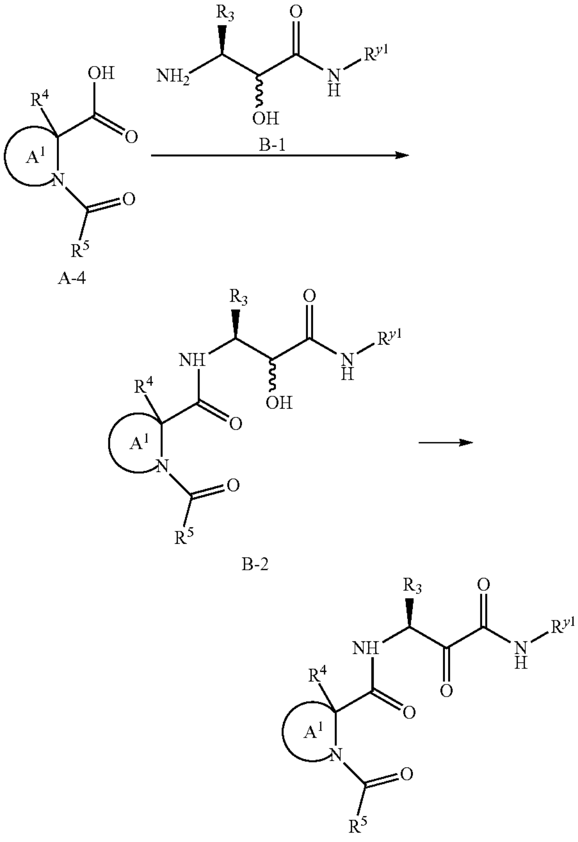

A-4

B-1

B-2

B-3

In Scheme B, a carboxylic acid of general Formula (A-4) can be coupled with an amino acid of general Formula (B-1), for example, under the influence of a coupling reagent (such as T3P) and a base (for example, DIPEA). The obtained compound of general Formula (B-2) can be oxidized, providing in a compound of general Formula (B-3). In Scheme B, $R^{y1}$ can be part of the ketoamide described herein with respect to $R^1$.

Scheme B1

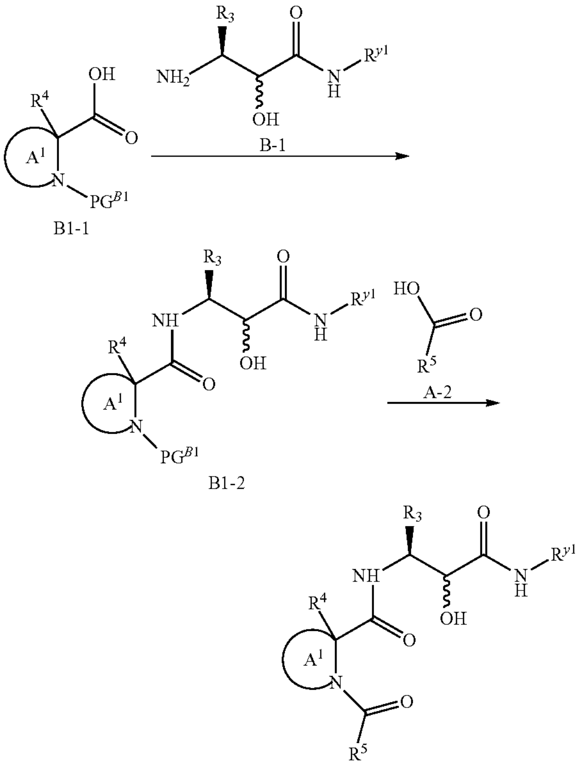

B1-1
B1-2
B-2

Alternatively, as depicted in Scheme B1, an amino acid of general Formula (B1-1) (with $PG^{B1}$ a protecting group of the nitrogen, for example, -Boc) can be coupled with a compound of general Formula (B-1), similar as described for the conversion of a compound of general Formula (A-4) to a compound of general Formula (B-2). The protecting group can be removed, for example, by treatment with an acid in case of $PG^{B1}$ being Boc, followed by coupling with a compound of general Formula (A-2), resulting in the formation of a compound of general formula (B-2).

Scheme B2

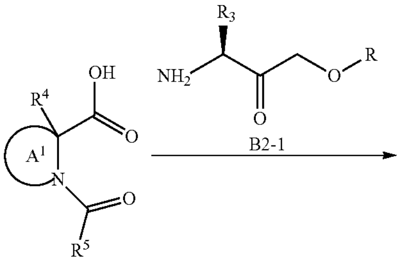

A-4

-continued

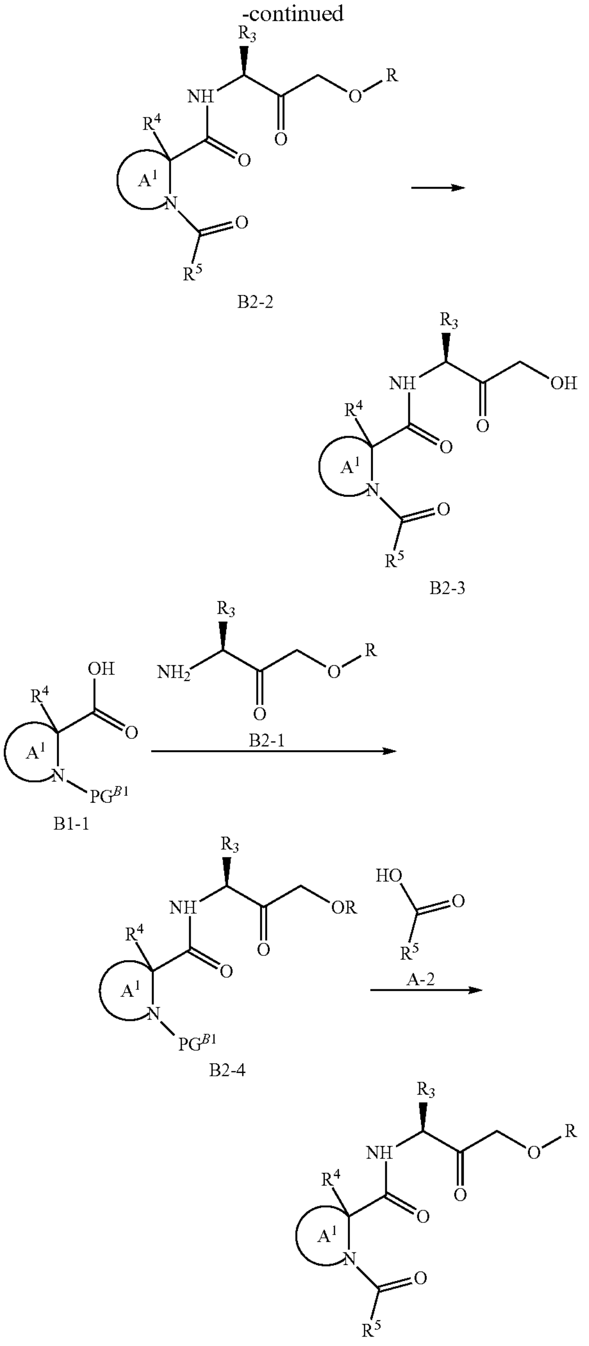

B2-2
B2-3
B1-1
B2-4
B2-2

As described herein, $R^1$ can be a substituted acyl, where the possible groups that can be present on the acyl include hydroxy, a substituted or an unsubstituted alkoxy (for example, —O-(an unsubstituted $C_{1-4}$ alkyl) and —O-(an unsubstituted $C_{3-6}$ cycloalkyl)), an unsubstituted $C_{1-4}$ alkyl (such as a heteroaryl substituted with an unsubstituted $C_{1-4}$ alkyl), a substituted or an unsubstituted phenoxy or a substituted or an unsubstituted benzyloxy). In Scheme B2, R can represent any of the aforementioned moieties that can be present on a substituted acyl for $R^1$. Compounds of general Formulae (B2-2) and (B2-3) can be prepared as described in Scheme B2. An amino-ketone compound of general Formula (B2-1) can be coupled to a carboxylic acid of general Formula (A-4) or (B1-1) under typical amide coupling conditions. A compound of general Formula (B2-2) can be optionally further converted in a hydroxyketone of general Formula (B2-3), for example, in case where R represents a benzyl group, by catalytic hydrogenolysis. The $PG^{B1}$ of a compound of general Formula (B2-4) can be deprotected (for example in the case wherein $PG^{B1}$ is a Boc-group, by treatment with HCl in $Et_2O$). The amine can then be coupled with a carboxylic acid of general Formula (A-2) under typical amide bound formation conditions, to provide a compound of general Formula (B2-2).

Scheme B3

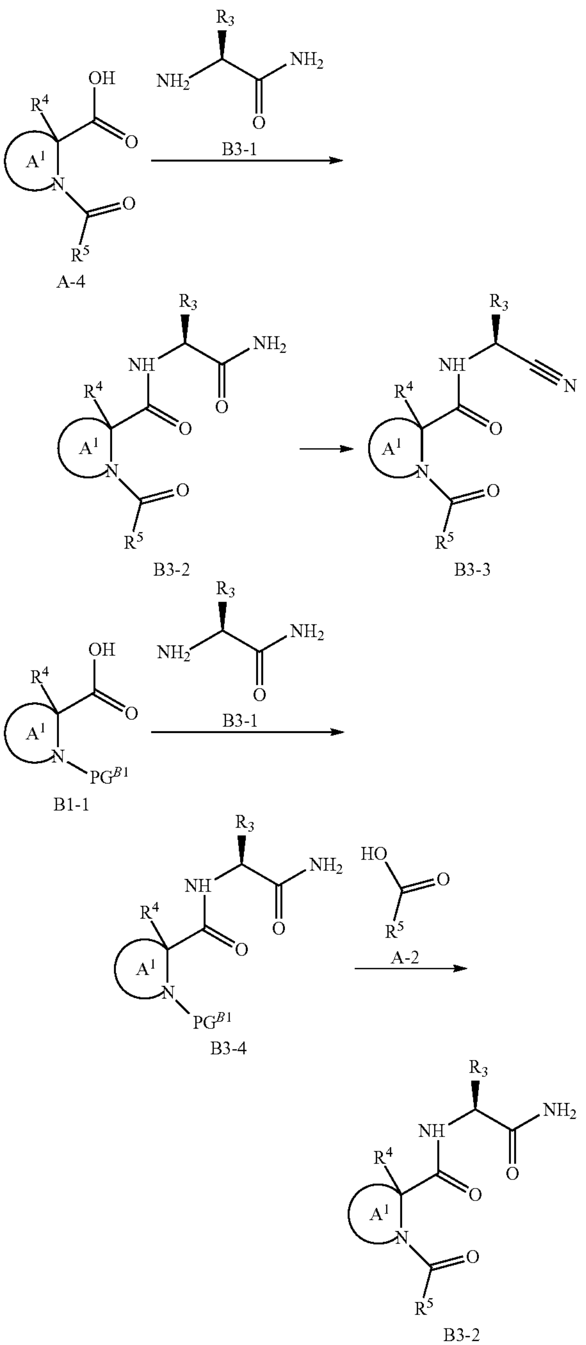

A-4
B3-2
B3-3
B1-1
B3-4
B3-2

Similar as described in Scheme B2 for a compound of Formula (B2-2), using an amide of general Formula (B3-1) in place of a compound of general Formula (B2-1). a compound of general Formula (B3-2) can be obtained. Conversion of a compound of general Formula (B3-2) to a compound of general Formula B3-3 can, for example, occur under the influence of trifluoroacetic anhydride (TFAA) and pyridine in $CH_2Cl_2$, or by application of the Burgess reagent.

Scheme B4

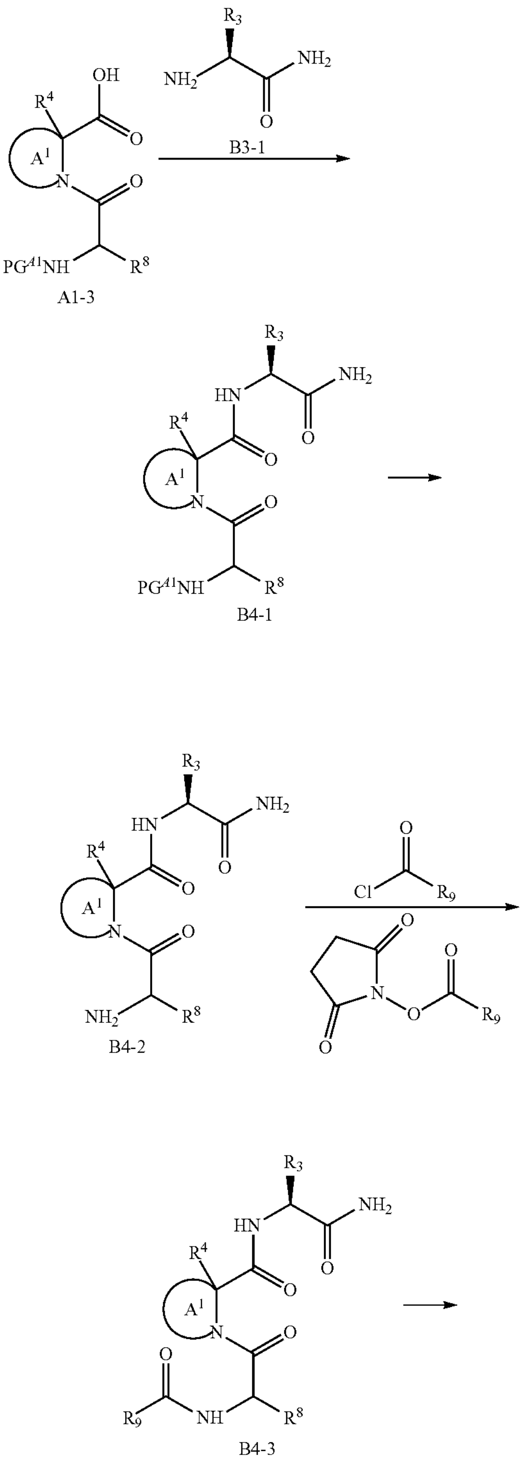

A1-3
B4-1
B4-2
B4-3

-continued

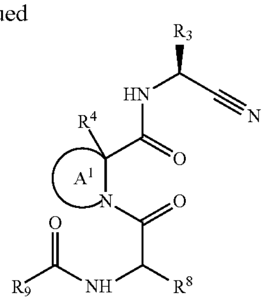

B4-4

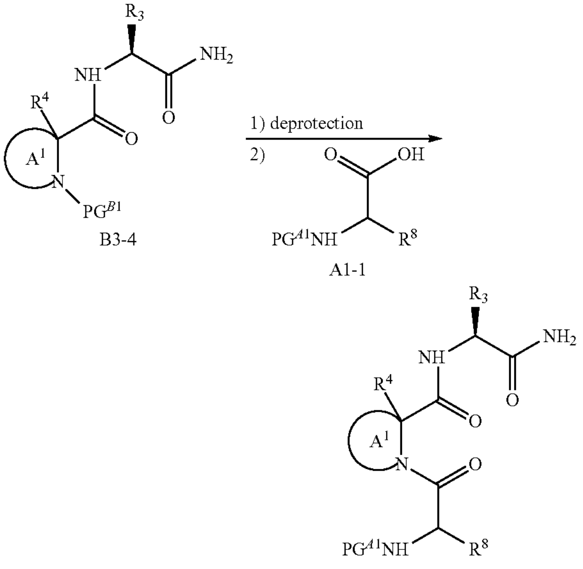

B3-4

A1-1

B4-1

For the purpose of the generic synthesis the transformations described in Scheme B3 include transformations as described in Scheme B4, where a compound of general Formula (A1-3) can be coupled with amine of general Formula (B3-1), resulting in a compound of general Formula (B4-1), where $PG^{A1}$ can be a protecting group which can be removed (for example, in the case $PG^{A1}$ is Boc, by treatment with HCl or TFA). Compound of general Formula (B4-2) can be converted in a compound of general Formula (B4-3), similar as outlined for the conversion of a compound of general Formula (A1-4) to a compound of general Formula (A1-5). The compound of general Formula (B4-3) can be converted to a compound of general Formula (B4-4), similar as outlined for the conversion of a compound of general Formula (B3-2) to a compound of general Formula (B3-3). A compound of general Formula (B4-1) can be obtained by deprotection of $PG^{B1}$ of a compound of general Formula (B3-4), followed by coupling with a compound of general Formula (A1-1).

Scheme C

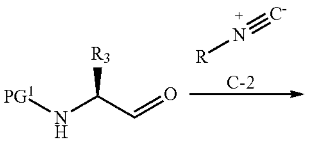

C-2

C-1

-continued

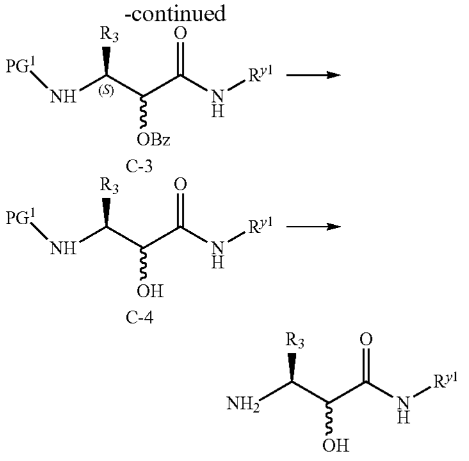

C-3

C-4

B-1

A compound of general Formula (B-1) can be prepared as outlined in Scheme C. An aldehyde of general Formula (C-1) ($PG^1$ can be a nitrogen protecting group, for example -Boc) and an isonitrile of general Formula (C-2), in the presence of a carboxylic acid (for example, benzoic acid), can be condensed in a Passerini-like reaction towards a compound of general Formula (C-3). After hydrolysis, a compound of general Formula (C-4) can be obtained. The $PG^1$ can be removed, for example, by treatment with HCl when $PG^1$ can be Boc.

Scheme C1

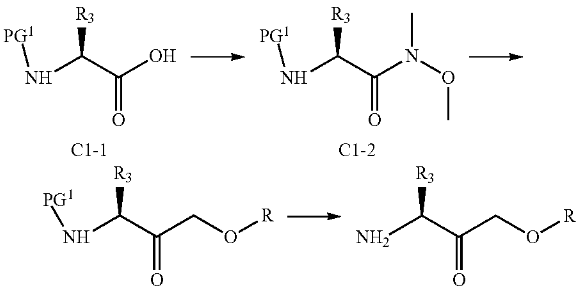

C1-1

C1-2

C1-3

B2-1

An amino ketone of general Formula (B2-1), can be prepared as outline in Scheme C1. A protected amino acid of general Formula (C1-1) can be converted to its corresponding Weinreb amide under typical amide coupling conditions. Addition of an organometallic reagent to the Weinreb amide, followed by work-up, can result in a ketone of general Formula (C1-3). An example, wherein R can be benzyl, is the formation of an organometallic reagent by mixing Mg, $HgCl_2$ and benzylchloromethyl ether, followed by addition to a Weinreb amide of general Formula (C1-2), followed by work-up with saturated ammonium chloride. The protecting group ($PG^1$) can be removed (for example, when $PG^1$ is Boc, the protecting group can be removed using HCl) resulting in the formation of an amino ketone of general Formula (B2-1). When HCl is used for the deprotection, a compound of general Formula (B2-1) can be obtained as a HCl salt. Examples of a compound of general Formula (C1-1) are (S)-2-((tert-butoxycarbonyl)amino)-3-((S)-2-oxopiperidin-3-yl)propanoic acid and (S)-2-((tert-butoxycarbonyl)amino)-3-((S)-2-oxopyrrolidin-3-yl)propanoic acid.

Scheme D1
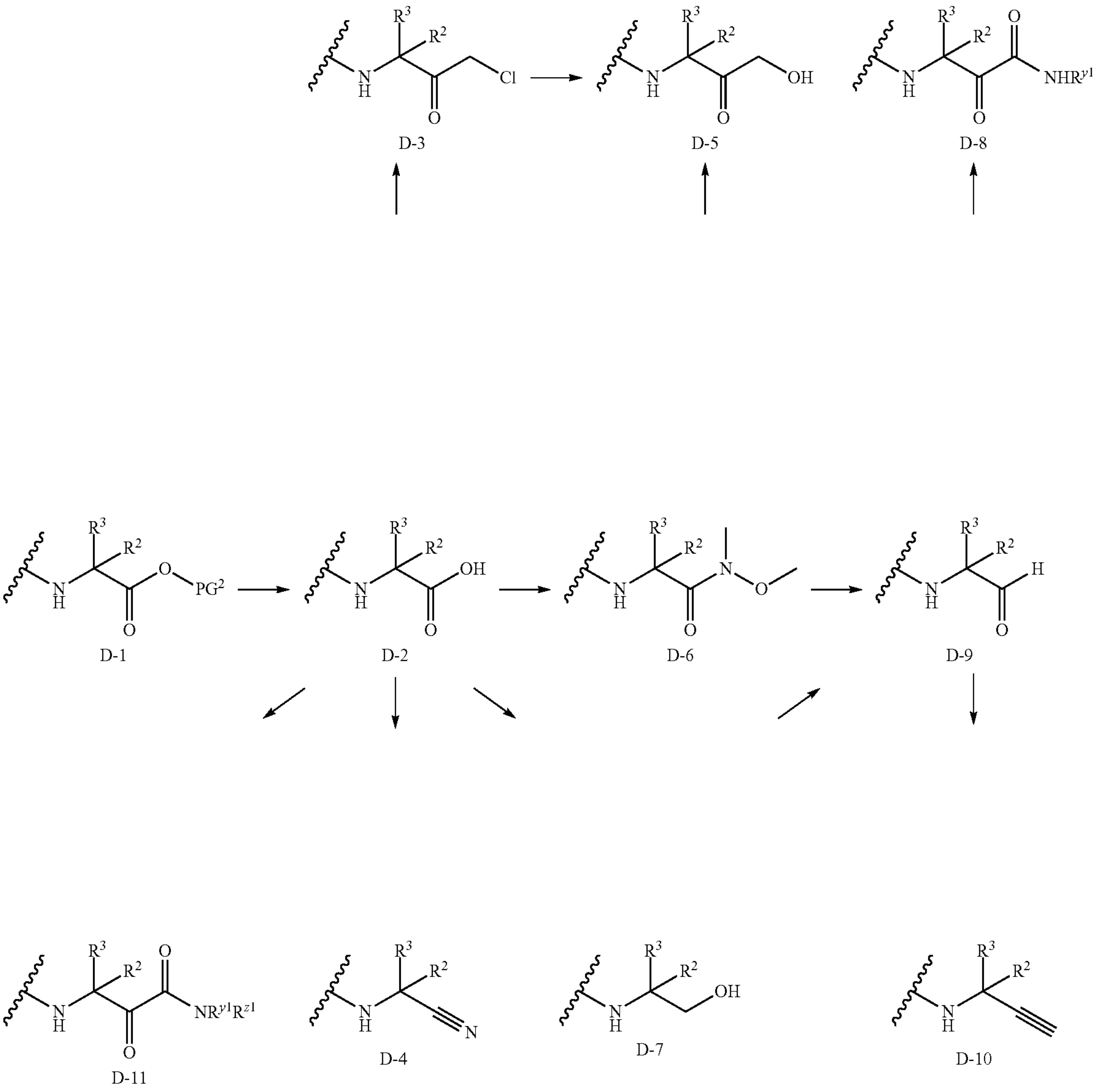
Scheme D2
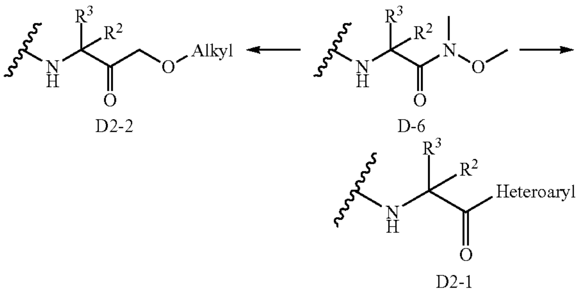
Other conversions for $R^1$ described herein are shown in Schemes D1 and D2. In Schemes D1 and D2, $PG^2$ represents an appropriate protecting group, and $R^{z1}$ and $R^{y1}$ are part of the ketoamide described herein with respect to $R^1$.

Scheme E

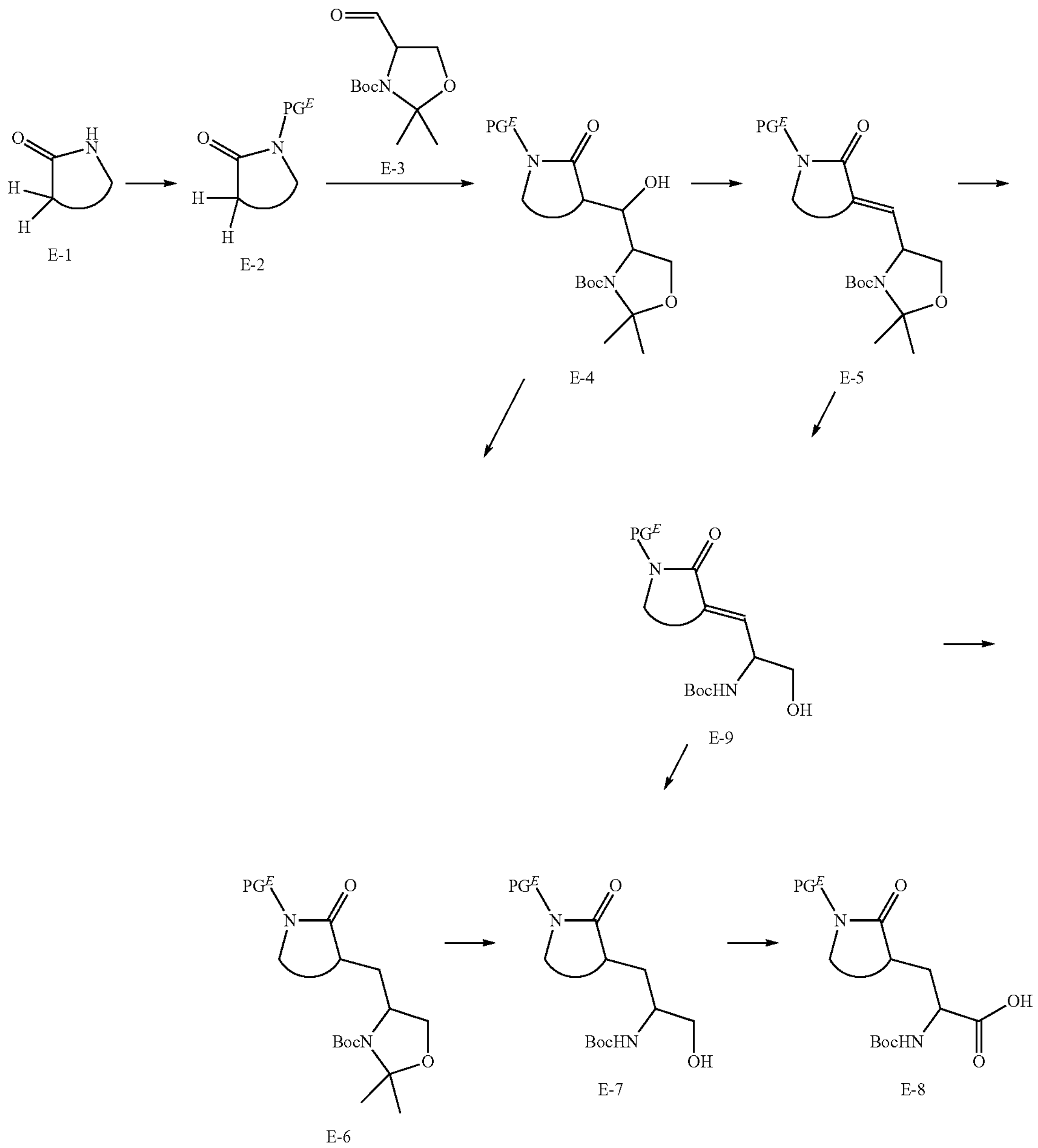

E-1 E-2 E-3 E-4 E-5 E-9 E-6 E-7 E-8

A method for preparing a sub-group of amino acids of general Formula (E-8) are provided in Scheme E. A lactam of general Formula (E-1) can be protected with a suitable protecting group, $PG^E$. An example of such a $PG^E$ group is a Boc-group. For the purpose of the Scheme E, this protecting group can be removed at any relevant stage; and therefore, $PG^E$ present hydrogen for any of compounds of general Formulae (E-4), (E-5), (E-6), (E-7), (E-8) and (E-9). The lactam of general Formula (E-2) can be reacted with an aldehyde of general Formula (E-3) (S or R-garner's aldehyde). The alcohol of general Formula (E-4) can be eliminated to provide an alkene compound of general Formula (E-5) (for example, by sequential conversion of the hydroxy to a corresponding mesylate, followed by elimination under basic conditions). The double bond can be reduced (for example, by hydrogenation, under influence of a homogeneous or a heterogenous catalyst, optionally diastereoselective) to provide a compound of general Formula (E-6). Removal of the acetonide in a compound of general Formula (E-6) to the Boc-protected amino alcohol of general Formula (E-7) can be followed by the oxidation to the carboxylic acid of general Formula (E-8). Alternatively, the acetonide can be deprotected in a compound of general Formula (E-5) to obtain a compound of general Formula (E-9). Reduction of the double bond of a compound of general Formula (E-9) (for example, by hydrogenation under influence of a homogeneous or a heterogenous catalyst, optionally diastereoselective) can be used to obtain a compound of general Formula (E-7). A compound of general Formula (E-4) can be deoxygenated, for example, by a Barton-type deoxygenation, to provide a compound of general Formula (E-6).

Scheme F

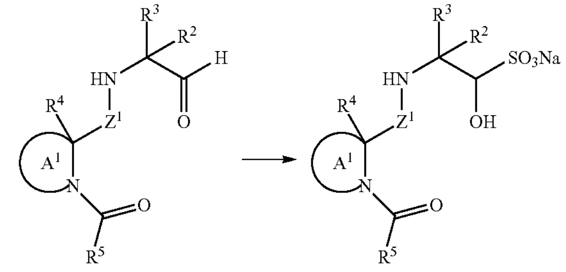

F-1 F-2

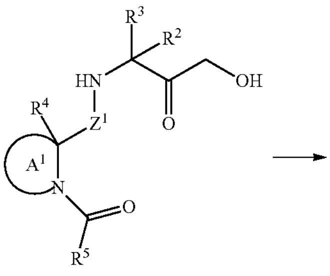

F-3

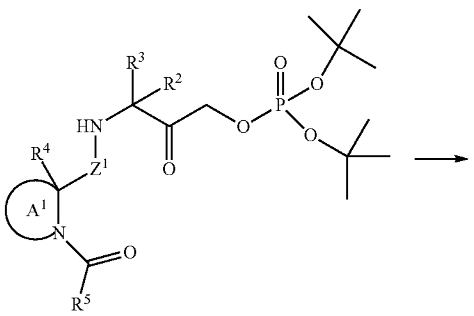

F-4

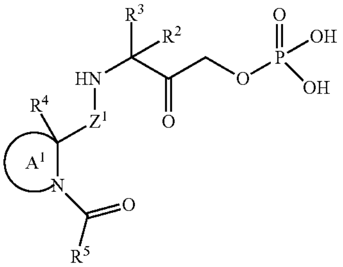

F-5

Compounds of Formula (I) can include a prodrug moiety. A method for including a prodrug moiety is depicted in Scheme F. For example an aldehyde of general Formula (F-1) can be transformed into the corresponding bisulfite adduct of general Formula (F-2), by treatment with $NaHSO_3$. A hydroxyketone of general Formula (F-3), can be transformed to the corresponding phosphate of general Formula (F-5), for example, by treatment with di-tert-butyl N,N-dipropan-2-ylphosphoramidite and tetrazole followed by oxidation with $H_2O_2$, that can provide a compound of general Formula (F-4). A compound of general Formula (F-4) can be deprotected (for example by treatment with TFA) to provide a compound of general Formula (F-5).

As shown in Scheme G, the synthesis of an amino ester of general Formula (G2) can be accomplished via a Diels-Alder reaction, such as described in Arakawa et al., Chemical & Pharmaceutical Bulletin (2003) 51(8), 1015-1020 (-$PG_{G1}$ can be -Bz and -$PG_{G2}$ can be —$CH_3$). Also described herein in the synthesis of intermediates, is the use of -$PG_{G1}$ is -Boc and -$PG_{G2}$ is -t-Butyl or Me. A compound of general Formula (G2) can be deprotected using methods known to those skilled in the art and depending on the protecting group used for $PG_{G1}$ and $PG_{G2}$. Alternatively, a compound of general Formula (G2) can be converted to a compound of general Formula (G3), by hydrogenation of the double bond, or to a compound of general Formula (G4), by cyclopropanation of the double bond. The cyclopropanation can, for example, be performed by application of a Simmons-smith cyclopropanation, by treatment with $CH_2N_2$ in the presence of $Pd(OAc)_2$, or other methods described known to those skilled in the art. Alternatively, deuterated intermediates can be used.

Scheme G

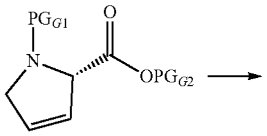

G1

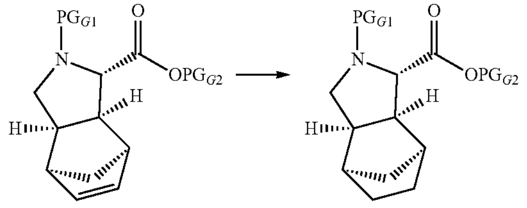

G2 G3

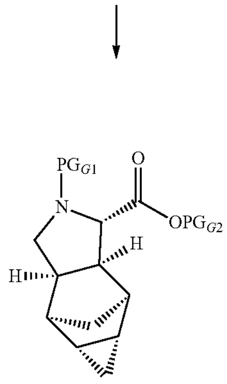

G4

Scheme H

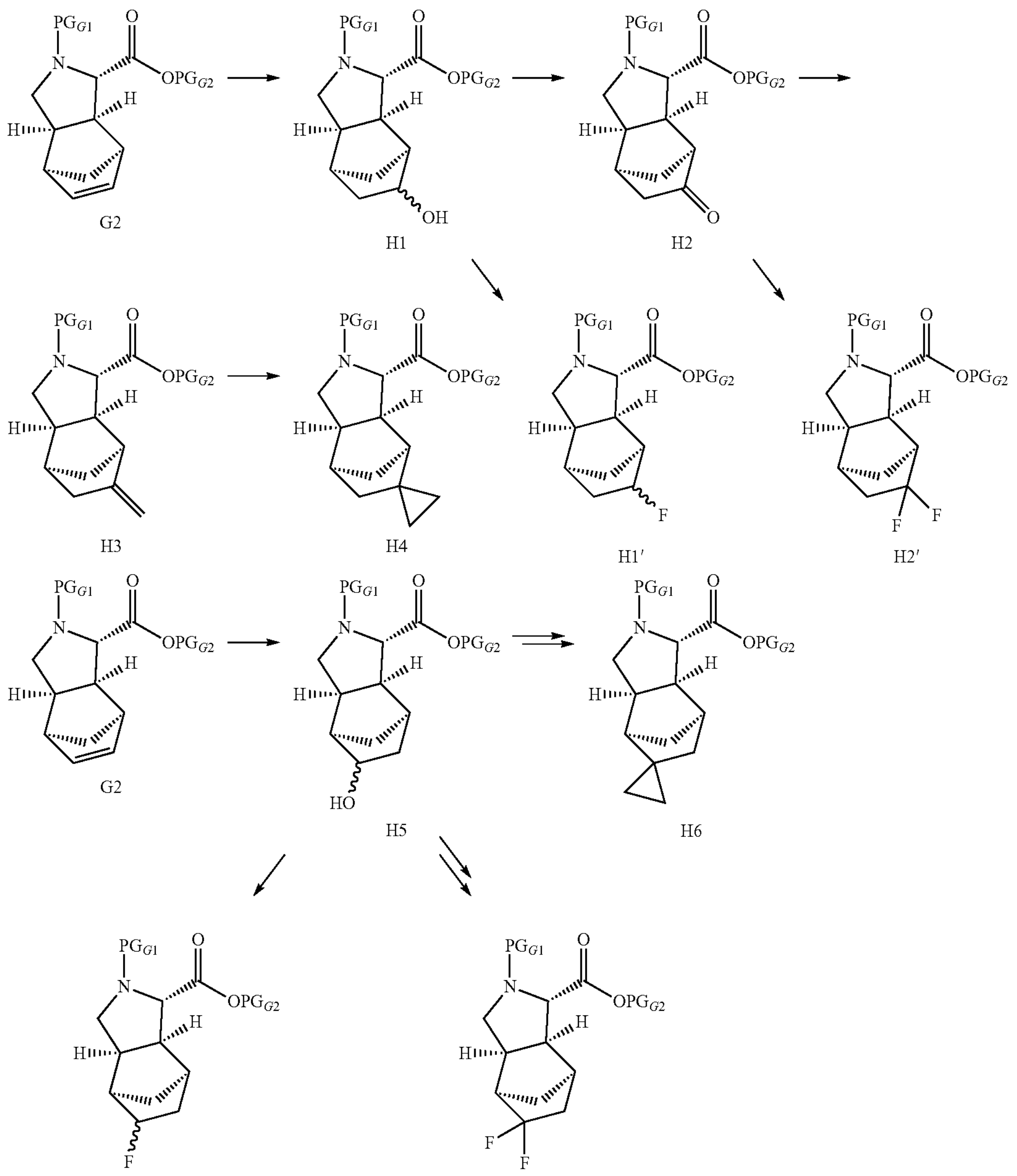

G2, H1, H2, H3, H4, H1', H2', G2, H5, H6, H5', H7

Other intermediates are described in Scheme H. The intermediate of general Formula (G2), can be selectively hydroxylated, for example, by hydrosilylation with trichlorosilane in the presence of a chiral Pd-catalyst, followed by $SiCl_3$/OH exchange (for example, Breuning et al, Beilstein Journal of Organic Chemistry (2009) 5(81):1-5). Oxidation of the alcohol of general Formula (H1) can provide a ketone of general Formula (H2). The ketone of general Formula (H2) can be converted to an alkene of general Formula (H3), for example, by using a Wittig or a Tebbe reagent. Transformation of the double bond towards the cyclopropyl can be done by treatment with $CH_2N_2$ in the presence of $Pd(OAc)_2$, or other methods described in the literature and known to those skilled in the art, and can result in a compound of general Formula (H4). A similar approach can be done with the isomer of a compound of general Formula (H1), a compound of general Formula (H5) can be obtained by using an enantiomeric chiral Pd-catalyst. A compound of general Formula (H5) can then be converted to a compound of general Formula (H6), similar as outlined for the conversion of a compound of general Formula (H1) to a compound of general Formula (H4). Alternatively, the ketone of compound of general Formula (H2) can be converted to a compound of general Formula (H2') by fluorination, for example by application of a DAST reagent. The isomeric compound of general Formula (H7) can be obtained starting from a related isomer. The alcohols of general Formulae (H1) and (H5) can be converted to the related fluoro derivatives of general Formulae (H1') and (H5'), by treatment with a fluorination reagent like DAST (diethylaminosulfur trifluoride).

Scheme I

I1

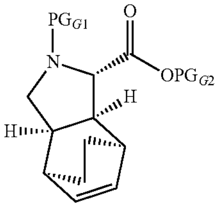

I2

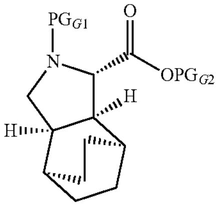

I3

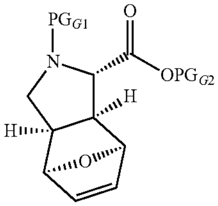

I4

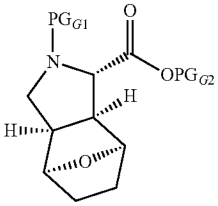

I5

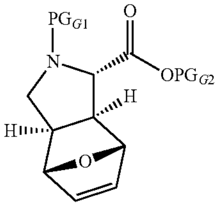

I6

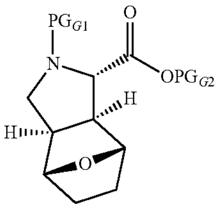

I7

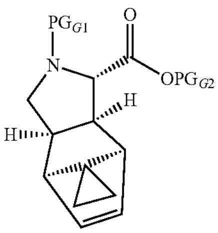

-continued

I8

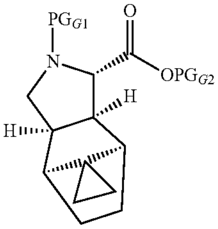

I9

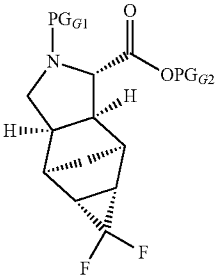

I10

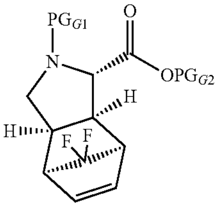

I11

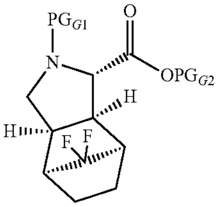

I12

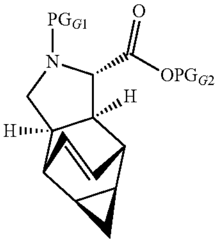

Other compounds of general Formulae (I1), (I2) (Johnson et al., Synthetic Communications (2011) 41(18):2769-2793), (I3), (I4), (I5), (I6), (I7), (I8), (I9), (I10), (I11) and (I12) as depicted in Scheme I can be obtained by methods described in literature (for example, de Graaff et al., Org. Biomol. Chem. (2015) 13:10108-10112; and Johnson et al., Synthetic Communications (2011) 41(18):2769-2793) and/or by applying methodologies as described herein. Compounds general Formulae (I1), (I2), (I3), (I4), (I5), (I6), (I7), (I8), (I9), (I10), (I11) and (I12) can be used to obtain compounds of Formula (I), along with pharmaceutically acceptable salts, using similar methods as described herein.

Scheme IA

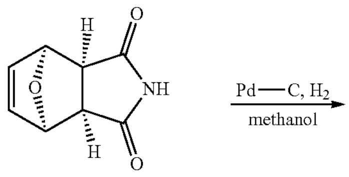

IA1
endo

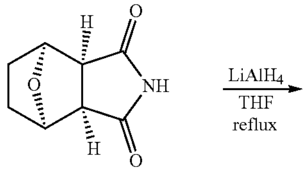

IA2
endo

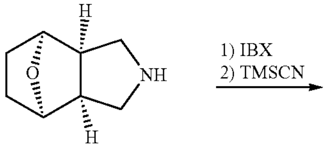

IA3

-continued

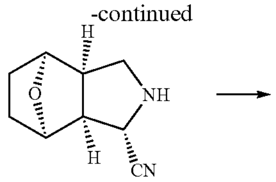

IA4

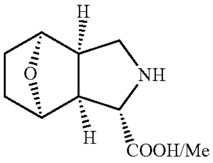

IA5

As an example, as depicted in Scheme IA, a compound of Formula (IA1) (Rulisek et al., J. Org. Chem. (2005) 70(16): 6295-6302) can be hydrogenated to a compound of Formula (IA2). After reduction of a compound of Formula (IA2), (for example, with $LiAlH_4$ (Johnson et al., Synthetic Communications (2011) 41(18):2769-2793), can result in a compound of Formula (IA3). A compound of Formula (IA3) can be oxidized using IBX (de Graaff et al., Org. Biomol. Chem. (2015) 13:10108-10112) followed by introduction of nitrile (Liu et al., Org. Process Res. Dev. (2016) 20(2):320-324) to provide a compound of Formula (IA4). The nitrile can next be converted to a carboxylic acid or ester of a compound of Formula (IA5). In the above scheme, racemic material can be obtained upon nitrile introduction from a compound of Formula (IA3) to a compound of Formula (IA4). Alternatively, achiral method can be used to provide enantioenriched compound(s).

Scheme J

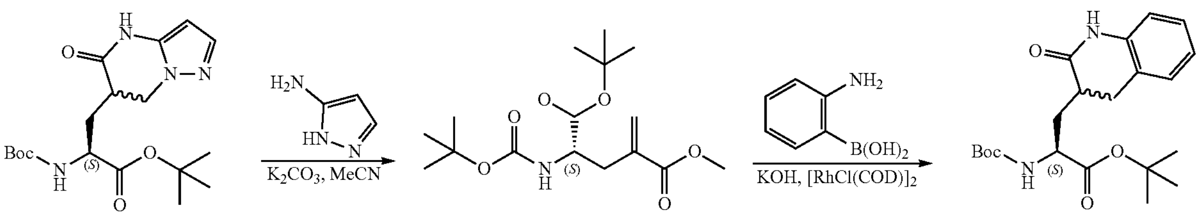

J2 J1 J3

An intermediate, a compound of Formula (J1) (Moody et al., J. Chem. Soc., Perkin Trans. 1 (1997) 23:3519-3530), can be used to prepare amino acids of general Formulae (J2) and (J3) using similar procedures as described for Scheme H.

Pharmaceutical Compositions

Some embodiments described herein relate to a pharmaceutical composition, that can include an effective amount of a compound described herein (e.g., a compound, or a pharmaceutically acceptable salt thereof, as described herein) and a pharmaceutically acceptable carrier, excipient or combination thereof. A pharmaceutical composition described herein is suitable for human and/or veterinary applications.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

Proper formulation is dependent upon the route of administration chosen. Techniques for formulation and administration of the compounds described herein are known to those skilled in the art. Multiple techniques of administering a compound exist in the art including, but not limited to, oral, rectal, topical, aerosol, injection, inhalation and parenteral delivery, including intramuscular, subcutaneous, intravenous, intramedullary injections, intrathecal, direct intraventricular, intraperitoneal, intranasal and intraocular injections. Pharmaceutical compositions will generally be tailored to the specific intended route of administration.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes may be targeted to and taken up selectively by the organ.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. As described herein, compounds used in a pharmaceutical composition may be provided as salts with pharmaceutically compatible counterions.

Methods of Use

Some embodiments described herein relate to a method of treating a coronavirus infection that can include administering to a subject identified as suffering from the coronavirus infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a coronavirus infection. Still other embodiments described herein relate to the use of a compound, or a pharmaceutically acceptable salt thereof, as described herein or a pharmaceutical composition that includes a compound, or a pharmaceutically acceptable salt thereof, as described herein for treating a coronavirus infection.

Some embodiments disclosed herein relate to a method of treating a coronavirus infection that can include contacting a cell infected with the coronavirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a coronavirus infection. Still other embodiments described herein relate to the use of a compound, or a pharmaceutically acceptable salt thereof, as described herein described herein, or a pharmaceutical composition that includes an effective amount of a compound, or a pharmaceutically acceptable salt thereof, as described herein for treating a coronavirus infection.

Some embodiments disclosed herein relate to a method of inhibiting replication of a coronavirus that can include contacting a cell infected with the coronavirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for inhibiting replication of a coronavirus. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein, for inhibiting replication of a coronavirus.

In some embodiments, the coronavirus can be an α-coronavirus or a β-coronavirus. A compound described herein may be effective against one or more variants of a coronavirus. Examples of variants include, but are not limited, to alpha-variant (B.1.1.7), beta-variant (B.1.351), gamma variant (P.1) and delta-variant (B.1.617.2). In some embodiments, the coronavirus can be selected from CoV 229E, CoV NL63, CoV OC43, CoV HKU1, Middle East Respiratory Syndrome (MERS)-CoV, Severe Acute Respiratory Syndrome (SARS)-CoV, and SARS-CoV-2.

Some embodiments described herein relate to a method of treating a picornavirus infection that can include administering to a subject identified as suffering from the picornavirus infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a picornavirus infection. Still other embodiments described herein relate to the use of a compound, or a pharmaceutically acceptable salt thereof, as described herein or a pharmaceutical composition that includes a compound, or a pharmaceutically acceptable salt thereof, as described herein for treating a picornavirus infection.

Some embodiments disclosed herein relate to a method of treating a picornavirus infection that can include contacting a cell infected with the picornavirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a picornavirus infection. Still other embodiments described herein relate to the use of a compound, or a pharmaceutically acceptable salt thereof, as described herein described herein, or a pharmaceutical composition that includes an effective amount of a compound, or a pharmaceutically acceptable salt thereof, as described herein for treating a picornavirus infection.

Some embodiments disclosed herein relate to a method of inhibiting replication of a picornavirus that can include contacting a cell infected with the picornavirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for inhibiting replication of a picornavirus. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein, for inhibiting replication of a picornavirus.

In some embodiments, the picornavirus can be a rhinovirus, including rhinovirus A, B and/or C. In some embodiments, a compound described herein, including a compound of Formula (I), or a pharmaceutically acceptable salt thereof, can be used to treat one or serotypes of a rhinovirus.

Some embodiments described herein relate to a method of treating a norovirus infection that can include administering to a subject identified as suffering from the norovirus infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a norovirus infection. Still other embodiments described herein relate to the use of a compound, or a pharmaceutically acceptable salt thereof, as described herein or a pharmaceutical composition that includes a compound, or a pharmaceutically acceptable salt thereof, as described herein for treating a norovirus infection.

Some embodiments disclosed herein relate to a method of treating a norovirus infection that can include contacting a cell infected with the norovirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a norovirus infection. Still other embodiments described herein relate to the use of a compound, or a pharmaceutically acceptable salt thereof, as described herein described herein, or a pharmaceutical composition that includes an effective amount of a compound, or a pharmaceutically acceptable salt thereof, as described herein for treating a norovirus infection.

Some embodiments disclosed herein relate to a method of inhibiting replication of a norovirus that can include contacting a cell infected with the norovirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for inhibiting replication of a norovirus. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein, for inhibiting replication of a norovirus.

Some embodiments disclosed herein relate to a method of treating a respiratory condition that is developed because of a coronavirus and/or a picornavirus infection that can include administering to a subject suffering from the respiratory condition and/or contacting a cell infected with the coronavirus and/or the picornavirus in a subject suffering from the respiratory condition with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a respiratory condition due to a coronavirus infection and/or a picornavirus infection with an effective amount of the compound, or a pharmaceutically acceptable salt thereof. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating a respiratory condition due to a coronavirus infection and/or a picornavirus infection.

A subject infected with a coronavirus can be asymptotic. A coronavirus infection can manifest itself via one or more symptoms. Examples of symptoms include, but are not limited to, coughing, sore throat, runny nose, sneezing, headache, fever, shortness of breath, myalgia, abdominal pain, fatigue, difficulty breathing, persistent chest pain or pressure, difficulty waking, loss of smell and taste, muscle or joint pain, chills, nausea or vomiting, nasal congestion, diarrhea, haemoptysis, conjunctival congestion, sputum production, chest tightness and/or palpitations. A coronavirus infection can cause complications. A non-limiting list of complications include, but are not limited to, sinusitis, otitis media, pneumonia, acute respiratory distress syndrome, disseminated intravascular coagulation, pericarditis and/or kidney failure.

As with a coronavirus, a subject infected with a picornavirus can be asymptotic. Alternatively, a subject can exhibit one or more of symptoms. Examples of symptoms of a picornavirus infection include, but are not limited to, aseptic meningitis, rash, conjunctivitis, runny nose a headache a cough a fever a sore throat, chest and/or abdominal pain and paralysis. As provided herein, subjects infected with a norovirus can exhibit one or more the symptoms including, but not limited to, nausea, non-bloody diarrhea, vomiting and abdominal pain. An example of a complication that can be attributed to a norovirus infection is dehydration, including severe dehydration.

Various indicators for determining the effectiveness of a method for treating a coronavirus, picornavirus and/or norovirus infection are also known to those skilled in the art. Examples of suitable indicators include, but are not limited to, a reduction in viral load indicated by reduction in coronavirus (or load) (e.g., reduction $<10^5$ copies/mL in serum), a reduction in plasma viral load, a reduction in viral replication, a reduction in time to seroconversion (virus undetectable in patient serum), an increase in the rate of sustained viral response to therapy a reduction of morbidity or mortality in clinical outcomes, reduction in the need for a ventilator and/or total time on a ventilator, reduction in hospitalization rates and/or reduction in time in an ICU (intensive care unit) and/or hospital.

As used herein, the terms “treat,” “treating,” “treatment,” “therapeutic,” and “therapy” do not necessarily mean total cure or abolition of the disease or condition. Any alleviation of any undesired signs or symptoms of a disease or condition, to any extent can be considered treatment and/or therapy. Furthermore, treatment may include acts that may worsen the subject’s overall feeling of well-being or appearance.

As used herein, a “subject” refers to an animal that is the object of treatment, observation or experiment. “Animal” includes cold- and warm-blooded vertebrates and invertebrates such as fish, shellfish, reptiles and, in particular, mammals. “Mammal” includes, without limitation, mice, rats, rabbits, guinea pigs, dogs, cats, sheep, goats, cows, horses, camels, non-human primates, such as monkeys, chimpanzees, and apes, and, in particular, humans. In some embodiments, the subject can be human, for example, a human subject that is 60 years old or older.

The term “effective amount” is used to indicate an amount of an active compound, or pharmaceutical agent, that elicits the biological or medicinal response indicated. For example, an effective amount of compound can be the amount needed to alleviate or ameliorate symptoms of disease or prolong the survival of the subject being treated. This response may occur in a tissue, system, animal or human and includes alleviation of the signs or symptoms of the disease being treated. Determination of an effective amount is well within the capability of those skilled in the art, in view of the disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

In some embodiments, the subject can be asymptomatic, for example, the subject can be infected with coronavirus but does not exhibit any symptoms of the viral infection. In some embodiments, the subject can be have a pre-existing condition, such as asthma, hypertension, immunocompromised subjects (such as subjects with cancer, HIV and/or genetic immune deficiencies, bone marrow transplant subjects, solid organ transplant subjects, subjects who have had stem cells for cancer treatment and/or subjects who use oral or intravenous corticosteroids or other medicines called immunosuppressants), liver disease, subjects at risk for severe illness, chronic kidney disease being treated with dialysis, chronic lung disease, diabetes, hemoglobin disorders, serious heart conditions (for example, heart failure, coronary artery disease, congenital heart disease, cardiomyopathies, and pulmonary hypertension), severe obesity (such as subjects with a body mass index (BMI) of 40 or above) and people who live in a nursing home or long-term care facility. Additional examples and/or further information is provided by the CDC (https://www.cdc.gov/coronavirus/2019-ncov/need-extra-precautions/groups-at-higher-risk-.html).

A compound described herein, including a compound of Formula (I), or a pharmaceutically acceptable salt thereof, can be administered after a subject is infected with a coronavirus. In addition and/or alternatively, a compound described herein, including a compound of Formula (I), or a pharmaceutically acceptable salt thereof, can be administered prophylactically.

Examples of agents that have been used to treat a coronavirus infection include Remdesivir. However, there can be drawbacks associated with compounds being used to treat a coronavirus including, but not limited to, one or more adverse side effects, the need for subcutaneous administration and/or high cost. Potential advantages of a compound of Formula (I), or a pharmaceutically acceptable salt thereof, can be less adverse side effects, delay in the onset of an adverse side effect and/or reduction in the severity of an adverse side effect.

A coronavirus infection can be treated by inhibiting certain mechanisms. In some embodiments, a compound described herein (such as a compound of Formula (I), or a pharmaceutically acceptable salt thereof) can be selective for a coronavirus protease. For example, a compound of Formula (I), or a pharmaceutically acceptable salt thereof, can be selective for a coronavirus protease compared to a host protease, for example, one or more host proteases selected from Cathepsin L, Cathepsin B, Cathepsin D, Cathepsin K, Leukocyte Elastase, Chymotrypsin, Trypsin, Thrombin, Pepsin, Caspase 2, Elastase and Calpain. In some embodiments, the selectivity for a coronavirus protease over a host protease (such as those described herein) can be >2-fold. In some embodiments, the selectivity for a coronavirus protease over a host protease (such as those described herein) can be >10-fold. In some embodiments, the selectivity for a coronavirus protease over a host protease (such as those described herein) can be >100-fold.

Studies have shown that the entry of SARS-CoV-2 into the target cells is a process that can be mediated by multiple proteases including cysteine cathepsins L and/or transmembrane protease serine 2 (TMPRSS2) (Shang et al., PNAS (2020) 117:11727, and Hoffmann et al., Cell (2020) 181: 271-280). The cathepsin L inhibitor K117777, which lacks an inhibitory effect on the 3CLpro, can result in potent inhibition of SARS-CoV-2 in VeroE6, A549-ACE2 and/or HeLa-ACE2 (Mellott et al., bioRxiv (2020) 2020.2010.2023.347534). It has also been shown that the potent antiviral effect of K117777 is abolished when TMPRSS2 was expressed in A549-ACE2 (Steuten et al., bioRxiv (2020) 2020.2011.2021.392753). Off target activity of 3CLpro inhibitors, for example, on cathepsin L, may lead to an inaccurate assessment of the 3CLpro component of a compound's cellular potency. As an example, a compound described herein (such as a compound of Formula (I), or a pharmaceutically acceptable salt thereof) can have greater selectivity for a coronavirus protease over a host protease, such as cathepsin L. The selectivity can be determined by those skilled in the art, for example, using $IC_{50}$ and/or Ki values. In some embodiments, a compound described herein does not significantly inhibit cathepsin L (for example, $IC_{50} \geq 10000$ nM or >3.3 μM), but inhibits a coronavirus protease (for example, SARS-Cov-2 3Clpro).

A drawback with anti-viral treatment can be the development of resistance, including cross-resistance. Resistance can be a cause for treatment failure. The term "resistance" as used herein refers to a viral strain displaying a delayed, lessened and/or null response to an anti-viral agent. In some embodiments, a compound, or a pharmaceutically acceptable salt thereof, as described herein can be provided to a subject infected with a coronavirus strain that is resistant to one or more other anti-viral agents. In some embodiments, development of coronavirus resistant strains is delayed when a subject is treated with a compound, or a pharmaceutically acceptable salt thereof, as described herein compared to the development of a coronavirus resistant strain when treated with one or more other anti-viral agents.

Combination Therapies

In some embodiments, a compound, or a pharmaceutically acceptable salt thereof, as described herein can be used in combination with one or more additional agent(s) for treating and/or inhibiting replication a coronavirus. Additional agents include, but are not limited to, an ACE inhibitor, an anticoagulant, an anti-inflammatory, an ARB, an ASO, a Covid-19 convalescent plasma, an entry inhibitor, an $H_2$ pump antagonist, an H-conducting channel, an HIV protease inhibitor, an HMG-CoA reductase inhibitor, an immune globulin, an immunosuppressant, an immunotherapeutic agent, a monoclonal antibody, a neuraminidase inhibitor, a nucleoside inhibitor, a nucleoside analog inhibitor, a polymerase inhibitor, a protease inhibitor, an siRNA, a statin, a tissue plasminogen activator, an antibiotic, an antimicrobial and a vaccine. Examples of additional agents include Ascorbic acid, Anakin, Azithromycin, Baloxavir, Baricitinib, Chloroquine Phosphate, Colchicine, a corticosteroid, Epoprostenol, Famotidine, Favipiravir, an IGIV, an interferon (for example, recombinant interferon alpha 2b, IFN-α and/or PEG-IFN-α-2a), an IVIG, Ivermectin, γ-globulin, lopinavir, Methylprednisolone, Molnupiravir (MK-4482 or EIDD-2801), Niclosamide, Nitazoxanide, Nitric oxide, Oseltamivir, Peramivir, RANTES, ribavirin, Remdesivir, Ruxolitinib, Sarilumab, Siltuximab, Sirolimus, a statin, Tacrolimus, Tocilizumab, Umifenovir, Zanamivir, Casirivimab, imdevimab, bamlanivimab, etesevimab and AT-527 (Good et al., Antimicrobial Agents and Chemotherapy (2021) 65(4):e02479-20)

In some embodiments, a compound, or a pharmaceutically acceptable salt thereof, as described herein can be administered with one or more additional agent(s) together in a single pharmaceutical composition. In some embodiments, a compound, or a pharmaceutically acceptable salt thereof, can be administered with one or more additional agent(s) as two or more separate pharmaceutical compositions. Further, the order of administration of a compound, or a pharmaceutically acceptable salt thereof, as described herein with one or more additional agent(s) can vary.

EXAMPLES

Additional embodiments are disclosed in further detail in the following examples, which are not in any way intended to limit the scope of the claims.

Compounds

Compounds of Formula (I), along with pharmaceutically acceptable salts thereof, can be prepared in various ways, including those synthetic schemes shown and described herein, are provided below. Those skilled in the art will be able to recognize modifications of the disclosed syntheses and to devise routes based on the disclosures herein; all such modifications and alternate routes are within the scope of the claims.

Synthesis of Intermediates

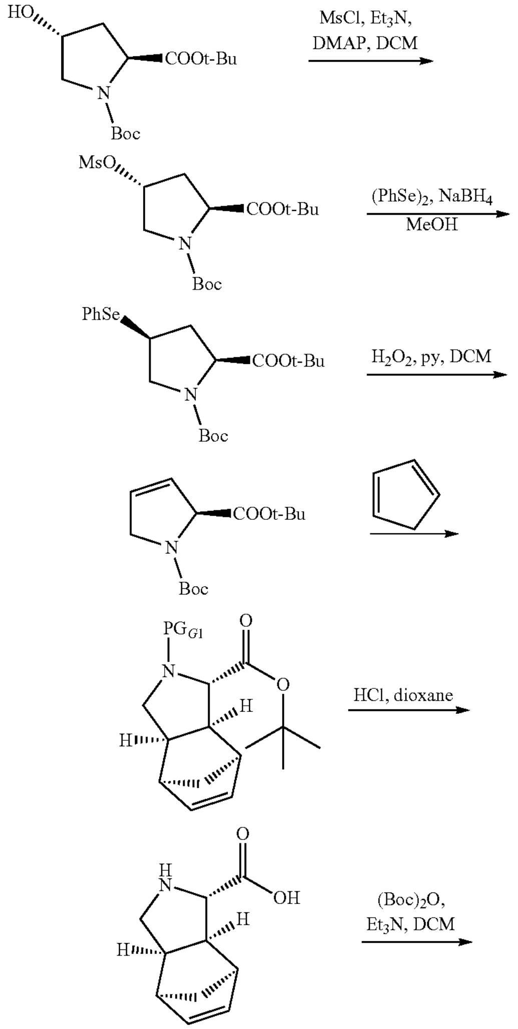

-continued

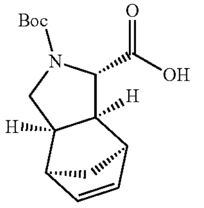

To a solution of 1,2-di-tert-butyl (2S,4R)-4-hydroxypyrrolidine-1,2-dicarboxylate (15 g, 52.2 mmol, 1.0 eq.) in DCM (250 mL) was added triethylamine (9.51 g, 93.9 mmol, 1.8 eq.) and DMAP (1.91 g, 15.7 mmol, 0.3 eq.). MsCl (8.97 g, 78.3 mmol, 1.5 eq.) was added dropwise at 0° C. The mixture was stirred at room temperature (rt) for 2 h, and the reaction was quenched with water (100 mL). The solution was extracted with DCM (3×150 mL). The organic layers were combined, washed with brine (100 mL), dried over anhydrous sodium sulfate, filtered and concentrated under reduced pressure. The residue was chromatographed on a silica gel column with EA:PE (1:10) to provide 1,2-di-tert-butyl (2S,4R)-4-(methanesulfonyloxy)pyrrolidine-1,2-dicarboxylate (17.8 g, 89%) as a colorless oil. LC-MS (ESI, m/z): 366 $[M+H]^+$.

To a solution of 1,2-di-tert-butyl (2S,4R)-4-(methanesulfonyloxy)pyrrolidine-1,2-dicarboxylate (17.8 g, 48.7 mmol, 1.0 eq.) in MeOH (400 mL) was added (phenyldiselanyl)benzene (9.12 g, 29.2 mmol, 0.6 eq.). Sodium borohydride (2.4 g, 63.3 mmol, 1.3 eq.) was added at 0° C. in several portions. The mixture was refluxed overnight and then concentrated under reduced pressure. Water (100 mL) was added, and the mixture was extracted with EA (3×150 mL). The organic layers were combined, washed with brine (100 mL), dried over anhydrous sodium sulfate, filtered and concentrated under reduced pressure. The residue was chromatographed on a silica gel column with EA:PE (1:5) to provide 1,2-di-tert-butyl (2S,4S)-4-(phenylselanyl)pyrrolidine-1,2-dicarboxylate (7.5 g, 32%) as a colorless oil. LC-MS (ESI, m/z): 428 $[M+H]^+$.

To a solution of 1,2-di-tert-butyl (2S,4S)-4-(phenylselanyl)pyrrolidine-1,2-dicarboxylate (7.5 g, 17.6 mmol, 1.0 eq.) in DCM (100 mL) was added pyridine (2.4 mL, 30.5 mmol, 1.7 eq.) and 30% aqueous $H_2O_2$ (5.6 mL, 71.6 mmol, 4.0 eq.). The mixture was stirred at rt for 12 h, and the reaction was quenched with water (20 mL). The solution was extracted with DCM (3×150 mL). The organic layers were combined, washed with 1 M citric acid (80 mL), sat. aq. $Na_2SO_3$ (100 mL) and brine (100 mL), dried over anhydrous sodium sulfate, filtered and concentrated under reduced pressure. The residue was chromatographed on a silica gel column with EA:PE (1:9) to provide 1,2-di-tert-butyl (2S)-2,5-dihydropyrrole-1,2-dicarboxylate (2.8 g, 53%) as a colorless oil. $^1$H NMR (300 MHz, DMSO-$d_6$) δ 6.02-6.09 (m, 1H), 5.76-5.83 (m, 1H), 4.72-4.78 (m, 1H), 4.05-4.09 (m, 2H), 1.17-1.42 (m, 18H). LC-MS (ESI, m/z): 270 $[M+H]^+$.

A solution of 1,2-di-tert-butyl (2S)-2,5-dihydropyrrole-1,2-dicarboxylate (2.8 g, 10.4 mmol, 1.0 eq.) in dicyclopentadiene (60 mL) was stirred at 170° C. for 48 h under nitrogen and then resolved with DCM (200 mL). After removal of the solvent, the residue was chromatographed on a silica gel column with EA:PE (1:9) to provide the product (2.5 g, crude) as a yellow oil. The crude oil was chromatographed on a C18 column with $H_2O$:MeCN (2:1) to provide di-tert-butyl (1S,3aR,4S,7R,7aS)-1,3,3a,4,7,7a-hexahydro-2H-4,7-methanoisoindole-1,2-dicarboxylate (690 mg, 19%) as a white solid. $^1$H NMR (300 MHz, DMSO-$d_6$) δ 6.14-6.21 (m, 2H), 3.55-3.60 (m, 1H), 3.23-3.27 (m, 1H), 2.95-3.02 (m, 2H), 2.74-2.87 (m, 3H), 1.24-1.48 (m, 20H). LC-MS (ESI, m/z): 270 $[M+H]^+$.

To a solution of i-tert-butyl (1S,3aR,4S,7R,7aS)-1,3,3a,4,7,7a-hexahydro-2H-4,7-methanoisoindole-1,2-dicarboxylate (690 mg, 2.1 mmol, 1.0 eq.) in dioxane (10 mL) was added hydrochloric acid (10 mL, 9M). The mixture was stirred at rt overnight and then concentrated under reduced pressure to provide (1S,3aR,4S,7R,7aS)-2,3,3a,4,7,7a-hexahydro-1H-4,7-methanoisoindole-1-carboxylic acid (320 mg, crude) as a black solid. LC-MS (ESI, m/z): 180 $[M+H]^+$.

To a solution of (1S,3aR,4S,7R,7aS)-2,3,3a,4,7,7a-hexahydro-1H-4,7-methanoisoindole-1-carboxylic acid (320 mg, 1.79 mmol, 1.0 eq.) in DCM (8 mL) was added di-tert-butyl dicarbonate (429 mg, 1.97 mmol, 1.1 eq.) and triethylamine (542 mg, 5.34 mmol, 3.0 eq.). The mixture was stirred at rt for 3 h and then concentrated under reduced pressure to provide (1S,3aR,4S,7R,7aS)-2-(tert-butoxycarbonyl)-2,3,3a,4,7,7a-hexahydro-1H-4,7-methanoisoindole-1-carboxylic acid (430 mg, crude) as a brown solid. LC-MS (ESI, m/z): 280 $[M+H]^+$.

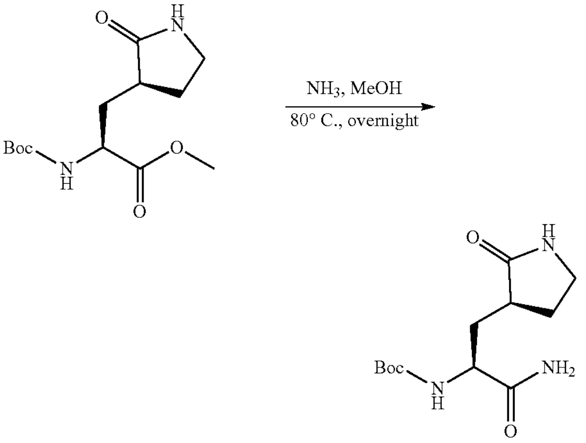

A mixture of methyl (2S)-2-[(tert-butoxycarbonyl)amino]-3-[(3S)-2-oxopyrrolidin-3-yl]propanoate (10.0 g, 34.9 mmol, 1.00 eq.) in ammonia (150 mL, 7 M in MeOH) was stirred overnight at 80° C. and concentrated under reduced pressure to afford tert-butyl N-[(1S)-1-carbamoyl-2-[(3S)-2-oxopyrrolidin-3-yl]ethyl]carbamate (10.0 g, crude) as a light brown solid. $^1$H NMR (400 MHz, DMSO-$d_6$) δ 7.65 (s, 1H), 7.29 (s, 1H), 7.01 (s, 1H), 6.88-6.95 (m, 1H), 3.84-4.15 (m, 1H), 3.09-3.21 (m, 2H), 2.08-2.26 (m, 2H), 1.84-1.96 (m, 1H), 1.60-1.74 (m, 1H), 1.44-1.54 (m, 1H), 1.38 (s, 9H). LC-MS (ESI, m/z): 272 $[M+H]^+$.

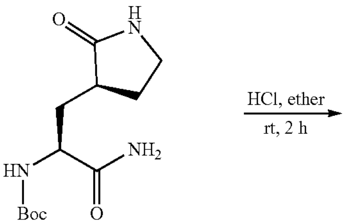

-continued

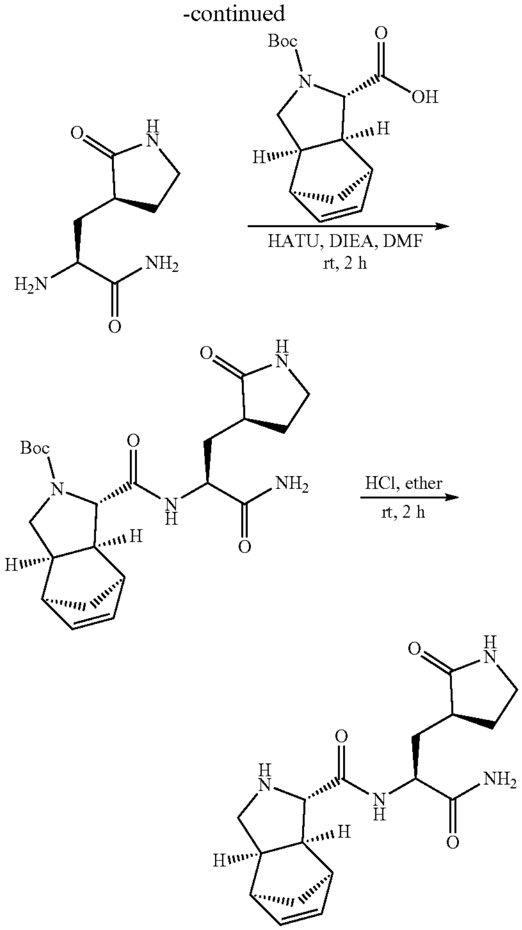

A solution of tert-butyl ((S)-1-amino-1-oxo-3-((S)-2-oxopyrrolidin-3-yl)propan-2-yl)carbamate (710 mg, 2.62 mmol, 1.0 eq.) in hydrochloric acid in ether (12 mL, 2 mol/L) was stirred at rt for 2 h and concentrated under reduced pressure to provide (S)-2-amino-3-((S)-2-oxopyrrolidin-3-yl)propenamide (500 mg, crude) as a white solid. LC-MS (ESI, m/z): 172 [M+H]$^+$.

To a solution of (1S,3aR,4S,7R,7aS)-2-(tert-butoxycarbonyl)-2,3,3a,4,7,7a-hexahydro-1H-4,7-methanoisoindole-1-carboxylic acid (979 mg, 3.5 mmol, 1.2 eq.) in DMF (2 mL) was added N,N,N',N'-Tetramethyl-O-(7-azabenzotriazol-1-yl)uronium hexafluorophosphate (1.44 g, 3.8 mmol, 1.3 eq.) and N,N-diisopropylethylamine (2.64 g, 20.4 mmol, 7.0 eq.). The mixture was stirred at 0° C. for 30 min and then (S)-2-amino-3-((S)-2-oxopyrrolidin-3-yl)propanamide (500 mg, 2.92 mmol, 1.0 eq.) was added. The mixture was stirred at rt for 2 h, and the reaction was quenched with water (5 mL). The mixture was extracted with EA (3×10 mL). The organic layers were combined, washed with brine (3×10 mL), dried over anhydrous sodium sulfate, filtered and concentrated under reduced pressure. The residue was chromatographed on a C18 column with water:MeCN (2:1) to provide tert-butyl (1S,3aR,4S,7R,7aS)-1-(((S)-1-amino-1-oxo-3-((S)-2-oxopyrrolidin-3-yl)propan-2-yl)carbamoyl)-1,3,3a,4,7,7a-hexahydro-2H-4,7-methanoisoindole-2-carboxylate (1.05 g, 75%) as a brown yellow solid. LC-MS (ESI, m/z): 433 [M+H]$^+$.

A solution of tert-butyl (1S,3aR,4S,7R,7aS)-1-(((S)-1-amino-1-oxo-3-((S)-2-oxopyrrolidin-3-yl)propan-2-yl)carbamoyl)-1,3,3a,4,7,7a-hexahydro-2H-4,7-methanoisoindole-2-carboxylate (300 mg, 0.69 mmol, 1.0 eq.) in hydrochloric acid in ether (5 mL, 2 mol/L) was stirred at rt for 2 h and then concentrated under reduced pressure to provide (1S,3aR,4S,7R,7aS)—N—((S)-1-amino-1-oxo-3-((S)-2-oxopyrrolidin-3-yl)propan-2-yl)-2,3,3a,4,7,7a-hexahydro-1H-4,7-methanoisoindole-1-carboxamide (200 mg, crude) as a white solid. LC-MS (ESI, m/z): 333 [M+H]$^+$.

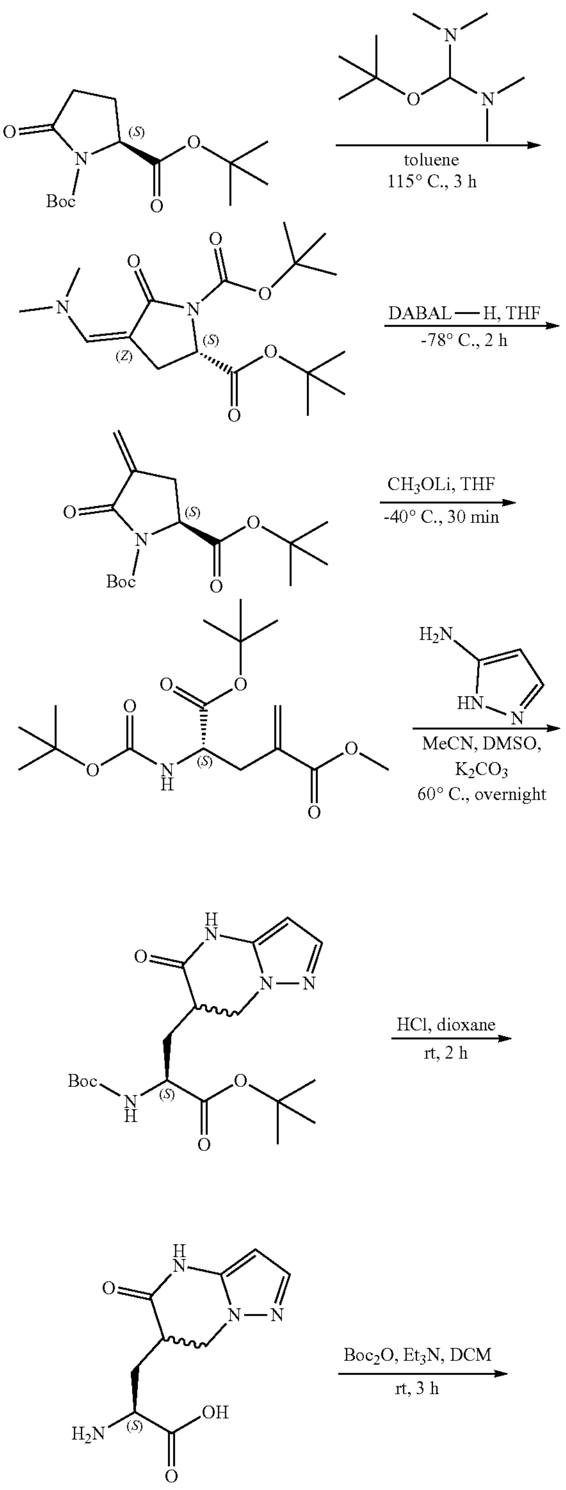

-continued

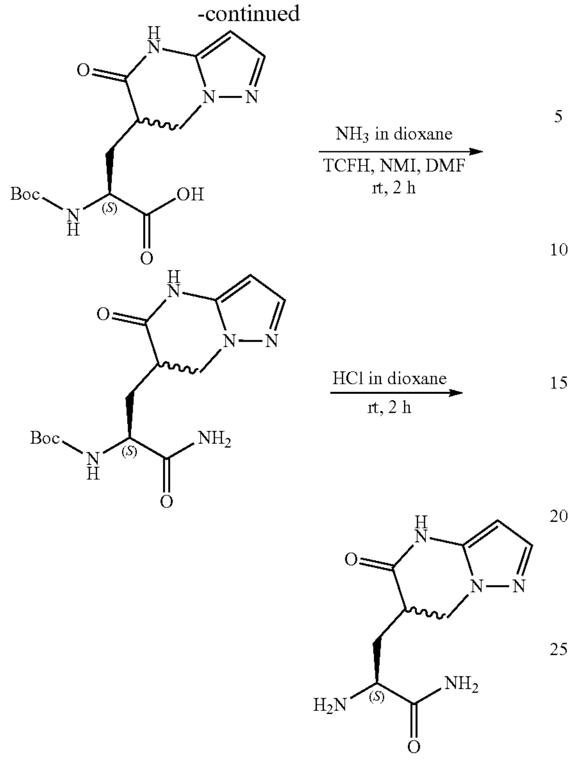

To a solution of 1,2-di-tert-butyl (2S)-5-oxopyrrolidine-1,2-dicarboxylate 1,2-di-tert-butyl (2S)-5-oxopyrrolidine-1,2-dicarboxylate (50 g, 175 mmol, 1.0 eq.) in toluene (500 mL) was added [tert-butoxy(dimethylamino)methyl]dimethylamine (36.7 g, 210 mmol, 1.2 eq.). The mixture was stirred at 115° C. for 3 h under nitrogen and concentrated under reduced pressure to provide di-tert-butyl (S,Z)-4-((dimethylamino)methylene)-5-oxopyrrolidine-1,2-dicarboxylate (46 g, crude) as an orange oil. LC-MS (ESI, m/z): 341 $[M+H]^+$.

To a solution of di-tert-butyl (S,Z)-4-((dimethylamino)methylene)-5-oxopyrrolidine-1,2-dicarboxylate (46 g, 135 mmol, 1.0 eq.) in THF (900 mL) was added DIBAl-H (203 mL, 1M in toluene, 203 mmol, 1.5 eq.) dropwise at −78° C. under $N_2$. The mixture was stirred at −78° C. for 2 h, and was then poured into hydrochloric acid (800 mL, 2 mol/L) slowly at 0° C. The solution was extracted with EA (3×600 mL). The organic layers were combined, dried over anhydrous sodium sulfate, filtered and concentrated under reduced pressure. The residue was chromatographed on a silica gel column with EA:PE (1:5) to provide di-tert-butyl (S)-4-methylene-5-oxopyrrolidine-1,2-dicarboxylate (16 mg, 36%) as a colorless oil. $^1$H NMR (300 MHz, DMSO-$d_6$) δ 5.98-6.00 (m, 1H), 5.58-5.59 (m, 1H), 4.50-4.54 (m, 1H), 3.04-3.34 (m, 1H), 2.57-2.64 (m, 1H), 1.36-1.44 (m, 18H). LC-MS (ESI, m/z): 298 $[M+H]^+$.

To a solution of di-tert-butyl (S)-4-methylene-5-oxopyrrolidine-1,2-dicarboxylate (12 g, 40.4 mmol, 1.0 eq.) in THF (200 mL) was added methoxylithium (22 mL, 2.2M in methanol, 48.4 mmol, 1.2 eq.) at −40° C. under $N_2$. The mixture was stirred at −40° C. for 30 min. The reaction quenched with sat. aq. sodium chloride (100 mL). The solution was extracted with EA (3×100 mL). The organic layers were combined, dried over anhydrous sodium sulfate, filtered and concentrated under reduced pressure. The residue was chromatographed on a silica gel column with EA:PE (1:4) to provide 1-(tert-butyl) 5-methyl (S)-2-((tert-butoxycarbonyl)amino)-4-methylenepentanedioate (12 g, 81%) as a colorless viscous oil. LC-MS (ESI, m/z): 330 $[M+H]^+$.

To a solution of 1-(tert-butyl) 5-methyl (S)-2-((tert-butoxycarbonyl)amino)-4-methylenepentanedioate (7 g, 21 mmol, 1.0 eq.) in MeCN (70 mL) and DMSO (70 mL) was added 2H-pyrazol-3-amine (2.1 g, 25.5 mmol, 1.2 eq.), $K_2CO_3$ (2.94 mg, 21 mmol, 1.0 eq.). The mixture was stirred at 60° C. overnight and then concentrated under reduced pressure. The residue was chromatographed on a C18 column with MeCN:$H_2O$ (3:2) to provide tert-butyl (2S)-2-((tert-butoxycarbonyl)amino)-3-(5-oxo-4,5,6,7-tetrahydropyrazolo[1,5-a]pyrimidin-6-yl)propanoate (1.7 g, 19%) as a brown yellow oil. $^1$H NMR (300 MHz, DMSO-$d_6$) δ 10.76 (s, 1H), 7.18-7.27 (m, 2H), 5.56-5.57 (m, 1H), 4.26-4.36 (m, 1H), 3.89-4.13 (m, 1H), 2.75-2.79 (m, 1H), 2.10-2.25 (m, 1H), 1.61-1.80 (m, 1H), 1.27-1.53 (m, 18H). LC-MS (ESI, m/z): 381 $[M+H]^+$.

To a solution of tert-butyl (2S)-2-((tert-butoxycarbonyl)amino)-3-(5-oxo-4,5,6,7-tetrahydropyrazolo[1,5-a]pyrimidin-6-yl)propanoate (800 mg, 3.55 mmol, 1.0 eq.) in dioxane (8 mL) was added hydrochloric acid (8 mL, 9M). The mixture was stirred at rt for 2 h and then concentrated under reduced pressure to provide (2S)-2-amino-3-(5-oxo-4,5,6,7-tetrahydropyrazolo[1,5-a]pyrimidin-6-yl)propanoic acid (400 mg, crude) as an off-white semi-solid. LC-MS (ESI, m/z): 225 $[M+H]^+$.

To a solution of (2S)-2-amino-3-(5-oxo-4,5,6,7-tetrahydropyrazolo[1,5-a]pyrimidin-6-yl)propanoic acid (400 mg, 1.78 mmol, 1.0 eq.) in DCM (6 mL) was added di-tert-butyl dicarbonate (430 mg, 1.96 mmol, 1.1 eq.) and triethylamine (180 mg, 5.36 mmol, 3.0 eq.). The mixture was stirred at rt for 3 h and then concentrated under reduced pressure to provide (2S)-2-((tert-butoxycarbonyl)amino)-3-(5-oxo-4,5,6,7-tetrahydropyrazolo[1,5-a]pyrimidin-6-yl)propanoic acid (530 mg, crude) as a brown yellow semi-solid. LC-MS (ESI, m/z): 325 $[M+H]^+$.

To a solution of (2S)-2-((tert-butoxycarbonyl)amino)-3-(5-oxo-4,5,6,7-tetrahydropyrazolo[1,5-a]pyrimidin-6-yl) propanoic acid (530 mg, 1.63 mmol, 1.0 eq.) in DMF (8 mL) was added N,N,N,N-tetramethylchloroformamidinium hexafluorophosphate (550 mg, 1.96 mmol, 1.2 eq.), NMI (671 mg, 8.17 mmol, 5.0 eq.) and $NH_3$ in dioxane (40 mL, 10.0 eq., 0.4 mol/L). The mixture was stirred at rt for 2 h and then chromatographed on a C18 column with MeCN:$H_2O$ (1:4) to provide tert-butyl ((2S)-1-amino-1-oxo-3-(5-oxo-4,5,6,7-tetrahydropyrazolo[1,5-a]pyrimidin-6-yl)propan-2-yl) carbamate (280 mg, 48%) as a brown yellow oil. LC-MS (ESI, m/z): 324 $[M+H]^+$.

To a solution of tert-butyl ((2S)-1-amino-1-oxo-3-(5-oxo-4,5,6,7-tetrahydropyrazolo[1,5-a]pyrimidin-6-yl)propan-2-yl)carbamate (280 mg, 0.87 mmol, 1.0 eq.) in hydrochloric acid (4 mL, 2 mol/L in dioxane) was stirred at rt for 2 h and then concentrated under reduced pressure to provide (2S)-2-amino-3-(5-oxo-4,5,6,7-tetrahydropyrazolo[1,5-a]pyrimidin-6-yl)propanamide (180 mg, crude) as an off-white semi-solid. LC-MS (ESI, m/z): 224 $[M+H]^+$.

(S)-3-((R*)-1-(tert-butoxycarbonyl)-5,5-dimethyl-2-oxopyrrolidin-3-yl)-2-((tert-butoxycarbonyl)amino) propanoic acid

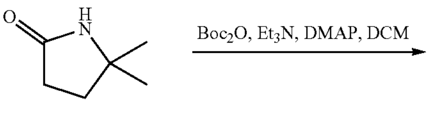

-continued

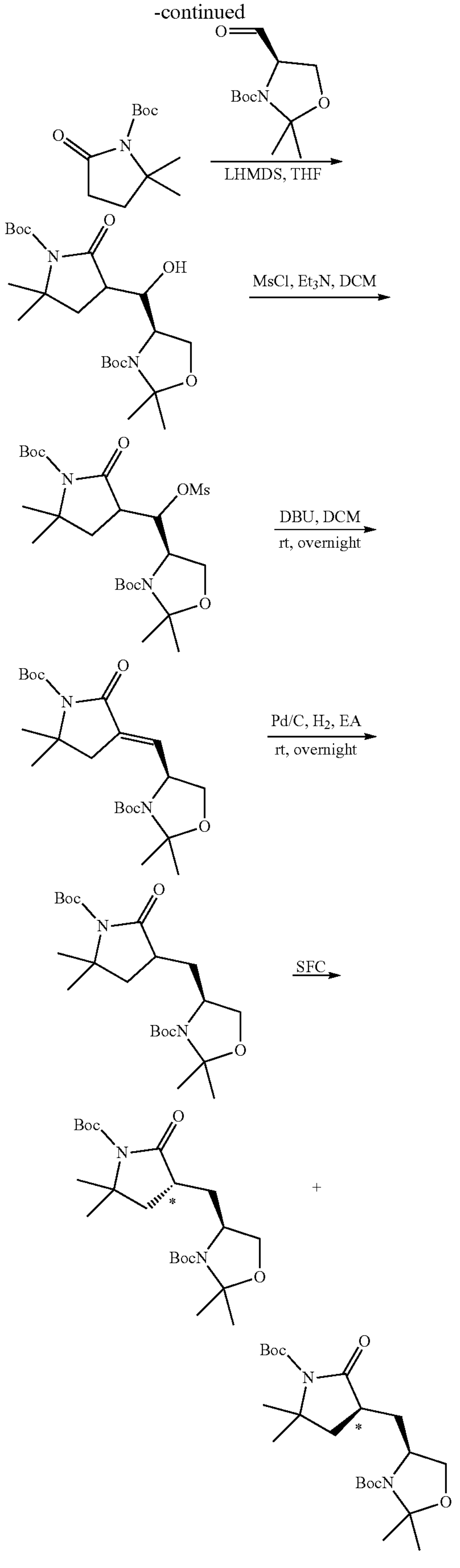

-continued

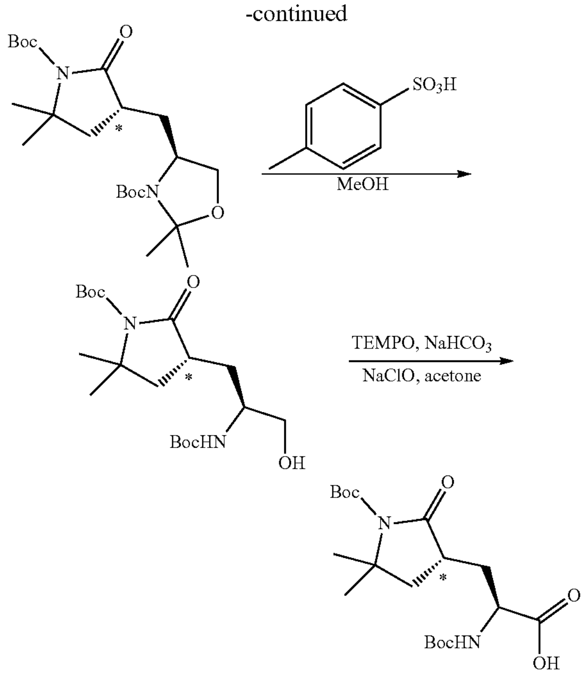

The chiral center noted with "*" is tentatively assigned.

A 100 mL round-bottom flask was charged with 5,5-dimethylpyrrolidin-2-one (3.5 g, 30.9 mmol, 1.0 eq.), DCM (50 mL), di-tert-butyl dicarbonate (10.8 g, 49.5 mmol, 1.6 eq.), triethylamine (6.24 g, 61.8 mmol, 2.0 eq.) and DMAP (0.38 g, 3.09 mmol, 0.1 eq.). The solution was stirred overnight at 40° C., and the reaction was quenched with water (150 mL). The solution was extracted with EA (5×300 mL). The organic layers were combined, washed with brine (2×100 mL), dried over anhydrous sodium sulfate, filtered and concentrated under reduced pressure. The residue was chromatographed on a silica gel column with EA:PE (13:87) to provide tert-butyl 2,2-dimethyl-5-oxopyrrolidine-1-carboxylate (4.0 g, 58%) as a white solid. LC-MS (ESI, m/z): 214 $[M+H]^+$.

A 100 mL round-bottom flask was charged with tert-butyl 2,2-dimethyl-5-oxopyrrolidine-1-carboxylate (3.6 g, 16.9 mmol, 1.00 eq.) and THF (50 mL). The solution was cooled to −78° C. and LiHMDS (20.2 mL, 1M in THF, 20.2 mmol, 1.2 eq.) was added. The mixture was stirred for 1 h at −78° C., and a solution of tert-butyl (4R)-4-formyl-2,2-dimethyl-1,3-oxazolidine-3-carboxylate (5.81 g, 25.3 mmol, 1.5 eq.) in THF (10 mL) was added under Ar. Stirring was continued at −78° C. for 1 h. The reaction was quenched with a sat. ammonium chloride solution (50 mL). The solution was extracted with dichloromethane (3×150 mL). The organic layers were combined, washed with brine (2×50 mL), dried over anhydrous sodium sulfate, filtered and concentrated under reduced pressure. The residue was chromatographed on a silica gel column with EA:PE (1:4) to provide tert-butyl (4R)-4-{[1-(tert-butoxycarbonyl)-5,5-dimethyl-2-oxopyrrolidin-3-yl](hydroxy)methyl}-2,2-dimethyl-1,3-oxazolidine-3-carboxylate (7.2 g, 89%) as a colorless oil. LC-MS (ESI, m/z): 443 $[M+H]^+$.

A 100 mL round-bottom flask was charged with tert-butyl (4R)-4-{[1-(tert-butoxycarbonyl)-5,5-dimethyl-2-oxopyrrolidin-3-yl](hydroxy)methyl}-2,2-dimethyl-1,3-oxazolidine-3-carboxylate (1 g, 2.26 mmol, 1.00 eq.), DCM (10 mL), triethylamine (1.14 g, 11.3 mmol, 5.0 eq.) and MsCl (0.31 g, 4.52 mmol, 2.0 eq.). The mixture was stirred overnight at rt, and the reaction was quenched with water (30 mL). The solution was extracted with dichloromethane (4×50 mL). The organic layers were combined, washed with brine (3×20 mL), dried over anhydrous sodium sulfate, filtered and concentrated under reduced pressure to provide tert-butyl (4R)-4-{[1-(tert-butoxycarbonyl)-5,5-dimethyl-2-oxopyrrolidin-3-yl](methanesulfonyloxy)methyl}-2,2-dimethyl-1,3-oxazolidine-3-carboxylate (960 mg, crude) as a yellow oil. LC-MS (ESI, m/z): 521 $[M+H]^+$.

A 100 mL round-bottom flask was charged with tert-butyl (4R)-4-{[1-(tert-butoxycarbonyl)-5,5-dimethyl-2-oxopyrrolidin-3-yl](methanesulfonyloxy)methyl}-2,2-dimethyl-1,3-oxazolidine-3-carboxylate (900 mg, 1.73 mmol, 1.0 eq.), DCM (20 mL) and DBU (1.32 g, 8.64 mmol, 5.0 eq.). The mixture was stirred overnight at rt, and the reaction was quenched with water (30 mL). The solution was extracted with dichloromethane (3×80 mL). The organic layers were combined, washed with brine (2×30 mL), dried over anhydrous sodium sulfate, filtered and concentrated under reduced pressure. The residue was chromatographed on a silica gel column with EA:PE (1:4) to provide tert-butyl (4S)-4-{[1-(tert-butoxycarbonyl)-5,5-dimethyl-2-oxopyrrolidin-3-ylidene]methyl}-2,2-dimethyl-1,3-oxazolidine-3-carboxylate (635 mg, 82%) as a colorless oil. LC-MS (ESI, m/z): 425 $[M+H]^+$.

A 250 mL round-bottom flask was charged with tert-butyl (4S)-4-{[1-(tert-butoxycarbonyl)-5,5-dimethyl-2-oxopyrrolidin-3-ylidene]methyl}-2,2-dimethyl-1,3-oxazolidine-3-carboxylate (4.4 g, 10.4 mmol, 1.0 eq.), EA (50 mL) and 10% palladium on activated carbon (5.51 g). The contents of the flask were placed under an atmosphere of hydrogen (3 atm). The mixture was stirred overnight at rt. The solids were filtered off. The organic layer was concentrated under reduced pressure to provide tert-butyl (4S)-4-{[1-(tert-butoxycarbonyl)-5,5-dimethyl-2-oxopyrrolidin-3-yl]methyl}-2,2-dimethyl-1,3-oxazolidine-3-carboxylate (4.3 g, 78%) as a colorless oil. LC-MS (ESI, m/z): 427 $[M+H]^+$.

Tert-butyl (4S)-4-((1-(tert-butoxycarbonyl)-5,5-dimethyl-2-oxopyrrolidin-3-yl)methyl)-2,2-dimethyloxazolidine-3-carboxylate (3.6 g) was purified by prep-SFC using the following gradient conditions: Column: Lux Sum Cellulose-2, 3*25 cm, 5 m; Mobile Phase A: $CO_2$, Mobile Phase B: IPA(0.5% 2M $NH_3$-MeOH); Flow rate: 60 mL/min; Gradient: isocratic 10% B; Column Temperature(° C.): 35; Back Pressure(bar): 100; Wave Length: 220 nm; RT1 (min): 4.81; RT2(min): 6.43; Sample Solvent: MeOH—Preparative; Injection Volume: 1.5 mL; Number Of Runs: 27. Purification resulted in tert-butyl (S)-4-(((S*)-1-(tert-butoxycarbonyl)-5,5-dimethyl-2-oxopyrrolidin-3-yl)methyl)-2,2-dimethyloxazolidine-3-carboxylate (990 mg) as an off-white solid (Lux Celloluse-2 4.6*50 mm, 3 m, 35° c. Co-Solvent: IPA (0.1% DEA), 10% to 50% in 2.0 min, hold 1.0 min at 50%): Rt: 0.969 min), and tert-butyl (S)-4-(((R*)-1-(tert-butoxycarbonyl)-5,5-dimethyl-2-oxopyrrolidin-3-yl)methyl)-2,2-dimethyloxazolidine-3-carboxylate (1.6 g) as an off-white solid Lux Celloluse-2 4.6*50 mm, 3 m, 35° C. Co-Solvent: IPA (0.1% DEA), 10% to 50% in 2.0 min, hold 1.0 min at 50%): Rt: 1.411 min).

A 40 mL vial was charged with tert-butyl (S)-4-(((R*)-1-(tert-butoxycarbonyl)-5,5-dimethyl-2-oxopyrrolidin-3-yl)methyl)-2,2-dimethyloxazolidine-3-carboxylate (1.6 g, 3.75 mmol, 1.0 eq.), para-toluene sulfonate (64.6 mg, 0.375 mmol, 0.1 eq.) and MeOH (20 mL). The mixture was stirred overnight at rt. The reaction was quenched with water (20 mL). The solution was extracted with EA (3×30 mL). The organic layers were combined, washed with brine (50 mL), dried over anhydrous sodium sulfate, filtered and concentrated under reduced pressure to provide tert-butyl(S)-4-((S)-2-((tert-butoxycarbonyl)amino)-3-hydroxypropyl)-2,2-dimethyl-5-oxopyrrolidine-1-carboxylate (1.47 g, crude) as an off-white semi-solid. LC-MS (ESI, m/z): 387 $[M+H]^+$.

To a solution of tert-butyl (S)-4-((R*)-2-((tert-butoxycarbonyl)amino)-3-hydroxypropyl)-2,2-dimethyl-5-oxopyrrolidine-1-carboxylate (1.7 g, 4.40 mmol, 1.0 eq.) in acetone (22 mL) was added 5% sodium bicarbonate solution (22 mL, 13.1 mmol, 3.0 eq.) and 2,2,6,6-Tetramethylpiperidinooxy (0.14 g, 0.88 mmol, 0.2 eq.). Chlorosylsodium (1.15 g, 15.4 mmol, 3.5 eq.) was added dropwise at 0° C. The mixture was stirred at rt overnight, and the reaction was quenched with water (20 mL). The solution was washed with Et2O (2×20 mL). The pH value of the aqueous solution was adjusted to 2 with concentrated hydrochloric acid (1 mol/L). The solution was extracted with EtOAc (3×50 mL). The organic layers were combined, washed with brine (50 mL), dried over anhydrous sodium sulfate, filtered and concentrated under reduced pressure to provide (S)-3-((R*)-1-(tert-butoxycarbonyl)-5,5-dimethyl-2-oxopyrrolidin-3-yl)-2-((tert-butoxycarbonyl)amino)propanoic acid (1.2 g, 61%) as a white solid.

tert-butyl ((S)-1-hydroxy-3-((S*)-5-oxo-4-azaspiro[2.4]heptan-6-yl)propan-2-yl)carbamate

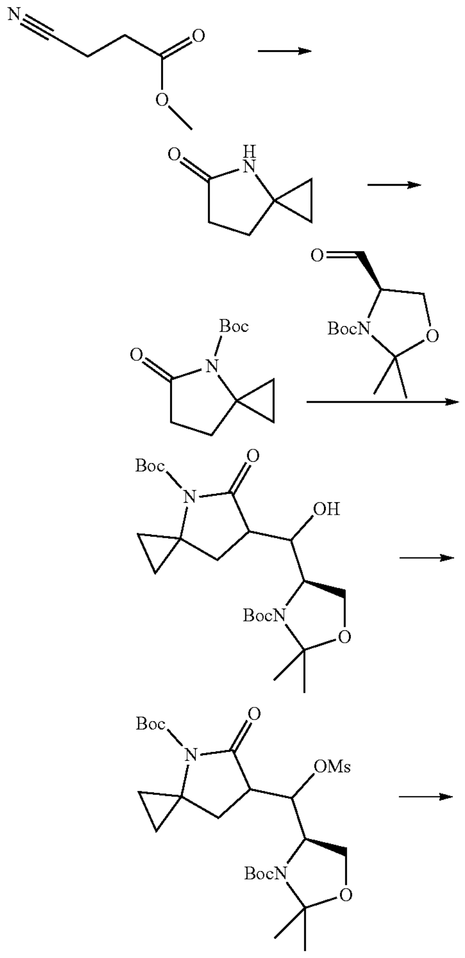

-continued

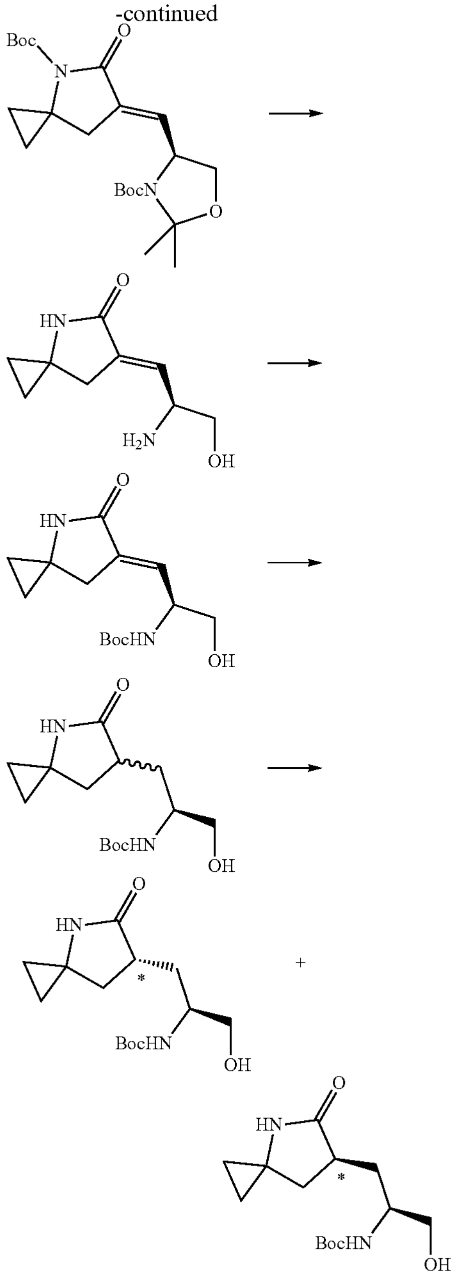

The absolute configuration of the chiral center noted with "*" is tentatively assigned.

To a solution of methyl 3-cyanopropanoate (10 g, 88.4 mmol, 1.0 eq.) in $Et_2O$ (100 mL) was added $Ti(O^iPr)_4$ (5.03 g, 17.7 mmol, 0.2 eq.). EtMgBr (194 mL, 1M in THF, 194 mmol, 2.2 eq.) was then added dropwise under $N_2$. The mixture was stirred at rt for 2 h, and the reaction was quenched with water (20 mL). The mixture was extracted with EA (3×60 mL). The organic layers were combined, washed with brine (50 mL), dried over anhydrous sodium sulfate, filtered and concentrated under reduced pressure. The residue was chromatographed on a silica gel column with PE:MeOH (12:1) to provide 4-azaspiro[2.4]heptan-5-one (8.5 g, 69%) as a colorless oil. LC-MS (ESI, m/z): 112 $[M+H]^+$.

A 250 mL round-bottom flask was charged with 4-azaspiro[2.4]heptan-5-one (8.5 g, 76.5 mmol, 1.0 eq.), DCM (100 mL), di-tert-butyl dicarbonate (26.7 g, 122 mmol, 1.6 eq.), triethylamine (0.77 g, 7.65 mmol, 0.1 eq.) and DMAP (0.93 g, 7.65 mmol, 0.1 eq.). The solution was stirred overnight at 40° C., and the reaction was quenched with water (70 mL). The solution was extracted with DCM (3×100 mL). The organic layers were combined, washed with brine (80 mL), dried over anhydrous sodium sulfate, filtered and concentrated under reduced pressure. The residue was chromatographed on a silica gel column with EA:PE (1:12) to provide tert-butyl 5-oxo-4-azaspiro[2.4]heptane-4-carboxylate (11 g, 58%) as a white solid. LC-MS (ESI, m/z): 212 $[M+H]^+$.

A 500 mL round-bottom flask was charged with tert-butyl 5-oxo-4-azaspiro[2.4]heptane-4-carboxylate (11 g, 52.1 mmol, 1.0 eq.) and THF (150 mL). The solution was cooled to −78° C. and LiHMDS (62.5 mL, 1M in THF, 62.5 mmol, 1.2 eq.) was added. The mixture was stirred for 1 h at −78° C. and a solution of tert-butyl (4R)-4-formyl-2,2-dimethyl-1,3-oxazolidine-3-carboxylate (17.9 g, 78.1 mmol, 1.5 eq.) in THF (50 mL) under Ar was added. Stirring was continued at −78° C. for 1 h. The reaction was quenched with sat. ammonium chloride solution (100 mL). The solution was extracted with EA (3×200 mL). The organic layers were combined, washed with brine (200 mL), dried over anhydrous sodium sulfate, filtered and concentrated under reduced pressure. The residue was chromatographed on a silica gel column with EA:PE (1:8) to provide tert-butyl (4R)-4-((4-(tert-butoxycarbonyl)-5-oxo-4-azaspiro[2.4]heptan-6-yl)(hydroxy)methyl)-2,2-dimethyloxazolidine-3-carboxylate (19.7 g, 69%) as a colorless oil. LC-MS (ESI, m/z): 441 $[M+H]^+$.

A 500 mL round-bottom flask was charged with tert-butyl (4R)-4-((4-(tert-butoxycarbonyl)-5-oxo-4-azaspiro[2.4]heptan-6-yl)(hydroxy)methyl)-2,2-dimethyloxazolidine-3-carboxylate (19.7 g, 44.7 mmol, 1.0 eq.), DCM (250 mL), triethylamine (27.2 g, 268 mmol, 6.0 eq.) and MsCl (20.5 g, 179 mmol, 4.0 eq.). The mixture was stirred overnight at rt, and the reaction was quenched with water (100 mL). The solution was extracted with DCM (4×150 mL). The organic layers were combined, washed with brine (100 mL), dried over anhydrous sodium sulfate, filtered and concentrated under reduced pressure to provide tert-butyl (4R)-4-((4-(tert-butoxycarbonyl)-5-oxo-4-azaspiro[2.4]heptan-6-yl)((methylsulfonyl)oxy)methyl)-2,2-dimethyloxazolidine-3-carboxylate (22 g, crude) as an orange oil. LC-MS (ESI, m/z): 519 $[M+H]^+$.

A 500 mL round-bottom flask was charged with tert-butyl (4R)-4-((4-(tert-butoxycarbonyl)-5-oxo-4-azaspiro[2.4]heptan-6-yl)((methylsulfonyl)oxy)methyl)-2,2-dimethyloxazolidine-3-carboxylate (22 g, 42.4 mmol, 1.0 eq.), DCM (200 mL) and DBU (14.2 g, 93.3 mmol, 2.2 eq.). The mixture was stirred overnight at rt, and the reaction was quenched with water (80 mL). The solution was extracted with DCM (3×100 mL). The organic layers were combined, washed with brine (80 mL), dried over anhydrous sodium sulfate, filtered and concentrated under reduced pressure. The residue was chromatographed on a silica gel column with EA:PE (1:12) to provide tert-butyl 6-{[(4S)-3-(tert-butoxycarbonyl)-2,2-dimethyl-1,3-oxazolidin-4-yl]methylidene}-5-oxo-4-azaspiro[2.4]heptane-4-carboxylate (11.3 g, 57%) as a colorless oil. LC-MS (ESI, m/z): 423 $[M+H]^+$.

A 250 mL vial was charged with tert-butyl 6-{[(4S)-3-(tert-butoxycarbonyl)-2,2-dimethyl-1,3-oxazolidin-4-yl]methylidene}-5-oxo-4-azaspiro[2.4]heptane-4-carboxylate (11.3 g, 26.7 mmol, 1.0 eq.), 4-methylbenzenesulfonic acid (5.53 g, 32.1 mmol, 1.2 eq.) and MeOH (120 mL). The mixture was stirred overnight at rt, and then concentrated under reduced pressure to provide 6-[(2S)-2-amino-3-hydroxypropylidene]-4-azaspiro[2.4]heptan-5-one (5.8 g, crude) as an orange oil. LC-MS (ESI, m/z): 183 $[M+H]^+$.

To a solution of 6-[(2S)-2-amino-3-hydroxypropylidene]-4-azaspiro[2.4]heptan-5-one (5.8 g, 31.829 mmol, 1.00 eq.) in DCM (90 mL) was added triethylamine (25.8 g, 255 mmol, 8.0 eq.) and di-tert-butyl dicarbonate (20.8 g, 95.5 mmol, 3.0 eq.). The mixture was stirred at rt overnight, and the reaction was quenched with water (30 mL). The mixture was extracted with $CDCl_3$:isopropyl alcohol=3:1 (3×50 mL). The organic layers were combined, dried over anhydrous sodium sulfate, filtered and concentrated under reduced pressure. The residue was chromatographed on a silica gel column with MeOH:DCM (1:25) to provide tert-butyl N-[(2S)-1-hydroxy-3-[(6E)-5-oxo-4-azaspiro[2.4]heptan-6-ylidene]propan-2-yl]carbamate (3.9 g, 39%) as a brown yellow solid. LCMS (ESI, m/z): 283 $[M+H]^+$.

To a solution of tert-butyl N-[(2S)-1-hydroxy-3-[5-oxo-4-azaspiro[2.4]heptan-6-ylidene]propan-2-yl]carbamate (3.9 g, 13.8 mmol, 1.0 eq.) in THF (30 mL) and MeOH (90 mL) was added $NiCl_2 \cdot 6H_2O$ (23 g, 96.7 mmol, 7.0 eq.). $NaBH_4$ (11 g, 290 mmol, 21.0 eq.) was added in several portions at 0° C. The mixture was stirred at rt overnight, and the reaction was quenched with water (30 mL). The mixture was extracted with $CDCl_3$:isopropyl alcohol=3:1 (3×60 mL). The organic layers were combined, dried over anhydrous sodium sulfate, filtered and concentrated under reduced pressure. The residue was chromatographed on a C18 column with MeCN:$H_2O$ (4:1) to provide tert-butyl N-[(2S)-1-hydroxy-3-{5-oxo-4-azaspiro[2.4]heptan-6-yl}propan-2-yl]carbamate (1.7 g, 39%) as a brown yellow solid. LCMS (ESI, m/z): 285 $[M+H]^+$.

Tert-butyl N-[(2S)-1-hydroxy-3-{5-oxo-4-azaspiro[2.4]heptan-6-yl}propan-2-yl]carbamate (1.7 g) was purified by SFC using the following gradient conditions: Column: NB-Lux Sum i-Cellulose-5, 2.12*25 cm, 5 u m; Mobile Phase A: $CO_2$, Mobile Phase B: MeOH(0.1% 2M $NH_3$-MeOH); Flow rate: 100 mL/min; Gradient: isocratic 25% B; Column Temperature(° C.): 35; Back Pressure(bar): 100; Wave Length: 220 nm; RT1 (min): 3.37; RT2(min): 4.02; Sample Solvent: MeOH—Preparative; Injection Volume: 1 mL; Number Of Runs: 40. Purification resulted in 590 mg of first eluding tert-butyl ((S)-1-hydroxy-3-((R*)-5-oxo-4-azaspiro[2.4]heptan-6-yl)propan-2-yl)carbamate as a brown yellow solid and 640 mg of last eluding tert-butyl ((S)-1-hydroxy-3-((S*)-5-oxo-4-azaspiro[2.4]heptan-6-yl)propan-2-yl)carbamate as a brown yellow solid.

(3S)-3-amino-N-cyclopropyl-2-hydroxy-4-((S)-2-oxopyrrolidin-3-yl)butanamide

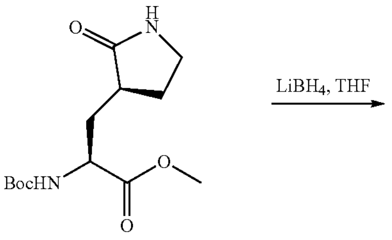

-continued

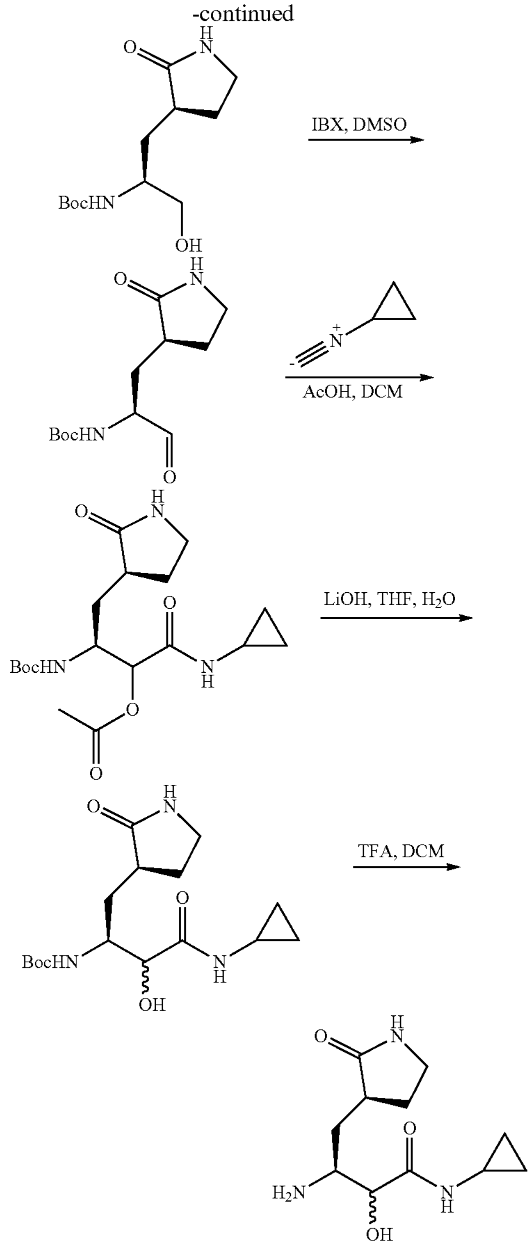

To a stirred mixture of methyl (2S)-2-[(tert-butoxycarbonyl)amino]-3-[(3S)-2-oxopyrrolidin-3-yl]propanoate (3.0 g, 10.5 mmol, 1.0 eq.) in tetrahydrofuran (50 mL) was added lithium borohydride (26.2 mL, 52.4 mmol, 5.0 eq.) dropwise at 0° C. The mixture was stirred for 1 h at 0° C. and then concentrated under reduced pressure. The mixture was diluted with water (20 mL), and then extracted with isopropanol:trichloromethane (1:5, 4×50 mL). The organic layers were combined, dried over anhydrous sodium sulfate, filtered and concentrated under reduced pressure. The residue was purified by silica gel column chromatography, eluted with dichloromethane:methanol (19:1) to afford tert-butyl N-[(2S)-1-hydroxy-3-[(3S)-2-oxopyrrolidin-3-yl]propan-2-yl]carbamate (2.6 g, crude) as a white solid. The crude product was precipitated by the addition of PE:EA (4:1, 40 mL) to afford tert-butyl N-[(2S)-1-hydroxy-3-[(3S)-2-oxopyrrolidin-3-yl]propan-2-yl]carbamate (2.4 g, 79%) as a white solid. LC-MS (ESI, m/z): 259 $[M+H]^+$.

To a stirred mixture of tert-butyl N-[(2S)-1-hydroxy-3-[(3S)-2-oxopyrrolidin-3-yl]propan-2-yl]carbamate (2.4 g, 9.29 mmol, 1.0 eq.) in dimethyl sulfoxide (40 mL) was added 2-iodoxybenzoic acid (7.80 g, 27.8 mmol, 3.0 eq.) in portions at rt. The mixture was stirred for 3 h at rt, and then basified to pH=8 with sat. sodium bicarbonate (aq.). The mixture was diluted with water (20 mL) and extracted with EA (4×200 mL). The organic layers were combined, washed with brine (3×100 mL), dried over anhydrous sodium sulfate, filtered and concentrated under reduced pressure to afford tert-butyl N-[(2S)-1-oxo-3-[(3S)-2-oxopyrrolidin-3-yl]propan-2-yl]carbamate (1.5 g, 63%) as a yellow solid. LC-MS (ESI, m/z): 257 [M+H]$^+$.

To a stirred mixture of tert-butyl N-[(2S)-1-oxo-3-[(3S)-2-oxopyrrolidin-3-yl]propan-2-yl]carbamate (900 mg, 3.51 mmol, 1.0 eq.) in dichloromethane (10 mL) were added isocyanocyclopropane (471 mg, 7.02 mmol, 2.0 eq.) and acetic acid (633 mg, 10.5 mmol, 3.0 eq.) dropwise at 0° C. The mixture was stirred for 5 h at rt and then concentrated under reduced pressure. The residue was purified by silica gel column chromatography, eluted with dichloromethane: methanol (49:1) to afford (2S)-2-[(tert-butoxycarbonyl)amino]-1-(cyclopropylcarbamoyl)-3-[(3S)-2-oxopyrrolidin-3-yl]propyl acetate (820 mg, 55%) as a yellow solid. LC-MS (ESI, m/z): 384 [M+H]$^+$.

To a stirred mixture of (2S)-2-[(tert-butoxycarbonyl)amino]-1-(cyclopropylcarbamoyl)-3-[(3S)-2-oxopyrrolidin-3-yl]propyl acetate (810 mg, 2.11 mmol, 1.0 eq.) in tetrahydrofuran (8 mL) was added lithium hydroxide (253 mg, 10.5 mmol, 5.0 eq., in water 8 mL) at 0° C. The mixture was stirred for 1 h at 0° C. The mixture was acidified to pH=6 with hydrochloric acid (2M). The mixture was extracted with EA (4×60 mL). The organic layers were combined, dried over anhydrous sodium sulfate, filtered and concentrated under reduced pressure to afford tert-butyl N-[(2S)-1-(cyclopropylcarbamoyl)-1-hydroxy-3-[(3S)-2-oxopyrrolidin-3-yl]propan-2-yl]carbamate (680 mg, 94%) as a yellow solid. LCMS (ESI, m/z): 342 [M+H]$^+$.

To a stirred mixture of tert-butyl N-[(2S)-1-(cyclopropylcarbamoyl)-1-hydroxy-3-[(3S)-2-oxopyrrolidin-3-yl]propan-2-yl]carbamate (400 mg, 1.17 mmol, 1.0 eq.) in dichloromethane (6 mL) was added trifluoroacetic acid (2 mL) dropwise at rt. The mixture was stirred for 1 h at rt and then concentrated under reduced pressure to afford (3S)-3-amino-N-cyclopropyl-2-hydroxy-4-[(3S)-2-oxopyrrolidin-3-yl]butanamide (290 mg, crude) as a brown solid. LC-MS (ESI, m/z): 242 [M+H]$^+$.

tert-butyl (1S,3aR,4S,7R,7aS)-1-(((2S)-4-(cyclopropylamino)-3-hydroxy-4-oxo-1-((S)-2-oxopyrrolidin-3-yl)butan-2-yl)carbamoyl)-1,3,3a,4,7,7a-hexahydro-2H-4,7-methanoisoindole-2-carboxylate

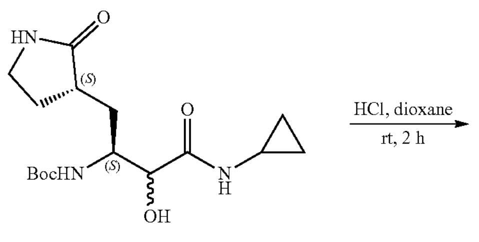

-continued

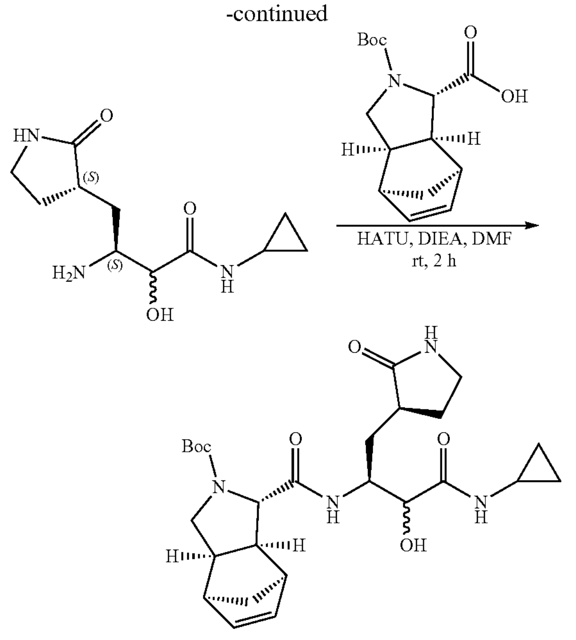

A solution of tert-butyl ((2S)-4-(cyclopropylamino)-3-hydroxy-4-oxo-1-((S)-2-oxopyrrolidin-3-yl)butan-2-yl)carbamate (800 mg, 2.34 mmol, 1.0 eq.) in hydrochloric acid (14 mL, 4 M in dioxane) was stirred at rt for 2 h and then concentrated under reduced pressure to provide (3S)-3-amino-N-cyclopropyl-2-hydroxy-4-((S)-2-oxopyrrolidin-3-yl)butanamide (550 mg, crude) as an off-white solid. LC-MS (ESI, m/z): 242 [M+H]$^+$.

To a solution of (1S,3aR,4S,7R,7aS)-2-(tert-butoxycarbonyl)-2,3,3a,4,7,7a-hexahydro-1H-4,7-methanoisoindole-1-carboxylic acid (700 mg, 2.5 mmol, 1.1 eq.) in DMF (8 mL) were added N,N,N',N'-Tetramethyl-O-(7-azabenzotriazol-1-yl)uronium hexafluorophospate (1.13 g, 2.96 mmol, 1.3 eq.) and N,N-diisopropylethylamine (2.06 g, 16 mmol, 7.0 eq.). The mixture was stirred at 0° C. for 30 min and (3S)-3-amino-N-cyclopropyl-2-hydroxy-4-((S)-2-oxopyrrolidin-3-yl)butanamide (550 mg, 2.28 mmol, 1.0 eq.) was added. The mixture was stirred at rt for 2 h, and the reaction was quenched with water (10 mL). The mixture was extracted with EA (3×20 mL). The organic layers were combined, washed with brine (3×10 mL), dried over anhydrous sodium sulfate, filtered and concentrated under reduced pressure. The residue was chromatographed on a silica gel column with MeOH:DCM (1:12) to provide tert-butyl (1S,3aR,4S,7R,7aS)-1-(((2S)-4-(cyclopropylamino)-3-hydroxy-4-oxo-1-((S)-2-oxopyrrolidin-3-yl)butan-2-yl)carbamoyl)-1,3,3a,4,7,7a-hexahydro-2H-4,7-methanoisoindole-2-carboxylate (900 mg, 70%) as a brown yellow solid. LC-MS (ESI, m/z): 503 [M+H]$^+$.

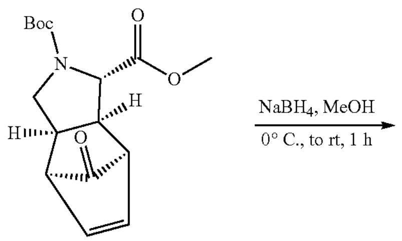

-continued

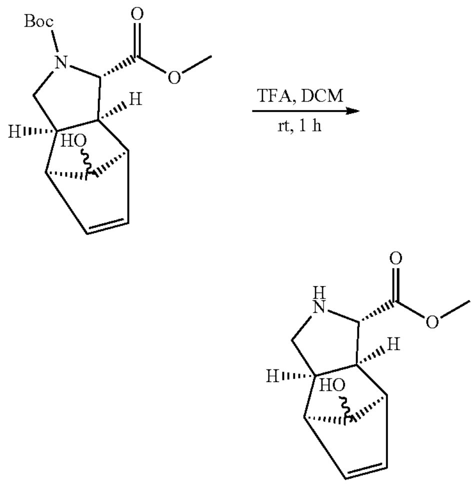

To a solution of 2-(tert-butyl) 1-methyl (1S,3aS,4S,7R,7aR)-8-oxo-1,3,3a,4,7,7a-hexahydro-2H-4,7-methanoisoindole-1,2-dicarboxylate (950 mg, 3.09 mmol, 1.0 eq.) in methanol (10 mL) was added sodium borohydride (114 mg, 3.09 mmol, 1.0 eq.) at 0° C. The mixture was stirred for 1 h at rt. The reaction was quenched with sat. ammonium chloride (aq.). The mixture was extracted with EA (3×80 mL). The organic layers were combined, washed with brine (2×50 mL), dried over anhydrous sodium sulfate, filtered and concentrated under reduced pressure to afford 2-(tert-butyl) 1-methyl (1S,3aS,4S,7R,7aR,8R)-8-hydroxy-1,3,3a,4,7,7a-hexahydro-2H-4,7-methanoisoindole-1,2-dicarboxylate (700 mg, crude) as a yellow oil. LC-MS (ESI, m/z): 210 [M-Boc+H]$^+$.

To a stirred mixture of 2-(tert-butyl) 1-methyl (1S,3aS,4S,7R,7aR)-8-hydroxy-1,3,3a,4,7,7a-hexahydro-2H-4,7-methanoisoindole-1,2-dicarboxylate (450 mg, 1.45 mmol, 1.0 eq.) in DCM (4.5 mL) was added trifluoroacetic acid (1.5 mL) at rt. The mixture was stirred for 1 h at rt and then concentrated under reduced pressure to afford methyl (1S,3aS,4S,7R,7aR,8R)-8-hydroxy-2,3,3a,4,7,7a-hexahydro-1H-4,7-methanoisoindole-1-carboxylate (305 mg, crude) as a yellow oil. LC-MS (ESI, m/z): 210 [M+H]$^+$.

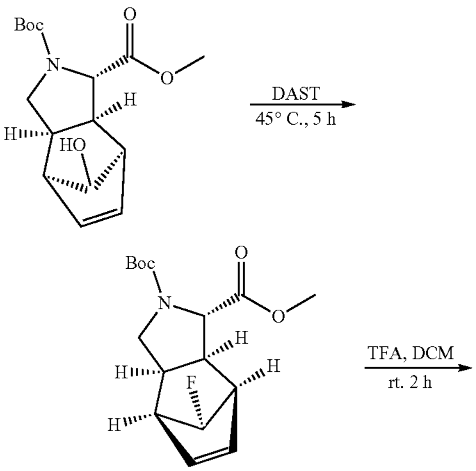

-continued

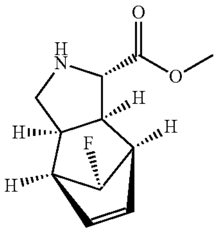

A mixture of 2-(tert-butyl) 1-methyl (1S,3aS,4S,7R,7aR,8R)-8-hydroxy-1,3,3a,4,7,7a-hexahydro-2H-4,7-methanoisoindole-1,2-dicarboxylate (1.0 g, 3.23 mmol, 1.0 eq.) in diethylaminosulfur trifluoride (20 mL) was stirred for 5 h at 45° C. The mixture was diluted with dichloromethane (100 mL). The reaction was quenched with sat. sodium bicarbonate (80 mL) at 0° C. The mixture was extracted with dichloromethane (3×80 mL). The organic layers were combined, washed with brine (2×50 mL), dried over anhydrous sodium sulfate, filtered and concentrated under reduced pressure. The crude product was purified by prep-HPLC (Column: XSelect CSH Prep C18 OBD Column, 19*150 mm, 5 m; Mobile Phase A: Water (0.05% TFA), Mobile Phase B: ACN; Flow rate: 25 mL/min; Gradient: 32% B to 52% B in 10 min, 52% B; Wave Length: 254 nm; RT1 (min): 8.78/9.3) to provide 2-(tert-butyl) 1-methyl (1S,3aS,4S,7R,7aR,8S)-8-fluoro-1,3,3a,4,7,7a-hexahydro-2H-4,7-methanoisoindole-1,2-dicarboxylate (350 mg, 35%) as a white oil. $^1$H NMR (400 MHz, DMSO-$d_6$) δ 6.05-6.24 (m, 2H), 4.25-4.57 (m, 1H), 3.81-4.03 (m, 1H), 3.56-3.76 (m, 3H), 3.34-3.48 (m, 1H), 3.10-3.26 (m, 1H), 2.83-3.09 (m, 4H), 1.19-1.51 (m, 9H). LC-MS (ESI, m/z): 256 [M−56+H]$^+$.

To a stirred mixture of 2-(tert-butyl) 1-methyl (1S,3aS,4S,7R,7aR,8*S)-8-fluoro-1,3,3a,4,7,7a-hexahydro-2H-4,7-methanoisoindole-1,2-dicarboxylate (350 mg, 1.12 mmol, 1.0 eq.) in dichloromethane (3 mL) was added trifluoroacetic acid (1 mL) at rt. The mixture was stirred for 2 h at rt. The mixture was concentrated under reduced pressure to provide methyl (1S,3aS,4S,7R,7aR,8*S)-8-fluoro-2,3,3a,4,7,7a-hexahydro-1H-4,7-methanoisoindole-1-carboxylate (240 mg, crude) as a yellow oil. LC-MS (ESI, m/z): 212 [M+H]$^+$.

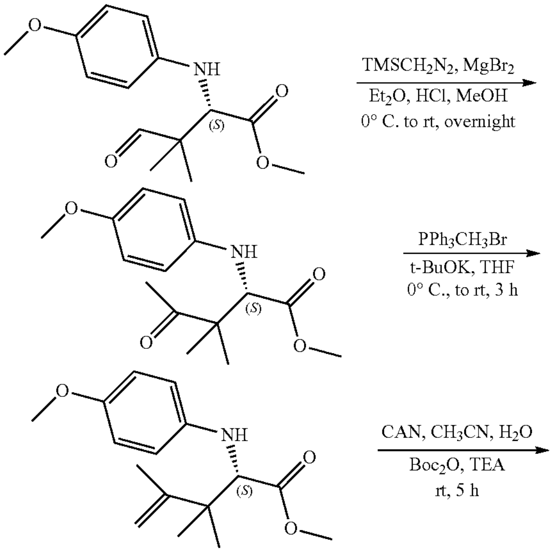

-continued

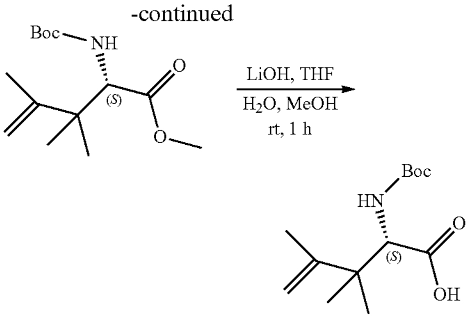

To a solution of methyl (S)-2-((4-methoxyphenyl)amino)-3,3-dimethyl-4-oxobutanoate (12.0 g, 45.2 mmol, 1.0 eq.) and magnesium bromide (29.2 g, 113 mmol, 2.5 eq.) in $Et_2O$ (200 mL) was added (trimethylsilyl)diazomethane (11.4 g, 99.5 mmol, 2.2 eq.) at 0° C. The mixture was stirred for 0.5 h at 0° C. and then stirred overnight at rt. MeOH (60 mL) and hydrochloric acid (40 mL, 2 M) were added at 0° C. The mixture was stirred for 1 h at rt. The mixture was extracted with EA (3×100 mL). The organic layers were combined, washed with brine (2×50 mL), dried over anhydrous sodium sulfate, filtered and concentrated under reduced pressure to afford the crude product. The crude product was chromatographed on a silica gel column with EA:PE (17%) to provide methyl (S)-2-((4-methoxyphenyl)amino)-3,3-dimethyl-4-oxopentanoate (3.2 g, 22%) as a yellow solid. $^1$H NMR (400 MHz, DMSO-$d_6$) δ 6.68-6.75 (m, 4H), 5.26-5.31 (m, 1H), 4.38-4.67 (m, 1H), 3.64 (s, 3H), 3.59 (s, 3H), 2.16 (s, 3H), 1.06-1.15 (m, 6H). LC-MS (ESI, m/z): 280 $[M+H]^+$.

To a stirred mixture of methyltriphenylphosphanium bromide (7.37 g, 20.6 mmol, 1.8 eq.) in THF (50 mL) was added potassium tert-butoxide (2.31 g, 20.6 mmol, 1.8 eq.) at 0° C. under nitrogen. After stirring for 1 h, methyl (S)-2-((4-methoxyphenyl)amino)-3,3-dimethyl-4-oxopentanoate (3.2 g, 11.456 mmol, 1.0 eq.) was added. The mixture was stirred for 3 h at rt. The reaction was quenched with water (50 mL). The mixture was extracted with EA (3×100 mL). The organic layers were combined, washed with brine (2×50 mL), dried over anhydrous sodium sulfate, filtered and concentrated under reduced pressure to afford the crude product. The crude product was chromatographed on a silica gel column with EA:PE (5%) to provide methyl (S)-2-((4-methoxyphenyl)amino)-3,3,4-trimethylpent-4-enoate (820 mg, 25%) as a yellow solid. $^1$H NMR (400 MHz, DMSO-$d_6$) δ 6.69-6.73 (m, 2H), 6.59-6.64 (m, 2H), 5.01-5.10 (m, 1H), 4.78-4.81 (m, 2H), 3.99-4.02 (m, 1H), 3.63 (s, 3H), 2.56 (s, 3H), 1.76 (s, 3H), 1.11-1.16 (m, 6H). LC-MS (ESI, m/z): 278 $[M+H]^+$.

To a stirred mixture of methyl (S)-2-((4-methoxyphenyl)amino)-3,3,4-trimethylpent-4-enoate (800 mg, 2.88 mmol, 1.0 eq.) in $CH_3CN$ (20 mL) and $H_2O$ (5 mL) was added ceric ammonium nitrate (7.94 g, 14.4 mmol, 5.0 eq.). The mixture was stirred for 1 h at rt. To the mixture was added THF (5 mL). The mixture was basified to pH=8 with triethylamine. Di-tert-butyl dicarbonate (3.78 g, 17.3 mmol, 6.0 eq.) was added. The mixture was stirred for 5 h at rt and then diluted with $H_2O$ (30 mL). The mixture was extracted with EA (3×50 mL). The organic layers were combined, washed with brine (2×20 mL), dried over anhydrous sodium sulfate, filtered and concentrated under reduced pressure to afford the crude product. The crude product was chromatographed on a silica gel column with EA:PE (9%-13%) to provide methyl (S)-2-((tert-butoxycarbonyl)amino)-3,3,4-trimethylpent-4-enoate (160 mg, 20%) as a yellow oil. $^1$H NMR (400 MHz, Chloroform-d) δ 5.01-5.11 (m, 1H), 4.77-4.86 (m, 2H), 4.37-4.39 (m, 1H), 3.67-3.71 (m, 3H), 1.82 (s, 3H), 1.45 (s, 9H), 1.10-1.12 (m, 6H). LC-MS (ESI, m/z): 272 $[M+H]^+$.

To a mixture of methyl (S)-2-((tert-butoxycarbonyl)amino)-3,3,4-trimethylpent-4-enoate (160 mg, 0.590 mmol, 1.0 eq.) in THF (2 mL), $H_2O$ (1 mL) and MeOH (0.5 mL) was added lithium hydroxide (70.6 mg, 2.95 mmol, 5.0 eq.). The mixture was stirred for 1 h at rt and then concentrated under reduced pressure to remove MeOH and THF. The mixture was acidified to pH=5 with hydrochloric acid (1 M). The mixture was extracted with EA (3×50 mL). The organic layers were combined, dried over anhydrous sodium sulfate, filtered and concentrated under reduced pressure to provide the desired product (S)-2-((tert-butoxycarbonyl)amino)-3,3,4-trimethylpent-4-enoic acid (130 mg, crude) as an off-white solid. LC-MS (ESI, m/z): 258 $[M+H]^+$.

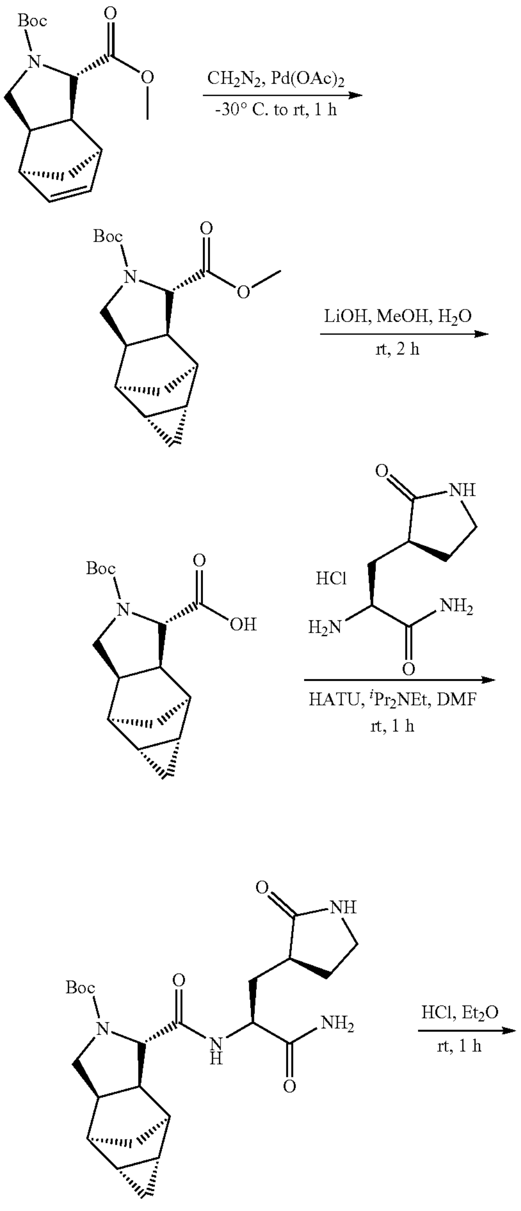

-continued

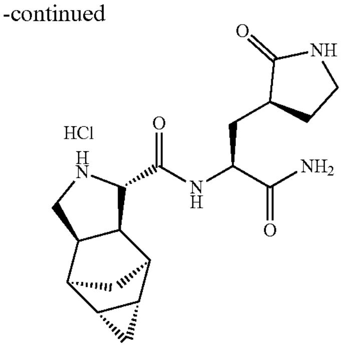

To a solution of 4-tert-butyl 3-methyl (1R,2S,3S,6R,7S)-4-azatricyclo[5.2.1.0^{2,6}]dec-8-ene-3,4-dicarboxylate (300 mg, 1.02 mmol, 1.0 eq.) in $Et_2O$ (2.5 mL) at −30° C. was added diazomethane (30 mL, 30.0 eq.) and palladium (II) acetate (45.9 mg, 0.205 mmol, 0.2 eq.). The mixture was stirred for 1 h at rt and then filtered. The filter cake was washed with diethyl ether (3×50 mL). The filtrate was concentrated under reduced pressure to afford the crude product. The crude product was chromatographed on a silica gel column with ethyl acetate (EA):petroleum ether (PE) (1:8) to provide 4-tert-butyl 3-methyl (1R,2S,3S,6R,7S,8S,10R)-4-azatetracyclo[5.3.1.0^{2,6}0.0^{8,10}]undecane-3,4-dicarboxylate (200 mg, 58%) as a light yellow solid. $^1H$ NMR (400 MHz, DMSO-$d_6$) δ 4.25-4.50 (m, 1H), 3.53-3.72 (m, 4H), 3.22-3.30 (m, 1H), 2.52-2.64 (m, 2H), 2.22-2.42 (m, 2H), 1.21-1.47 (m, 9H), 1.03-1.16 (m, 1H), 0.70-0.95 (m, 3H), 0.39-0.54 (m, 1H), −0.09-0.05 (m, 1H). LC-MS (ESI, m/z): 208 $[M+H-Boc]^+$.

To a stirred mixture of 4-tert-butyl 3-methyl (1R,2S,3S,6R,7S,8S,10R)-4-azatetracyclo[5.3.1.0^{2,6}0.0^{8,10}] undecane-3,4-dicarboxylate (245 mg, 0.797 mmol, 1.0 eq.) in MeOH (3 mL) and $H_2O$ (3 mL) were added lithium hydroxide (95.4 mg, 3.98 mmol, 5.0 eq.). The mixture was stirred for 2 h at rt. The mixture was acidified to pH 4 with hydrochloric acid (1M) and then extracted with ethyl acetate (3×10 mL). The mixture was concentrated under reduced pressure to afford (1R,2S,3S,6R,7S,8S,10R)-4-(tert-butoxycarbonyl)-4-azatetracyclo[5.3.1.0^{2,6}0.0^{8,10}]undecane-3-carboxylic acid (200 mg, 85%) as a light yellow solid. $^1H$ NMR (400 MHz, DMSO-$d_6$) δ 12.57 (s, 1H), 4.17-4.39 (m, 1H), 3.47-3.76 (m, 1H), 3.12-3.31 (m, 1H), 2.51-2.59 (m, 2H), 2.20-2.44 (m, 2H), 1.27-1.49 (m, 9H), 1.05-1.22 (m, 1H), 0.69-0.93 (m, 3H), 0.40-0.51 (m, 1H), −0.06-0.00 (m, 1H). LC-MS (ESI, m/z): 238 $[M+H-56]^+$.

To a stirred mixture of (1R,2S,3S,6R,7S,8S,10R)-4-(tert-butoxycarbonyl)-4-azatetracyclo[5.3.1.0^{2,6}0.0^{8,10}] undecane-3-carboxylic acid (200 mg, 0.682 mmol, 1.0 eq.) in DMF (2 mL) was added o-(7-Azabenzotriazol-1-yl)-N,N,N',N'-tetramethyluronium hexafluorophosphate (311 mg, 0.818 mmol, 1.2 eq.) and N-ethyl-N-isopropylpropan-2-amine (528 mg, 4.09 mmol, 6.0 eq.) at rt. The mixture was stirred for 10 min at 0° C. and then (2S)-2-amino-3-[(3S)-2-oxopyrrolidin-3-yl]propanamide hydrochloride (141 mg, 0.682 mmol, 1.0 eq.) was added. The mixture was stirred for 1 h at rt. The mixture was purified by C18 column with $CH_3CN$:Water (0.05% FA). The compound fraction was concentrated under reduced pressure to provide tert-butyl (1R,2S,3S,6R,7S,8S,10R)-3-{[(1S)-1-carbamoyl-2-[(3S)-2-oxopyrrolidin-3-yl]ethyl]carbamoyl}-4-azatetracyclo [5.3.1.0^{2,6}.0^{8,10}]undecane-4-carboxylate (200 mg, 55%) as a white solid. LC-MS (ESI, m/z): 447 $[M+H]^+$.

To a stirred mixture of tert-butyl (1R,2S,3S,6R,7S,8S,10R)-3-{[(1S)-1-carbamoyl-2-[(3S)-2-oxopyrrolidin-3-yl] ethyl]carbamoyl}-4-azatetracyclo[5.3.1.0^{2,6}0.0^{8,10}] undecane-4-carboxylate (200 mg, 0.448 mmol, 1.0 eq.) in DCM (1 mL) was added hydrochloric acid (3 mL, 2M in $Et_2O$) at rt. The mixture was stirred for 1 h at rt and then concentrated under reduced pressure to afford (2S)-2-[(1R,2S,3S,6R,7S,8S,10R)-4-azatetracyclo[5.3.1.0^{2,6}0.0^{8,10}]undecan-3-ylformamido]-3-[(3S)-2-oxopyrrolidin-3-yl]propanamide hydrochloride (200 mg, crude) as a white solid. LC-MS (ESI, m/z): 347 $[M+H]^+$.

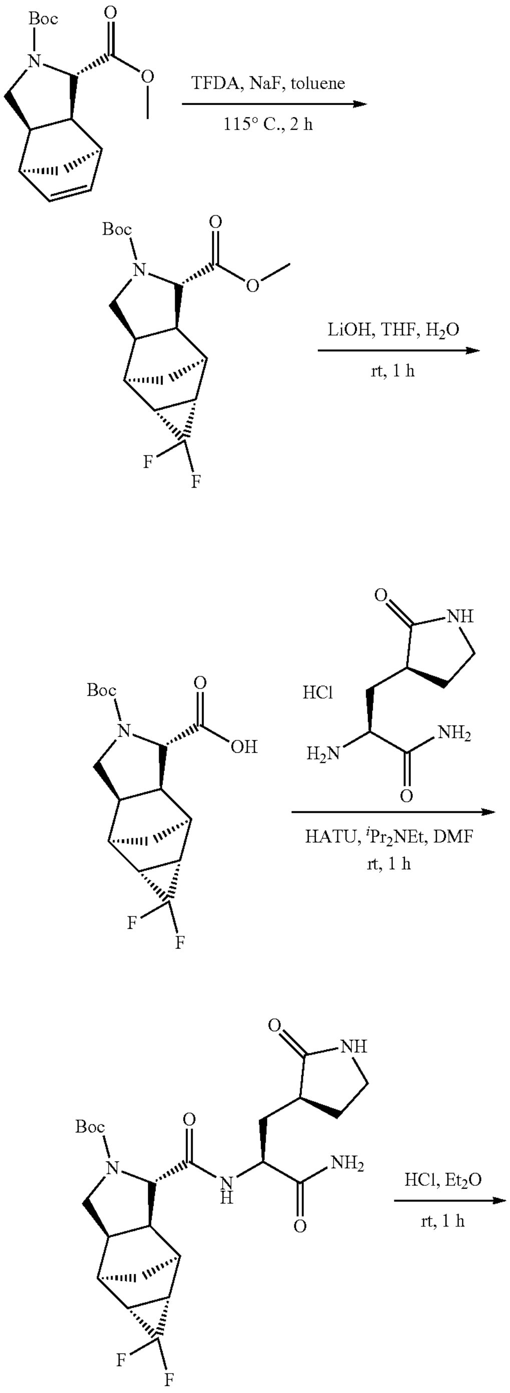

-continued

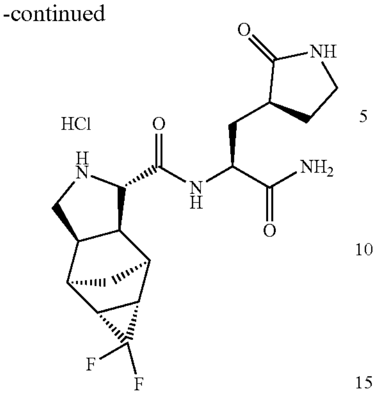

To a stirred mixture of 4-tert-butyl 3-methyl (1R,2S,3S,6R,7S)-4-azatricyclo[5.2.1.0^{2,6}]dec-8-ene-3,4-dicarboxylate (1 g, 3.40 mmol, 1.0 eq.) in toluene (4 mL) was added sodium fluoride (50.0 mg, 1.19 mmol, 0.35 eq.). Trimethylsilyl 2,2-difluoro-2-sulfoacetate (4.27 g, 17.0 mmol, 5.0 eq.) was added slowly for 2 h at 115° C. under nitrogen. The reaction was quenched with water (30 mL). The mixture was extracted with ethyl acetate (3×30 mL)> The organic layers were combined, washed with brine (2×30 mL), dried over anhydrous sodium sulfate, filtered and concentrated under reduced pressure to afford the crude product. The crude product was purified by C18 column with $CH_3CN$:Water (0.05% FA). The desired fraction was concentrated under reduced pressure to provide 4-tert-butyl 3-methyl (1S,2S,3S,6R,7R,8R,10S)-9,9-difluoro-4-azatetracyclo[5.3.1.0^{2,6}].0^{8,10}]undecane-3,4-dicarboxylate (180 mg, 13%) as a light yellow oil. LC-MS (ESI, m/z): 288 $[M-56+H]^+$.

To a stirred mixture of 4-tert-butyl 3-methyl (1S,2S,3S,6R,7R,8R,10S)-9,9-difluoro-4-azatetracyclo[5.3.1.0^{2,6}0.0^{8,10}]undecane-3,4-dicarboxylate (180 mg, 0.524 mmol, 1.0 eq.) in THF (3 mL) and $H_2O$ (1 mL) was added lithium hydroxide (37.6 mg, 1.57 mmol, 3.0 eq.) at rt. The mixture was stirred for 1 h at rt. The mixture was acidified to pH=4 with hydrochloric acid (2M) and then extracted with ethyl acetate (3×10 mL). The combined organic layers were dried over anhydrous sodium sulfate. After filtration, the filtrate was concentrated under reduced pressure to afford (1S,2S,3S,6R,7R,8R,10S)-4-(tert-butoxycarbonyl)-9,9-difluoro-4-azatetracyclo[5.3.1.0^{2,6}.0^{8,10}]undecane-3-carboxylic acid (150 mg, crude) as a light yellow oil. LC-MS (ESI, m/z): 328 $[M-H]^-$.

To a stirred mixture of (1S,2S,3S,6R,7R,8R,10S)-4-(tert-butoxycarbonyl)-9,9-difluoro-4-azatetracyclo[5.3.1.0^{2,6}0.0^{8,10}]undecane-3-carboxylic acid (150 mg, 0.455 mmol, 1.0 eq.) and o-(7-Azabenzotriazol-1-yl)-N,N,N',N'-tetramethyluronium hexafluorophosphate (207 mg, 0.546 mmol, 1.2 eq.) in DMF (3 mL) was added N-ethyl-N-isopropylpropan-2-amine (353 mg, 2.73 mmol, 6.0 eq.). The mixture was stirred for 10 min at 0° C. (2S)-2-amino-3-[(3S)-2-oxopyrrolidin-3-yl]propanamide hydrochloride (104 mg, 0.501 mmol, 1.1 eq.) was added. The mixture was stirred for 1 h at rt. The mixture was purified by C18 column with $CH_3CN$:Water (0.05% FA). The desired fraction was concentrated under reduced pressure to provide tert-butyl (1S,2S,3S,6R,7R,8R,10S)-3-{[(1S)-1-carbamoyl-2-[(3S)-2-oxopyrrolidin-3-yl]ethyl]carbamoyl}-9,9-difluoro-4-azatetracyclo[5.3.1.0^{2,6}0.0^8,101]undecane-4-carboxylate (160 mg, 65%) as a white solid. LC-MS (ESI, m/z): 483 $[M+H]^+$.

To a stirred mixture of tert-butyl (1S,2S,3S,6R,7R,8R,10S)-3-{[(1S)-1-carbamoyl-2-[(3S)-2-oxopyrrolidin-3-yl]ethyl]carbamoyl}-9,9-difluoro-4-azatetracyclo[5.3.1.0^{2,6}0.0^{8,10}]undecane-4-carboxylate (160 mg, 0.332 mmol, 1.0 eq.) in DCM (1 mL) were added hydrogen chloride (5 mL, 2M in $Et_2O$). The mixture was stirred for 1 h at rt and then concentrated under reduced pressure to afford (2S)-2-{[(1S,2S,3S,6R,7R,8R,10S)-9,9-difluoro-4-azatetracyclo[5.3.1.0^{2,6}0.0^{8,10}]undecan-3-yl]formamido}-3-[(3S)-2-oxopyrrolidin-3-yl]propanamide hydrochloride (140 mg, crude) as a white solid. LC-MS (ESI, m/z): 383 $[M+H]^+$.

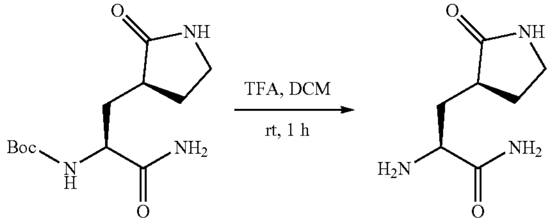

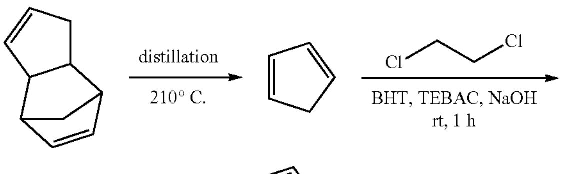

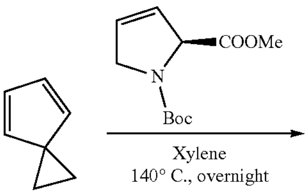

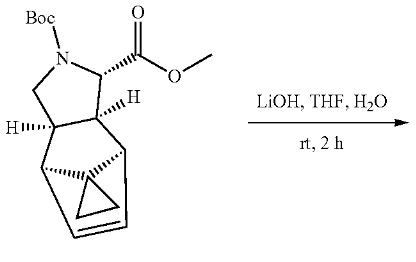

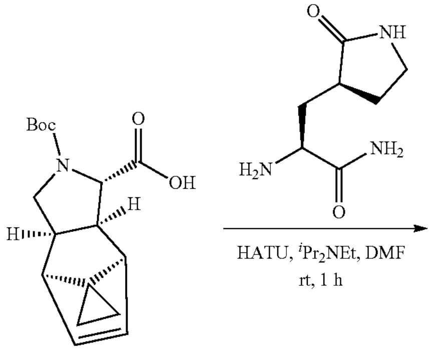

-continued

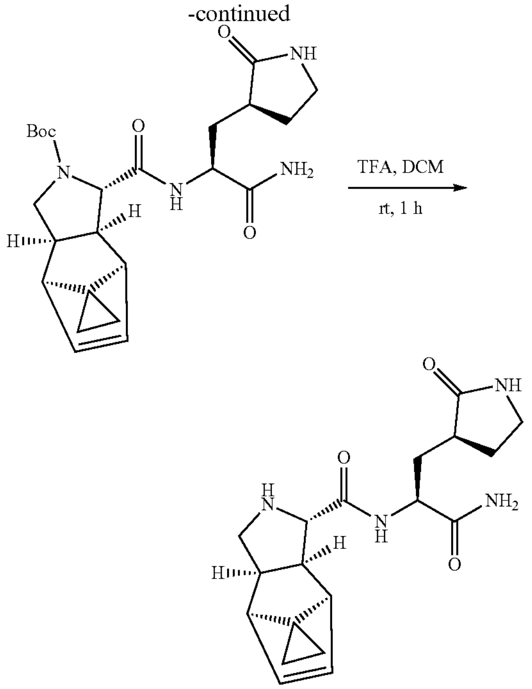

The tricyclo[5.2.1.0^{2,6}]deca-3,8-diene (110 g, 832 mmol, 1.0 eq.) was stirred at 210° C. The cyclopentadiene was distillation at 37° C.-43° C. The fraction was collected to provide the product (46 g, 83%) as a colorless liquid. $^1$H NMR (400 MHz, DMSO-$d_6$) δ 6.60-6.69 (m, 2H), 4.43-6.56 (m, 2H), 3.04-3.05 (m, 2H).

To a stirred mixture of cyclopentadiene (42.0 g, 635 mmol, 1.0 eq.) and ional (0.130 g, 0.572 mmol, 0.0009 eq.) in ethylene dichloride (62.8 g, 635 mmol, 1.0 eq.). After stirred for 20 min, sodium hydroxide (139 g, 3462 mmol, 5.45 eq.) and benzyltriethylazanium chloride (1.30 g, 5.72 mmol, 0.009 eq.) were added. The mixture was stirred for 1 h at rt. The reaction was quenched with water (50 mL). The mixture was extracted with EtOAc (3×50 mL). The organic layers were combined, washed with brine (2×50 mL), dried over anhydrous sodium sulfate, filtered and concentrated under reduced pressure to afford the crude product. The crude product was stirred at 130° C. Spiro[2.4]hepta-4,6-diene was distillation at 60° C.~65° C. under 0.7 MPa. The desired fraction was collected to provide spiro[2.4]hepta-4,6-diene (10 g, 14%) as a colorless liquid. $^1$H NMR (400 MHz, DMSO-$d_6$) δ 6.47-6.69 (m, 2H), 6.14-6.24 (m, 2H), 1.71-1.72 (m, 4H).

To a stirred mixture of 1-tert-butyl 2-methyl (2R)-2,5-dihydropyrrole-1,2-dicarboxylate (6.00 g, 26.4 mmol, 1.0 eq.) in xylene (6 mL) was added spiro[2.4]hepta-4,6-diene (4.87 g, 52.8 mmol, 1.0 eq.). The mixture was stirred for 2 d at 140° C. and then concentrated under reduced pressure. The crude product was chromatographed on a silica gel column with EA:PE (30:70) to provide the crude product. The crude product was purified by C18 column with $CH_3CN$:Water (0.05% TFA). The desired fraction was concentrated under reduced pressure to provide 4'-tert-butyl 3'-methyl (1'R,2'S,3'S,6'R,7'S)-4'-azaspiro[cyclopropane-1,10'-tricyclo[5.2.1.0^{2,6}]decan]-8'-ene-3',4'-dicarboxylate (1.98 g, 23%) as a yellow oil. $^1$H NMR (400 MHz, DMSO-$d_6$) δ 6.03-6.36 (m, 2H), 3.70-3.89 (m, 1H), 3.55-3.69 (m, 3H), 3.22-3.37 (m, 1H), 2.70-3.10 (m, 3H), 2.33-2.42 (m, 1H), 2.22-2.29 (m, 1H), 1.08-1.53 (m, 9H), 0.22-0.48 (m, 4H). LC-MS (ESI, m/z): 220 $[M+H-Boc]^+$.

To a stirred mixture of 4'-tert-butyl 3'-methyl (1'R,2'S,3'S,6'R,7'S)-4'-azaspiro[cyclopropane-1,10'-tricyclo[5.2.1.0^{2,6}]decan]-8'-ene-3',4'-dicarboxylate (1.00 g, 3.13 mmol, 1.0 eq.) in THF (10 mL) was added lithium hydroxide (300 mg, 12.5 mmol, 4.0 eq., in water 10 mL). The mixture was stirred for 2 h at rt. The pH was adjusted to 6 with hydrochloric acid (2 M). The mixture was extracted with EtOAc (3×30 mL). The organic layers were combined, washed with brine (2×30 mL), dried over anhydrous sodium sulfate, filtered and concentrated under reduced pressure to provide (1'R,2'S,3'S,6'R,7'S)-4'-(tert-butoxycarbonyl)-4'-azaspiro [cyclopropane-1,10'-tricyclo [5.2.1.0^{2,6}]decan]-8'-ene-3'-carboxylic acid (917 mg, 89%) as a light yellow oil. LC-MS (ESI, m/z): 250 $[M+H-56]^+$.

To a stirred mixture of (2S)-2-amino-3-[(3S)-2-oxopyrrolidin-3-yl]propanamide (500 mg, 2.92 mmol, 1.0 eq.) and o-(7-azabenzotriazol-1-yl)-N,N,N',N'-tetramethyluronium hexafluorophosphate (1.33 g, 3.51 mmol, 1.2 eq.) in DMF (10 mL) was added N-ethyl-N-isopropylpropan-2-amine (3.02 g, 23.4 mmol, 8.0 eq.) at 0° C. After stirred for 20 min at 0° C., (2S)-2-amino-3-[(3S)-2-oxopyrrolidin-3-yl]propanamide (500 mg, 2.92 mmol, 1.0 eq.) was added. The mixture was stirred for 1 h at rt. The reaction was quenched with water (30 mL). The mixture was extracted with EtOAc (3×30 mL). The organic layers were combined, washed with brine (2×30 mL), dried over anhydrous sodium sulfate, filtered and concentrated under reduced pressure to afford the crude product. The crude product was chromatographed on a silica gel column with MeOH:DCM (1:11) to provide tert-butyl (1'R,2'S,3'S,6'R,7'S)-3'-{[(1S)-1-carbamoyl-2-[(3S)-2-oxopyrrolidin-3-yl]ethyl]carbamoyl}-4'-azaspiro [cyclopropane-1,10'-tricyclo[5.2.1.0^{2,6}]decan]-8'-ene-4'-carboxylate (758 mg, 55%) as a yellow solid. LC-MS (ESI, m/z): 359 $[M-H-Boc]^+$.

To a stirred mixture of tert-butyl (1'R,2'S,3'S,6'R,7'S)-3'-{[(1S)-1-carbamoyl-2-[(3S)-2-oxopyrrolidin-3-yl]ethyl]carbamoyl}-4'-azaspiro[cyclopropane-1,10'-tricyclo [5.2.1.0^{2,6}]decan]-8'-ene-4'-carboxylate (750 mg, 1.63 mmol, 1.0 eq.) in DCM (10 mL) was added trifluoroacetic acid (3 mL). The mixture was stirred for 1 h at rt and then concentrated under reduced pressure to afford (2S)-2-[(1'R,2'S,3'S,6'R,7'S)-4'-azaspiro[cyclopropane-1,10'-tricyclo [5.2.1.0^{2,6}]decan]-8'-en-3'-ylformamido]-3-[(3S)-2-oxopyrrolidin-3-yl]propanamide (586 mg, crude) as a brown oil. LC-MS (ESI, m/z): 359 $[M+H]^+$.

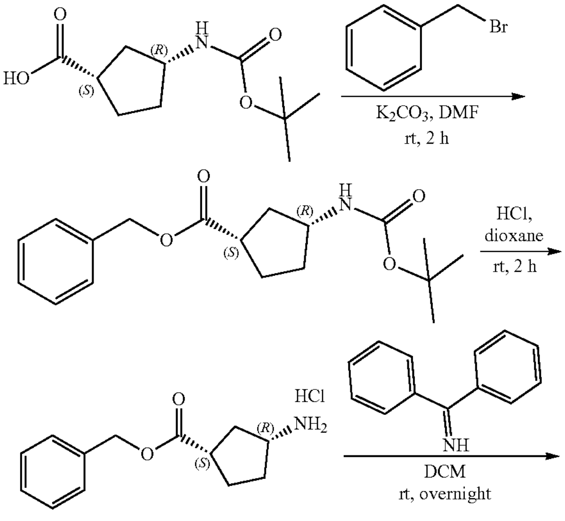

-continued

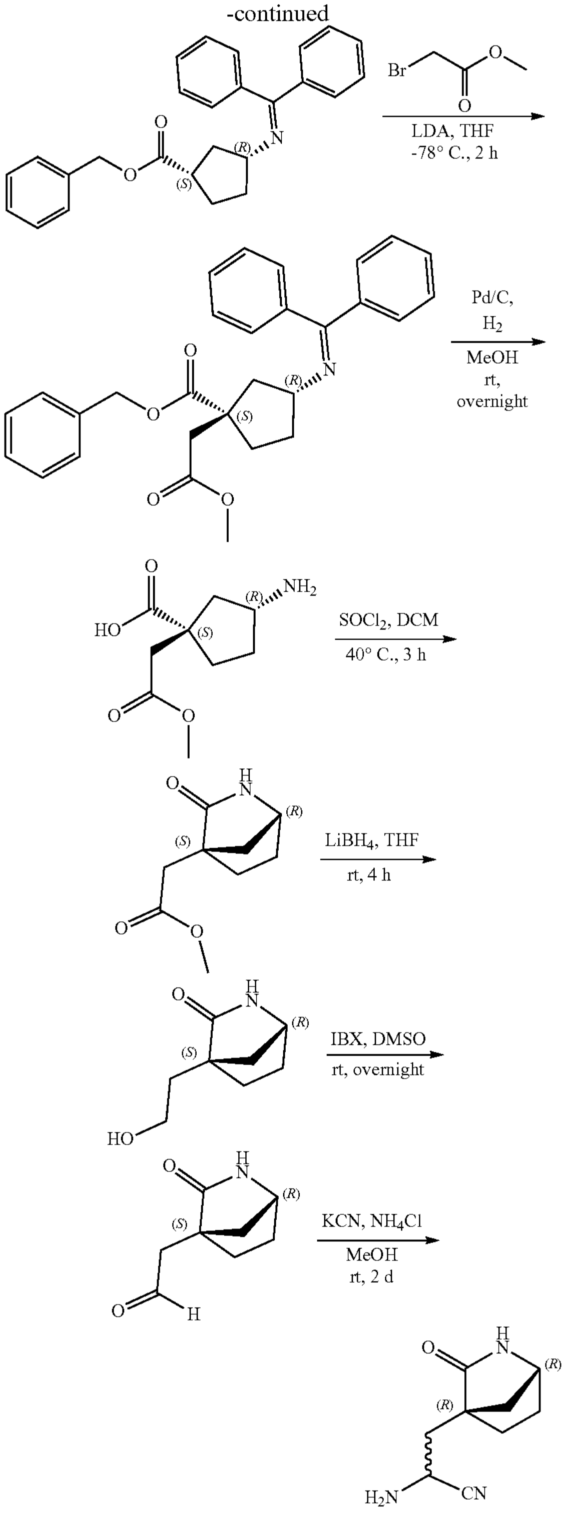

To a mixture of (1S,3R)-3-((tert-butoxycarbonyl)amino) cyclopentane-1-carboxylic acid (35.0 g, 109 mmol, 1.0 eq.) and potassium carbonate (31.7 g, 229 mmol, 1.5 eq.) in DMF (250 mL) was added benzyl bromide (31.3 g, 183 mmol, 1.2 eq.) at rt. The mixture was stirred 2 h at rt. The mixture was filtered through a celite pad and washed with ethyl acetate (3×100 mL). The filtrate was quenched with water (200 mL). The mixture was extracted with ethyl acetate (3×500 mL). The organic layers were combined, washed with brine (2×300 mL), dried over anhydrous sodium sulfate, filtered and concentrated under reduced pressure to afford the crude product. The crude product was chromatographed on a silica gel column with EA:PE (25%-30%) to provide benzyl (1S,3R)-3-((tert-butoxycarbonyl) amino)cyclopentane-1-carboxylate (40.0 g, 85%) as a white solid. LC-MS (ESI, m/z): 320 $[M+H]^+$.

To a mixture of benzyl (1S,3R)-3-((tert-butoxycarbonyl) amino)cyclopentane-1-carboxylate (40.0 g, 125 mmol, 1.0 eq.) in 1,4-dioxane (200 mL) was added hydrogen chloride (400 mL, 4 M in 1,4-dioxane) at rt. The mixture was stirred 2 h at rt and then concentrated under reduced pressure to provide benzyl (1S,3R)-3-aminocyclopentane-1-carboxylate hydrochloride (25.1 g, crude) as a white solid. $^1H$ NMR (300 MHz, DMSO-$d_6$) δ 8.26 (br, 3H), 7.31-7.42 (m, 5H), 5.12 (s, 2H), 3.42-3.53 (m, 1H), 2.80-2.95 (m, 1H), 2.23-2.33 (m, 1H), 1.60-1.99 (m, 5H). LC-MS (ESI, m/z): 220 $[M+H]^+$.

To a mixture of benzyl (1S,3R)-3-aminocyclopentane-1-carboxylate hydrochloride (25.1 g, 97.8 mmol, 1.0 eq.) in DCM (400 mL) was added diphenylmethanimine (19.5 g, 108 mmol, 1.1 eq.). The mixture was stirred for overnight at rt. The mixture was filtered through a celite pad and washed with DCM (3×100 mL). The mixture was concentrated under reduced pressure to afford then crude product. The crude product was chromatographed on a silica gel column with EA:PE (11%-13%) to provide benzyl (1S,3R)-3-((diphenylmethylene)amino)cyclopentane-1-carboxylate (33.0 g, crude) as a yellow oil. LC-MS (ESI, m/z): 384 $[M+H]^+$.

To a mixture of benzyl (1S,3R)-3-((diphenylmethylene) amino)cyclopentane-1-carboxylate (33.0 g, 86.2 mmol, 1.0 eq.) in THF (400 mL) was added dropwise lithium diisopropylamide (56.1 mL, 112 mmol, 1.3 eq., 2 M in THF) at −78° C. under nitrogen. After stirred for 1 h at −78° C., methyl 2-bromoacetate (26.4 g, 172 mmol, 2.5 eq.) was added. The mixture was stirred for 1 h at −78° C. The mixture was warmed to 0° C. and stirred for 2 h at 0° C. under nitrogen. The reaction was quenched with water (200 mL). The mixture was extracted with ethyl acetate (3×300 mL). The organic layers were combined, washed with brine (2×200 mL), dried over anhydrous sodium sulfate, filtered and concentrated under reduced pressure to afford the crude product. The crude product was chromatographed on a silica gel column with EA:PE (12%-15%) to provide benzyl (1S,3R)-3-((diphenylmethylene)amino)-1-(2-methoxy-2-oxoethyl)cyclopentane-1-carboxylate (10.7 g, crude) as a yellow oil. LC-MS (ESI, m/z): 456 $[M+H]^+$.

To a mixture of benzyl (1S,3R)-3-((diphenylmethylene) amino)-1-(2-methoxy-2-oxoethyl)cyclopentane-1-carboxylate (10.7 g, 23.5 mmol, 1.0 eq.) in MeOH (150 mL) was added 10% palladium on activated carbon (3.5 g). The mixture was stirred overnight at rt under hydrogen and then filtered. The filter cake was washed with MeOH (3×150 mL). The filtrate was concentrated under reduced pressure to afford (1S,3R)-3-amino-1-(2-methoxy-2-oxoethyl)cyclopentane-1-carboxylic acid (4.5 g, crude) as a yellow solid. LC-MS (ESI, m/z):202 $[M+H]^+$.

To a mixture of (1S,3R)-3-amino-1-(2-methoxy-2-oxoethyl)cyclopentane-1-carboxylic acid (4.5 g, 22.4 mmol, 1.0 eq.) in DCM (50 mL) was added thionyl chloride (4.26 g, 35.8 mmol, 1.6 eq.). The mixture was stirred 3 h at 40° C. The reaction was quenched with water (20 mL). The mixture was extracted with DCM (3×100 mL). The organic layers were combined, washed with brine (2×50 mL), dried over anhydrous sodium sulfate, filtered and concentrated under reduced pressure to afford the crude product. The crude product was chromatographed on a silica gel column with EA:PE (70%-85%) to provide methyl 2-((1R,4S)-3-oxo-2-azabicyclo[2.2.1]heptan-4-yl)acetate (400 mg, 9%) as a yellow oil. $^1$H NMR (400 MHz, $CDCl_3$) δ 5.99 (br, 1H), 3.89-3.90 (m, 1H), 3.71 (s, 3H), 2.86-2.91 (m, 1H), 2.68-2.72 (m, 1H), 2.05-2.09 (m, 1H), 1.92-1.99 (m, 1H), 1.82-1.88 (m, 1H), 1.65-1.73 (m, 1H), 1.60-1.63 (m, 1H), 1.51-1.59 (m, 1H). LC-MS (ESI, m/z): 184 $[M+H]^+$.

To a mixture of methyl 2-((1R,4S)-3-oxo-2-azabicyclo[2.2.1]heptan-4-yl)acetate (400 mg, 2.18 mmol, 1.0 eq.) in THF (5 mL) was added lithium borohydride (4.4 mL, 8.73 mmol, 4.0 eq., 2 M in THF) at 0° C. The mixture was stirred for 4 h at rt. The reaction was quenched with water (10 mL). The mixture was extracted with ethyl acetate (6×50 mL). The organic layers were combined, washed with brine (2×20 mL), dried over anhydrous sodium sulfate, filtered and concentrated under reduced pressure to afford the crude product. The crude product was chromatographed on a silica gel column with MeOH:DCM (2%-4%) to provide (1R,4S)-4-(2-hydroxyethyl)-2-azabicyclo[2.2.1]heptan-3-one (240 mg, 70%) as a light yellow oil. $^1$H NMR (400 MHz, $CDCl_3$) δ 6.13 (br, 1H), 3.92 (s, 1H), 3.75-3.86 (m, 2H), 3.11 (br, 1H), 2.06-2.14 (m, 1H), 1.92-2.03 (m, 3H), 1.65-1.77 (m, 3H), 1.41-1.44 (m, 1H). LC-MS (ESI, m/z): 156 $[M+H]^+$.

To a mixture of (1R,4S)-4-(2-hydroxyethyl)-2-azabicyclo[2.2.1]heptan-3-one (120 mg, 0.773 mmol, 1.0 eq.) in DMSO (2 mL) was added 2-iodoxybenzoic acid (650 mg, 2.31 mmol, 3.0 eq.). The mixture was stirred for overnight at rt. The reaction was quenched with saturated aqueous sodium bicarbonate (10 mL). The mixture was extracted with ethyl acetate (5×30 mL). The organic layers were combined, washed with brine (2×20 mL), saturated aqueous sodium bicarbonate (2×20 mL), dried over anhydrous sodium sulfate, filtered and concentrated under reduced pressure to afford 2-((1R,4S)-3-oxo-2-azabicyclo[2.2.1]heptan-4-yl)acetaldehyde (80.0 mg, crude) as a yellow oil. LC-MS (ESI, m/z): 154 $[M+H]^+$.

To a solution of 2-((1R,4S)-3-oxo-2-azabicyclo[2.2.1]heptan-4-yl)acetaldehyde (80.0 mg, 0.522 mmol, 1.0 eq.) in $CH_3OH$ (2 mL) was added ammonium chloride (83.8 mg, 1.57 mmol, 3.0 eq.). After stirred 2 h at rt, zyankali (44.1 mg, 0.679 mmol, 1.3 eq.) was added. The mixture was stirred for 2 d at rt. The mixture was filtered through a celite pad and washed with $CH_3OH$ (3×20 mL) and DCM (3×20 mL). The filtrate was concentrated under reduced pressure to afford 2-amino-3-((1R,4R)-3-oxo-2-azabicyclo[2.2.1]heptan-4-yl)propanenitrile (80.0 mg, crude) as a yellow oil. LC-MS (ESI, m/z): 180 $[M+H]^+$.

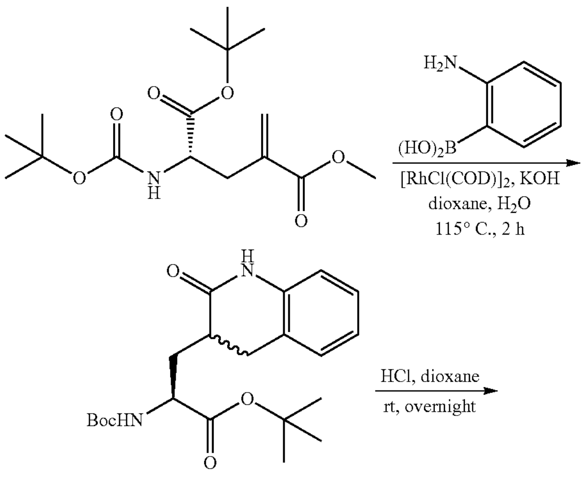

-continued

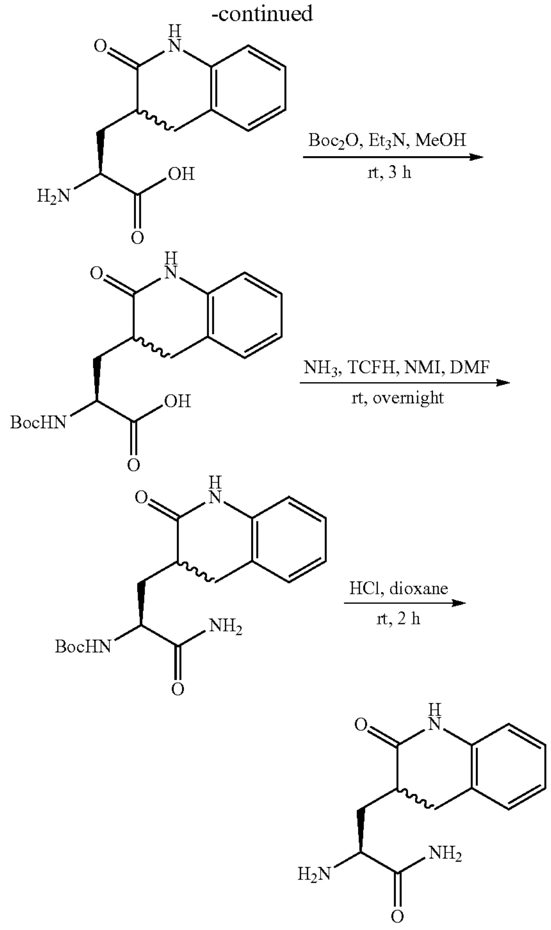

To a solution of 1-(tert-butyl) 5-methyl (S)-2-((tert-butoxycarbonyl)amino)-4-methylenepentanedioate (2 g, 6.07 mmol, 1.0 eq.) in dioxane (30 mL) was added 2-aminophenylboronic acid (1.66 g, 12.1 mmol, 2.0 eq.), Chloro(1,5-cyclooctadiene)rhodium(I) dimer (89.8 mg, 0.18 mmol, 0.03 eq.), potassium hydroxide solution (0.6 mL, 1.52 mmol, 0.25 eq.), was stirred at 115° C. for 2 h under $N_2$. The reaction was quenched with water (20 mL). The mixture was extracted with EA (3×30 mL). The organic layers were combined, washed with brine (50 mL), dried over anhydrous sodium sulfate, filtered and concentrated under reduced pressure. The residue was chromatographed on a silica gel column with EA:PE (1:4) to provide tert-butyl (2S)-2-((tert-butoxycarbonyl)amino)-3-(2-oxo-1,2,3,4-tetrahydroquinolin-3-yl)propanoate (1.5 g, 57%) as a white solid. $^1$H NMR (300 MHz, DMSO-$d_6$) δ 10.13 (s, 1H), 7.01-7.24 (m, 3H), 6.82-6.92 (m, 2H), 3.86-4.12 (m, 1H), 2.86-2.95 (m, 1H), 2.59-2.71 (m, 1H), 2.38-2.49 (m, 1H), 2.07-2.18 (m, 1H), 1.54-1.69 (m, 1H), 1.35-1.44 (m, 18H). LC-MS (ESI, m/z): 391 $[M+H]^+$.

To a solution of tert-butyl (2S)-2-((tert-butoxycarbonyl)amino)-3-(2-oxo-1,2,3,4-tetrahydroquinolin-3-yl)propanoate (1.3 g, 3.33 mmol, 1.0 eq.) in dioxane (15 mL) was added hydrochloric acid (15 mL, 9 mol/L in dioxane). The mixture was stirred at rt overnight and then concentrated under reduced pressure to provide (2S)-2-amino-3-(2-oxo-1,2,3,4-tetrahydroquinolin-3-yl)propanoic acid (700 mg, crude) as a white solid. LC-MS (ESI, m/z): 235 $[M+H]^+$.

To a solution of (2S)-2-amino-3-(2-oxo-1,2,3,4-tetrahydroquinolin-3-yl)propanoic acid (700 mg, 2.99 mmol, 1.0 eq.)

in MeOH (10 mL) was added di-tert-butyl dicarbonate (717 mg, 3.29 mmol, 1.1 eq.) and triethylamine (907 mg, 8.96 mmol, 3.0 eq.). The mixture was stirred at rt for 3 h and then concentrated under reduced pressure to provide (2S)-2-((tert-butoxycarbonyl)amino)-3-(2-oxo-1,2,3,4-tetrahydroquinolin-3-yl)propanoic acid (800 mg, crude) as an off-white solid. LC-MS (ESI, m/z): 335 $[M+H]^+$.

To a solution of (2S)-2-((tert-butoxycarbonyl)amino)-3-(2-oxo-1,2,3,4-tetrahydroquinolin-3-yl)propanoic acid (800 mg, 2.39 mmol, 1.0 eq.) in DMF (10 mL) was added N,N,N,N-tetramethylchloroformamidinium hexafluorophosphate (4.03 g, 14.4 mmol, 6.0 eq.), NMI (4.91 g, 59.8 mmol, 25.0 eq.), $NH_3$ (120 mL, 0.4 mol/L in dioxane, 47.8 mmol, 20.0 eq.). The mixture was stirred at rt overnight and then chromatographed on a C18 column with MeCN:$H_2O$ (1:4) to provide tert-butyl ((2S)-1-amino-1-oxo-3-(2-oxo-1,2,3,4-tetrahydroquinolin-3-yl)propan-2-yl)carbamate (600 mg, 68%) as a brown yellow solid. $^1H$ NMR (400 MHz, DMSO-$d_6$) δ 10.12-10.14 (m, 1H), 7.12-7.24 (m, 3H), 6.84-7.01 (m, 4H), 4.01-4.11 (m, 1H), 2.88-3.18 (m, 1H), 2.63-2.72 (m, 1H), 2.41-2.45 (m, 1H), 2.05-2.18 (m, 1H), 1.49-1.67 (m, 1H), 1.36-1.48 (m, 9H). LC-MS (ESI, m/z): 334 $[M+H]^+$.

A solution of tert-butyl ((2S)-1-amino-1-oxo-3-(2-oxo-1,2,3,4-tetrahydroquinolin-3-yl)propan-2-yl)carbamate (150 mg, 0.450 mmol, 1 eq.) in hydrochloric acid (3 mL, 4M in dioxane) was stirred at rt for 2 h and then concentrated under reduced pressure to provide (2S)-2-amino-3-(2-oxo-1,2,3,4-tetrahydroquinolin-3-yl)propenamide (100 mg, crude) as an off-white solid. LC-MS (ESI, m/z): 234 $[M+H]^+$.

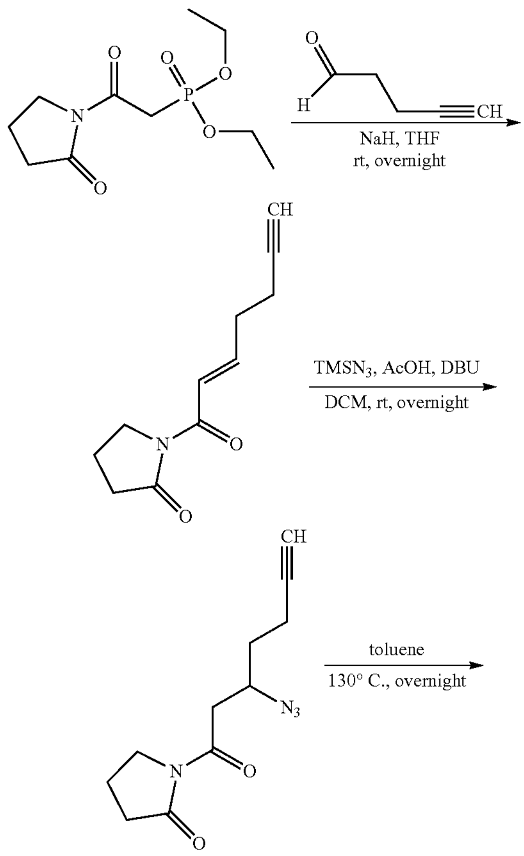

-continued

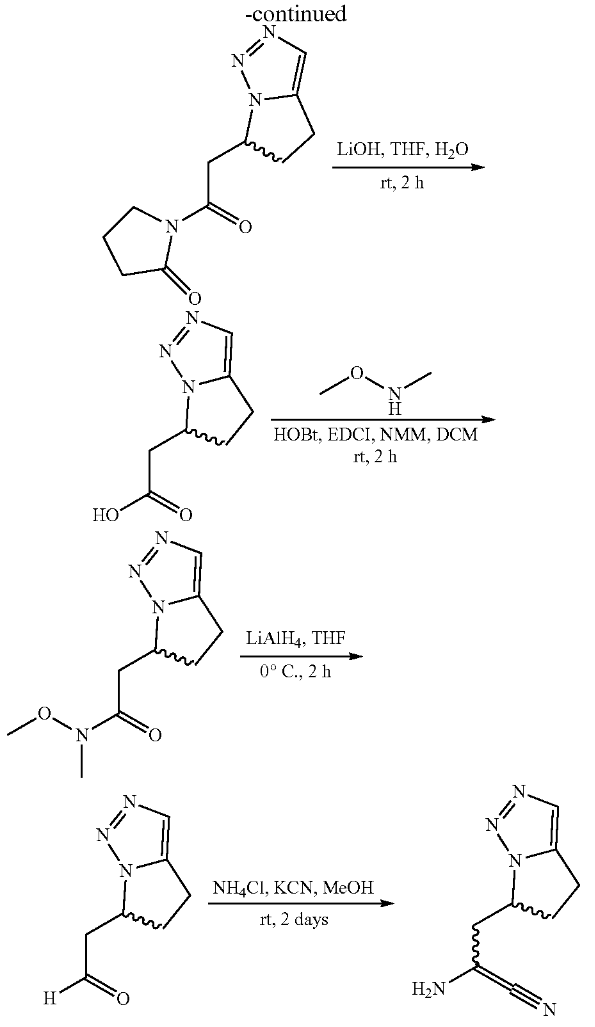

To a mixture of diethyl 2-oxo-2-(2-oxopyrrolidin-1-yl)ethylphosphonate (Gansauer et al., Ang. Chem. Int. Ed. (2009) 48(47), 8882-8885, S8882/1-S8882/32; 5.29 g, 20.1 mmol, 1.1 eq.) in THF (50 mL) was added sodium hydride (804 mg, 20.1 mmol, 1.1 eq., 60% in mineral oil) at 0° C. After stirred for 20 min at 0° C., a mixture of pent-4-ynal (1.50 g, 18.3 mmol, 1.0 eq.) in DCM (5 mL) was added. The mixture was stirred overnight at rt. The reaction was quenched with saturated aqueous ammonium chloride (100 mL). The mixture was extracted with DCM (3×100 mL). The organic layers were combined, washed with brine (2×100 mL), dried over anhydrous sodium sulfate, filtered and concentrated under reduced pressure to afford the crude product. The crude product was diluted with DCM (60 mL) and made into a slurry with 100-200 silica gel mesh (3 g). The slurry was loaded onto a column after removing the DCM. The sample was purified by column chromatography (Column size 5×24 cm, column volume: 300 mL, silica gel size (100~200 mesh) quantity: 120 g) and eluted with EtOAc/PE(0%~-50% over 30 min). The collected fractions: 33%-35% EtOAc/PE fractions were chosen as the pure fractions. Those fractions were combined and concentrated under reduced pressure to provide 1-[(2E)-hept-2-en-6-ynoyl]pyrrolidin-2-one (2.00 g, 55%) as a light yellow oil. $^1H$ NMR (300 MHz, $CDCl_3$-d) δ 7.28-7.37 (m, 1H), 7.06-7.19 (m, 1H), 3.80-3.91 (m, 2H), 2.57-2.67 (m, 2H), 2.45-2.56 (m, 2H), 2.32-2.42 (m, 2H), 1.95-2.14 (m, 3H). LC-MS (ESI, m/z): 192 $[M+H]^+$.

To a mixture of trimethylsilyl azide (6.02 g, 52.3 mmol, 5.0 eq.) in DCM (50 mL) was added acetic acid (3.14 g, 52.3 mmol, 5.0 eq.). The mixture was stirred for 20 min at rt, and 1-[(2E)-hept-2-en-6-ynoyl]pyrrolidin-2-one (2.00 g, 10.5 mmol, 1.0 eq.) and 1,8-diazabicyclo[5.4.0]undec-7-ene (318 mg, 2.09 mmol, 0.2 eq.) in DCM (50 mL) were added. The mixture was stirred overnight at rt. The reaction quenched with saturated aqueous sodium bicarbonate (100 mL). The mixture was extracted with DCM (3×100 mL). The organic layers were combined, washed with brine (2×100 mL), dried over anhydrous sodium sulfate, filtered and concentrated under reduced pressure to afford the crude product. The crude product was diluted with DCM (60 mL) and made into a slurry with 100~200 silica gel mesh (5 g). The slurry was loaded to a column after removing the DCM. The sample was purified by column chromatography (Column size 5×24 cm, column volume: 300 mL, silica gel size (100-200 mesh) quantity: 120 g) and eluted with EtOAc/PE (0%-50% over 30 min). The collected fractions: 33%-35% EtOAc/PE fractions were chosen as the pure fractions. Those fractions were combined and concentrated under reduced pressure to provide 1-(3-azidohept-6-ynoyl)pyrrolidin-2-one (2.4 g, 96%) as a light yellow oil. $^1$H NMR (300 MHz, $CDCl_3$-d) δ 4.05-4.22 (m, 1H), 3.78-3.96 (m, 2H), 3.15-3.28 (m, 1H), 2.98-3.10 (m, 1H), 2.55-2.66 (m, 2H), 2.31-2.46 (m, 2H), 1.93-2.17 (m, 3H), 1.64-1.85 (m, 2H). LC-MS (ESI, m/z): 235 $[M+H]^+$.

A solution of 1-(3-azidohept-6-ynoyl)pyrrolidin-2-one (2.40 g, 10.2 mmol, 1.0 $CDCl_3$) in toluene (20 mL) was stirred overnight at 130° C. The mixture was concentrated under reduced pressure to afford the crude product. The crude product was diluted with DCM (50 mL) and made into a slurry with 100-200 silica gel mesh (5 g). The slurry was loaded to a column after removing the DCM. The sample was purified by column chromatography (Column size 5×24 cm, column volume: 300 mL, silica gel size (100~200 mesh) quantity: 120 g) and eluted with MeOH:DCM (0%-5% over 20 min). The collected fractions: 2%-3% MeOH:DCM fractions were chosen as the pure fractions. Those fractions were combined and concentrated under reduced pressure to provide 1-(2-{4H,5H,6H-pyrrolo[1,2-c][1,2,3]triazol-6-yl}acetyl)pyrrolidin-2-one (2.20 g, 73%) as a brown semi solid. $^1$H NMR (300 MHz, $CDCl_3$-d) δ 7.38 (s, 1H), 5.00-5.11 (m, 1H), 3.78-3.91 (m, 3H), 3.28-3.40 (m, 1H), 3.04-3.17 (m, 1H), 2.87-2.99 (m, 2H), 2.57-2.64 (m, 2H), 2.44-2.55 (m, 1H), 2.02-2.13 (m, 2H). LC-MS (ESI, m/z): 235 $[M+H]^+$.

To a mixture of 1-(2-{4H,5H,6H-pyrrolo[1,2-c][1,2,3]triazol-6-yl}acetyl)pyrrolidin-2-one (1.00 g, 4.27 mmol, 1.0 eq.) in THF (5 mL):water (5 mL) was added lithium hydroxide (307 mg, 12.8 mmol, 3.0 eq.). The mixture was stirred for 2 h at rt. The mixture was concentrated under reduced pressure to remove the THF and adjusted to pH=6 with HCl (2 M). The mixture was extracted with EtOAc (5×20 mL). The organic layers were combined, washed with brine (2×10 mL), dried over anhydrous sodium sulfate, filtered and concentrated under reduced pressure to afford 4H,5H,6H-pyrrolo[1,2-c][1,2,3]triazol-6-ylacetic acid (600 mg, crude) as a yellow semi-solid. LC-MS (ESI, m/z): 168 $[M+H]^+$.

To a mixture of 4H,5H,6H-pyrrolo[1,2-c][1,2,3]triazol-6-ylacetic acid (600 mg, 3.59 mmol, 1.0 eq.) in DCM (15 mL) were added N,O-dimethylhydroxylamine hydrochloride (350 mg, 3.59 mmol, 1.0 eq.), 1-hydroxybenzotriazole (485 mg, 3.59 mmol, 1.0 eq.), 1-(3-dimethylaminopropyl)-3-ethylcarbodiimide hydrochloride (757 mg, 3.95 mmol, 1.1 eq.) and N-methylmorphline (1.09 g, 10.77 mmol, 3.0 eq.) at rt. The mixture was stirred for 2 h at rt. The reaction was quenched with water (30 mL). The mixture was extracted with DCM (4×30 mL). The organic layers were combined, washed with brine (30 mL), dried over anhydrous sodium sulfate, filtered and concentrated under reduced pressure to afford the crude product. The crude product was diluted with DCM (30 mL) and made into a slurry with 100-200 silica gel mesh (3 g). The slurry was loaded to a column after removing the DCM. The sample was purified by column chromatography (Column size 5×24 cm, column volume: 300 mL, silica gel size (100~200 mesh) quantity: 120 g) and eluted with MeOH:DCM (0%-10% over 20 min). The collected fractions: 3% MeOH:DCM fractions were chosen as the pure fractions. Those fractions were combined and concentrated under reduced pressure to provide N-methoxy-N-methyl-2-{4H,5H,6H-pyrrolo[1,2-c][1,2,3]triazol-6-yl}acetamide (340 mg, 40%) as a yellow oil. $^1$H NMR (300 MHz, $CDCl_3$-d) δ 7.43 (s, 1H), 4.91-5.05 (m, 1H), 3.70 (s, 3H), 3.46-3.56 (m, 1H), 3.22 (s, 3H), 3.08-3.20 (m, 1H), 2.80-2.98 (m, 3H), 2.45-2.59 (m, 1H). LC-MS (ESI, m/z): 211 $[M+H]^+$.

To a mixture of N-methoxy-N-methyl-2-{4H,5H,6H-pyrrolo[1,2-c][1,2,3]triazol-6-yl}acetamide (300 mg, 1.43 mmol, 1.0 eq.) in THF (6 mL) was added dropwise lithium aluminum hydride (0.68 mL, 1.71 mmol, 1.2 eq., 2.5 M in THF) at 0° C. under nitrogen. The mixture was stirred for 2 h at 0° C. The reaction was quenched with saturated aqueous ammonium chloride (20 mL). The mixture was extracted with chloroform:isopropyl alcohol (5/1, 4×20 mL). The organic layers were combined, washed with brine (2×20 mL), dried over anhydrous sodium sulfate, filtered and concentrated under reduced pressure to afford 2-{4H,5H,6H-pyrrolo[1,2-c][1,2,3]triazol-6-yl}acetaldehyde (216 mg, crude) as a yellow oil. LC-MS (ESI, m/z): 152 $[M+H]^+$.

To a mixture of 2-{4H,5H,6H-pyrrolo[1,2-c][1,2,3]triazol-6-yl}acetaldehyde (216 mg, 1.43 mmol, 1.0 eq.) in MeOH (5 mL) was added ammonium chloride (153 mg, 2.86 mmol, 2.0 eq.). After being stirred for 2 h at rt, potassium cyanide (140 mg, 2.14 mmol, 1.5 eq.) was added. The mixture was stirred for 2 days at rt, and then filtered. The filtrate was concentrated under reduced pressure to remove the MeOH. The residue was diluted with DCM (5 mL) and filtered. The filtrate was concentrated under reduced pressure to provide 2-amino-3-{4H,5H,6H-pyrrolo[1,2-c][1,2,3]triazol-6-yl}propanenitrile (190 mg, crude) as a yellow oil. LC-MS (ESI, m/z): 178 $[M+H]^+$.

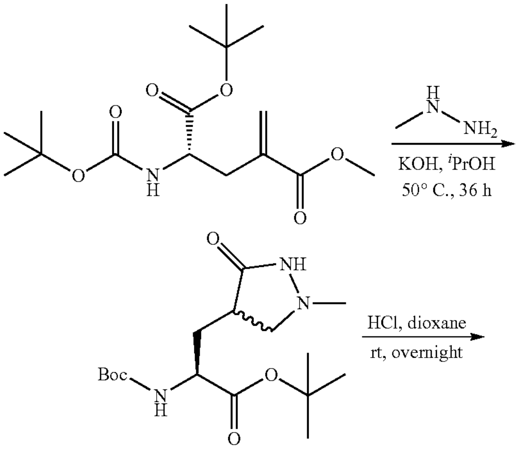

-continued

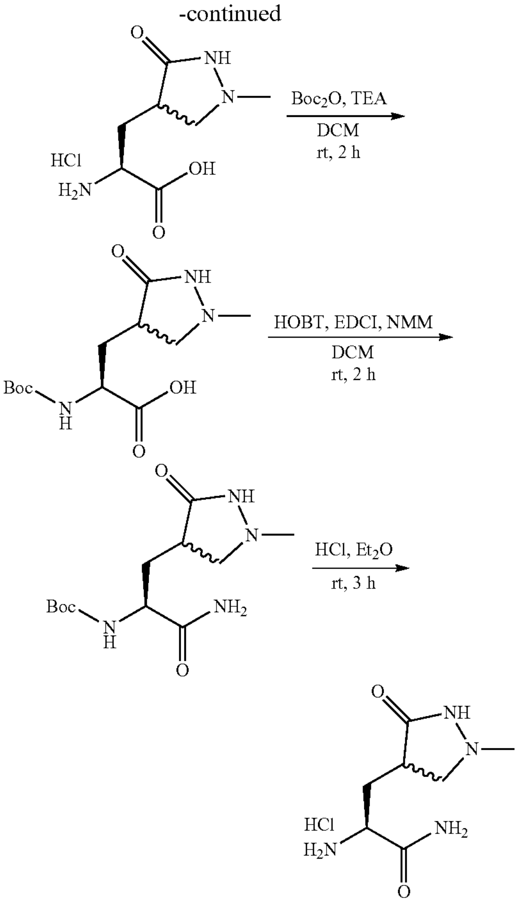

To a mixture of 1-(tert-butyl) 5-methyl (S)-2-((tert-butoxycarbonyl)amino)-4-methylenepentanedioate (5.0 g, 15.2 mmol, 1.0 eq.) in $^{PrOH}$ (50 mL) were added methyl hydrazine (3.50 g, 75.9 mmol, 5.0 eq.) and potassium hydroxide (42.6 mg, 0.759 mmol, 0.05 eq.) at rt. The mixture was stirred for 36 h at 50° C. and then concentrated under reduced pressure to afford the crude product. The crude product was chromatographed on a silica gel column with EA:PE (90%-100%) to provide the crude product. The crude product was separated by prep-achiral-SFC-HPLC column (Column: GreenSep Basic, 3*15 cm, 5 m; Mobile Phase A: $CO_2$, Mobile Phase B: MeOH (0.1% 2M $NH_3$-MeOH); Flow rate: 75 mL/min; Gradient: isocratic 13% B; Column Temperature(° C.): 35; Back Pressure(bar): 100; Wave Length: 220 nm; RT1 (min): 1.56; RT2(min): 3.85; Sample Solvent: MeOH—HPLC; Injection Volume: 1.5 mL;) to provide tert-butyl (S)-2-((tert-butoxycarbonyl)amino)-3-(-1-methyl-3-oxopyrazolidin-4-yl)propanoate (1.75 g, 33%) as white solid. $^1$H NMR (400 MHz, $CDCl_3$) δ 5.31-5.58 (m, 1H), 4.13-4.25 (m, 1H), 3.40-3.65 (m, 1H), 2.85-2.99 (m, 2H), 2.66-2.67 (m, 3H), 2.02-2.38 (m, 1H), 1.75-1.93 (m, 1H), 1.46-1.51 (m, 18H). LC-MS (ESI, m/z): 344 $[M+H]^+$.

To a solution of tert-butyl (S)-2-((tert-butoxycarbonyl)amino)-3-(1-methyl-3-oxopyrazolidin-4-yl)propanoate (800 mg, 2.33 mmol, 1.0 eq.) in 1,4-dioxane (8 mL) was added hydrogen chloride (8 mL, 9 M in $H_2O$). The mixture was stirred for overnight at rt and then concentrated under reduced pressure to afford (S)-2-amino-3-(1-methyl-3-oxopyrazolidin-4-yl)propanoic acid hydrochloride (500 mg, crude) as a yellow solid. LC-MS (ESI, m/z): 188 $[M+H]^+$.

To a solution of (S)-2-amino-3-(1-methyl-3-oxopyrazolidin-4-yl)propanoic acid hydrochloride (500 mg, 2.23 mmol, 1.0 eq.) in DCM (10 mL) were added di-tert-butyl dicarbonate (537 mg, 2.46 mmol, 1.1 eq.) and triethylamine (679 mg, 6.71 mmol, 3.0 eq.). The mixture was stirred for 2 h at rt. The reaction was quenched with water (10 mL). The mixture was concentrated under reduced pressure to remove DCM and adjusted to pH=6 with HCl (1 M). The mixture was extracted with $CHCl_3$:$^{PrOH}$ (4:1) (3×100 mL). The organic layers were combined, dried over anhydrous sodium sulfate, filtered and concentrated under reduced pressure to afford (S)-2-((tert-butoxycarbonyl)amino)-3-(1-methyl-3-oxopyrazolidin-4-yl)propanoic acid (400 mg, crude) as a yellow solid. LC-MS (ESI, m/z): 288 $[M+H]^+$.

To a mixture of (S)-2-((tert-butoxycarbonyl)amino)-3-((R)-1-methyl-3-oxopyrazolidin-4-yl)propanoic acid (400 mg, 1.39 mmol, 1.0 eq.) in DCM (8 mL) was added 1-hydroxybenzotriazole (225 mg, 1.67 mmol, 1.2 eq.), 1-(3-dimethylaminopropyl)-3-ethylcarbodiimide hydrochloride (294 mg, 1.53 mmol, 1.1 eq.), ammonia (0.04 mL, 0.280 mmol, 2.0 eq., 7 M in MeOH) and N-methylmorphline (422 mg, 4.18 mmol, 3.0 eq.) stirred at 0° C. The mixture was stirred for 2 h at rt. The reaction was quenched with water (10 mL). The mixture was extracted with $CHCl_3$:$^{PrOH}$ (4:1) (5×100 mL). The organic layers were combined, dried over anhydrous sodium sulfate, filtered and concentrated under reduced pressure to afford the crude product. The crude product was chromatographed on a silica gel column with MeOH:DCM (12%) to provide tert-butyl ((S)-1-amino-3-(1-methyl-3-oxopyrazolidin-4-yl)-1-oxopropan-2-yl)carbamate (110 mg, crude) as a yellow solid. $^1$H NMR (400 MHz, $CDCl_3$) δ 6.87-6.99 (m, 2H), 5.85-5.99 (m, 2H), 4.36-4.42 (m, 1H), 3.38-3.56 (m, 1H), 2.84-3.14 (m, 2H), 2.64-2.68 (m, 3H), 1.94-2.16 (m, 2H), 1.45-1.48 (m, 9H). LC-MS (ESI, m/z): 287$[M+H]^+$.

A mixture of tert-butyl ((S)-1-amino-3-(1-methyl-3-oxopyrazolidin-4-yl)-1-oxopropan-2-yl)carbamate (110 mg, 0.384 mmol, 1.0 eq.) in hydrogen chloride (3 mL, 2 M in diethyl ether) was stirred for 3 h at rt and then concentrated under reduced pressure to afford (S)-2-amino-3-((R)-1-methyl-3-oxopyrazolidin-4-yl)propanamide hydrochloride (70 mg, crude) as a yellow solid. LC-MS (ESI, m/z): 187 $[M+H]^+$.

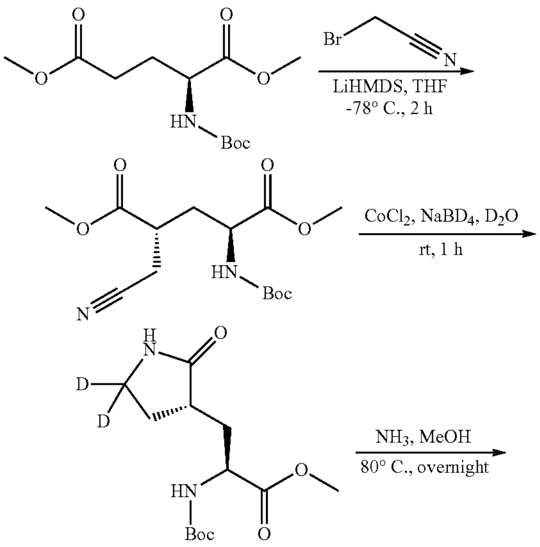

-continued

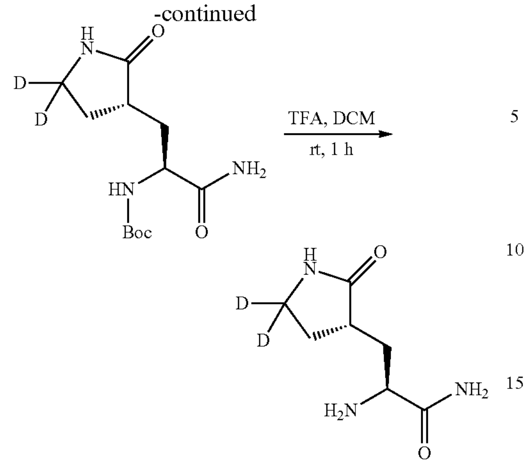

To a mixture of 1,5-dimethyl (2S)-2-[(tert-butoxycarbonyl)amino]pentanedioate (60.0 g, 217 mmol, 1.0 eq.) in THF (500 mL) was added lithium bis(trimethylsilyl)amide (80.2 g, 479 mmol, 2.2 eq.) at −78° C. under nitrogen atmosphere. After stirred for 1 h at −78° C., 2-bromoacetonitrile (28.7 g, 239 mmol, 1.1 eq.) was added. The mixture was stirred for 2 h at −78° C. under nitrogen. The reaction was quenched with methanol (200 mL) and hydrochloric acid (300 mL, 2M). The mixture was extracted with ethyl acetate (3×250 mL). The organic layers were combined, washed with brine (2×250 mL), dried over anhydrous sodium sulfate, filtered and concentrated under reduced pressure to afford the crude product. The crude product was chromatographed on a silica gel column with EA:PE (1:1) to provide 1,5-dimethyl (2S,4R)-2-[(tert-butoxycarbonyl)amino]-4-(cyanomethyl)pentanedioate (41.4 g, 57%) as a yellow oil. LC-MS (ESI, m/z): 315 $[M+H]^+$.

To a stirred mixture of 1,5-dimethyl (2S,4R)-2-[(tert-butoxycarbonyl)amino]-4-(cyanomethyl)pentanedioate (1.50 g, 4.77 mmol, 1.0 eq.) and cobalt(II) chloride (1.24 g, 9.54 mmol, 2.0 eq.) in $D_2O$ (15 mL) was added sodium borodeuteride (2.00 g, 47.7 mmol, 10 eq.). The mixture was stirred for 1 h at rt. The reaction was quenched with water (30 mL). The mixture was extracted with EtOAc (3×30 mL). The organic layers were combined, washed with brine (2×30 mL), dried over anhydrous sodium sulfate, filtered and concentrated under reduced pressure to afford the crude product. The crude product was chromatographed on a silica gel column with MeOH:DCM (1:20) to provide methyl (S)-2-((tert-butoxycarbonyl)amino)-3-((S)-2-oxopyrrolidin-3-yl-5,5-d2)propanoate (190 mg, 13%) as yellow solid. $^1H$ NMR (400 MHz, DMSO-$d_6$) δ 7.53-7.73 (m, 1H), 7.28-7.49 (m, 1H), 3.96-4.11 (m, 1H), 3.54-3.71 (m, 3H), 2.20-2.32 (m, 1H), 2.07-2.18 (m, 1H), 1.91-2.06 (m, 1H), 1.50-1.70 (m, 2H), 1.30-1.44 (m, 9H). LC-MS (ESI, m/z): 189 $[M-Boc+H]^+$.

Methyl (S)-2-((tert-butoxycarbonyl)amino)-3-((S)-2-oxopyrrolidin-3-yl-5,5-d2)propanoate (190 mg, 0.659 mmol, 1.0 eq.) was stirred with $NH_3$ in MeOH (10 mL, 7 M $NH_3$ in MeOH). The mixture was stirred overnight at 80° C. and then concentrated under reduced pressure to afford tert-butyl ((S)-1-amino-1-oxo-3-((S)-2-oxopyrrolidin-3-yl-5,5-d2)propan-2-yl)carbamate (140 mg, crude) as a brown oil. LC-MS (ESI, m/z): 274 $[M+H]^+$.

To a stirred mixture of tert-butyl ((S)-1-amino-1-oxo-3-((S)-2-oxopyrrolidin-3-yl-5,5-d2)propan-2-yl)carbamate (140 mg, 0.512 mmol, 1.0 eq.) in DCM (4 mL) was added trifluoroacetic acid (1.5 mL). The mixture was stirred for 1 h at rt and then concentrated under reduced pressure to afford (S)-2-amino-3-((S)-2-oxopyrrolidin-3-yl-5,5-d2)propanamide (88 mg, crude) as a brown oil. LC-MS (ESI, m/z): 174 $[M+H]^+$.

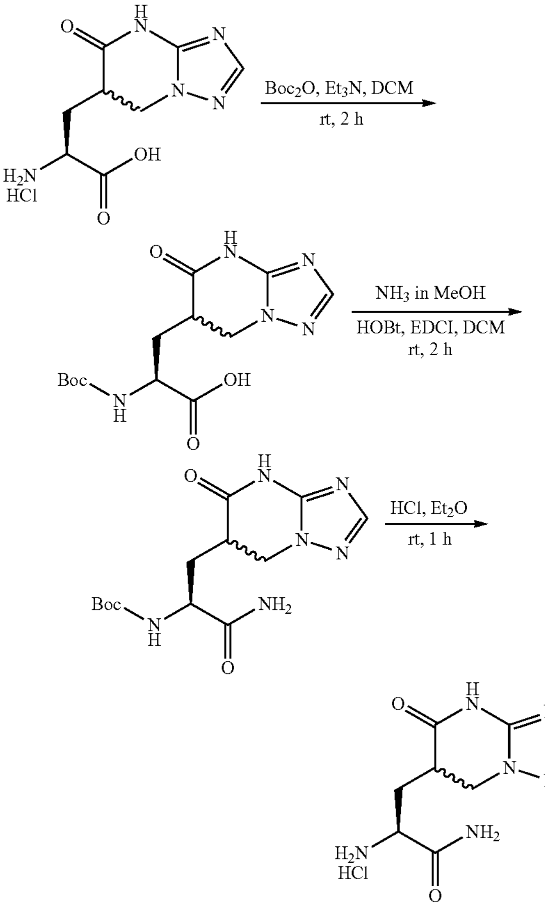

To a mixture of 1-tert-butyl 5-methyl (2S)-2-[(tert-butoxycarbonyl)amino]-4-methylidenepentanedioate (1.00 g, 3.04 mmol, 1 eq.) in DMSO (5 mL)/MeCN (5 mL) were added 2-amino-1,3,4-triazole (383 mg, 4.55 mmol, 1.5 eq.) and potassium carbonate (634 mg, 4.55 mmol, 1.5 eq.). The mixture was stirred overnight at 70° C. The reaction was quenched with water (50 mL). The mixture was extracted with EtOAc (3×50 mL). The organic layers were combined, washed with brine (2×50 mL), dried over anhydrous sodium sulfate, filtered and concentrated under reduced pressure to afford the crude product. The crude product was chromatographed on a silica gel column with EtOAc:PE (7:3) to provide tert-butyl (2S)-2-[(tert-butoxycarbonyl)amino]-3-{5-oxo-4H,6H,7H-[1,2,4]triazolo[1,5-a]pyrimidin-6-yl}propanoate (620 mg, 49%) as a white solid. $^1H$ NMR (400 MHz, DMSO-$d_6$) δ 11.42-11.53 (m, 1H), 7.67-7.75 (m, 1H), 7.19-7.32 (m, 1H), 4.30-4.42 (m, 1H), 3.88-4.14 (m, 2H), 2.88-3.04 (m, 1H), 2.18-2.29 (m, 1H), 1.52-1.88 (m, 1H), 1.31-1.48 (m, 18H). LC-MS (ESI, m/z): 382 $[M+H]^+$.

To a mixture of tert-butyl (2S)-2-[(tert-butoxycarbonyl)amino]-3-{5-oxo-4H,6H,7H-[1,2,4]triazolo[1,5-a]pyrimidin-6-yl}propanoate (900 mg, 2.36 mmol, 1.0 eq.) in 1,4-dioxane (15 mL) was added hydrochloric acid (15 mL, 9 M). The mixture was stirred overnight at rt. The mixture was concentrated under reduced pressure to afford (2S)-2-amino-3-{5-oxo-4H,6H,7H-[1,2,4]triazolo[1,5-a]pyrimidin-6-yl}propanoic acid hydrochloride (616 mg, crude) as an off-white solid. LC-MS (ESI, m/z): 226 [M+H]$^+$.

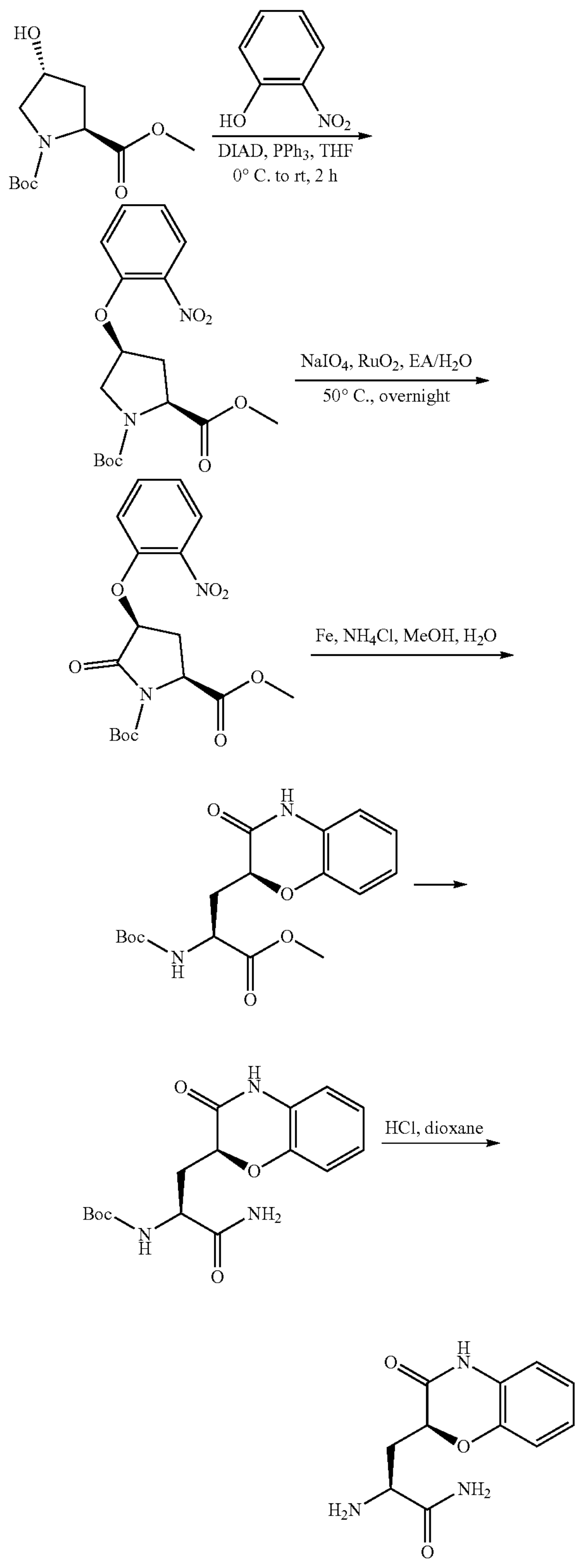

A solution of sodium periodate (21.0 g, 98.3 mmol, 7.2 eq.) and ruthenium(IV) oxide (1.03 g, 6.82 mmol, 0.5 eq.) in $H_2O$ (150 mL) was stirred for 5 min at rt under nitrogen. Then 1-(tert-butyl) 2-methyl (2S,4S)-4-(2-nitrophenoxy) pyrrolidine-1,2-dicarboxylate (5.00 g, 13.6 mmol, 1.0 eq.) in ethyl acetate (150 mL) was added. The mixture was stirred for overnight at 50° C. The mixture was diluted with ethyl acetate (200 mL) and filtered through a celite pad. The filtrate was washed with saturated aqueous sodium bisulfite (100 mL). The organic layer was washed with brine (100 mL), dried over anhydrous sodium sulfate, filtered and concentrated under reduced pressure to afford the crude product. The crude product was chromatographed on a silica gel column with EA:PE (46:100) to provide the crude product. The crude product was purified by prep-HPLC (Column: XSelect CSH Prep C18 OBD Column, 5 um, 19*150 mm; Mobile Phase A: Water (10 mmol/L $NH_4HCO_3$), Mobile Phase B: ACN; Flow rate: 25 mL/min; Gradient: 25% B to 70% B in 7 min; 254 nm; Rt: 5.30 min) to provide 1-(tert-butyl) 2-methyl (2S,4S)-4-(2-nitrophenoxy)-5-oxopyrrolidine-1,2-dicarboxylate (650 mg, 12%) as white solid. $^1$H NMR (400 MHz, Chloroform-d) δ 7.83-7.86 (m, 1H), 7.54-7.64 (m, 2H), 7.12-7.17 (m, 1H), 4.90-4.94 (m, 1H), 4.67-4.71 (m, 1H), 3.87 (s, 3H), 2.78-2.87 (m, 1H), 2.45-2.54 (m, 1H), 1.49-1.59 (m, 9H). LCMS (ESI, m/z): 381 [M+H]$^+$.

To a solution of 1-(tert-butyl) 2-methyl (2S,4S)-4-(2-nitrophenoxy)-5-oxopyrrolidine-1,2-dicarboxylate (650 mg, 1.71 mmol, 1.0 eq.) in methanol (8 mL) and $H_2O$ (2 mL) was added iron (477 mg, 8.55 mmol, 5.0 eq.) and ammonium chloride (219 mg, 4.10 mmol, 2.4 eq.). The mixture was stirred for 24 h at 70° C. The mixture was filtered through a celite pad and washed with methanol (3×50 mL). The filtrate was dried over anhydrous sodium sulfate, filtered and concentrated under reduced pressure to afford methyl (S)-2-((tert-butoxycarbonyl)amino)-3-((S)-3-oxo-3,4-dihydro-2H-benzo[b][1,4]oxazin-2-yl)propanoate (500 mg, crude) as a yellow solid. $^1$H NMR (400 MHz, DMSO-$d_6$) δ 10.72-10.77 (m, 1H), 7.25-7.49 (m, 1H), 6.70-7.00 (m, 4H), 4.44-4.74 (m, 1H), 4.03-4.30 (m, 1H), 3.51-3.70 (m, 3H), 1.98-2.22 (m, 2H), 1.25-1.57 (m, 9H). LCMS (ESI, m/z): 351 [M+H]$^+$.

A mixture of methyl (S)-2-((tert-butoxycarbonyl)amino)-3-((S)-3-oxo-3,4-dihydro-2H-benzo[b][1,4]oxazin-2-yl) propanoate (500 mg, 1.43 mmol, 1.0 eq.) in ammonia (8 mL, 7 M in methanol) was stirred for overnight at 70° C. The mixture was concentrated under reduced pressure to afford tert-butyl ((S)-1-amino-1-oxo-3-((S)-3-oxo-3,4-dihydro-2H-benzo[b][1,4]oxazin-2-yl)propan-2-yl)carbamate (460 mg, crude) as a red solid. LCMS (ESI, m/z): 336 [M+H]$^+$.

To a mixture of tert-butyl ((S)-1-amino-1-oxo-3-((S)-3-oxo-3,4-dihydro-2H-benzo[b][1,4]oxazin-2-yl)propan-2-yl) carbamate (300 mg, 0.895 mmol, 1.0 eq.) in 1,4-dioxane (4 mL) was added hydrogen chloride (6 mL, 4 M in 1,4-dioxane). The mixture was stirred for 3 h at rt and then concentrated under reduced pressure to afford (S)-2-amino-3-((S)-3-oxo-3,4-dihydro-2H-benzo[b][1,4]oxazin-2-yl) propanamide hydrochloride (250 mg, crude) as a yellow solid. LCMS (ESI, m/z): 236 [M+H]$^+$.

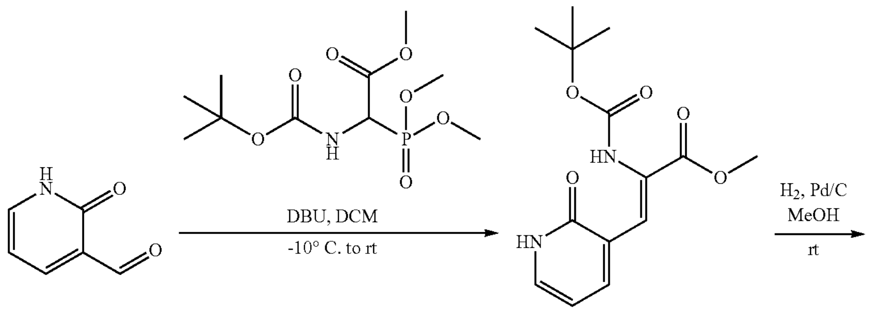

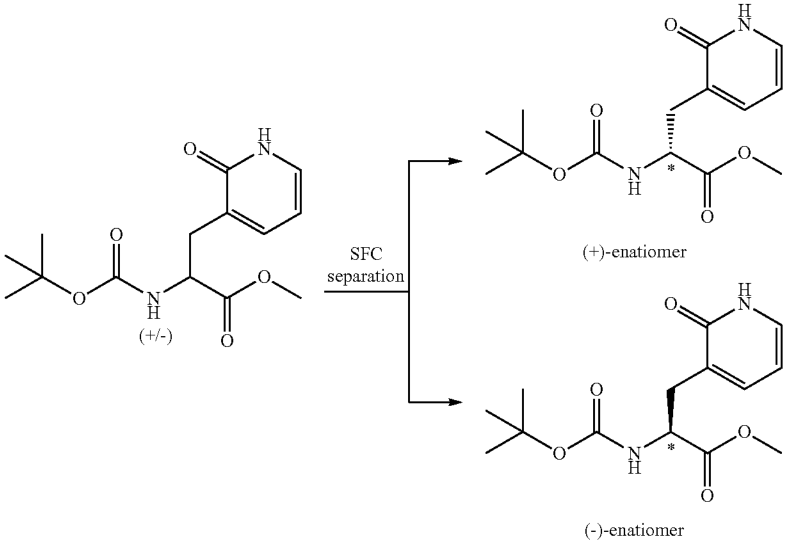

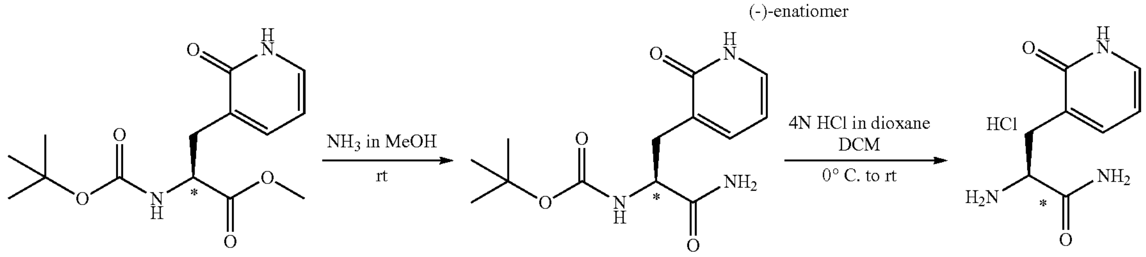

To a solution of methyl 2-((tert-butoxycarbonyl)amino)-2-(dimethoxyphosphoryl)acetate 1 (1.5 g, 12.2 mmol, 1.0 eq.) in DCM (20 mL) cooled at −10° C. was added DBU (2.2 mL, 14.6 mmol, 1.2 eq.). The mixture was stirred at −10° C. for 30 min. 2-Oxo-1,2-dihydropyridine-3-carbaldehyde (4.34 g, 14.6 mmol, 1.2 eq.) was added, and the mixture was stirred at rt for 16 h. The mixture was diluted with water (20 mL) and extracted with EA (2×20 mL). The organic phases were combined, washed with brine (2×20 mL), dried over $Na_2SO_4$, filtered and concentrated under reduced pressure. The residue was purified by flash chromatography on silica gel using a gradient of MeOH (1 to 10%) in DCM to afford methyl 2-((tert-butoxycarbonyl)amino)-3-(2-oxo-1,2-dihydropyridin-3-yl)acrylate (1.5 g, 42%) as an off-white solid.

To a solution of methyl 2-((tert-butoxycarbonyl)amino)-3-(2-oxo-1,2-dihydropyridin-3-yl)acrylate (1.5 g, 5.10 mmol, 1.0 eq.) in MeOH (15 mL) was added 10% Pd/C (1.0 g). The mixture was stirred for 3 h under hydrogen bladder pressure and then filtered through celite bed. The filtrate was concentrated under reduced pressure. The residue was purified by flash chromatography on silica gel using a gradient of MeOH (1 to 10%) in DCM to afford methyl 2-((tert-butoxycarbonyl)amino)-3-(2-oxo-1,2-dihydropyridin-3-yl)propanoate (1.4 g, 91%) as a white solid.

Methyl 2-((tert-butoxycarbonyl)amino)-3-(2-oxo-1,2-dihydropyridin-3-yl)propanoate (1.2 g) was purified by prep-SFC using the following conditions: Column: Chiralpak-IG, 25*200 mm, 5 m; Mobile Phase A: $CO_2$, Mobile Phase B: MeOH; Flow rate: 100 g/min; Gradient: isocratic 15% B; Column Temperature: 30° C.; Back Pressure: 110 bar. Purification resulted in methyl (R*)-2-((tert-butoxycarbonyl)amino)-3-(2-oxo-1,2-dihydropyridin-3-yl)propanoate (500 mg) and methyl (S*)-2-((tert-butoxycarbonyl)amino)-3-(2-oxo-1,2-dihydropyridin-3-yl)propanoate (480 mg).

Methyl (R*)-2-((tert-butoxycarbonyl)amino)-3-(2-oxo-1,2-dihydropyridin-3-yl)propanoate: $^1H$ NMR (500 MHz, DMSO-$d_6$) δ 11.64 (s, 1H), 7.22-7.31 (m, 3H), 6.12 (t, 1H), 4.24-4.29 (m, 1H), 3.58 (s, 3H), 2.87 (dd, 1H), 2.54-2.60 (m, 1H), 1.20-1.37 (m, 9H). $[\alpha]^{25}_{D}$: +70.2° (c 0.1, MeOH). SFC: Chiralpak-IG, 4.6*150 mm, 3 m, 30° C., co-Solvent: 0.5% DEA in MeOH, hold 12 min at 20%, Rt: 1.74 min.

Methyl (S*)-2-((tert-butoxycarbonyl)amino)-3-(2-oxo-1,2-dihydropyridin-3-yl)propanoate: $^1H$ NMR (400 MHz, DMSO-$d_6$) δ 11.63 (s, 1H), 7.22-7.31 (m, 3H), 6.12 (t, 1H), 4.24-4.29 (m, 1H), 3.58 (s, 3H), 2.87 (dd, 1H), 2.58 (dd, 1H), 1.23-1.33 (m, 9H). $[\alpha]^{25}_{D}$: −97.9° (c 0.1, MeOH). SFC: Chiralpak-IG, 4.6*150 mm, 3 m, 30° C., co-Solvent: 0.5% DEA in MeOH, hold 12 min at 20%, Rt: 3.73 min.

A solution of methyl (S*)-2-((tert-butoxycarbonyl) amino)-3-(2-oxo-1,2-dihydropyridin-3-yl)propanoate (300 mg, 1.01 mmol, 1.0 eq.) in 7M $NH_3$ in MeOH (10 mL) was stirred at rt for 32 h in a sealed tube. The mixture was concentrated under reduced pressure. The residue was purified by flash chromatography on silica gel using a gradient of MeOH (1 to 10%) in DCM to afford tert-butyl (S*)-(1-amino-1-oxo-3-(2-oxo-1,2-dihydropyridin-3-yl)propan-2-yl)carbamate (260 mg, 91%) as a white solid.

To a solution of tert-butyl (S*)-(1-amino-1-oxo-3-(2-oxo-1,2-dihydropyridin-3-yl)propan-2-yl)carbamate (260 mg, 0.925 mmol, 1.0 eq.) in DCM (3 mL) cooled at 0° C. was added 4N HCl in dioxane (0.920 mL, 3.70 mmol, 4.0 eq.). The mixture was stirred at rt for 2 h and then concentrated under reduced pressure to afford (S*)-2-amino-3-(2-oxo-1,2-dihydropyridin-3-yl)propanamide hydrochloride (150 mg, 89%) as a white solid.

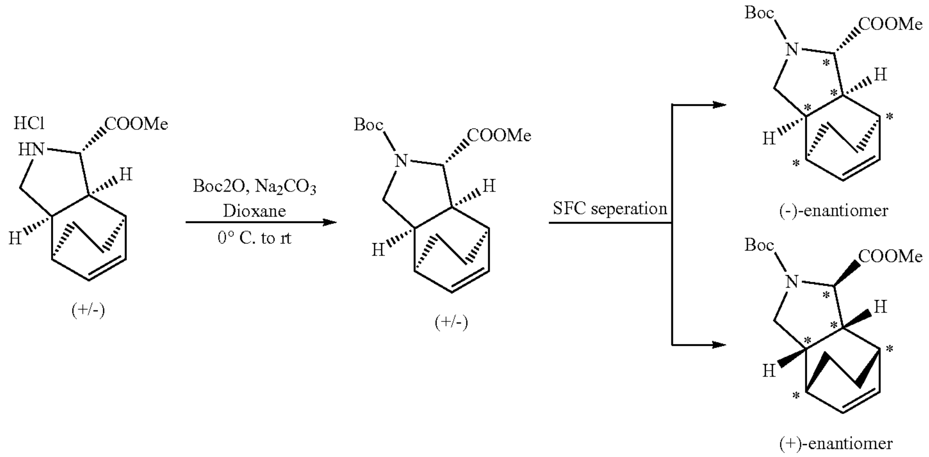

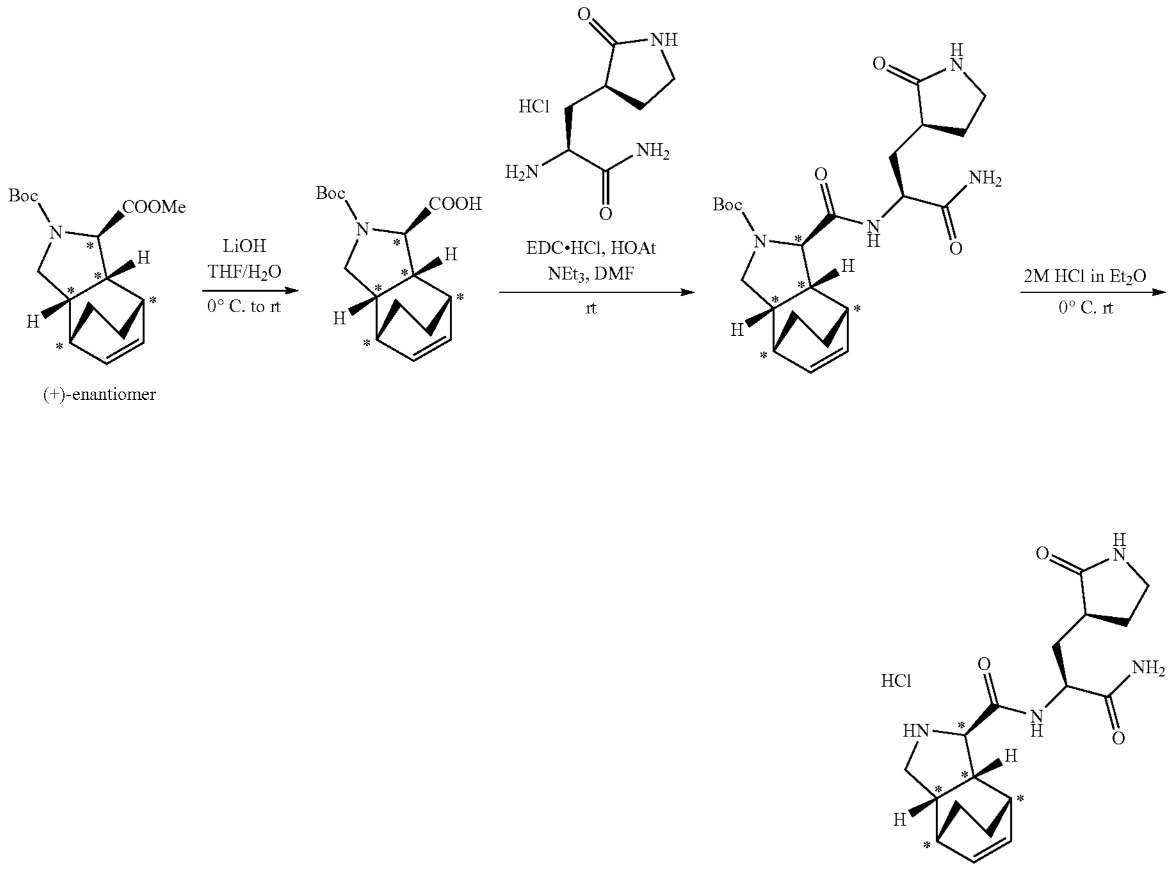

The chiral centers noted with "*" are tentatively assigned.

To a solution of (+/−)-methyl (1S,3aR,4S,7R,7aS)-2,3,3a,4,7,7a-hexahydro-1H-4,7-ethanoisoindole-1-carboxylate hydrochloride (1 g, 4.10 mmol, 1.0 eq.) in dioxane (15 mL) cooled at 0° C. were added $Na_2CO_3$ (870 mg, 8.21 mmol, 2.0 eq.) and $Boc_2O$ (1.8 g, 8.21 mmol, 2.0 eq.). The mixture was stirred at rt for 24 h. After cooling to 0° C., $Na_2CO_3$ (870 mg, 8.21 mmol, 2.0 eq.) and $Boc_2O$ (1.8 g, 8.21 mmol, 2.0 eq.) were added. The mixture was stirred at rt for 24 h. The mixture was diluted with EA (50 mL) and washed with water. The phases were separated. The aqueous phase was extracted twice with EA. The organic phases were combined, washed with brine, dried over $Na_2SO_4$, filtered and concentrated under reduced pressure. The residue was purified by flash chromatography on silica gel using a gradient of EA (0 to 30%) in PE to afford (+/−)-2-(tert-butyl) 1-methyl (1S,3aR,4S,7R,7aS)-1,3,3a,4,7,7a-hexahydro-2H-4,7-ethanoisoindole-1,2-dicarboxylate (1.1 g, 74%) as a brown oil.

(+/−)-2-(tert-Butyl) 1-methyl (1S,3aR,4S,7R,7aS)-1,3,3a,4,7,7a-hexahydro-2H-4,7-ethanoisoindole-1,2-dicarboxylate (900 mg) was purified by prep-SFC using the following conditions: Column: Lux Cellulose-2, 30*250 mm, 5 m; Mobile Phase A: $CO_2$, Mobile Phase B: MeOH; Flow rate: 60 g/min; Gradient: isocratic 10% B; Column Temperature: 30° C.; Back Pressure: 100 bar. Purification resulted in 2-(tert-butyl) 1-methyl (1S*,3aR*,4S*,7R*,7aS*)-1,3,3a,4,7,7a-hexahydro-2H-4,7-ethanoisoindole-1,2-dicarboxylate (370 mg) and 2-(tert-butyl) 1-methyl (1R*,3aS*,4R*,7S*,7aR*)-1,3,3a,4,7,7a-hexahydro-2H-4,7-ethanoisoindole-1,2-dicarboxylate (370 mg).

2-(tert-Butyl) 1-methyl (1S*,3aR*,4S*,7R*,7aS*)-1,3,3a,4,7,7a-hexahydro-2H-4,7-ethanoisoindole-1,2-dicarboxylate: $^1H$ NMR (400 MHz, $CDCl_3$) δ 6.22-6.33 (m, 2H), 3.87-4.02 (m, 1H), 3.71 (s, 3H), 3.52-3.70 (m, 1H), 3.14-3.28 (m, 1H), 2.78 (m, 1H), 2.59 (m, 1H), 2.40-2.52 (m, 2H), 1.32-1.50 (m, 11H), 1.18-1.30 (m, 2H). $[\alpha]^{25}_D$: −29.1° (c 0.1, $CHCl_3$). SFC: Lux Cellulose-2, 4.6*150 mm, 3 m, Mobile Phase A: $CO_2$, Mobile Phase B: 0.5% DEA in MeOH; Flow rate: 3 g/min; Gradient: isocratic 15% B; Column Temperature: 30° C.; Back Pressure: 100 bar, Rt: 0.98 min.

2-(tert-Butyl) 1-methyl (1R*,3aS*,4R*,7S*,7aR*)-1,3,3a,4,7,7a-hexahydro-2H-4,7-ethanoisoindole-1,2-dicarboxylate: $^1H$ NMR (400 MHz, $CDCl_3$) δ 6.22-6.33 (m, 2H), 3.87-4.02 (m, 1H), 3.71 (s, 3H), 3.52-3.70 (m, 1H), 3.14-3.28 (m, 1H), 2.78 (m, 1H), 2.59 (m, 1H), 2.40-2.52 (m, 2H), 1.32-1.50 (m, 11H), 1.18-1.30 (m, 2H). $[\alpha]^{25}_D$: +21.6° (c 0.1, $CHCl_3$). SFC: Lux Cellulose-2, 4.6*150 mm, 3 m, Mobile Phase A: $CO_2$, Mobile Phase B: 0.5% DEA in MeOH; Flow rate: 3 g/min; Gradient: isocratic 15% B; Column Temperature: 30° C.; Back Pressure: 100 bar, Rt: 1.12 min.

To a solution of 2-(tert-butyl) 1-methyl (1R*,3aS*,4R*,7S*,7aR*)-1,3,3a,4,7,7a-hexahydro-2H-4,7-ethanoisoindole-1,2-dicarboxylate (100 mg, 0.325 mmol, 1.0 eq.) in THF (1 mL) and water (1 mL) cooled at 0° C. was added LiOH (21 mg, 0.500 mmol, 1.5 eq.). The mixture was stirred for 2 h at rt and then partially concentrated under reduced pressure to remove THF. The residue was acidified by addition of 1N HCl until pH=2. The mixture was extracted with EA (3×10 mL). The organic phases were combined, dried over $Na_2SO_4$, filtered and concentrated under reduced pressure to afford (1R*,3aS*,4R*,7S*,7aR*)-2-(tert-butoxycarbonyl)-2,3,3a,4,7,7a-hexahydro-1H-4,7-ethanoisoindole-1-carboxylic acid (82 mg, 86%) as an oil.

To a solution of (1R*,3aS*,4R*,7S*,7aR*)-2-(tert-butoxycarbonyl)-2,3,3a,4,7,7a-hexahydro-1H-4,7-ethanoisoindole-1-carboxylic acid (160 mg, 0.546 mmol, 1.0 eq.) in DMF (1.6 mL) cooled at 0° C. were added (S)-2-amino-3-((S)-2-oxopyrrolidin-3-yl)propanamide hydrochloride (141 mg, 0.655 mmol, 1.2 eq.), EDC·HCl (208 mg, 1.09 mmol, 2.0 eq.), HOAt (74 mg, 0.546 mmol, 1.0 eq.) and $NEt_3$ (0.380 mL, 2.73 mmol, 5.0 eq.). The mixture was stirred at rt for 16 h. The mixture was diluted with water (10 mL) and extracted with EA (2×10 mL). The organic phases were combined, washed with brine (2×10 mL), dried over $Na_2SO_4$, filtered and concentrated under reduced pressure. The residue was purified by flash chromatography on C18 using 0.01% FA in ACN to afford tert-butyl (1R*,3aS*,4R*,7S*,7aR*)-1-(((S)-1-amino-1-oxo-3-((S)-2-oxopyrrolidin-3-yl)propan-2-yl)carbamoyl)-1,3,3a,4,7,7a-hexahydro-2H-4,7-ethanoisoindole-2-carboxylate (180 mg, 74%) as a white solid. LC-MS (ESI, m/z): 447 $[M+H]^+$.

A solution of tert-butyl (1R*,3aS*,4R*,7S*,7aR*)-1-(((S)-1-amino-1-oxo-3-((S)-2-oxopyrrolidin-3-yl)propan-2-yl)carbamoyl)-1,3,3a,4,7,7a-hexahydro-2H-4,7-ethanoisoindole-2-carboxylate (170 mg, 0.381 mmol, 1.0 eq.) in 2M HCl in ether (20 mL) was stirred at rt for 5 h. The mixture was concentrated under reduced pressure to afford quantitatively (1R*,3aS*,4R*,7S*,7aR*)—N—((S)-1-amino-1-oxo-3-((S)-2-oxopyrrolidin-3-yl)propan-2-yl)-2,3,3a,4,7,7a-hexahydro-1H-4,7-ethanoisoindole-1-carboxamide hydrochloride as a white solid.

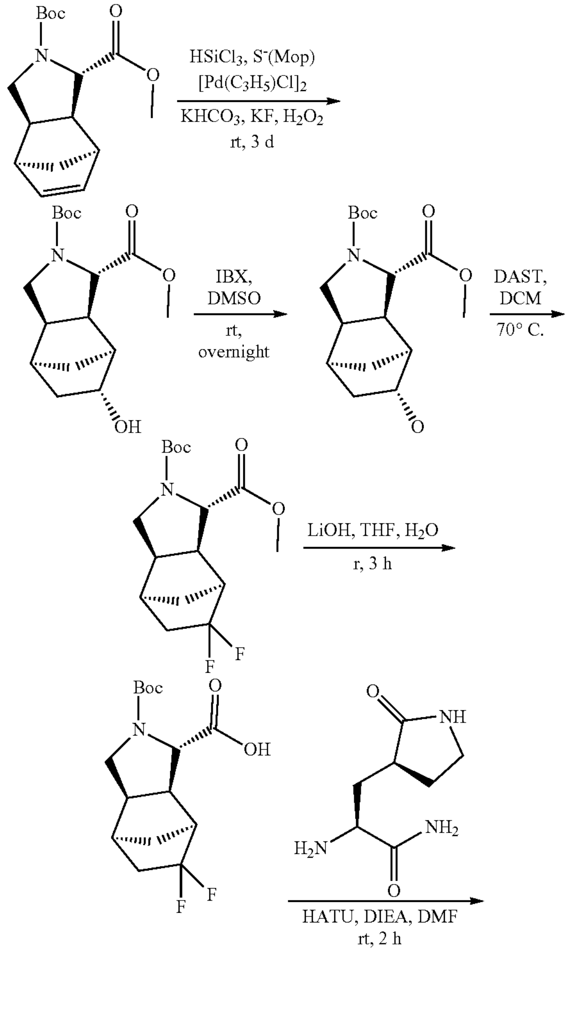

-continued

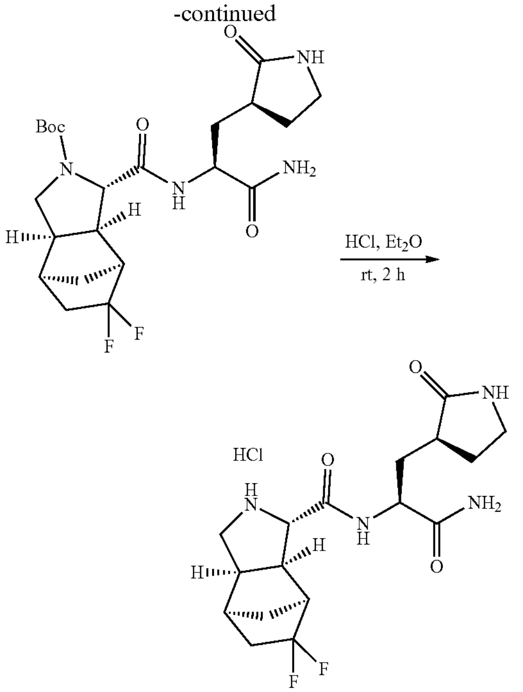

The 4-tert-butyl 3-methyl (1R,2S,3S,6R,7S)-4-azatricyclo[5.2.1.0^{2,6}]dec-8-ene-3,4-dicarboxylate (4.00 g, 13.6 mmol, 1.0 eq.) was dissolved in toluene (8 mL) under nitrogen and cooled to 0° C. (S)-MOP (S)-(−)-2-Diphenylphosphino-2'-methoxy-1,1'-binaphthyl (15.9 mg, 0.034 mmol, 0.0025 eq.), [Pd($C_3$H5)Cl]2 allylpalladium chloride dimer (3.00 mg, 0.008 mmol, 0.0006 eq.) and trichlorosilane (5.87 g, 43.5 mmol, 3.2 eq.) were added consecutively. The mixture was warmed to rt and then stirred for 3 d. The mixture was concentrated under reduced pressure. The residue was re-dissolved in THF (36 mL) and MeOH (36 mL). The mixture was poured into a suspension of potassium fluoride (6.26 g, 108 mmol, 8.0 eq.) and $KHCO_3$ (13.6 g, 136 mmol, 10.0 eq.) in THF (36 mL) and MeOH (36 mL) at 0° C. Then $H_2O_2$ (20 mL) was added. The mixture was stirred for 1 d at rt. The mixture was extracted with EtOAc (3×100 mL). The organic layers were combined, washed with brine (2×50 mL), dried over anhydrous sodium sulfate, filtered and concentrated under reduced pressure to afford the crude product. The crude product was chromatographed on a silica gel column with EA:PE (40:60) to provide 4-tert-butyl 3-methyl (1S,2R,3S,6R,7S)-9-hydroxy-4-azatricyclo [5.2.1.0^{2,6}]decane-3,4-dicarboxylate (2.00 g, 47%) as a yellow oil. LC-MS (ESI, m/z): 256 $[M-56+H]^+$.

To a stirred mixture of 4-tert-butyl 3-methyl (1S,2R,3S,6R,7S)-9-hydroxy-4-azatricyclo[5.2.1.0^{2,6}]decane-3,4-dicarboxylate (2.00 g, 6.43 mmol, 1.0 eq.) in DMSO (20 mL) was added 2-iodoxybenzoic acid (5.29 g, 18.9 mmol, 3.0 eq.). The mixture was stirred for overnight at rt. The reaction was quenched with sat. sodium bicarbonate (50 mL). The mixture was extracted with EtOAc (3×80 mL). The organic layers were combined, washed with brine (2×50 mL), dried over anhydrous sodium sulfate, filtered and concentrated under reduced pressure to afford the crude product. The crude product was chromatographed on a silica gel column with EA:PE (50:50) to provide 4-tert-butyl 3-methyl (1S,2R,3S,6R,7S)-9-oxo-4-azatricyclo[5.2.1.0^{2,6}]decane-3,4-dicarboxylate (1.5 g, 78%) as a white oil. LC-MS (ESI, m/z): 310 $[M+H]^+$.

A mixture of 4-tert-butyl 3-methyl (1S,2R,3S,6R,7S)-9-oxo-4-azatricyclo[5.2.1.0^{2,6}]decane-3,4-dicarboxylate (1.00 g, 3.23 mmol, 1.0 eq.) in diethylaminosulfur trifluoride (20 mL) was stirred for 6 h at 70° C. The mixture was diluted with dichloromethane (50 mL). The reaction was quenched with sat. sodium bicarbonate (100 mL) at 0° C. The mixture was extracted with dichloromethane (3×100 mL). The organic layers were combined, washed with brine (2×60 mL), dried over anhydrous sodium sulfate, filtered and concentrated under reduced pressure. The residue was purified by silica gel column chromatography with PE:EA (7:3) to afford 4-tert-butyl 3-methyl (1S,2R,3S,6R,7S)-9,9-difluoro-4-azatricyclo [5.2.1.0^{2,6}]decane-3,4-dicarboxylate (300 mg, 28%) as a yellow oil. LC-MS (ESI, m/z): 310 $[M+H]^+$.

To a stirred mixture of 4-tert-butyl 3-methyl (1S,2R,3S,6R,7S)-9,9-difluoro-4-azatricyclo[5.2.1.0^{2,6}]decane-3,4-dicarboxylate (300 mg, 0.905 mmol, 1.0 eq.) in THF (3 mL) and $H_2O$ (3 mL) was added lithium hydroxide (108 mg, 4.52 mmol, 5.0 eq.) at rt. The mixture was stirred for 2 h and acidified to pH=3 with hydrochloric acid (1M in $H_2O$). The aqueous layer was extracted with ethyl acetate (3×30 mL). The organic layers were combined, washed with brine (2×20 mL), dried over anhydrous sodium sulfate, filtered and concentrated under reduced pressure to afford (1S,2R,3S,6R,7S)-4-(tert-butoxycarbonyl)-9,9-difluoro-4-azatricyclo [5.2.1.0^{2,6}]decane-3-carboxylic acid (270 mg, crude) as a light yellow solid. LC-MS (ESI, m/z): 318 $[M+H]^+$.

To a mixture of (1S,2R,3S,6R,7S)-4-(tert-butoxycarbonyl)-9,9-difluoro-4-azatricyclo[5.2.1.0^{2,6}]decane-3-carboxylic acid (270 mg, 0.851 mmol, 1.0 eq.) in N,N-dimethylformamide (3 mL) was added o-(7-azabenzotriazol-1-yl)-N,N,N',N'-tetramethyluronium hexafluorophosphate (387 mg, 1.02 mmol, 1.2 eq.) and N-ethyl-N-isopropylpropan-2-amine (658 mg, 5.10 mmol, 6.0 eq.) at 0° C. The mixture was stirred for 20 min at 0° C., and then (2S)-2-amino-3-[(3S)-2-oxopyrrolidin-3-yl]propanamide (145 mg, 0.851 mmol, 1.0 eq.) was added at 0° C. The mixture was purified by C18 column with $CH_3CN$/Water (0.05% TFA). The desired fraction was concentrated under reduced pressure to provide tert-butyl (1S,2R,3S,6R,7S)-3-{[(1S)-1-carbamoyl-2-[(3S)-2-oxopyrrolidin-3-yl]ethyl]carbamoyl}-9,9-difluoro-4-azatricyclo[5.2.1.0^{2,6}]decane-4-carboxylate (200 mg, 50%) as a light yellow solid. LC-MS (ESI, m/z): 471 $[M+H]^+$.

A mixture of tert-butyl (1S,2R,3S,6R,7S)-3-{[(1S)-1-carbamoyl-2-[(3S)-2-oxopyrrolidin-3-yl]ethyl]carbamoyl}-9,9-difluoro-4-azatricyclo [5.2.1.0^{2,6}]decane-4-carboxylate (200 mg, 0.425 mmol, 1.0 eq.) in hydrogen chloride (1 mL, 2 M in $Et_2O$) was stirred for 1 h at rt. The mixture was concentrated under reduced pressure to afford (2S)-2-{[(1S,2R,3S,6R,7S)-9,9-difluoro-4-azatricyclo[5.2.1.0^{2,6}]decan-3-yl]formamido}-3-[(3S)-2-oxopyrrolidin-3-yl]propanamide hydrochloride (160 mg, crude) as a yellow solid. LC-MS (ESI, m/z): 371 $[M+H]^+$.

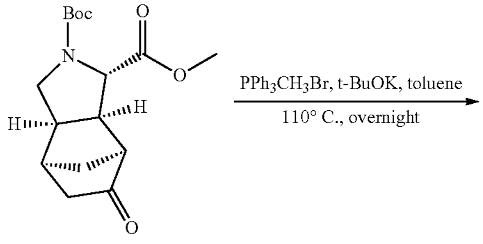

-continued

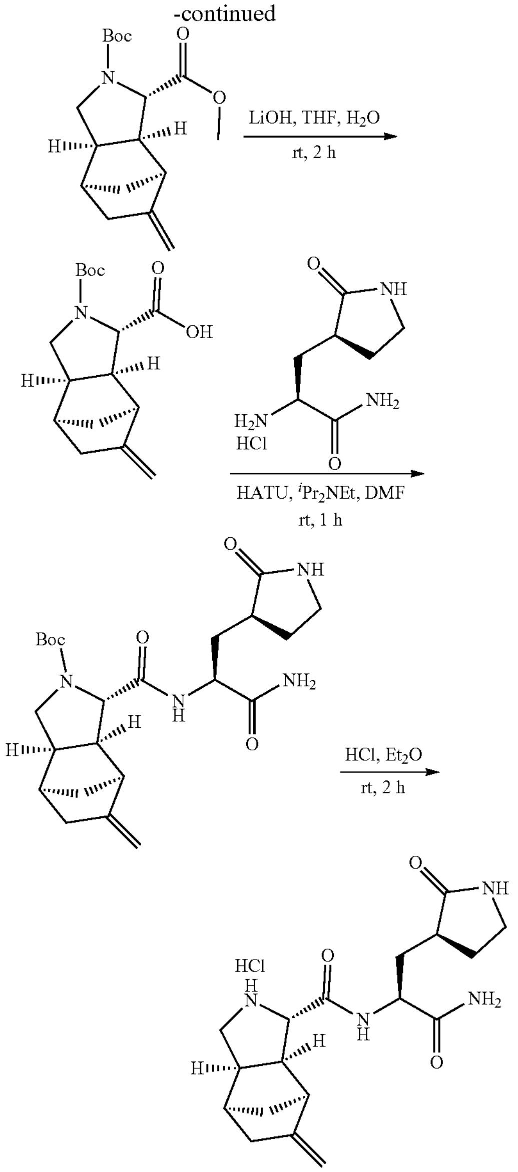

To a mixture of bromo(methyl)triphenyl-$\lambda^5$-phosphane (2.96 g, 8.27 mmol, 1.6 eq.) in toluene (48 mL) was added potassium tert-butoxide (928 mg, 8.27 mmol, 1.6 eq.). After stirred for 2 h at 110° C., 4-tert-butyl 3-methyl (1S,2R,3S,6R,7S)-9-oxo-4-azatricyclo[5.2.1.0^{2,6}]decane-3,4-dicarboxylate (1.60 g, 5.17 mmol, 1.0 eq.) was added. The mixture was stirred overnight at 110° C. The reaction was quenched with ice-water (50 mL). The mixture was extracted with EtOAc (3×50 mL). The organic layers were combined, washed with brine (2×50 mL), dried over anhydrous sodium sulfate, filtered and concentrated under reduced pressure to afford the crude product. The crude product was chromatographed on a silica gel column with EA:PE (15:85) to provide 4-tert-butyl 3-methyl (1S,2S,3S,6R,7S)-9-methylidene-4-azatricyclo[5.2.1.0^{2,6}]decane-3,4-dicarboxylate (480 mg, 29%) as a light yellow oil. $^1$H NMR (400 MHz, Chloroform-d) δ 4.89-4.96 (m, 1H), 4.71-4.80 (m, 1H), 4.17-4.33 (m, 1H), 3.72 (s, 3H), 3.52-3.66 (m, 1H), 3.35-3.44 (m, 1H), 2.56-2.85 (m, 3H), 2.33-2.42 (m, 1H), 1.98-2.22 (m, 2H), 1.62-1.71 (m, 1H), 1.52-1.60 (m, 1H), 1.36-1.50 (m, 9H). LC-MS (ESI, m/z): 208[M−100+H]$^+$.

To a mixture of 4-tert-butyl 3-methyl (1S,2S,3S,6R,7S)-9-methylidene-4-azatricyclo[5.2.1.0^{2,6}]decane-3,4-dicarboxylate (220 mg, 0.716 mmol, 1.0 eq.) in tetrahydrofuran (2 mL)/water (2 mL) was added lithium hydroxide (86.0 mg, 3.58 mmol, 5.0 eq.). The mixture was stirred for 3 h at rt. The reaction was quenched with water (5 mL) and extracted with EtOAc (5 mL). The aqueous phase was adjusted to pH=6 with HCl (1M). The mixture was extracted with EtOAc (3×5 mL). The organic layers were combined, washed with brine (2×5 mL), dried over anhydrous sodium sulfate, filtered and concentrated under reduced pressure to afford (1S,2S,3S,6R,7S)-4-(tert-butoxycarbonyl)-9-methylidene-4-azatricyclo[5.2.1.0^{2,6}]decane-3-carboxylic acid (170 mg, 76%, crude) as a yellow oil. LC-MS (ESI, m/z): 194 [M-Boc+H]$^+$.

To a mixture of (1S,2S,3S,6R,7S)-4-(tert-butoxycarbonyl)-9-methylidene-4-azatricyclo[5.2.1.0^{2,6}]decane-3-carboxylic acid (201 mg, 0.684 mmol, 1.0 eq.) and o-(7-azabenzotriazol-1-yl)-N,N,N',N'-tetramethyluronium hexafluorophosphate (312 mg, 0.821 mmol, 1.2 eq.) in DMF (5 mL) was added N-ethyl-N-isopropylpropan-2-amine (530 mg, 4.10 mmol, 6.0 eq.) at 0° C. After stirred for 15 min at 0° C., (2S)-2-amino-3-[(3S)-2-oxopyrrolidin-3-yl]propanamide hydrochloride (142 mg, 0.684 mmol, 1.0 eq.) was added. The mixture was stirred for 1 h at rt. The mixture was purified by C18 column with $CH_3CN$/Water (0.05% TFA). The desired fraction was concentrated under reduced pressure to provide tert-butyl (1S,2S,3S,6R,7S)-3-{[(1S)-1-carbamoyl-2-[(3S)-2-oxopyrrolidin-3-yl]ethyl]carbamoyl}-9-methylidene-4-azatricyclo[5.2.1.0^{2,6}]decane-4-carboxylate (180 mg, 50%) as a light yellow solid. LC-MS (ESI, m/z): 447 [M+H]$^+$.

A mixture of tert-butyl (1S,2S,3S,6R,7S)-3-{[(1S)-1-carbamoyl-2-[(3S)-2-oxopyrrolidin-3-yl]ethyl]carbamoyl}-9-methylidene-4-azatricyclo[5.2.1.0^{2,6}]decane-4-carboxylate (160 mg, 0.358 mmol, 1.0 eq.) in hydrogen chloride (5 mL, 2 M in $Et_2O$) was stirred for 2 h at rt. The mixture was concentrated under reduced pressure to afford (2S)-2-{[(1S,2S,3S,6R,7S)-9-methylidene-4-azatricyclo[5.2.1.0^{2,6}]decan-3-yl]formamido}-3-[(3S)-2-oxopyrrolidin-3-yl]propanamide hydrochloride (137 mg, crude) as an off-white solid. LC-MS (ESI, m/z): 540 [M+H]$^+$.

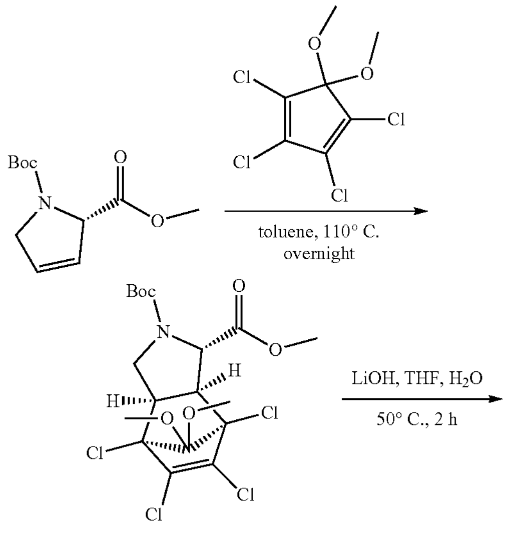

-continued

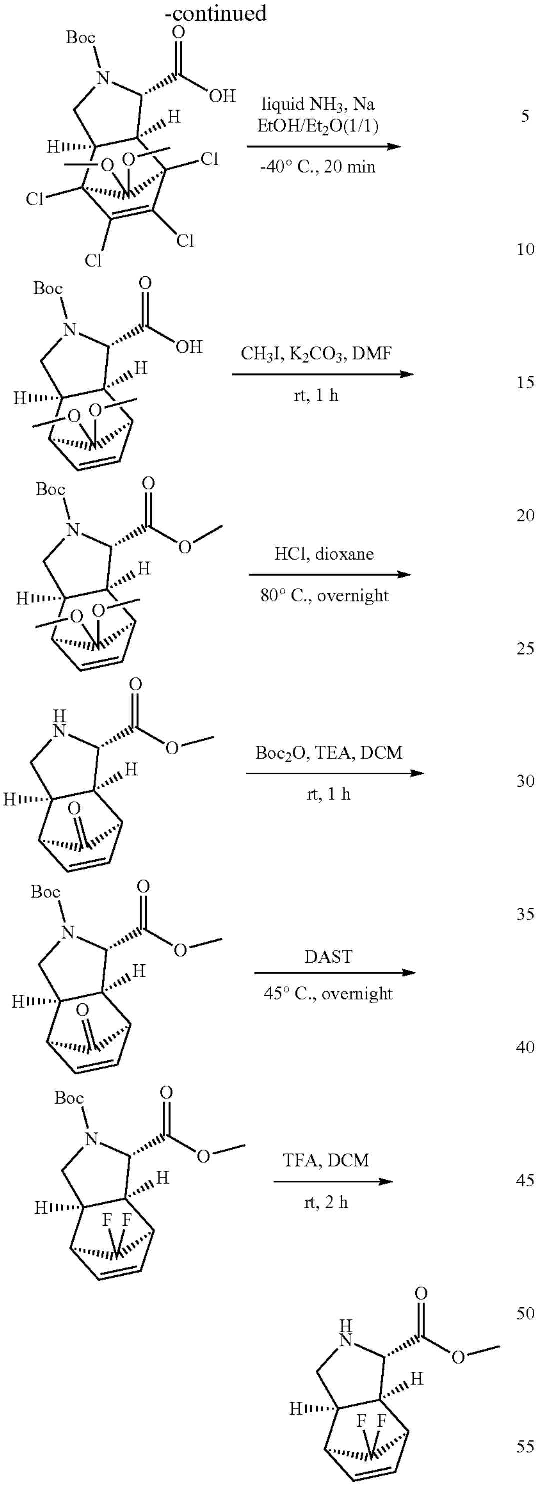

A mixture of 1,2,3,4-tetrachloro-5,5-dimethoxycyclopenta-1,3-diene (17.4 g, 66.0 mmol, 1.5 eq.) and 1-tert-butyl 2-methyl (2S)-2,5-dihydropyrrole-1,2-dicarboxylate (10.0 g, 44.0 mmol, 1.0 eq.) in toluene (10 mL) was stirred overnight at 110° C. under nitrogen and then concentrated under reduced pressure. The residue was chromatographed on a silica gel column with EA:PE (17:100) to provide the crude product. The crude product was purified by C18 column with $CH_3CN$/Water (0.05% TFA). The desired fraction was concentrated under reduced pressure to provide 4-tert-butyl 3-methyl (1S,2S,3S,6R,7R)-1,7,8,9-tetrachloro-10,10-dimethoxy-4-azatricyclo[5.2.1.0^{2,6}]dec-8-ene-3,4-dicarboxylate (7.5 g, 31%) as a yellow solid. $^1$H NMR (400 MHz, DMSO-$d_6$) δ 4.02-4.23 (m, 1H), 3.65-3.77 (m, 3H), 3.51-3.58 (m, 3H), 3.45-3.49 (m, 3H), 3.31-3.44 (m, 4H), 1.23-1.47 (m, 9H). LC-MS (ESI, m/z): 392 [M-Boc+H]$^+$.

To a stirred solution of 4-tert-butyl 3-methyl (1S,2S,3S,6R,7R)-1,7,8,9-tetrachloro-10,10-dimethoxy-4-azatricyclo[5.2.1.0^{2,6}]dec-8-ene-3,4-dicarboxylate (7.50 g, 15.2 mmol, 1.0 eq.) in THF (40 mL)/water (40 mL) was added lithium hydroxide (1.46 g, 61.0 mmol, 4.0 eq.). The mixture was stirred for 2 h at 50° C. and then concentrated under reduced pressure to removed tetrahydrofuran. The mixture was adjusted to pH=6 with hydrochloric acid (2M) and extracted with EtOAc (3×100 mL). The organic layers were combined, washed with brine (2×100 mL), dried over anhydrous sodium sulfate, filtered and concentrated under reduced pressure to afford (1S,2S,3S,6R,7R)-4-(tert-butoxycarbonyl)-1,7,8,9-tetrachloro-10,10-dimethoxy-4-azatricyclo[5.2.1.0^{2,6}]dec-8-ene-3-carboxylic acid (6.3 g, 86%, crude) as an off-white solid. $^1$H NMR (400 MHz, DMSO-$d_6$) δ 3.99-4.08 (m, 1H), 3.50-3.58 (m, 3H), 3.43-3.47 (m, 3H), 3.22-3.42 (m, 4H), 1.25-1.48 (m, 9H). LC-MS (ESI, m/z): 378 [M-Boc+H]$^+$.

To a stirred solution of sodium (6×1.68 g, 438 mmol, 35.0 eq.) in liquid $NH_3$ (6×34 mL) was added (1S,2S,3S,6R,7R)-4-(tert-butoxycarbonyl)-1,7,8,9-tetrachloro-10,10-dimethoxy-4-azatricyclo[5.2.1.0^{2,6}]dec-8-ene-3-carboxylic acid (6×1.00 g, 12.5 mmol, 1.0 eq.) in EtOH/ether (6×16 mL, 1:1 ratio) dropwise under nitrogen at −40° C. for 20 min. The mixture was stirred for 20 min at −40° C. and then $NH_4C_1$(s) (6×2 g) was added. The mixture was warmed to rt in 2 h and then diluted with water (6×50 mL). The mixture was extracted with EtOAc (300 mL). The aqueous phase was adjusted to pH=6 with hydrochloric acid (2M). The mixture was extracted with EtOAc (3×300 mL). The organic layers were combined, washed with brine (2×200 mL), dried over anhydrous sodium sulfate, filtered and concentrated under reduced pressure to afford (1R,2R,3S,6S,7S)-4-(tert-butoxycarbonyl)-10,10-dimethoxy-4-azatricyclo[5.2.1.0^{2,6}]dec-8-ene-3-carboxylic acid (3.4 g, crude) as a brown oil. LC-MS (ESI, m/z): 240 [M-Boc+H]$^+$.

To a stirred mixture of (1R,2R,3S,6S,7S)-4-(tert-butoxycarbonyl)-10,10-dimethoxy-4-azatricyclo[5.2.1.0^{2,6}]dec-8-ene-3-carboxylic acid (3.40 g, 10.0 mmol, 1.0 eq.) and potassium carbonate (2.22 g, 16.0 mmol, 1.6 eq.) in DMF (30 mL) was added iodomethane (1.49 g, 10.5 mmol, 1.05 eq.). The mixture was stirred for 1 h at rt. The reaction was quenched with water (100 mL). The mixture was extracted with EtOAc (3×100 mL). The organic layers were combined, washed with brine (2×100 mL), dried over anhydrous sodium sulfate, filtered and concentrated under reduced pressure to afford the crude product. The crude product was chromatographed on a silica gel column with EA:PE (31:100) to provide 4-tert-butyl 3-methyl (1R,2R,3S,6S,7S)-10,10-dimethoxy-4-azatricyclo[5.2.1.0^{2,6}]dec-8-ene-3,4-dicarboxylate (1.62 g, 41%) as a yellow oil. $^1$H NMR (400 MHz, DMSO-$d_6$) δ 6.07-6.23 (m, 2H), 3.70-3.86 (m, 1H), 3.60-3.69 (m, 3H), 3.26-3.33 (m, 1H), 3.08-3.12 (m, 3H), 3.01-3.07 (m, 2H), 2.97-3.00 (m, 3H), 2.78-2.96 (m, 3H), 1.23-1.44 (m, 9H). LC-MS (ESI, m/z): 254 [M-Boc+H]$^+$.

To a stirred mixture of 4-tert-butyl 3-methyl (1R,2R,3S,6S,7S)-10,10-dimethoxy-4-azatricyclo[5.2.1.0^{2,6}]dec-8-ene-3,4-dicarboxylate (1.62 g, 4.58 mmol, 1.0 eq.) in dioxane (3 mL) was added hydrogen chloride (20 mL, 4M in dioxane). The mixture was stirred for overnight at 80° C.

and then concentrated under reduced pressure to afford methyl (1R,2R,3S,6S,7S)-10-oxo-4-azatricyclo[5.2.1.0^{2,6}]dec-8-ene-3-carboxylate (949 mg, crude) as an off-white solid. LC-MS (ESI, m/z): 208 $[M+H]^+$.

To a stirred mixture of methyl (1R,2R,3S,6S,7S)-10-oxo-4-azatricyclo[5.2.1.0^{2,6}]dec-8-ene-3-carboxylate (949 mg, 4.57 mmol, 1.0 eq.) in DCM (10 mL) was added triethylamine (1.39 g, 13.7 mmol, 3.0 eq.) and di-tert-butyl dicarbonate (1.30 g, 5.95 mmol, 1.3 eq.). The mixture was stirred for 1 h at rt. The reaction was quenched with water (50 mL). The mixture was extracted with DCM (3×50 mL). The organic layers were combined, washed with brine (2×50 mL), dried over anhydrous sodium sulfate, filtered and concentrated under reduced pressure to afford the crude product. The crude product was chromatographed on a silica gel column with EA:PE (29:100) to provide 4-tert-butyl 3-methyl (1R,2R,3S,6S,7S)-10-oxo-4-azatricyclo[5.2.1.0^{2,6}]dec-8-ene-3,4-dicarboxylate (800 mg, 56%) as an off-white solid. $^1H$ NMR (400 MHz, DMSO-$d_6$) δ 6.46-6.71 (m, 2H), 3.80-4.00 (m, 1H), 3.57-3.75 (m, 3H), 3.38-3.48 (m, 1H), 2.95-3.27 (m, 5H), 1.11-1.49 (m, 9H). LC-MS (ESI, m/z): 208 $[M-Boc+H]^+$.

A mixture of 2-(tert-butyl) 1-methyl (1S,3aS,4S,7R,7aR)-8-oxo-1,3,3a,4,7,7a-hexahydro-2H-4,7-methanoisoindole-1,2-dicarboxylate (500 mg, 1.63 mmol, 1.0 eq.) in diethylaminosulfur trifluoride (10 mL) was stirred for overnight at 45° C. The mixture was diluted with dichloromethane (30 mL). The reaction was quenched with sat. sodium bicarbonate (50 mL) at 0° C. The mixture was extracted with dichloromethane (3×80 mL). The organic layers were combined, washed with brine (2×30 mL), dried over anhydrous sodium sulfate, filtered and concentrated under reduced pressure. The residue was purified by silica gel column chromatography with PE:EA (7:3) to afford 2-(tert-butyl) 1-methyl (1S,3aS,4S,7R,7aR)-8,8-difluoro-1,3,3a,4,7,7a-hexahydro-2H-4,7-methanoisoindole-1,2-dicarboxylate (350 mg, 65%) as a yellow oil. LC-MS (ESI, m/z): 230 $[M-Boc+H]^+$.

To a stirred mixture of 2-(tert-butyl) 1-methyl (1S,3aS,4S,7R,7aR)-8,8-difluoro-1,3,3a,4,7,7a-hexahydro-2H-4,7-methanoisoindole-1,2-dicarboxylate (350 mg, 1.06 mmol, 1.0 eq.) in dichloromethane (4 mL) was added trifluoroacetic acid (1.3 mL) at rt. The mixture was stirred for 2 h at rt and then concentrated under reduced pressure to provide methyl (1S,3aS,4S,7R,7aR)-8,8-difluoro-2,3,3a,4,7,7a-hexahydro-1H-4,7-methanoisoindole-1-carboxylate (243 mg, crude) as a yellow oil. LC-MS (ESI, m/z): 230 $[M+H]^+$.

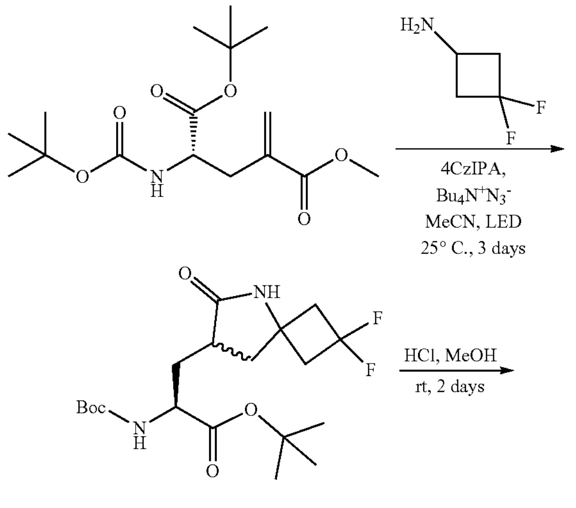

-continued

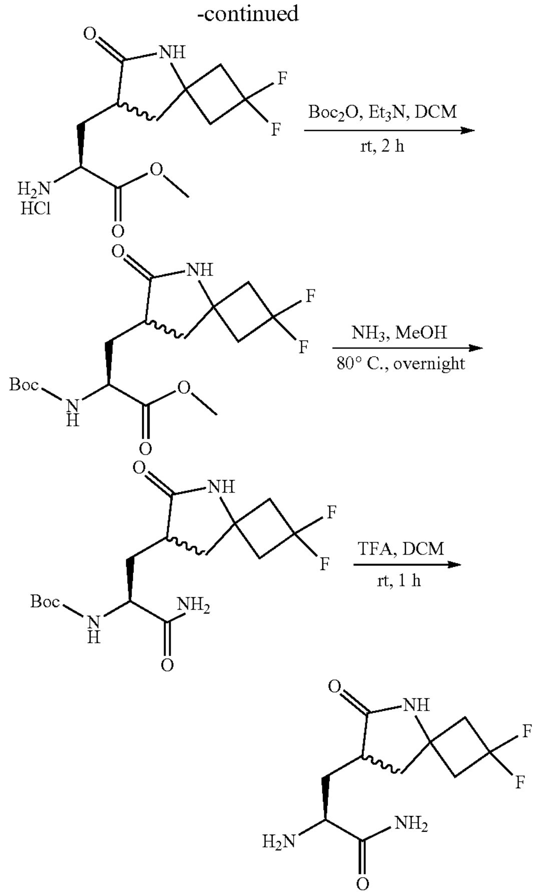

To a mixture of 1-tert-butyl 5-methyl (2S)-2-[(tert-butoxycarbonyl)amino]-4-methylidenepentanedioate (1.00 g, 3.03 mmol, 1.0 eq.), 2,4,5,6-Tetra-9H-carbazol-9-yl-1,3-benzenedicarbonitrile (24.0 mg, 0.030 mmol, 0.01 eq.) and tetrabutylammonium azide (86.0 mg, 0.303 mmol, 0.1 eq.) in acetonitrile (20 mL) was added 3,3-difluorocyclobutan-1-amine (325 mg, 3.03 mmol, 1.0 eq.) under nitrogen. The mixture was stirred for 3 days at 25° C. under nitrogen with a 450 nm LED lamp. The mixture was concentrated under reduced pressure to afford the crude product. The crude product was chromatographed on a silica gel column with MeOH:DCM (3:97) to provide tert-butyl (2S)-2-[(tert-butoxycarbonyl)amino]-3-{2,2-difluoro-6-oxo-5-azaspiro[3.4]octan-7-yl}propanoate (830 mg, 60%) as a brown solid. $^1H$ NMR (400 MHz, DMSO-$d_6$) δ 8.13-8.23 (m, 1H), 7.17-7.31 (m, 1H), 3.76-4.09 (m, 1H), 2.82-3.01 (m, 1H), 2.59-2.81 (m, 3H), 2.31-2.45 (m, 2H), 1.94-2.08 (m, 1H), 1.80-1.93 (m, 1H), 1.48-1.60 (m, 1H), 1.29-1.47 (m, 18H). LC-MS (ESI, m/z): 405 $[M+H]^+$.

A mixture of tert-butyl (2S)-2-[(tert-butoxycarbonyl)amino]-3-{2,2-difluoro-6-oxo-5-azaspiro[3.4]octan-7-yl}propanoate (800 mg, 1.98 mmol, 1.0 eq.) in hydrochloric acid (10 mL, 9 M)/methanol (10 mL) was stirred for 2 days at rt. The mixture was concentrated under reduced pressure to afford methyl (2S)-2-amino-3-{2,2-difluoro-6-oxo-5-azaspiro[3.4]octan-7-yl}propanoate hydrochloride (590 mg, crude) as a brown solid. LC-MS (ESI, m/z): 263 $[M+H]^+$.

To a mixture of methyl (2S)-2-amino-3-{2,2-difluoro-6-oxo-5-azaspiro[3.4]octan-7-yl}propanoate hydrochloride (590 mg, 1.98 mmol, 1.0 eq.) in DCM (10 mL) were added triethylamine (600 mg, 5.92 mmol, 3.0 eq.) and di-tert-butyl dicarbonate (517 mg, 2.37 mmol, 1.2 eq.). The mixture was stirred for 2 h at rt. The reaction was quenched with water (30 mL). The mixture was extracted with DCM (3×30 mL). The organic layers were combined, washed with brine (2×20 mL), dried over anhydrous sodium sulfate, filtered and concentrated under reduced pressure to provide methyl (2S)-2-[(tert-butoxycarbonyl)amino]-3-{2,2-difluoro-6-oxo-5-azaspiro[3.4]octan-7-yl}propanoate (720 mg, crude) as a brown oil. $^{1}$H NMR (400 MHz, DMSO-$d_6$) δ 8.23 (s, 1H), 7.23-7.45 (m, 1H), 4.00-4.31 (m, 1H), 3.55-3.69 (m, 3H), 2.59-3.05 (m, 4H), 2.27-2.47 (m, 2H), 1.94-2.17 (m, 1H), 1.77-1.89 (m, 1H), 1.52-1.62 (m, 1H), 1.32-1.40 (m, 9H). LC-MS (ESI, m/z): 363[M+H]$^+$.

A mixture of methyl (2S)-2-[(tert-butoxycarbonyl)amino]-3-{2,2-difluoro-6-oxo-5-azaspiro[3.4]octan-7-yl}propanoate (720 mg, 1.99 mmol, 1.0 eq.) in ammonia (10 mL, 7 M in MeOH) was stirred overnight at 80° C. The mixture was concentrated under reduced pressure to afford the crude product. The crude product was chromatographed on a silica gel column with MeOH:DCM (1:9) to provide tert-butyl N-[(1S)-1-carbamoyl-2-{2,2-difluoro-6-oxo-5-azaspiro[3.4]octan-7-yl}ethyl]carbamate (260 mg, 35%) as a light yellow solid. LC-MS (ESI, m/z): 348 [M+H]$^+$.

To a solution of tert-butyl N-[(1S)-1-carbamoyl-2-{2,2-difluoro-6-oxo-5-azaspiro[3.4]octan-7-yl}ethyl]carbamate (230 mg, 0.662 mmol, 1.0 eq.) in DCM (10 mL) was added trifluoroacetic acid (3 mL). The mixture was stirred for 1 h at rt and then concentrated under reduced pressure to afford (2S)-2-amino-3-{2,2-difluoro-6-oxo-5-azaspiro[3.4]octan-7-yl}propanamide (164 mg, crude) as a brown oil. LC-MS (ESI, m/z): 248 [M+H]$^+$.

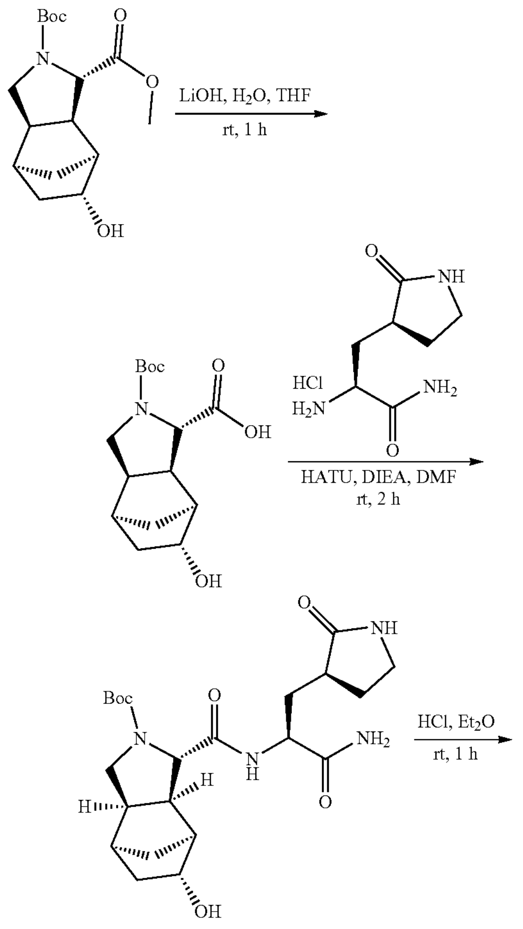

-continued

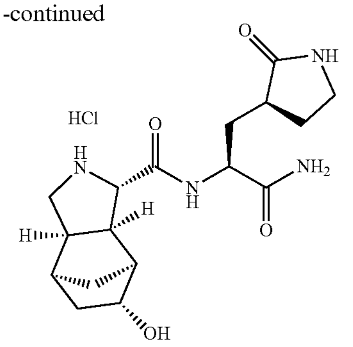

To a mixture of 4-tert-butyl 3-methyl (1S,2R,3S,6R,7S,9R)-9-hydroxy-4-azatricyclo[5.2.1.0^{2,6}]decane-3,4-dicarboxylate (200 mg, 0.642 mmol, 1.0 eq.) in tetrahydrofuran (2 mL)/water (2 mL) was added lithiumol (76.9 mg, 3.21 mmol, 5.0 eq.). The mixture was stirred for 1 h at rt and then acidified to pH=4 with hydrochloric acid (1M in $H_2O$). The mixture was extracted with EA (3×30 mL). The organic layers were combined, washed with brine (2×20 mL), dried over anhydrous sodium sulfate, filtered and concentrated under reduced pressure to afford (1S,2R,3S,6R,7S,9R)-4-(tert-butoxycarbonyl)-9-hydroxy-4-azatricyclo[5.2.1.0^{2,6}]decane-3-carboxylic acid) (190 mg, crude) as a white oil. LC-MS (ESI, m/z): 298 [M+H]$^+$.

A mixture of tert-butyl N-[(1S)-1-carbamoyl-2-[(3S)-2-oxopyrrolidin-3-yl]ethyl]carbamate (173 mg, 0.638 mmol, 1.0 eq.) in hydrogen chloride (3 mL, 2 M in $Et_2O$) was stirred for 1 h at rt. The mixture was concentrated under reduced pressure to afford methyl (2S)-2-amino-3-[(3S)-2-oxopyrrolidin-3-yl]propanamide hydrochloride (131 mg, crude) as a yellow solid. LC-MS (ESI, m/z): 172 [M-Boc+H]$^+$.

To a mixture of (1S,2R,3S,6R,7S,9R)-4-(tert-butoxycarbonyl)-9-hydroxy-4-azatricyclo[5.2.1.0^{2,6}]decane-3-carboxylic acid (189 mg, 0.636 mmol, 1.0 eq.) in N,N-dimethylformamide (2 mL) were added o-(7-azabenzotriazol-1-yl)-N,N,N',N'-tetramethyluronium hexafluorophosphate (290 mg, 0.763 mmol, 1.2 eq.) and N-ethyl-N-isopropylpropan-2-amine (493 mg, 3.82 mmol, 6.0 eq.) at 0° C. The mixture was stirred for 20 min at 0° C., and then (2S)-2-amino-3-[(3S)-2-oxopyrrolidin-3-yl]propanamide hydrochloride (132 mg, 0.636 mmol, 1.0 eq.) was added at 0° C. The mixture was stirred for 2 h at rt. The reaction was quenched with water (20 mL). The mixture was extracted with EtOAc (3×30 mL). The organic layers were combined, washed with brine (2×30 mL), dried over anhydrous sodium sulfate, filtered and concentrated under reduced pressure to afford the crude product. The mixture was purified by C18 column with $CH_3CN$/Water (0.05% TFA). The desired fraction was concentrated under reduced pressure to provide tert-butyl (1S,2R,3S,6R,7S,9R)-3-{[(1S)-1-carbamoyl-2-[(3S)-2-oxopyrrolidin-3-yl]ethyl]carbamoyl}-9-hydroxy-4-azatricyclo[5.2.1.0^{2,6}]decane-4-carboxylate (190 mg, 66%) as a light yellow solid. LC-MS (ESI, m/z): 451 [M+H]$^+$.

A mixture of tert-butyl (1S,2R,3S,6R,7S,9R)-3-{[(1S)-1-carbamoyl-2-[(3S)-2-oxopyrrolidin-3-yl]ethyl]carbamoyl}-9-hydroxy-4-azatricyclo [5.2.1.0^{2,6}]decane-4-carboxylate (190 mg, 0.422 mmol, 1.0 eq.) in hydrogen chloride (4 mL, 2 M in $Et_2O$) was stirred for 1 h at rt. The mixture was concentrated under reduced pressure to afford methyl (2S)-2-{[(1S,2R,3S,6R,7S,9R)-9-hydroxy-4-azatricyclo [5.2.1.0^{2,6}]decan-3-yl]formamido}-3-[(3S)-2-oxopyrrolidin-3-yl]propanamide hydrochloride (155 mg, crude) as a yellow solid. LC-MS (ESI, m/z): 351 [M+H]+.

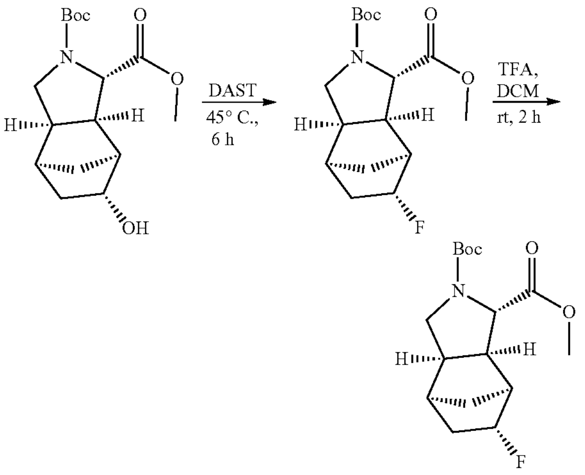

A mixture of 4-tert-butyl 3-methyl (1S,2R,3S,6R,7S,9R)-9-hydroxy-4-azatricyclo[5.2.1.0^{2,6}]decane-3,4-dicarboxylate (500 mg, 1.60 mmol, 1.0 eq.) in diethylaminosulfur trifluoride (10 mL) was stirred for 6 h at 45° C. The mixture was diluted with dichloromethane (80 mL), and the reaction quenched with sat. sodium bicarbonate (50 mL) at 0° C. The mixture was extracted with dichloromethane (3×80 mL). The organic layers were combined, washed with brine (2×50 mL), dried over anhydrous sodium sulfate, filtered and concentrated under reduced pressure. The residue was purified by silica gel column chromatography with PE:EA (7:3) to afford 4-tert-butyl 3-methyl (1S,2R,3S,6R,7S,9R)-9-fluoro-4-azatricyclo[5.2.1.0^{2,6}]decane-3,4-dicarboxylate (210 mg, 42%) as a yellow oil. LC-MS (ESI, m/z): 258 [M−56+H]+.

To a stirred mixture of 4-tert-butyl 3-methyl (1S,2R,3S,6R,7S,9R)-9-fluoro-4-azatricyclo[5.2.1.0^{2,6}]decane-3,4-dicarboxylate (210 mg, 0.670 mmol, 1.0 eq.) in dichloromethane (3 mL) was added trifluoroacetic acid (1 mL) at rt. The mixture was stirred for 2 h at rt and then concentrated under reduced pressure to provide methyl (1S,2R,3S,6R,7S,9R)-9-fluoro-4-azatricyclo[5.2.1.0^{2,6}]decane-3-carboxylate (155 mg, crude) as a yellow oil. LC-MS (ESI, m/z): 213 [M+H]+.

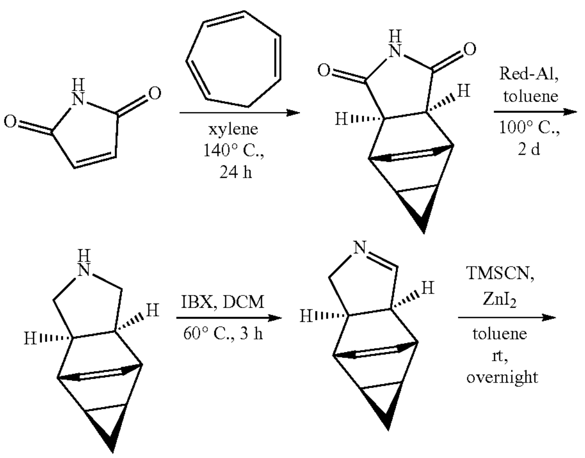

-continued

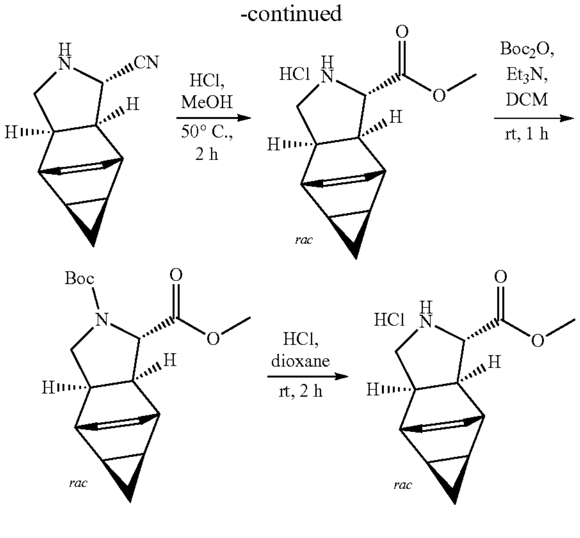

To a solution of cyclohepta-1,3,5-triene (3.13 g, 34.0 mmol, 1.1 eq.) in xylene (15 mL, 81.0 mmol, 2.6 eq.) was added 1H-pyrrole-2,5-dione (3.0 g, 30.9 mmol, 1.0 eq.). The mixture was stirred for 24 h at 140° C. and then cooled to rt. The cream-colored mixture was filtered, and the filter cake was washed with DCM (2×30 mL). The filter cake was combined to provide (3aR,4R,4aR,5aS,6S,6aS)-4,4a,5,5a,6,6a-hexahydro-4,6-ethenocyclopropa[f]isoindole-1,3(2H,3aH)-dione (5.0 g, 85%) as an off-white solid. $^1$H NMR (400 MHz, DMSO-$d_6$) δ 10.94 (s, 1H), 5.72-5.76 (m, 2H), 3.14-3.18 (m, 2H), 2.96-2.97 (m, 2H), 1.07-1.11 (m, 2H), 0.21-0.25 (m, 1H), 0.01-0.06 (m, 1H). LC-MS (ESI, m/z): 190 [M+H]+.

A solution of (3aR,4R,4aR,5aS,6S,6aS)-4,4a,5,5a,6,6a-hexahydro-4,6-ethenocyclopropa[f]isoindole-1,3(2H,3aH)-dione (5.00 g, 26.4 mmol, 1.0 eq.) in toluene was stirred at 0° C., and then sodium bis(2-methoxyethoxy) aluminum hydride (38.4 g, 133 mmol, 5.0 eq., 70% in toluene) was added dropwise. The mixture was stirred for 20 min at 0° C. The solution was stirred for 2 days at 100° C. and then cooled to rt. A sodium hydroxide aqueous solution (100 mL, 30%) was added dropwise at 0° C. The mixture was extracted with EA (3×150 mL). The organic layers were combined, dried over anhydrous sodium sulfate, filtered and concentrated under reduced pressure to afford (3aR,4R,4aR,5aS,6S,6aS)-1,2,3,3a,4,4a,5,5a,6,6a-decahydro-4,6-ethenocyclopropa[f]isoindole (3.5 g, crude) as a red oil. LC-MS (ESI, m/z): 162 [M+H]+.

To a solution of (3aR,4R,4aR,5aS,6S,6aS)-1,2,3,3a,4,4a,5,5a,6,6a-decahydro-4,6-ethenocyclopropa[f]isoindole (3.50 g, 21.7 mmol, 1.0 eq.) in DCM (60 mL) was added 2-Iodoxybenzoic acid (6.69 g, 23.9 mmol, 1.1 eq.). The mixture was stirred for 3 h at 60° C. The reaction was quenched with aqueous sodium thiosulfate (30 mL). The mixture was extracted with DCM (3×100 mL). The organic layers were combined, washed with saturated sodium bicarbonatebrine aqueous (2×50 mL), dried over anhydrous sodium sulfate, filtered and concentrated under reduced pressure to afford the crude product. The crude product was chromatographed on a silica gel column with EA:PE (60%-70%) to provide rac-(3aS,4S,4aS,5aR,6R,6aR)-1,3a,4,4a,5,5a,6,6a-octahydro-4,6-ethenocyclopropa[f]isoindole (1.7 g, crude) as an off-white solid. $^1$H NMR (400 MHz, Chloroform-d) δ 7.32-7.33 (m, 1H), 5.71-5.73 (m, 2H), 3.83-3.91 (m, 1H), 3.31-3.38 (m, 1H), 3.13-3.17 (m, 1H), 3.00-3.04

(m, 1H), 2.85-2.89 (m, 1H), 2.52-2.59 (m, 1H), 0.92-1.03 (m, 2H), 0.16-0.29 (m, 2H). LC-MS (ESI, m/z): 160 $[M+H]^+$.

To a solution of rac-(3aS,4S,4aS,5aR,6R,6aR)-1,3a,4,4a,5,5a,6,6a-octahydro-4,6-ethenocyclopropa[f]isoindole (1.7 g, 10.7 mmol, 1.0 eq.) in toluene (40 mL) was added zinc iodide (409 mg, 1.28 mmol, 0.12 eq.) and trimethylsilyl cyanide (4.77 g, 48.0 mmol, 4.5 eq.). The mixture was stirred overnight at rt. The reaction was quenched with water (30 mL). The mixture was extracted with EA (3×100 mL). The organic layers were combined, washed with brine (2×50 mL), dried over anhydrous sodium sulfate, filtered and concentrated under reduced pressure to afford the crude product. The crude product was chromatographed on a silica gel column with EA:PE (60%-80%) to provide rac-(3aR,4R,4aR,5aS,6S,6aS)-1,2,3,3a,4,4a,5,5a,6,6a-decahydro-4,6-ethenocyclopropa[f]isoindole-1-carbonitrile (1.1 g, 49%) as a light yellow oil. LC-MS (ESI, m/z): 187 $[M+H]^+$.

A mixture rac-(3aR,4R,4aR,5aS,6S,6aS)-1,2,3,3a,4,4a,5,5a,6,6a-decahydro-4,6-ethenocyclopropa[f]isoindole-1-carbonitrile (800 mg, 4.30 mmol, 1.0 eq.) in hydrogen chloride (7.5 mL, 4 M in MeOH) was stirred for 2 h at 50° C. The mixture was concentrated under reduced pressure to afford methyl rac-(3aR,4R,4aR,5aS,6S,6aS)-1,2,3,3a,4,4a,5,5a,6,6a-decahydro-4,6-ethenocyclopropa[f]isoindole-1-carboxylate hydrochloride (800 mg, crude) as a yellow solid. LC-MS (ESI, m/z): 220 $[M+H]^+$.

To a solution of methyl rac-(3aR,4R,4aR,5aS,6S,6aS)-1,2,3,3a,4,4a,5,5a,6,6a-decahydro-4,6-ethenocyclopropa[f]isoindole-1-carboxylate hydrochloride (800 mg, 3.65 mmol, 1.0 eq.) in DCM (10 mL) was added triethylamine (1.11 g, 10.9 mmol, 3.0 eq.) and di-tert-butyl dicarbonate (1.04 g, 4.74 mmol, 1.3 eq.). The mixture was stirred for 1 h at rt. The reaction was quenched with $H_2O$ (20 mL). The mixture was extracted with EA (3×50 mL). The organic layers were combined, washed with brine (2×30 mL), dried over anhydrous sodium sulfate, filtered and concentrated under reduced pressure to afford the crude product. The crude product was chromatographed on a silica gel column with EA:PE (10%-15%) to provide rac-2-(tert-butyl) 1-methyl (3aR,4R,4aR,5aS,6S,6aS)-3,3a,4,4a,5,5a,6,6a-octahydro-4,6-ethenocyclopropa[f]isoindole-1,2(1H)-dicarboxylate (830 mg, 71%) as a colorless oil. $^1H$ NMR (400 MHz, $CD_3OD$-$d_4$) δ 5.81-5.89 (m, 2H), 3.92-3.98 (m, 1H), 3.74-3.75 (m, 3H), 3.52-3.58 (m, 1H), 3.20-3.29 (m, 1H), 3.02-3.06 (m, 1H), 2.88-2.92 (m, 1H), 2.55-2.66 (m, 2H), 1.38-1.46 (m, 9H), 0.94-0.99 (m, 2H), 0.13-0.21 (m, 2H). LC-MS (ESI, m/z): 320 $[M+H]^+$.

To a mixture of rac-2-(tert-butyl) 1-methyl (3aR,4R,4aR,5aS,6S,6aS)-3,3a,4,4a,5,5a,6,6a-octahydro-4,6-ethenocyclopropa[f]isoindole-1,2(1H)-dicarboxylate (400 mg, 1.25 mmol, 1.0 eq.) in 1,4-dioxane (4 mL) was added hydrogen chloride (4 mL, 4 M in 1,4-dioxane) stirred at rt. The mixture was stirred for 2 h at rt and then concentrated under reduced pressure to afford rac-methyl (1S,3aR,4R,4aR,5aS,6S,6aS)-1,2,3,3a,4,4a,5,5a,6,6a-decahydro-4,6-ethenocyclopropa[f]isoindole-1-carboxylate hydrochloride (300 mg, crude) as a light yellow solid. LC-MS (ESI, m/z): 220 $[M+H]^+$.

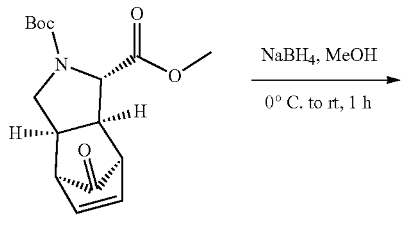

-continued

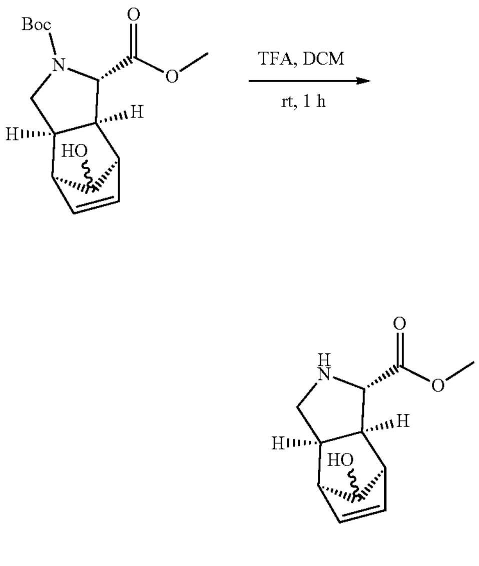

To a solution of 2-(tert-butyl) 1-methyl (1S,3aS,4S,7R,7aR)-8-oxo-1,3,3a,4,7,7a-hexahydro-2H-4,7-methanoisoindole-1,2-dicarboxylate (950 mg, 3.09 mmol, 1.0 eq.) in methanol (10 mL) was added sodium borohydride (114 mg, 3.09 mmol, 1.0 eq.) at 0° C. The mixture was stirred for 1 h at rt. The reaction was quenched with sat. ammonium chloride (aq.). The mixture was extracted with EA (3×80 mL). The organic layers were combined, washed with brine (2×50 mL), dried over anhydrous sodium sulfate, filtered and concentrated under reduced pressure to afford 2-(tert-butyl) 1-methyl (1S,3aS,4S,7R,7aR,8R)-8-hydroxy-1,3,3a,4,7,7a-hexahydro-2H-4,7-methanoisoindole-1,2-dicarboxylate (700 mg, crude) as a yellow oil. LC-MS (ESI, m/z): 210 $[M-Boc+H]^+$.

To a stirred mixture of 2-(tert-butyl) 1-methyl (1S,3aS,4S,7R,7aR)-8-hydroxy-1,3,3a,4,7,7a-hexahydro-2H-4,7-methanoisoindole-1,2-dicarboxylate (450 mg, 1.45 mmol, 1.0 eq.) in DCM (4.5 mL) was added trifluoroacetic acid (1.5 mL) at rt. The mixture was stirred for 1 h at rt and then concentrated under reduced pressure to afford methyl (1S,3aS,4S,7R,7aR,8R)-8-hydroxy-2,3,3a,4,7,7a-hexahydro-1H-4,7-methanoisoindole-1-carboxylate (305 mg, crude) as a yellow oil. LC-MS (ESI, m/z): 210 $[M+H]^+$.

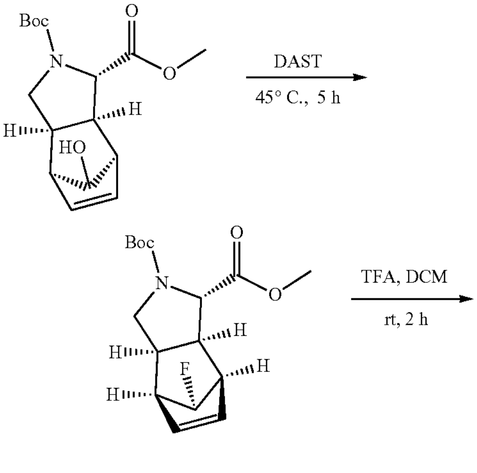

-continued

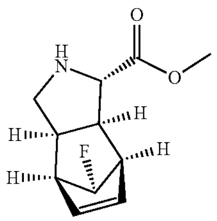

A mixture of 2-(tert-butyl) 1-methyl (1S,3aS,4S,7R,7aR,8R)-8-hydroxy-1,3,3a,4,7,7a-hexahydro-2H-4,7-methanoisoindole-1,2-dicarboxylate (1.0 g, 3.23 mmol, 1.0 eq.) in diethylaminosulfur trifluoride (20 mL) was stirred for 5 h at 45° C. The mixture was diluted with dichloromethane (100 mL). The reaction was quenched with sat. sodium bicarbonate (80 mL) at 0° C. The mixture was extracted with dichloromethane (3×80 mL). The organic layers were combined, washed with brine (2×50 mL), dried over anhydrous sodium sulfate, filtered and concentrated under reduced pressure. The crude product was purified by prep-HPLC (Column: XSelect CSH Prep C18 OBD Column, 19*150 mm, 5 m; Mobile Phase A: Water (0.05% TFA), Mobile Phase B: ACN; Flow rate: 25 mL/min; Gradient: 32% B to 52% B in 10 min, 52% B; Wave Length: 254 nm; RT1 (min): 8.78/9.3) to provide 2-(tert-butyl) 1-methyl (1S,3aS,4S,7R,7aR,8S)-8-fluoro-1,3,3a,4,7,7a-hexahydro-2H-4,7-methanoisoindole-1,2-dicarboxylate (350 mg, 35%) as a white oil. $^1$H NMR (400 MHz, DMSO-$d_6$) δ 6.05-6.24 (m, 2H), 4.25-4.57 (m, 1H), 3.81-4.03 (m, 1H), 3.56-3.76 (m, 3H), 3.34-3.48 (m, 1H), 3.10-3.26 (m, 1H), 2.83-3.09 (m, 4H), 1.19-1.51 (m, 9H). LC-MS (ESI, m/z): 256 $[M-56+H]^+$.

To a stirred mixture of 2-(tert-butyl) 1-methyl (1S,3aS,4S,7R,7aR,8*S)-8-fluoro-1,3,3a,4,7,7a-hexahydro-2H-4,7-methanoisoindole-1,2-dicarboxylate (350 mg, 1.12 mmol, 1.0 eq.) in dichloromethane (3 mL) was added trifluoroacetic acid (1 mL) at rt. The mixture was stirred for 2 h at rt. The mixture was concentrated under reduced pressure to provide methyl (1S,3aS,4S,7R,7aR,8*S)-8-fluoro-2,3,3a,4,7,7a-hexahydro-1H-4,7-methanoisoindole-1-carboxylate (240 mg, crude) as a yellow oil. LC-MS (ESI, m/z): 212 $[M+H]^+$.

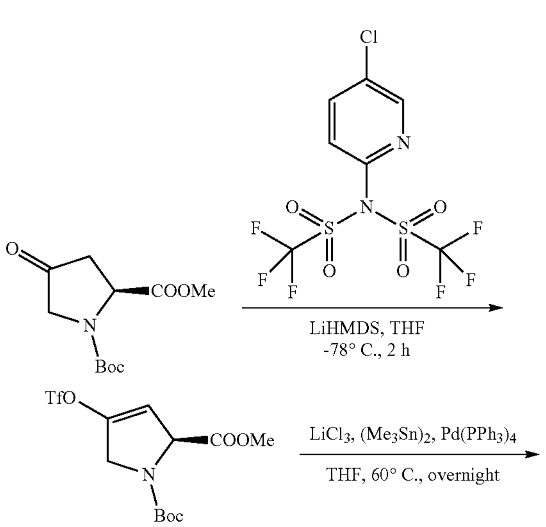

-continued

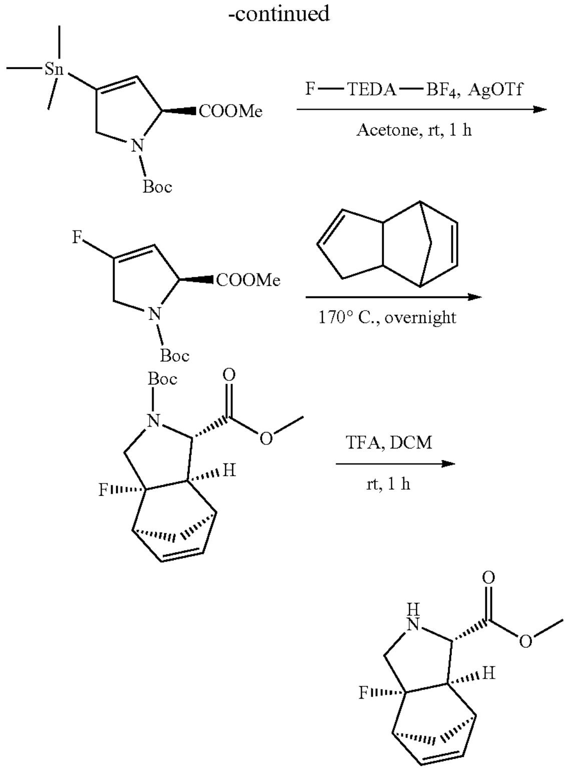

To a solution of 1-tert-butyl 2-methyl (2S)-4-oxopyrrolidine-1,2-dicarboxylate (15.0 g, 61.7 mmol, 1.0 eq.) in THF (240 mL) was added lithium bis(trimethylsilyl)amide (74 mL, 74.0 mmol, 1.2 eq., 1M in THF) at −78° C. under nitrogen. After stirring for 1 h at −78° C., a solution of comins' reagent (29.0 g, 74.0 mmol, 1.2 eq.) in THF (60 mL) was added dropwise. The mixture was stirred for 1 h at −78° C. under nitrogen. The reaction was quenched with water (600 mL). The mixture was extracted with EtOAc (3×500 mL). The organic layers were combined, washed with brine (2×500 mL), dried over anhydrous sodium sulfate, filtered and concentrated under reduced pressure to afford the crude product. The crude product was chromatographed on a silica gel column with EtOAc:PE (1:9) to provide the desired product 1-tert-butyl 2-methyl (2S)-4-(trifluoromethanesulfonyloxy)-2,5-dihydropyrrole-1,2-dicarboxylate (12.3 g, 48%) as a colorless oil. $^1$H NMR (400 MHz, Chloroform-d) δ 5.70-5.80 (m, 1H), 5.00-5.12 (m, 1H), 4.24-4.47 (m, 2H), 3.79 (s, 3H), 1.42-1.53 (m, 9H). LC-MS (ESI, m/z): 320 $[M-56+H]^+$.

To a mixture of 1-tert-butyl 2-methyl (2S)-4-(trifluoromethanesulfonyloxy)-2,5-dihydropyrrole-1,2-dicarboxylate (10.0 g, 26.6 mmol, 1.0 eq.), lithium chloride (3.95 g, 93.2 mmol, 3.5 eq.) and tetrakis(triphenylphosphine)platinum(0) (4.62 g, 4.00 mmol, 0.15 eq.) in THF (120 mL) was added hexamethyldistannane (13.1 g, 40.0 mmol, 1.5 eq.). The mixture was stirred overnight at 60° C. under nitrogen. The reaction was quenched with water (300 mL). The mixture was extracted with EtOAc (3×300 mL). The organic layers were combined, washed with brine (2×200 mL), dried over anhydrous sodium sulfate, filtered and concentrated under reduced pressure to afford the crude product. The crude product was chromatographed on a silica gel column with EtOAc:PE (6:94) to provide 1-tert-butyl 2-methyl (2S)-4-(trimethylstannyl)-2,5-dihydropyrrole-1,2-dicarboxylate (5.45 g, 49%) as a colorless oil. $^1$H NMR (400

MHz, Chloroform-d) δ 5.70-5.82 (m, 1H), 4.93-5.09 (m, 1H), 4.19-4.41 (m, 2H), 3.74-3.79 (m, 3H), 1.42-1.53 (m, 9H), 0.14-0.31 (m, 9H). LC-MS (ESI, m/z): 336 $[M-56+H]^+$.

To a mixture of silver trifluoromethanesulfonate (4.67 g, 18.2 mmol, 1.3 eq.) and 1-chloromethyl-4-fluoro-1,4-diazoniabicyclo[2.2.2]octane bis(tetrafluoroborate) (9.90 g, 27.9 mmol, 2.0 eq.) in dry acetone (165 mL) was added dropwise a solution of 1-tert-butyl 2-methyl (2S)-4-(trimethylstannyl)-2,5-dihydropyrrole-1,2-dicarboxylate (5.45 g, 14.0 mmol, 1.0 eq.) in dry acetone (55 mL) under nitrogen. The mixture was stirred for 1 h at rt. The reaction was quenched with saturated aqueous ammonium chloride (300 mL). The mixture was extracted with MTBE (3×300 mL). The organic layers were combined, washed with brine (2×200 mL), dried over anhydrous sodium sulfate, filtered and concentrated under reduced pressure to afford the crude product. The crude product was chromatographed on a silica gel column with EtOAc/PE (5:95) to provide 1-tert-butyl 2-methyl (2S)-4-fluoro-2,5-dihydropyrrole-1,2-dicarboxylate (780 mg, 20%) as a light yellow oil. $^1H$ NMR (400 MHz, Chloroform-d) δ 5.11-5.22 (m, 1H), 4.87-4.99 (m, 1H), 4.24-4.36 (m, 1H), 4.12-4.23 (m, 1H), 3.75-3.80 (m, 3H), 1.42-1.53 (m, 9H). LC-MS (ESI, m/z): 190 $[M-56+H]^+$.

A mixture of 1-tert-butyl 2-methyl (2S)-4-fluoro-2,5-dihydropyrrole-1,2-dicarboxylate (400 mg, 1.63 mmol, 1.0 eq.) in dicyclopentadiene (10 mL) was stirred overnight at 170° C. The mixture was chromatographed on a silica gel column with EtOAc:PE (3:7) to provide the crude product. The crude product was purified by C18 column with $CH_3CN$/Water (0.05% TFA). The desired fraction was concentrated under reduced pressure to provide 2-(tert-butyl) 1-methyl (1S,3aS,4S,7R,7aR)-3a-fluoro-1,3,3a,4,7,7a-hexahydro-2H-4,7-methanoisoindole-1,2-dicarboxylate (140 mg, crude) as a brown oil. LC-MS (ESI, m/z): 212 $[M-Boc+H]^+$.

To a solution of 2-(tert-butyl) 1-methyl (1S,3aS,4S,7R,7aR)-3a-fluoro-1,3,3a,4,7,7a-hexahydro-2H-4,7-methanoisoindole-1,2-dicarboxylate (140 mg, 0.450 mmol, 1.0 eq.) in DCM (1.5 mL) was added trifluoroacetic acid (0.5 mL). The mixture was stirred for 1 h at rt and then concentrated under reduced pressure to afford the methyl (1S,3aS,4S,7R,7aR)-3a-fluoro-2,3,3a,4,7,7a-hexahydro-1H-4,7-methanoisoindole-1-carboxylate (95 mg, crude) as a brown oil. LC-MS (ESI, m/z): 212 $[M+H]^+$.

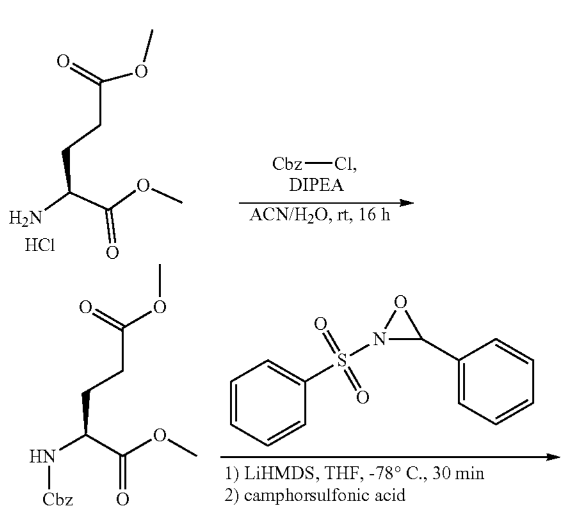

-continued

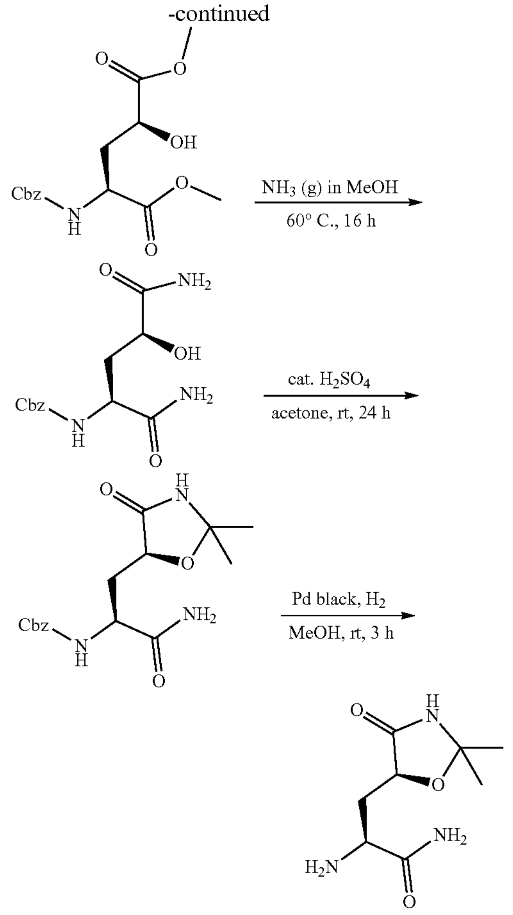

To a solution of dimethyl L-glutamate hydrogen chloride (5.00 g, 23.63 mmol, 1.0 eq.) in acetonitrile (200 mL) and water (30 mL) were added benzyl chloroformate (3.70 mL, 26.00 mmol, 1.1 eq.) and N,N-diisopropylethylamine (10.1 mL, 59.20 mmol, 2.5 eq.) under nitrogen. The mixture was stirred for 1 hour at rt and then concentrated under reduced pressure. The residue was purified by silica gel column chromatography, eluting with 0-50% tert-butyl methyl ether in dichloromethane to afford dimethyl ((benzyloxy)carbonyl)-L-glutamate (4.99 g, 68% yield) as colorless oil. $^1H$ NMR (400 MHz, DMSO-$d_6$) δ 7.77 (d, J=7.8 Hz, 1H), 7.24-7.45 (m, 5H), 5.04 (s, 2H), 4.06-4.09 (m, 1H), 3.63 (s, 2H), 3.58 (s, 3H), 2.31-2.48 (m, 2H), 1.93-2.06 (m, 1H), 1.82-1.90 (m, 1H). LC-MS (ESI, m/z): 310 $[M+H]^+$.

To a solution of dimethyl N-benzyloxycarbonyl-L-glutamate (1.40 g, 4.76 mmol, 1.0 eq.) and 3-phenyl-N-phenylsulfonyl oxaziridine (1.87 g, 7.14 mmol, 1.5 eq.) in tetrahydrofuran (50 mL) was added lithium bis(trimethylsilyl) amide (1M solution in THF, 14.3 mL, 14.3 mmol, 3.0 eq.) dropwise at −78° C. under nitrogen. After stirred for 30 mins at −78° C., the reaction was quenched by the addition of a solution of camphorsulfonic acid (4.76 g, 20.94 mmol, 4.4 eq.) in THF (21 mL). The mixture was diluted with EA (100 mL), then aqueous HCl solution (conc.aq HCl solution: water, v:v=1:4, 100 mL). The mixture was warmed to rt and then stirred for 16 h. The mixture was extracted with EA (3×100 mL). The combined organic layer was washed with brine (100 mL), dried over anhydrous sodium sulfate and filtered. The filtrate was concentrated under reduced pressure to afford dimethyl (2S,4S)-2-(((benzyloxy)carbonyl)amino)-4-hydroxypentanedioate (2.00 g, crude) as light brown semi-solid, which was used in the next step directly without any further purification. LC-MS (ESI, m/z): 326 $[M+H]^+$.

A suspension of dimethyl (2S,4S)-2-(((benzyloxy)carbonyl)amino)-4-hydroxypentanedioate (2.00 g crude, 1.00 eq.) in $NH_3$ (g) in MeOH (7M solution, 40 mL) was stirred for 16 h at 60° C. The mixture was cooled to rt. The precipitated white solid was collected by filtration, washed with MeOH (2×10 mL) and dried in high vacuo to afford benzyl ((2S,4S)-1,5-diamino-4-hydroxy-1,5-dioxopentan-2-yl)carbamate (902 mg, 67% yield for two steps) as a white solid. LC-MS (ESI, m/z): 296 $[M+H]^+$.

To a suspension of benzyl ((2S,4S)-1,5-diamino-4-hydroxy-1,5-dioxopentan-2-yl)carbamate (300 mg, 1.02 mmol, 1.0 eq.) in acetone (10 mL) was added conc. $H_2SO_4$ (0.1 mL). The mixture was stirred for 24 h at rt. The mixture was concentrated under reduced pressure. The residue was dissolved in DMSO and purified by reverse phase chromatography (Column: Agela Cis Column, 120 g; Mobile Phase A: Water (10 mM $NH_4HCO_3$+0.1% $NH_3 \cdot H_2O$), Mobile Phase B: ACN; Flow rate: 50 mL/min; Gradient: 0% B to 100% B in 60 min; Wavelength: 200 nm). The collected fraction was lyophilized directly to afford benzyl ((S)-1-amino-3-((S)-2,2-dimethyl-4-oxooxazolidin-5-yl)-1-oxopropan-2-yl)carbamate (144 mg, 42% yield) as a white solid. LC-MS (ESI, m/z): 336 $[M+H]^+$.

A mixture of benzyl ((S)-1-amino-3-((S)-2,2-dimethyl-4-oxooxazolidin-5-yl)-1-oxopropan-2-yl)carbamate (120 mg, 0.36 mmol, 1.0 eq.) and Pd black (67 mg, 0.63 mmol, 1.75 eq.) in methanol (20 mL) was degassed and refilled with hydrogen (3×). The mixture was stirred for 3 h at rt under hydrogen (hydrogen bag, 1-2 atm.). The mixture was filtered through a celite pad. The filtrate was concentrated under reduced pressure to afford (S)-2-amino-3-((S)-2,2-dimethyl-4-oxooxazolidin-5-yl)propanamide (70.0 mg, crude) as light yellow oil, which was used in the next step directly without any further purification. LC-MS (ESI, m/z): 20 2$[M+H]^+$.

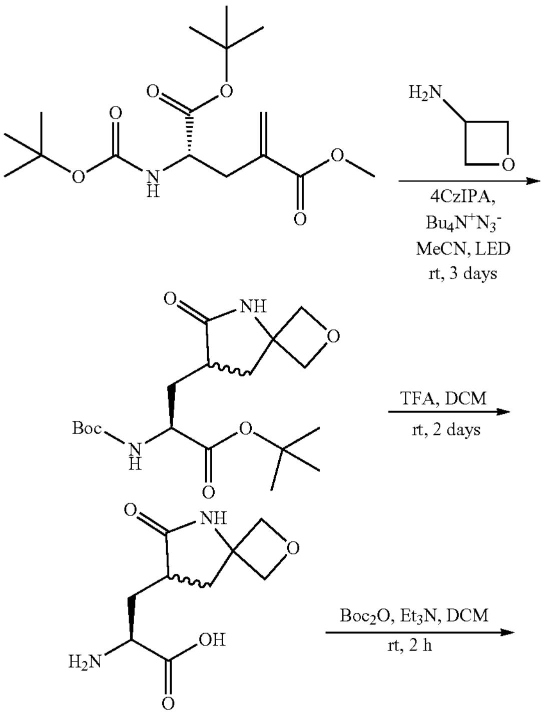

-continued

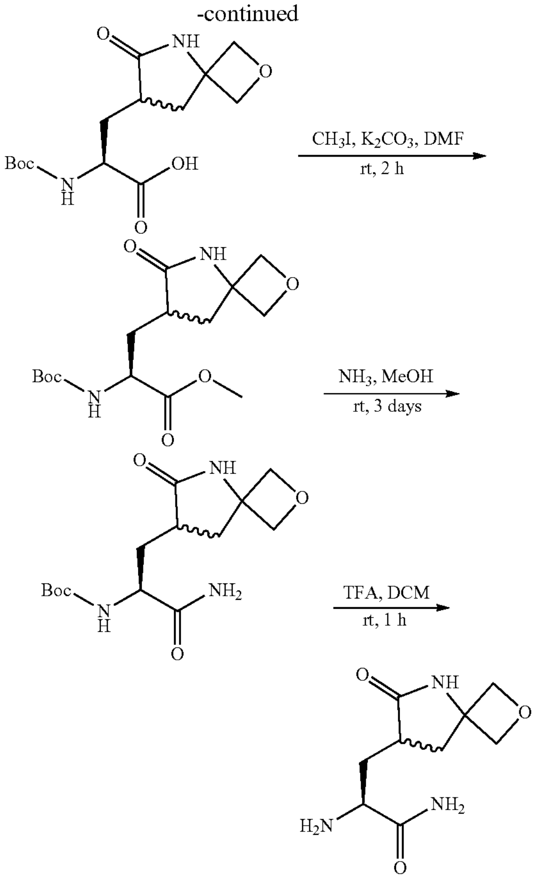

To a mixture of 1-tert-butyl 5-methyl (2S)-2-[(tert-butoxycarbonyl)amino]-4-methylidenepentanedioate (3.00 g, 9.11 mmol, 1.0 eq.), 2,4,5,6-tetra-9H-carbazol-9-yl-1,3-benzenedicarbonitrile (72.0 mg, 0.091 mmol, 0.01 eq.) and tetrabutylammonium azide (259 mg, 0.911 mmol, 0.1 eq.) in MeCN (40 mL) was added oxetan-3-amine (666 mg, 9.11 mmol, 1.0 eq.) under nitrogen. The mixture was stirred for 3 days at rt under nitrogen under 450 nm LED lamp. The mixture was concentrated under reduced pressure to afford the crude product. The crude product was chromatographed on a silica gel column with MeOH:DCM (1:12) to provide tert-butyl (2S)-2-[(tert-butoxycarbonyl)amino]-3-{6-oxo-2-oxa-5-azaspiro[3.4]octan-7-yl}propanoate (1.08 g, 32%) as a light yellow solid. $^1H$ NMR (400 MHz, DMSO-$d_6$) δ 8.52-8.62 (m, 1H), 6.70-7.40 (m, 1H), 4.60-4.70 (m, 1H), 4.40-4.59 (m, 3H), 3.75-4.10 (m, 1H), 2.54-2.65 (m, 1H), 2.27-2.39 (m, 1H), 1.80-2.10 (m, 2H), 1.48-1.60 (m, 1H), 1.32-1.47 (m, 18H). LC-MS (ESI, m/z): 371 $[M+H]^+$.

To a mixture of tert-butyl (2S)-2-[(tert-butoxycarbonyl)amino]-3-{6-oxo-2-oxa-5-azaspiro[3.4]octan-7-yl}propanoate (1.08 g, 2.70 mmol, 1.0 eq.) in DCM (30 mL) was added trifluoroacetic acid (15 mL). The mixture was stirred for 2 days at rt and then concentrated under reduced pressure to afford (2S)-2-amino-3-{6-oxo-2-oxa-5-azaspiro[3.4]octan-7-yl}propanoic acid (578 mg, crude) as a brown oil. LC-MS (ESI, m/z): 215 $[M+H]^+$.

To a mixture of (2S)-2-amino-3-{6-oxo-2-oxa-5-azaspiro[3.4]octan-7-yl}propanoic acid (578 mg, 2.70 mmol, 1.0 eq.) in DCM (10 mL) were added triethylamine (1.10 g, 10.9 mmol, 4.03 eq.) and di-tert-butyl dicarbonate (707 mg, 3.24 mmol, 1.2 eq.). The mixture was stirred for 2 h at rt and then concentrated under reduced pressure to afford (2S)-2-[(tert-butoxycarbonyl)amino]-3-{6-oxo-2-oxa-5-azaspiro[3.4]octan-7-yl}propanoic acid (850 mg, crude) as a brown oil. LC-MS (ESI, m/z): 315 $[M+H]^+$.

To a mixture of (2S)-2-[(tert-butoxycarbonyl)amino]-3-{6-oxo-2-oxa-5-azaspiro[3.4]octan-7-yl}propanoic acid (847 mg, 2.70 mmol, 1.0 eq.) in DMF (15 mL) were added potassium carbonate (1.2 g, 8.08 mmol, 3.0 eq.) and methyl iodide (459 mg, 3.23 mmol, 1.2 eq.). The mixture was stirred for 2 h at rt. The reaction was quenched with water (30 mL). The mixture was extracted with EtOAc (3×30 mL). The organic layers were combined, washed with brine (2×30 mL), dried over anhydrous sodium sulfate, filtered and concentrated under reduced pressure to afford methyl (2S)-2-[(tert-butoxycarbonyl)amino]-3-{6-oxo-2-oxa-5-azaspiro[3.4]octan-7-yl}propanoate (438 mg, crude) as a yellow oil. LC-MS (ESI, m/z): 329 $[M+H]^+$.

A mixture of methyl (2S)-2-[(tert-butoxycarbonyl)amino]-3-{6-oxo-2-oxa-5-azaspiro[3.4]octan-7-yl}propanoate (438 mg, 1.33 mmol, 1.0 eq.) in ammonia (15 mL, 7 M in MeOH) was stirred for 3 days at rt. The mixture was concentrated under reduced pressure to afford the crude product. The crude product was chromatographed on a silica gel column with MeOH:DCM (8:92) to provide tert-butyl N-[(1S)-1-carbamoyl-2-{6-oxo-2-oxa-5-azaspiro[3.4]octan-7-yl}ethyl]carbamate (180 mg, 40%) as a white solid. $^1H$ NMR (400 MHz, DMSO-$d_6$) δ 8.51-8.59 (m, 1H), 7.24-7.32 (m, 1H), 6.96-7.05 (s, 1H), 6.86-6.94 (m, 1H), 4.61-4.70 (m, 1H), 4.41-4.57 (m, 3H), 3.74-4.15 (m, 1H), 2.54-2.69 (m, 1H), 2.29-2.39 (m, 1H), 1.70-2.05 (m, 2H), 1.33-1.55 (m, 10H). LC-MS (ESI, m/z): 314 $[M+H]^+$.

To a mixture of tert-butyl N-[(1S)-1-carbamoyl-2-{6-oxo-2-oxa-5-azaspiro[3.4]octan-7-yl}ethyl]carbamate (100 mg, 0.319 mmol, 1.0 eq.) in DCM (3 mL) was added trifluoroacetic acid (1 mL). The mixture was stirred for 1 h at rt and then concentrated under reduced pressure to afford (2S)-2-amino-3-{2-oxa-5-azaspiro[3.4]octan-7-yl}propanamide (68 mg, crude) as a brown oil. LC-MS (ESI, m/z): 214 $[M+H]^+$.

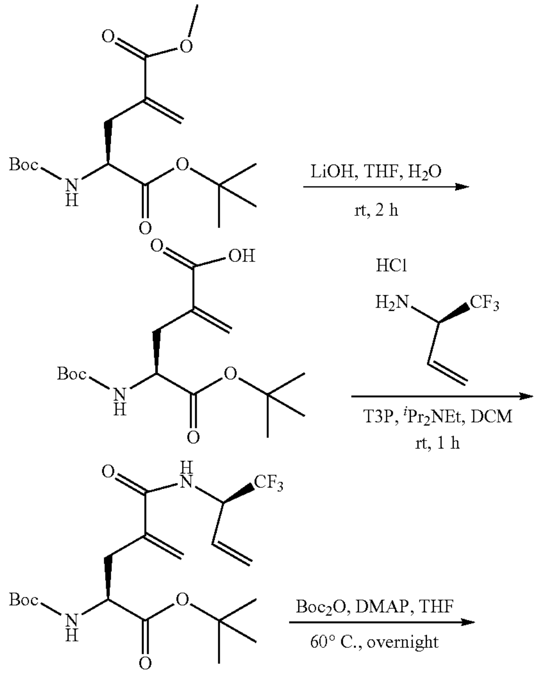

-continued

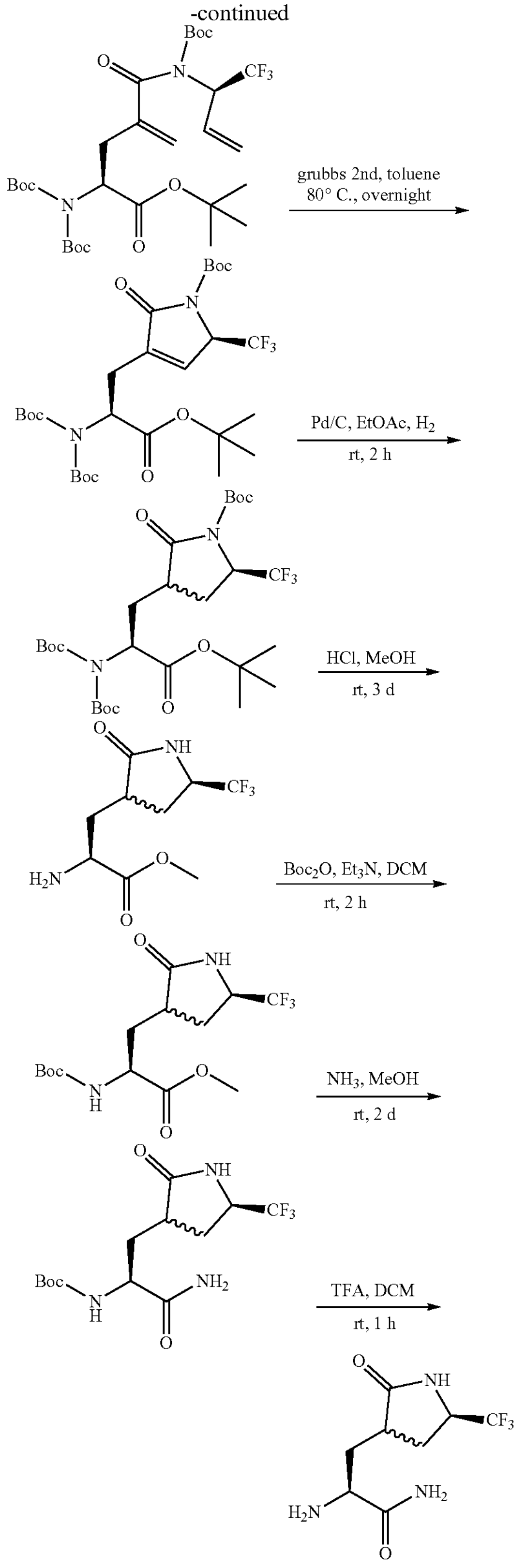

To a mixture of 1-tert-butyl 5-methyl (2S)-2-[(tert-butoxycarbonyl)amino]-4-methylidenepentanedioate (5.00 g, 15.2 mmol, 1.0 eq.) in THF (50 mL)/water (50 mL) was added lithium hydroxide (1.09 g, 45.5 mmol, 3.0 eq.). The mixture was stirred for 2 h at rt. Water (50 mL) was added, and the mixture was adjusted to pH=6 with hydrochloric acid (1 M). The mixture was extracted with EtOAc (3×100 mL). The organic layers were combined, dried over anhydrous sodium sulfate, filtered and concentrated under reduced pressure to afford the crude product. The crude product was purified by C18 column with $CH_3CN$/Water (0.05% TFA). The desired fraction was concentrated under reduced pressure to provide (4S)-5-(tert-butoxy)-4-[(tert-butoxycarbonyl)amino]-2-methylidene-5-oxopentanoic acid (2.56 g, 51%) as a light yellow semi-solid. $^1$H NMR (400 MHz, DMSO-$d_6$) δ 12.57 (s, 1H), 6.64-7.14 (m, 1H), 6.06-6.13 (m, 1H), 5.60-5.74 (m, 1H), 3.92-4.14 (m, 1H), 2.55-2.67 (m, 1H), 2.37-2.48 (m, 1H), 1.30-1.45 (m, 18H). LC-MS (ESI, m/z): 316 $[M+H]^+$.

To a mixture of (2R)-1,1,1-trifluorobut-3-en-2-amine hydrochloride (1.33 g, 8.23 mmol, 1.0 eq.) and (4S)-5-(tert-butoxy)-4-[(tert-butoxycarbonyl)amino]-2-methylidene-5-oxopentanoic acid (2.60 g, 8.23 mmol, 1.0 eq.) in DCM (40 mL) were added N-ethyl-N-isopropylpropan-2-amine (4.26 g, 32.9 mmol, 4.0 eq.) and 2,4,6-tripropyl-1,3,5,2,4,6-trioxatriphosphorinane-2,4,6-trioxide (5.24 g, 8.23 mmol, 1.0 eq., 50% in EtOAc). The mixture was stirred for 1 h at rt. The reaction was quenched with water (50 mL). The mixture was extracted with DCM (3×30 mL). The organic layers were combined, washed with brine (2×30 mL), dried over anhydrous sodium sulfate, filtered and concentrated under reduced pressure to afford the crude product. The crude product was chromatographed on a silica gel column with EtOAc:PE (13:87) to provide tert-butyl (2S)-2-[(tert-butoxycarbonyl)amino]-4-{[(2R)-1,1,1-trifluorobut-3-en-2-yl]carbamoyl}pent-4-enoate (1.66 g, 45%) as a light yellow semi-solid. LC-MS (ESI, m/z): 423 $[M+H]^+$.

To a mixture of tert-butyl (2S)-2-[(tert-butoxycarbonyl)amino]-4-{[(2R)-1,1,1-trifluorobut-3-en-2-yl]carbamoyl}pent-4-enoate (1.66 g, 3.93 mmol, 1.0 eq.) in THF (40 mL) were added di-tert-butyl dicarbonate (3.43 g, 15.7 mmol, 4.0 eq.) and N,N-dimethylpyridin-4-amine (240 mg, 1.96 mmol, 0.5 eq.). The mixture was stirred overnight at 60° C. The reaction was quenched with water (80 mL). The mixture was extracted with DCM (3×80 mL). The organic layers were combined, washed with brine (2×80 mL), dried over anhydrous sodium sulfate, filtered and concentrated under reduced pressure to afford the crude product. The crude product was chromatographed on a silica gel column with EtOAc:PE (7:93) to provide tert-butyl (2S)-2-[bis(tert-butoxycarbonyl)amino]-4-{[(tert-butoxycarbonyl)[(2R)-1,1,1-trifluorobut-3-en-2-yl]amino]carbonyl}pent-4-enoate (1.68 g, 67%) as a light yellow oil. LC-MS (ESI, m/z): 423 $[M-200+H]^+$.

To a mixture of tert-butyl (2S)-2-[bis(tert-butoxycarbonyl)amino]-4-{[(tert-butoxycarbonyl)[(2R)-1,1,1-trifluorobut-3-en-2-yl]amino]carbonyl}pent-4-enoate (1.0 g, 1.61 mmol, 1.0 eq.) in toluene (100 mL) was added Grubbs $2^{nd}$ (409 mg, 0.482 mmol, 0.3 eq.) under nitrogen. The mixture was stirred overnight at 80° C. The reaction was quenched with water (200 mL). The mixture was extracted with EtOAc (3×200 mL). The organic layers were combined, washed with brine (2×200 mL), dried over anhydrous sodium sulfate, filtered and concentrated under reduced pressure to afford the crude product. The crude product was chromatographed on a silica gel column with EtOAc:PE (11:89) to provide tert-butyl (5R)-3-[(2S)-2-[bis(tert-butoxycarbonyl)amino]-3-(tert-butoxy)-3-oxopropyl]-2-oxo-5-(trifluoromethyl)-5H-pyrrole-1-carboxylate (580 mg, 56%) as a light yellow semi-solid. LC-MS (ESI, m/z): 395 $[M-200+H]^+$.

To a mixture of tert-butyl (5R)-3-[(2S)-2-[bis(tert-butoxycarbonyl)amino]-3-(tert-butoxy)-3-oxopropyl]-2-oxo-5-(trifluoromethyl)-5H-pyrrole-1-carboxylate (1.00 g, 1.68 mmol, 1.0 eq.) in EtOAc (20 mL) was added 10% Palladium on activated carbon (500 mg). The mixture was stirred for 2 h at rt under hydrogen. The mixture was filtered through a celite pad, and the filtrate was concentrated under reduced pressure to tert-butyl (5R)-3-[(2S)-2-[bis(tert-butoxycarbonyl)amino]-3-(tert-butoxy)-3-oxopropyl]-2-oxo-5-(trifluoromethyl)pyrrolidine-1-carboxylate (980 mg, 96%) as a yellow oil. LC-MS (ESI, m/z): 397 $[M-200+H]^+$.

To a solution of tert-butyl (5R)-3-[(2S)-2-[bis(tert-butoxycarbonyl)amino]-3-(tert-butoxy)-3-oxopropyl]-2-oxo-5-(trifluoromethyl)pyrrolidine-1-carboxylate (200 mg, 0.335 mmol, 1.0 eq.) in MeOH (5 mL) was added hydrochloric acid (5 mL, 9 M in water). The mixture was stirred for 3 days at rt and then concentrated under reduced pressure to afford methyl (2S)-2-amino-3-[(5R)-2-oxo-5-(trifluoromethyl)pyrrolidin-3-yl]propanoate (85.0 mg, crude) as a light brown semi-solid. LC-MS (ESI, m/z): 255 $[M+H]^+$.

To a mixture of methyl (2S)-2-amino-3-[(5R)-2-oxo-5-(trifluoromethyl)pyrrolidin-3-yl]propanoate (85.0 mg, 0.334 mmol, 1.0 eq.) in DCM (5 mL) were added di-tert-butyl dicarbonate (88.0 mg, 0.401 mmol, 1.2 eq.) and triethylamine (102 mg, 1.00 mmol, 3.0 eq.). The mixture was stirred for 2 h at rt. The reaction was quenched with water (10 mL). The mixture was extracted with DCM (3×10 mL). The organic layers were combined, washed with brine (2×10 mL), dried over anhydrous sodium sulfate, filtered and concentrated under reduced pressure to provide methyl (2S)-2-[(tert-butoxycarbonyl)amino]-3-[(5R)-2-oxo-5-(trifluoromethyl)pyrrolidin-3-yl]propanoate (100 mg, 75%) as a light brown oil. LC-MS (ESI, m/z): 255 $[M\text{-}Boc+H]^+$.

A mixture of methyl (2S)-2-[(tert-butoxycarbonyl)amino]-3-[(5R)-2-oxo-5-(trifluoromethyl)pyrrolidin-3-yl]propanoate (100 mg, 0.282 mmol, 1.0 eq.) in ammonia (3 mL, 7 M in MeOH) was stirred for 2 days at rt. The mixture was concentrated under reduced pressure to afford the crude product. The crude product was chromatographed on a silica gel column with MeOH:DCM (6:94) to provide tert-butyl N-[(1S)-1-carbamoyl-2-[(5R)-2-oxo-5-(trifluoromethyl)pyrrolidin-3-yl]ethyl]carbamate (40.0 mg, 39%) as an off-white solid. LC-MS (ESI, m/z): 240 $[M\text{-}Boc+H]^+$.

To a mixture of tert-butyl N-[(1S)-1-carbamoyl-2-[(5R)-2-oxo-5-(trifluoromethyl)pyrrolidin-3-yl]ethyl]carbamate (40 mg, 0.118 mmol, 1.0 eq.) in DCM (1.5 mL) was added trifluoroacetic acid (0.5 mL). The resulting mixture was stirred for 1 h at rt and then concentrated under reduced pressure to afford (2S)-2-amino-3-[(5R)-2-oxo-5-(trifluoromethyl)pyrrolidin-3-yl]propanamide (28 mg, crude) as a brown oil. LC-MS (ESI, m/z): 240 $[M+H]^+$.

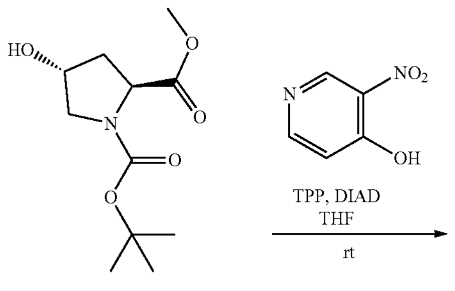

-continued

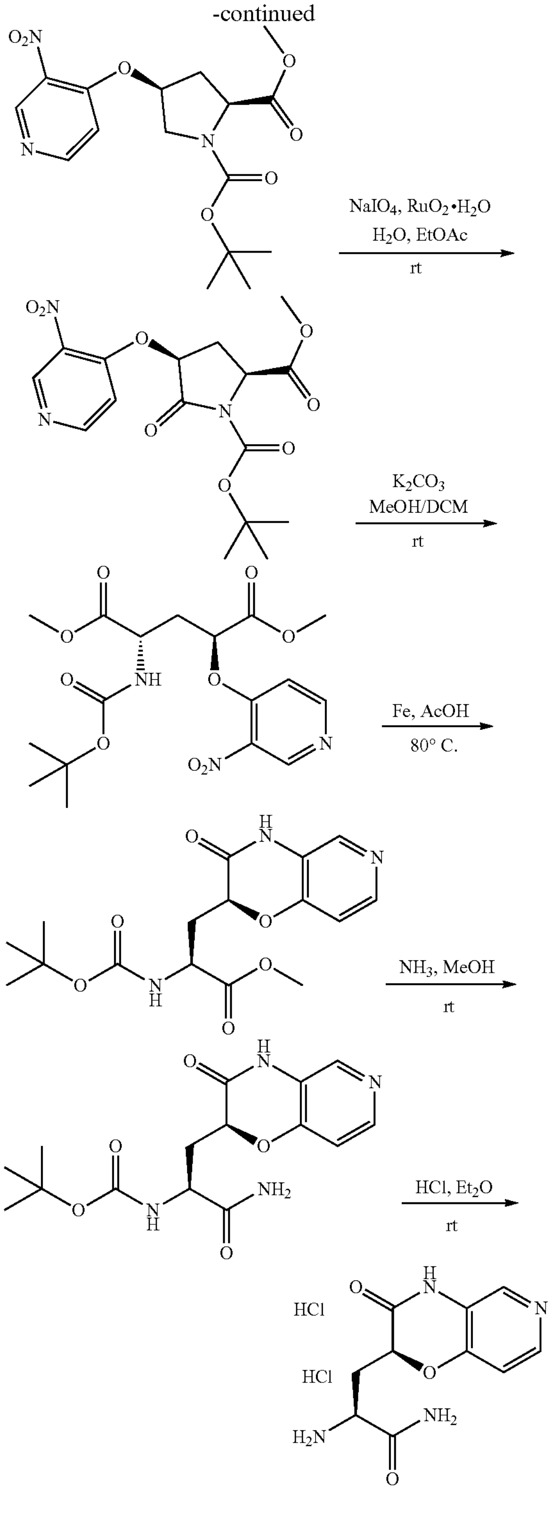

To a solution of 1-(tert-butyl) 2-methyl (2S,4R)-4-hydroxypyrrolidine-1,2-dicarboxylate (2.0 g, 8.16 mmol, 1.0 eq.) in THF (20 mL) cooled at 0° C. were added 3-nitropyridin-4-ol (1.7 g, 12.2 mmol, 1.5 eq.), triphenylphosphine (3.2 g, 12.2 mmol, 1.5 eq.) and DIAD (2.47 mL, 12.2 mmol, 1.5 eq.). The mixture was stirred at rt for 5 h and then concentrated under reduced pressure. The residue was purified by flash chromatography on silica gel using a gradient of EA (60 to 100%) in PE to afford 1-(tert-butyl) 2-methyl (2S,4S)-4-((3-nitropyridin-4-yl)oxy)pyrrolidine-1,2-dicarboxylate (2.5 g, 86%) as a yellow oil.

To a solution of $NaIO_4$ (7.2 g, 34.1 mmol, 5.0 eq.) in water (15 mL) was added $Ru_2O{\cdot}H_2O$ (135 g, 1.02 mmol, 0.15 eq.). The mixture was stirred at rt for 10 min. A solution of 1-(tert-butyl) 2-methyl (2S,4S)-4-((3-nitropyridin-4-yl)oxy) pyrrolidine-1,2-dicarboxylate (2.5 g, 6.81 mmol, 1.0 eq.) in EA (15 mL) was added. The mixture was stirred at rt for 16 h. The mixture was diluted with water (20 mL) and extracted with EA (2×20 mL). The organic phases were combined, diluted with IPA (50 mL), stirred for 10 min and filtered through celite. The filtrate was concentrated under reduced pressure. The residue was purified by flash chromatography on silica gel using a gradient of EA (60 to 100%) in PE to afford 1-(tert-butyl) 2-methyl (2S,4S)-4-((3-nitropyridin-4-yl)oxy)-5-oxopyrrolidine-1,2-dicarboxylate (2.3 g, 88%) as a pale yellow solid.

To a solution of 1-(tert-butyl) 2-methyl (2S,4S)-4-((3-nitropyridin-4-yl)oxy)-5-oxopyrrolidine-1,2-dicarboxylate (2.3 g, 6.04 mmol, 1.0 eq.) in MeOH (11.5 mL) and DCM (11.5 mL) cooled at 0° C. was added $K_2CO_3$ (83 mg, 0.603 mmol, 1.0 eq.). The mixture was stirred at rt for 1 h. The mixture was diluted with water (20 mL) and extracted with DCM (2×20 mL). The organic phases were combined, dried over $Na_2SO_4$, filtered and concentrated under reduced pressure. The residue was purified by flash chromatography on silica gel using a gradient of MeOH (1 to 10%) in DCM to afford dimethyl (2S,4S)-2-((tert-butoxycarbonyl)amino)-4-((3-nitropyridin-4-yl)oxy)pentanedioate (2.0 g, 80%) as a white solid.

To a solution of dimethyl (2S,4S)-2-((tert-butoxycarbonyl)amino)-4-((3-nitropyridin-4-yl)oxy)pentanedioate (2.0 g, 4.84 mmol, 1.0 eq.) in acetic acid (20 mL) was added Fe (1.35 g, 24.2 mmol, 5.0 eq.). The mixture was heated at 80° C. for 2 h and then concentrated under reduced pressure. The residue was basified with sat. $NaHCO_3$ and extracted with EA (2×20 mL). The organic phases were combined, dried over $Na_2SO_4$, filtered and concentrated under reduced pressure. The residue was purified by flash chromatography on silica gel using a gradient of MeOH (1 to 10%) in DCM to afford methyl (S)-2-((tert-butoxycarbonyl)amino)-3-((S)-3-oxo-3,4-dihydro-2H-pyrido[4,3-b][1,4]oxazin-2-yl)propanoate (1.4 g, 82%) as a white solid.

A solution of methyl (S)-2-((tert-butoxycarbonyl)amino)-3-((S)-3-oxo-3,4-dihydro-2H-pyrido[4,3-b][1,4]oxazin-2-yl)propanoate (500 mg, 1.42 mmol, 1.0 eq.) in 7M $NH_3$ in MeOH (5 mL) was stirred at rt for 48 h in a sealed tube. The mixture was concentrated under reduced pressure. The residue was purified by prep-HPLC (Column: X-SELECT-C18 Column, 19*250 mm, 5 m; Mobile Phase A: 10 mM $NH_4HCO_3$ in water, Mobile Phase B: ACN; Flow rate: 17 mL/min; Gradient: 2% B to 40% B in 8 min) to afford tert-butyl ((S)-1-amino-1-oxo-3-((S)-3-oxo-3,4-dihydro-2H-pyrido[4,3-b][1,4]oxazin-2-yl)propan-2-yl)carbamate (300 mg, 63%) as an off-white solid.

A solution of tert-butyl ((S)-1-amino-1-oxo-3-((S)-3-oxo-3,4-dihydro-2H-pyrido[4,3-b][1,4]oxazin-2-yl)propan-2-yl) carbamate (200 mg, 0.595 mmol, 1.0 eq.) in 2M HCl in $Et_2O$ (5 mL) was stirred at rt for 2 h. The mixture was concentrated under reduced pressure to afford (S)-2-amino-3-((S)-3-oxo-3,4-dihydro-2H-pyrido[4,3-b][1,4]oxazin-2-yl)propenamide dihydrochloride (150 mg, 82%) as a white solid.

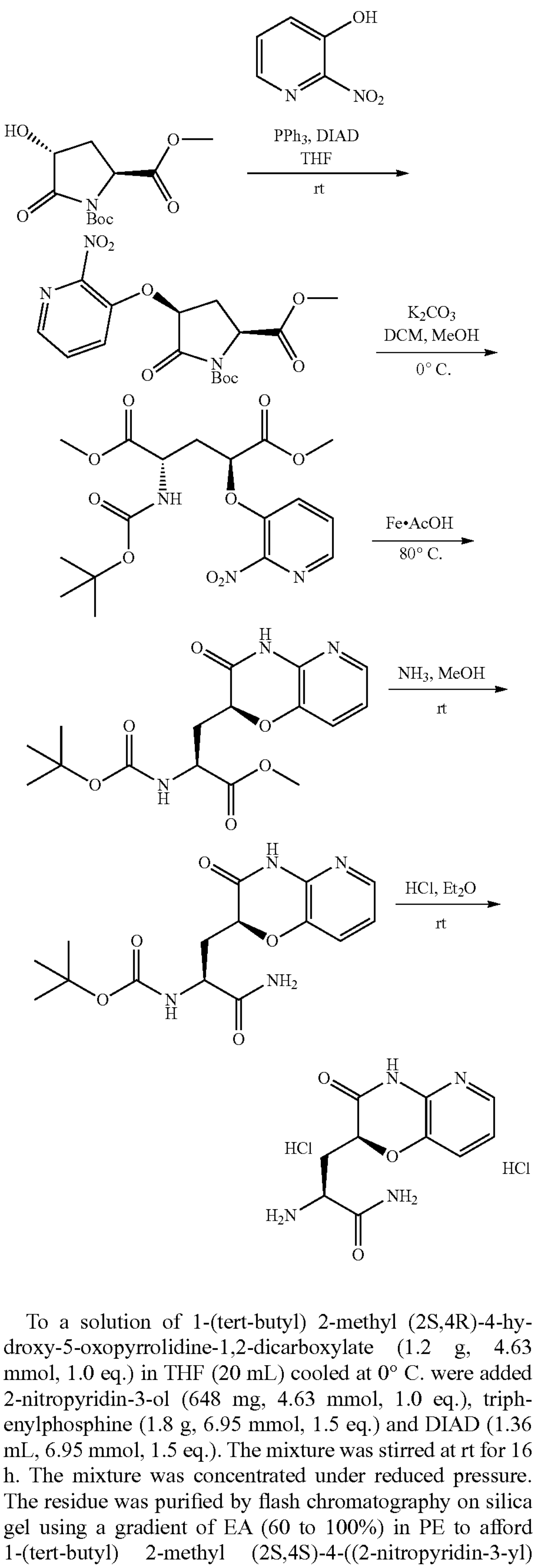

To a solution of 1-(tert-butyl) 2-methyl (2S,4R)-4-hydroxy-5-oxopyrrolidine-1,2-dicarboxylate (1.2 g, 4.63 mmol, 1.0 eq.) in THF (20 mL) cooled at 0° C. were added 2-nitropyridin-3-ol (648 mg, 4.63 mmol, 1.0 eq.), triphenylphosphine (1.8 g, 6.95 mmol, 1.5 eq.) and DIAD (1.36 mL, 6.95 mmol, 1.5 eq.). The mixture was stirred at rt for 16 h. The mixture was concentrated under reduced pressure. The residue was purified by flash chromatography on silica gel using a gradient of EA (60 to 100%) in PE to afford 1-(tert-butyl) 2-methyl (2S,4S)-4-((2-nitropyridin-3-yl)oxy)-5-oxopyrrolidine-1,2-dicarboxylate (1 g, 56%) as a yellow oil.

To a solution of 1-(tert-butyl) 2-methyl (2S,4S)-4-((2-nitropyridin-3-yl)oxy)-5-oxopyrrolidine-1,2-dicarboxylate (950 mg, 2.49 mmol, 1.0 eq.) in MeOH (10 mL) and DCM (10 mL) cooled at 0° C. was added $K_2CO_3$ (34 mg, 0.249 mmol, 0.1 eq.). The mixture was stirred at 0° C. for 1 h. Water (20 mL) was added, and the phases were separated. The aqueous phase was extracted with DCM (2×20 mL). The organic phases were combined, dried over $Na_2SO_4$, filtered and concentrated under reduced pressure. The residue was purified by flash chromatography on silica gel using a gradient of MeOH (1 to 10%) in DCM to afford dimethyl (2S,4S)-2-((tert-butoxycarbonyl)amino)-4-((2-nitropyridin-3-yl)oxy)pentanedioate (900 mg, 80%) as a white solid.

To a solution of dimethyl (2S,4S)-2-((tert-butoxycarbonyl)amino)-4-((2-nitropyridin-3-yl)oxy)pentanedioate (850 mg, 2.06 mmol, 1.0 eq.) in acetic acid (10 mL) was added Fe (576 mg, 10.3 mmol, 5.0 eq.). The mixture was heated at 80° C. for 2 h. The mixture was concentrated under reduced pressure. The residue was taken up with sat. $NaHCO_3$ and extracted with EA (2×20 mL). The organic phases were combined, dried over $Na_2SO_4$, filtered and concentrated under reduced pressure. The residue was purified by flash chromatography on silica gel using a gradient of MeOH (1 to 10%) in DCM to afford methyl (S)-2-((tert-butoxycarbonyl)amino)-3-((S)-3-oxo-3,4-dihydro-2H-pyrido[3,2-b][1,4]oxazin-2-yl)propanoate (550 mg, 76%) as a white solid.

A solution of methyl (S)-2-((tert-butoxycarbonyl)amino)-3-((S)-3-oxo-3,4-dihydro-2H-pyrido[3,2-b][1,4]oxazin-2-yl)propanoate (500 mg, 1.42 mmol, 1.0 eq.) in 7M $NH_3$ in MeOH (5 mL) was stirred at rt for 48 h in a sealed tube. The mixture was concentrated under reduced pressure. The residue was purified by prep-HPLC (Column: Sunfire-C18 Column, 19*150 mm, 5 m; Mobile Phase A: 10 mM $NH_4HCO_3$ in water, Mobile Phase B: ACN; Flow rate: 17 mL/min; Gradient: 20% B to 55% B in 8 min) to afford tert-butyl ((S)-1-amino-1-oxo-3-((S)-3-oxo-3,4-dihydro-2H-pyrido[3,2-b][1,4]oxazin-2-yl)propan-2-yl)carbamate (300 mg, 63%) as an off-white solid. $^1H$ NMR (400 MHz, DMSO-$d_6$) δ 11.25 (s, 1H), 7.91 (dd, 1H), 7.34 (d, 1H), 7.06-7.25 (d, 2H), 7.00 (m, 2H), 4.55 (m, 1H), 4.17 (m, 1H), 2.05-2.10 (m, 2H), 1.37 (s, 9H). LCMS (ESI, m/z): 337 $[M+H]^+$.

A solution of tert-butyl ((S)-1-amino-1-oxo-3-((S)-3-oxo-3,4-dihydro-2H-pyrido[3,2-b][1,4]oxazin-2-yl)propan-2-yl)carbamate (250 mg, 0.744 mmol, 1.0 eq.) in 2M HCl in $Et_2O$ (5 mL) was stirred at rt for 2 h. The mixture was concentrated under reduced pressure to afford (S)-2-amino-3-((S)-3-oxo-3,4-dihydro-2H-pyrido[3,2-b][1,4]oxazin-2-yl)propenamide dihydrochloride (150 mg, 85%) as a white solid.

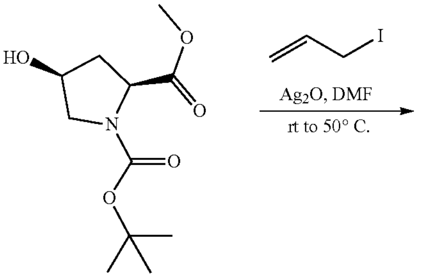

-continued

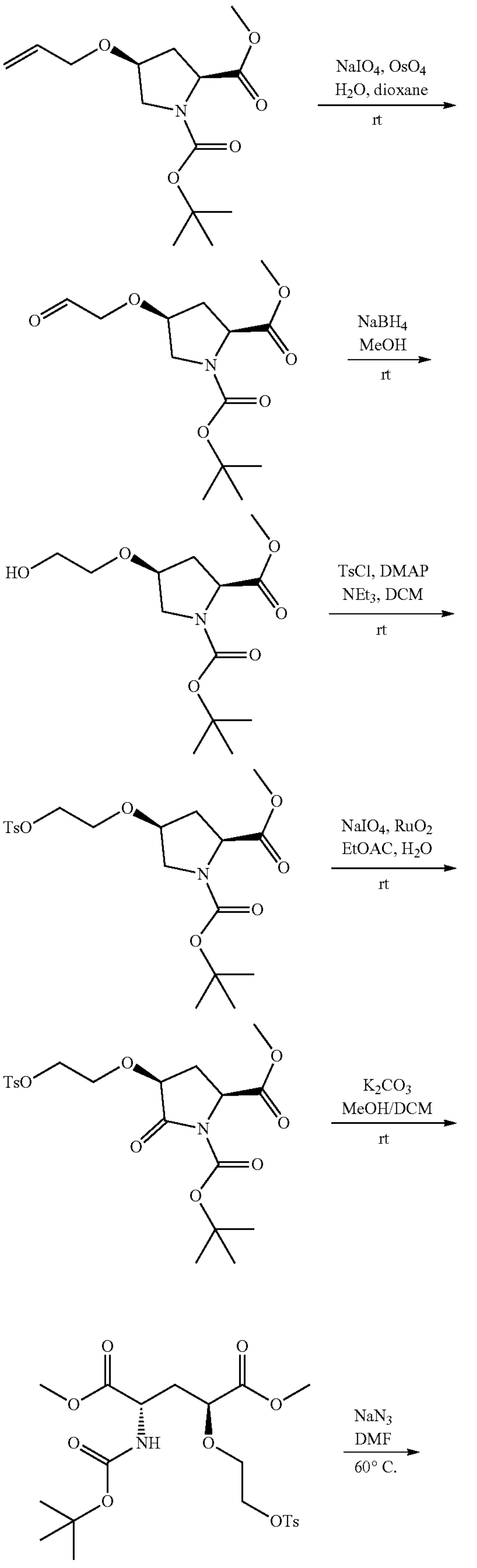

-continued

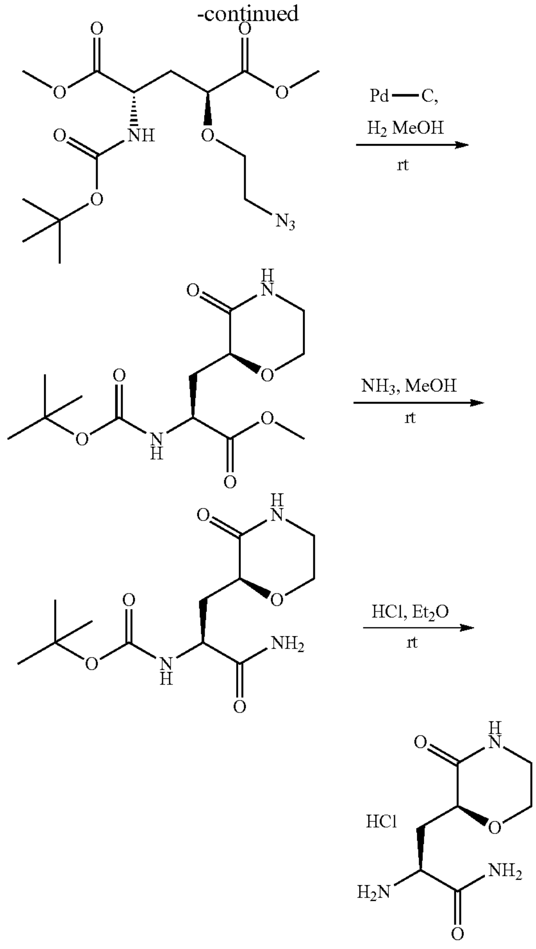

To a solution of 1-(tert-butyl) 2-methyl (2S,4S)-4-hydroxypyrrolidine-1,2-dicarboxylate (2.0 g, 8.16 mmol, 1.0 eq.) in DMF (20 mL) were added $Ag_2O$ (5.6 g, 24.5 mmol, 3.0 eq.) and allyl iodide (2.24 mL, 24.5 mmol, 3.0 eq.). The mixture was stirred at rt for 12 h and heated at 50° C. for 5 h. After cooling to rt, the mixture was filtered through celite. The filtrate was diluted with water (50 mL) and extracted with EA (3×50 mL). The organic phases were combined, washed with brine (3×50 mL), dried over $Na_2SO_4$, filtered and concentrated under reduced pressure. The residue was purified by flash chromatography on silica gel using a gradient of EA (10 to 15%) in PE to afford 1-(tert-butyl) 2-methyl (2S,4S)-4-(allyloxy)pyrrolidine-1,2-dicarboxylate (2.1 g, 91%) as a colorless oil.

To a solution of 1-(tert-butyl) 2-methyl (2S,4S)-4-(allyloxy)pyrrolidine-1,2-dicarboxylate (2.1 g, 7.39 mmol, 1.0 eq.) in dioxane (20 mL) were added 2.5% $OsO_4$ in tBuOH (0.2 mL) and a solution of $NaIO_4$ (3.16 g, 14.8 mmol, 2.0 eq.) in water (20 mL) over 10 min. The mixture was vigorously stirred at rt for 1 h. The mixture was diluted with water (50 mL) and extracted with EA (3×50 mL). The organic phases were combined, dried over $Na_2SO_4$, filtered and concentrated under reduced pressure. The residue was purified by flash chromatography on silica gel using a gradient of EA (40 to 50%) in PE to afford 1-(tert-butyl) 2-methyl (2S,4S)-4-(2-oxoethoxy)pyrrolidine-1,2-dicarboxylate (1.25 g, 60%) as a colorless oil.

To a solution of (1-(tert-butyl) 2-methyl (2S,4S)-4-(2-oxoethoxy)pyrrolidine-1,2-dicarboxylate (1.2 g, 4.21 mmol, 1.0 eq.) in methanol (12 mL) cooled at 0° C. was added portionwise $NaBH_4$ (160 mg, 4.21 mmol, 1.0 eq.). The mixture was stirred at rt for 1 h. The mixture was diluted with ice-cold water (10 mL) and extracted with DCM (2×20 mL). The organic phases were combined, washed with brine (2×10 mL), dried over $Na_2SO_4$, filtered and concentrated under reduced pressure. The residue was purified by flash chromatography on silica gel using a gradient of MeOH (5 to 10%) in DCM to afford 1-(tert-butyl) 2-methyl (2S,4S)-4-(2-hydroxyethoxy)pyrrolidine-1,2-dicarboxylate (1.1 g, 91%) as a colorless oil.

To a solution of 1-(tert-butyl) 2-methyl (2S,4S)-4-(2-hydroxyethoxy)pyrrolidine-1,2-dicarboxylate (1.1 g, 3.80 mmol, 1.0 eq.) in DCM (22 mL) cooled at 0° C. were added $NEt_3$ (1.6 mL, 11.4 mmol, 3.0 eq.), DMAP (46 mg, 0.376 mmol, 0.1 eq.) and TsCl (1.45 g, 7.61 mmol, 2.0 eq.). The mixture was stirred at rt overnight. The mixture was washed with ice-cold water (10 mL). The phases were separated. The aqueous phase was extracted with DCM (2×20 mL). The organic phases were combined, washed with brine (2×10 mL), dried over $Na_2SO_4$, filtered and concentrated under reduced pressure. The residue was purified by flash chromatography on silica gel using a gradient of EA (40 to 45%) in PE to afford 1-(tert-butyl) 2-methyl (2S,4S)-4-(2-(tosyloxy)ethoxy)pyrrolidine-1,2-dicarboxylate (1.4 g, 83%) as a colorless oil.

To a solution of $NaIO_4$ (10.1 g, 47.4 mmol, 15.0 eq.) in water (20 mL) was added $RuO_2 \cdot H_2O$ (84 mg, 0.632 mmol, 0.2 eq.). The mixture was stirred at rt for 10 min. A solution of 1-(tert-butyl) 2-methyl (2S,4S)-4-(2-(tosyloxy)ethoxy) pyrrolidine-1,2-dicarboxylate (1.4 g, 3.16 mmol, 1.0 eq.) in EA (20 mL) was added. The mixture was stirred at rt for 16 h. The mixture was diluted with ice-cold water (20 mL). The phases were separated. The aqueous phase was extracted with EA (2×30 mL). The organic phases were combined, washed with brine (2×10 mL), dried over $Na_2SO_4$, filtered and concentrated under reduced pressure. The residue was purified by flash chromatography on silica gel using a gradient of EA (40 to 45%) in PE to afford 1-(tert-butyl) 2-methyl (2S,4S)-5-oxo-4-(2-(tosyloxy)ethoxy)pyrrolidine-1,2-dicarboxylate (770 mg, 55%) as a colorless oil.

To a solution of 1-(tert-butyl) 2-methyl (2S,4S)-5-oxo-4-(2-(tosyloxy)ethoxy)pyrrolidine-1,2-dicarboxylate (550 mg, 1.20 mmol, 1.0 eq.) in MeOH (2.75 mL) and DCM (2.75 mL) cooled at 0° C. was added $K_2CO_3$ (33 mg, 0.239 mmol, 0.2 eq.). The mixture was stirred at rt for 1 h. Water (10 mL) was added and the phases were separated. The aqueous phase was extracted with DCM (2×20 mL). The organic phases were combined, dried over $Na_2SO_4$, filtered and concentrated under reduced pressure to afford dimethyl (2S,4S)-2-((tert-butoxycarbonyl)amino)-4-(2-tosyloxy) ethoxy)pentanedioate (570 mg) as an oil.

To a solution of dimethyl (2S,4S)-2-((tert-butoxycarbonyl)amino)-4-(2-tosyloxy)ethoxy)pentanedioate (570 mg, 1.16 mmol, 1.0 eq.) in DMF (5 mL) was added $NaN_3$ (151 mg, 2.33 mmol, 2.0 eq.). The mixture was heated at 60° C. for 2 h. After cooling to rt, the mixture was diluted with ice-cold water (10 mL) and extracted with EA (2×10 mL). The organic phases were combined, washed with brine (2×10 mL), dried over $Na_2SO_4$, filtered and concentrated under reduced pressure. The residue was purified by flash chromatography on silica gel using a gradient of EA (25 to 30%) in PE to afford dimethyl (2S,4S)-2-(2-azidoethoxy)-4-((tert-butoxycarbonyl)amino)pentanedioate (360 mg, 85%) as a colorless oil.

To a solution of dimethyl (2S,4S)-2-(2-azidoethoxy)-4-((tert-butoxycarbonyl)amino)pentanedioate (360 mg, 0.999 mmol, 1.0 eq.) in MeOH (10 mL) was added 10% Pd/C (70 mg, 50% wet). The mixture was stirred at rt under $H_2$ atmosphere for 2 h. The mixture was filtered through celite. The solid was washed with DCM (10 mL). The filtrate was concentrated under reduced pressure. The residue was purified by flash chromatography on silica gel using a gradient of MeOH (2 to 5%) in DCM to afford methyl (S)-2-((tert-butoxycarbonyl)amino)-3-((S)-3-oxomorpholin-2-yl)propanoate (225 mg, 74%) as a colorless oil. $^1H$ NMR (400 MHz, $CDCl_3$) δ 6.05 (bs, 1H), 5.37 (m, 1H), 4.50 (m, 1H), 4.17 (dd, 1H), 4.04 (m, 1H), 3.74 (m, 4H), 3.61 (m, 1H), 3.30 (m, 1H), 2.36-2.42 (m, 1H), 2.21-2.26 (m, 1H), 1.44 (s, 9H). LCMS (ESI, m/z): 303 $[M+H]^+$.

A solution of methyl (S)-2-((tert-butoxycarbonyl)amino)-3-((S)-3-oxomorpholin-2-yl)propanoate (225 mg, 0.733 mmol, 1.0 eq.) in 7M $NH_3$ in methanol (5 mL) was stirred at rt for 24 h in a sealed tube. The mixture was concentrated under reduced pressure to afford tert-butyl ((S)-1-amino-1-oxo-3-((S)-3-oxomorpholin-2-yl)propan-2-yl)carbamate (200 mg, 93%) as an off-white solid.

A solution of tert-butyl ((S)-1-amino-1-oxo-3-((S)-3-oxomorpholin-2-yl)propan-2-yl)carbamate (100 mg, 0.595 mmol, 1.0 eq.) in 2M HCl in $Et_2O$ (5 mL) was stirred at rt for 2 h. The mixture was concentrated under reduced pressure to afford (S)-2-amino-3-((S)-3-oxomorpholin-2-yl)propanamide hydrochloride (62 mg, 95%) as a white solid.

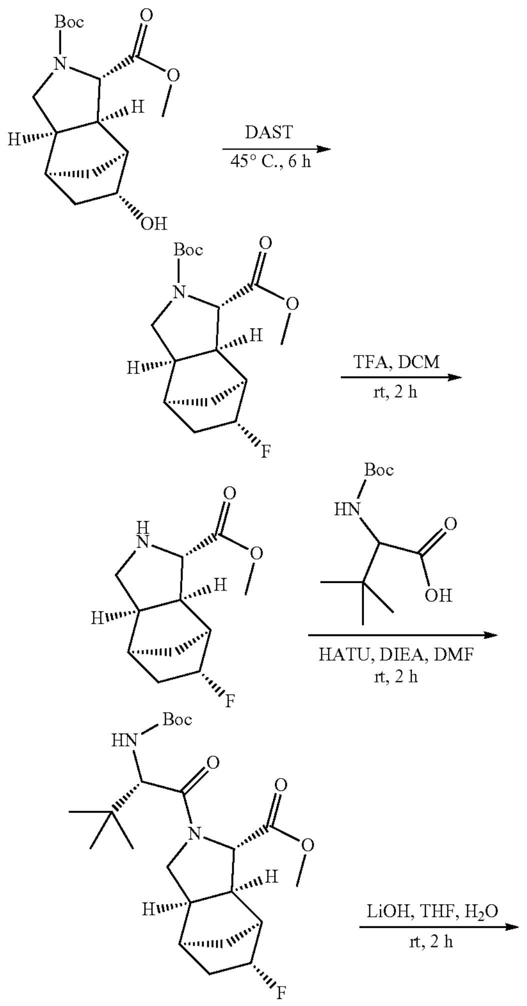

-continued

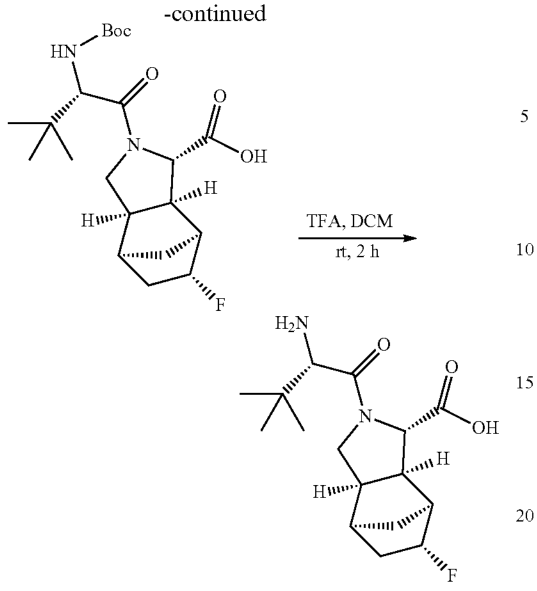

A mixture of 4-tert-butyl 3-methyl (1S,2R,3S,6R,7S,9R)-9-hydroxy-4-azatricyclo[5.2.1.0^{2,6}]decane-3,4-dicarboxylate (500 mg, 1.60 mmol, 1.0 eq.) in diethylaminosulfur trifluoride (10 mL) was stirred for 6 h at 45° C. The mixture was diluted with dichloromethane (80 mL), and the reaction quenched with sat. sodium bicarbonate (50 mL) at 0° C. The mixture was extracted with dichloromethane (3×80 mL). The organic layers were combined, washed with brine (2×50 mL), dried over anhydrous sodium sulfate, filtered and concentrated under reduced pressure. The residue was purified by silica gel column chromatography with PE:EA (7:3) to afford 4-tert-butyl 3-methyl (1S,2R,3S,6R,7S,9R)-9-fluoro-4-azatricyclo[5.2.1.0^{2,6}]decane-3,4-dicarboxylate (210 mg, 42%) as a yellow oil. LC-MS (ESI, m/z): 258 $[M-56+H]^+$.

To a stirred mixture of 4-tert-butyl 3-methyl (1S,2R,3S,6R,7S,9R)-9-fluoro-4-azatricyclo[5.2.1.0^{2,6}]decane-3,4-dicarboxylate (210 mg, 0.670 mmol, 1.0 eq.) in dichloromethane (3 mL) was added trifluoroacetic acid (1 mL) at rt. The mixture was stirred for 2 h at rt and then concentrated under reduced pressure to provide product methyl (1S,2R,3S,6R,7S,9R)-9-fluoro-4-azatricyclo[5.2.1.0^{2,6}]decane-3-carboxylate (155 mg, crude) as a yellow oil. LC-MS (ESI, m/z): 213 $[M+H]^+$.

To a mixture of (2S)-2-[(tert-butoxycarbonyl)amino]-3,3-dimethylbutanoic acid (155 mg, 0.671 mmol, 1.0 eq.) in N,N-dimethylformamide (2 mL) were added o-(7-azabenzotriazol-1-yl)-N,N,N',N'-tetramethyluronium hexafluorophosphate (305 mg, 0.805 mmol, 1.2 eq.) and N-ethyl-N-isopropylpropan-2-amine (520 mg, 4.026 mmol, 6.0 eq.) at 0° C. The mixture was stirred for 20 min at 0° C., and then methyl (1S,2R,3S,6R,7S,9R)-9-fluoro-4-azatricyclo[5.2.1.0^{2,6}]decane-3-carboxylate (143 mg, 0.671 mmol, 1.0 eq.) was added at 0° C. The mixture was stirred for 2 h at rt and then purified by a C18 column with $CH_3CN$/Water (0.05% TFA). The desired fraction was concentrated under reduced pressure to provide methyl (1S,2R,3S,6R,7S,9R)-4-[(2S)-2-[(tert-butoxycarbonyl)amino]-3,3-dimethylbutanoyl]-9-fluoro-4-azatricyclo[5.2.1.0^{2,6}]decane-3-carboxylate (190 mg, 66%) as a yellow solid. LC-MS (ESI, m/z): 427 $[M+H]^+$.

To a stirred methyl (1S,2R,3S,6R,7S,9R)-4-[(2S)-2-[(tert-butoxycarbonyl)amino]-3,3-dimethylbutanoyl]-9-fluoro-4-azatricyclo[5.2.1.0^{2,6}]decane-3-carboxylate (190 mg, 0.445 mmol, 1.0 eq.) in tetrahydrofuran (2 mL) and water (2 mL) was added lithium hydroxide (53.3 mg, 2.22 mmol, 5.0 eq.) at rt. The mixture was stirred for 2 h and acidified to pH=3 with hydrochloric acid (2M). The mixture was extracted with EA (3×50 mL). The organic layers were combined, washed with brine (2×20 mL) and dried over anhydrous sodium sulfate. The mixture was concentrated under reduced pressure to afford (1S,2R,3S,6R,7S,9R)-4-[(2S)-2-[(tert-butoxycarbonyl)amino]-3,3-dimethylbutanoyl]-9-fluoro-4-azatricyclo[5.2.1.0^{2,6}]decane-3-carboxylic acid ((1S,3aR,4S,6R,7S,7aR)-2-((S)-2-((tert-butoxycarbonyl)amino)-3,3-dimethylbutanoyl)-6-fluorooctahydro-1H-4,7-methanoisoindole-1-carboxylic acid, 180 mg, crude) as an orange solid. LC-MS (ESI, m/z): 413 $[M+H]^+$.

To a stirred mixture of (1S,2R,3S,6R,7S,9S)-4-[(2S)-2-[(tert-butoxycarbonyl)amino]-3,3-dimethylbutanoyl]-9-fluoro-4-azatricyclo[5.2.1.0^{2,6}]decane-3-carboxylic acid (160 mg, 0.388 mmol, 1.0 eq.) in dichloromethane (2 mL) was added trifluoroacetic acid (0.6 mL) at rt. The mixture was stirred for 2 h at rt and then concentrated under reduced pressure to give (1S,2R,3S,6R,7S,9S)-4-[(2S)-2-amino-3,3-dimethylbutanoyl]-9-fluoro-4-azatricyclo[5.2.1.0^{2,6}]decane-3-carboxylic acid (121 mg, crude) as a yellow oil. LC-MS (ESI, m/z): 313 $[M+H]^+$.

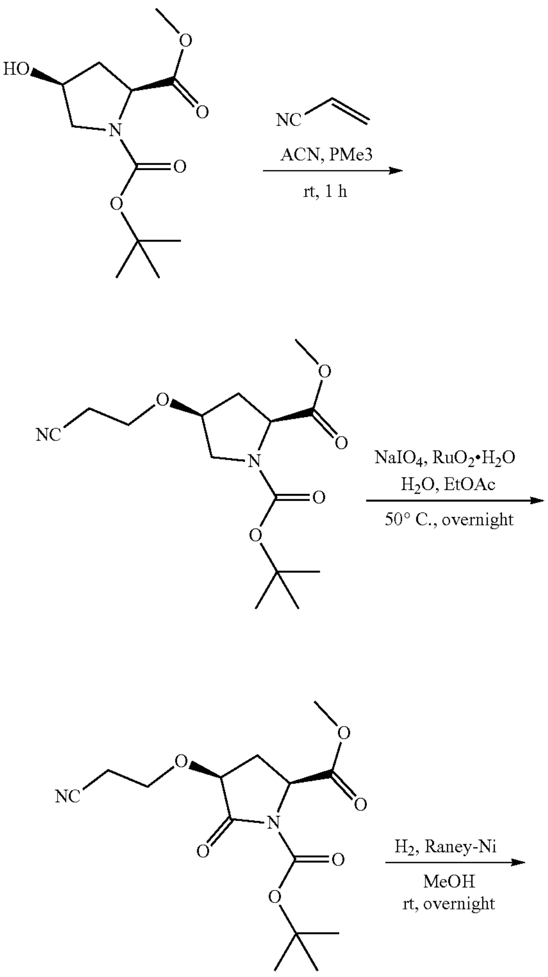

-continued

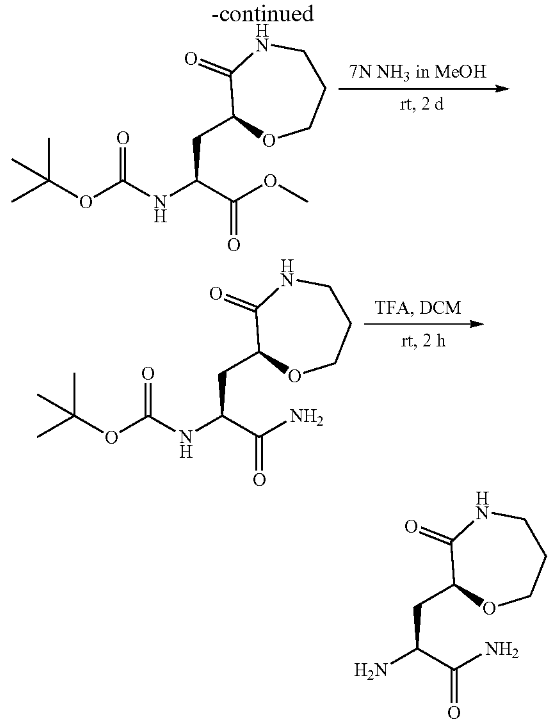

To a stirred mixture of 1-tert-butyl 2-methyl (2S,4S)-4-hydroxypyrrolidine-1,2-dicarboxylate (5.00 g, 20.3 mmol, 1.0 eq.) and trimethylphosphine (2.04 mL, 2.03 mmol, 0.1 eq.) in ACN (20 mL) was added acrylonitrile (10.8 g, 203 mmol, 10.0 eq.). The mixture was stirred for 1 h at rt. The crude product was purified by C18 column with $CH_3CN$/Water (0.05% TFA). The desired fraction was concentrated under reduced pressure to provide 1-tert-butyl 2-methyl (2S,4S)-4-(2-cyanoethoxy)pyrrolidine-1,2-dicarboxylate (3.9 g, 60%) as a yellow oil. $^1H$ NMR (400 MHz, DMSO-$d_6$) δ 4.24-4.40 (m, 1H), 4.10-4.23 (m, 1H), 3.60-3.70 (m, 3H), 3.50-3.59 (m, 3H), 2.20-2.30 (m, 1H), 2.63-2.70 (m, 2H), 2.25-2.48 (m, 1H), 2.00-2.10 (m, 1H), 1.25-1.48 (in, 9H). LC-MS (ESI, m/z): 199 [M-Boc+H]$^+$.

To a stirred mixture of 1-tert-butyl 2-methyl (2S,4S)-4-(2-cyanoethoxy)pyrrolidine-1,2-dicarboxylate (7.00 g, 23.4 mmol, 1.0 eq.) in EA (50 mL) were added sodium periodate (25.0 g, 116 mmol, 4.98 eq.) and ruthenium(IV) oxide hydrated (1.56 g, 11.7 mmol, 0.5 eq.) in water (50 mL). The mixture was stirred for overnight at 50° C. The mixture was diluted with EA (500 mL) and then filtered through a celite pad. The organic layer was washed with brine (500 mL), dried over anhydrous sodium sulfate, filtered and concentrated under reduced pressure to afford the crude product. The crude product was chromatographed on a silica gel column with EA:PE (80%) to provide 1-tert-butyl 2-methyl (2S,4S)-4-(2-cyanoethoxy)-5-oxopyrrolidine-1,2-dicarboxylate (5.4 g, crude) as a yellow oil. LC-MS (ESI, m/z): 213 [M-Boc+H]$^+$.

A mixture of 1-tert-butyl 2-methyl (2S,4S)-4-(2-cyanoethoxy)-5-oxopyrrolidine-1,2-dicarboxylate (4.40 g, 14.1 mmol, 1.0 eq.) and Raney nickel (2.30 g) in MeOH (20 mL) was stirred for overnight at rt under hydrogen. The mixture was filtered through a celite pad and washed with methanol (3x10 mL). The crude product was chromatographed on a silica gel column with MeOH:DCM (8:100) to provide methyl (2S)-2-[(tert-butoxycarbonyl)amino]-3-[(2S)-3-oxo-1,4-oxazepan-2-yl]propanoate (1.9 g, 40%) as a white solid. $^1H$ NMR (400 MHz, DMSO-$d_6$) δ 7.60-7.85 (m, 1H), 7.10-7.31 (m, 1H), 3.90-4.25 (m, 3H), 3.60-3.70 (m, 3H), 3.40-3.59 (m, 1H), 3.10-3.30 (m, 2H), 1.75-1.95 (m, 2H), 1.60-1.70 (m, 2H), 1.30-1.48 (m, 9H). LC-MS (ESI, m/z): 482 [M+H]$^+$.

A mixture of methyl (2S)-2-[(tert-butoxycarbonyl)amino]-3-[(2S)-3-oxo-1,4-oxazepan-2-yl]propanoate (1.90 g, 6.01 mmol, 1.0 eq.) in $NH_3$ (g) (20.0 mL, 7M in MeOH) was stirred for 2 d at rt and then concentrated under reduced pressure to afford tert-butyl N-[(1S)-1-carbamoyl-2-[(2S)-3-oxo-1,4-oxazepan-2-yl]ethyl]carbamate (1.4 g, 73%, crude) as a white solid. $^1H$ NMR (400 MHz, DMSO-$d_6$) δ 7.60-7.85 (m, 1H), 7.25-7.41 (m, 1H), 6.90-7.10 (m, 1H), 6.70-6.88 (m, 1H), 4.00-4.20 (m, 2H), 3.85-3.95 (m, 1H), 3.45-3.60 (m, 1H), 3.10-3.26 (m, 2H), 1.70-1.93 (m, 2H), 1.55-1.68 (m, 2H), 1.26-1.48 (m, 9H). LC-MS (ESI, m/z): 302 [M+H]$^+$.

To a stirred mixture of tert-butyl N-[(1S)-1-carbamoyl-2-[(2S)-3-oxo-1,4-oxazepan-2-yl]ethyl]carbamate (154 mg, 0.511 mmol, 1.0 eq.) in DCM (3 mL) was added trifluoroacetic acid (1 mL). The mixture was stirred for 2 h at rt and then concentrated under reduced pressure to afford (2S)-2-amino-3-[(2S)-3-oxo-1,4-oxazepan-2-yl]propanamide (103 mg, crude) as a brown oil. LC-MS (ESI, m/z): 202 [M+H]$^+$.

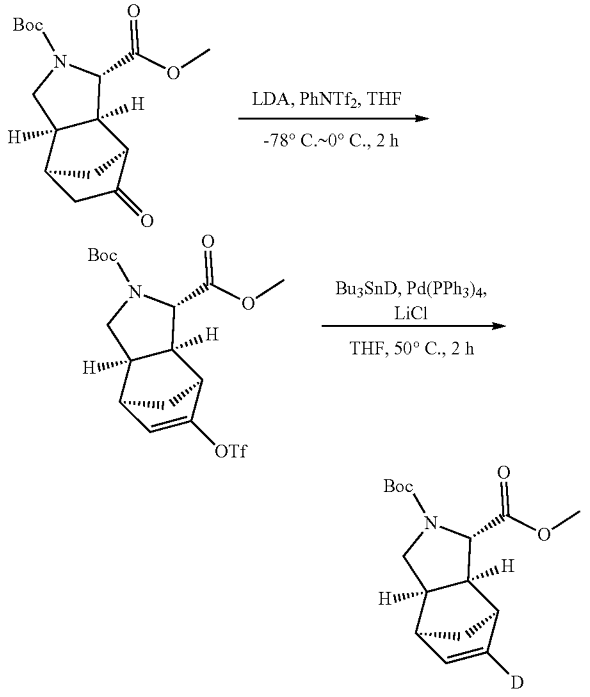

To a stirred mixture of 4-tert-butyl 3-methyl (1S,2R,3S,6R,7S)-9-oxo-4-azatricyclo[5.2.1.0^{2,6}]decane-3,4-dicarboxylate (600 mg, 1.93 mmol, 1.0 eq.) in THF (6 mL) was added lithium diisopropylamide (1.94 mL, 3.87 mmol, 2.0 eq.) dropwise at −78° C. under nitrogen. The mixture was stirred for 1 h at 0° C. and then 1,1,1-trifluoro-N-phenyl-N-((trifluoromethyl)sulfonyl)methanesulfonamide (1.03 g, 2.90 mmol, 1.5 eq.) was added slowly at −78° C. The mixture was stirred for 2 h at 0° C. The reaction was quenched with water (20 mL). The mixture was extracted with EtOAc (3x30 mL). The organic layers were combined, washed with brine (2x20 mL), dried over anhydrous sodium sulfate, filtered and concentrated under reduced pressure to afford the crude product. The crude product was chromatographed on a silica gel column with EA:PE (3:7) to provide the crude product. The crude product was purified by Cis column with $CH_3CN$/Water (0.05% FA). The desired fraction was concentrated under reduced pressure to provide 4-tert-butyl 3-methyl (1S,2R,3S,6R,7R)-9-(trifluoromethanesulfonyloxy)-4-azatricyclo[5.2.1.0^{2,6}]dec-8-ene-3,4-dicarboxylate (400 mg, 44%) as a light yellow oil. LC-MS (ESI, m/z): 342 $[M-Boc+H]^+$.

To a mixture of 4-tert-butyl 3-methyl (1S,2R,3S,6R,7R)-9-(trifluoromethanesulfonyloxy)-4-azatricyclo[5.2.1.0^{2,6}]dec-8-ene-3,4-dicarboxylate (180 mg, 0.408 mmol, 1.0 eq.), lithium chloride (138 mg, 3.26 mmol, 8.0 eq.) and tetrakis(triphenylphosphine)platinum(0) (80.0 mg, 0.069 mmol, 0.17 eq.) in THF (2 mL) was added tributylstannane-d (834 mg, 2.86 mmol, 7.0 eq.) under nitrogen. The mixture was stirred for 2 h at 50° C. The reaction was quenched with water (10 mL). The mixture was extracted with EtOAc (3×20 mL). The organic layers were combined, washed with brine (2×10 mL), dried over anhydrous sodium sulfate, filtered and concentrated under reduced pressure to afford the crude product. The crude product was purified by C18 column with $CH_3CN$/Water (0.05% $NH_4HCO_3$+$NH_3 \cdot H_2O$, pH-13). The desired fraction was concentrated under reduced pressure to provide 2-(tert-butyl) 1-methyl (1S,3aR,4S,7R,7aS)-1,3,3a,4,7,7a-hexahydro-2H-4,7-methanoisoindole-1,2-dicarboxylate-6-d (60.0 mg, 44%) as a light yellow semi-solid. $^1H$ NMR (400 MHz, $CDCl_3$-d) δ 6.14-6.30 (m, 1H), 3.82-3.98 (m, 1H), 3.61-3.77 (m, 3H), 3.35-3.53 (m, 1H), 3.01-3.24 (m, 2H), 2.73-2.98 (m, 3H), 1.50-1.58 (m, 1H), 1.32-1.49 (m, 10H). LC-MS (ESI, m/z): 195 $[M-Boc+H]^+$.

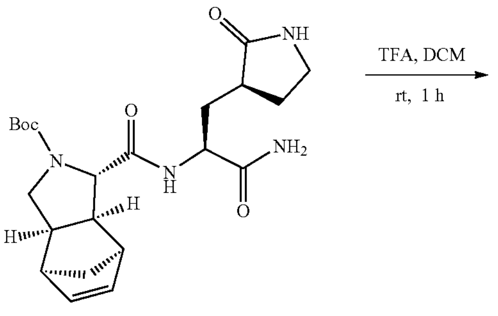

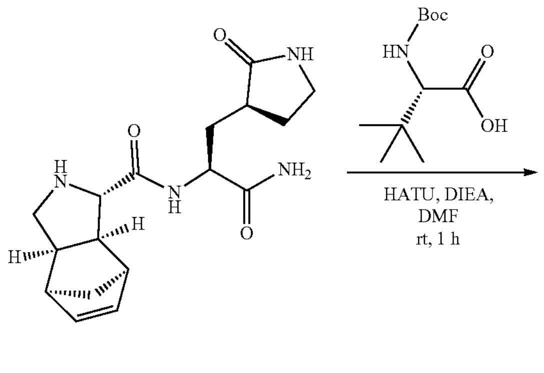

-continued

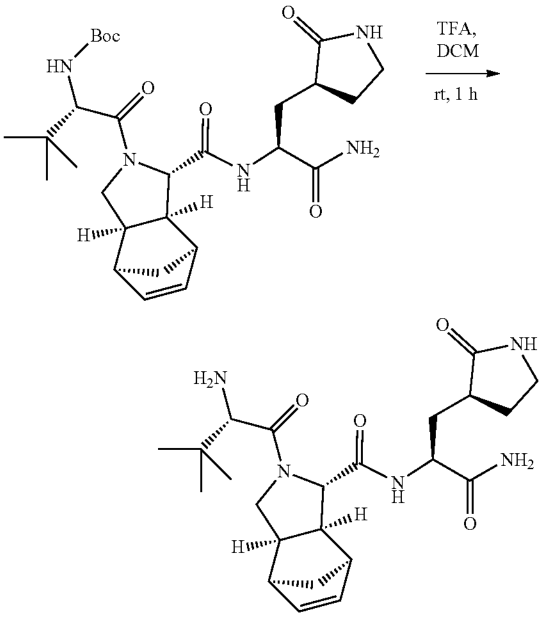

To a stirred mixture of tert-butyl (1R,2S,3S,6R,7S)-3-{[(1S)-1-carbamoyl-2-[(3S)-2-oxopyrrolidin-3-yl]ethyl]carbamoyl}-4-azatricyclo[5.2.1.0^{2,6}]dec-8-ene-4-carboxylate (500 mg, 1.15 mmol, 1.0 eq.) in DCM (6 mL) was added trifluoroacetic acid (2 mL). The mixture was stirred for 1 h at rt and then concentrated under reduced pressure to afford (2S)-2-[(R,2S,3S,6R,7S)-4-azatricyclo[5.2.1.0^{2,6}]dec-8-en-3-ylformamido]-3-[(3S)-2-oxopyrrolidin-3-yl]propanamide (380 mg, crude) as a yellow oil. LC-MS (ESI, m/z): 333 $[M+H]^+$.

To a stirred mixture of (2S)-2-[(1R,2S,3S,6R,7S)-4-azatricyclo[5.2.1.0^{2,6}]dec-8-en-3-ylformamido]-3-[(3S)-2-oxopyrrolidin-3-yl]propanamide (76.0 mg, 0.229 mmol, 1.0 eq.), (2S)-2-[(tert-butoxycarbonyl)amino]-3,3-dimethylbutanoic acid (52.9 mg, 0.229 mmol, 1.0 eq.) and o-(7-azabenzotriazol-1-yl)-N,N,N',N'-tetramethyluronium hexafluorophosphate (104 mg, 0.275 mmol, 1.2 eq.) in DMF (2 mL) were added N-ethyl-N-isopropylpropan-2-amine (236 mg, 1.83 mmol, 8.0 eq.) at 0° C. The mixture was stirred for 1 h at rt. The crude product was purified by C18 column with $CH_3CN$:Water (0.05% TFA). The compound fraction was concentrated under reduced pressure to provide tert-butyl N-[(2S)-1-[(1R,2S,3S,6R,7S)-3-{[(1S)-1-carbamoyl-2-[(3S)-2-oxopyrrolidin-3-yl]ethyl]carbamoyl}-4-azatricyclo [5.2.1.0^{2,6}]dec-8-en-4-yl]-3,3-dimethyl-1-oxobutan-2-yl]carbamate (105 mg, 78%) as a white solid. LC-MS (ESI, m/z): 546 $[M+H]^+$.

To a stirred mixture of tert-butyl N-[(2S)-1-[(1R,2S,3S,6R,7S)-3-{1[(1S)-1-carbamoyl-2-[(3S)-2-oxopyrrolidin-3-yl]ethyl]carbamoyl}-4-azatricyclo[5.2.1.0^{2,6}]dec-8-en-4-yl]-3,3-dimethyl-1-oxobutan-2-yl]carbamate (100 mg, 0.183 mmol, 1.0 eq.) in DCM (3 mL) was added trifluoroacetic acid (1 mL). The mixture was stirred for 1 h at rt and then concentrated under reduced pressure to afford (2S)-2-{[(1R,2S,3S,6R,7S)-4-[(2S)-2-amino-3,3-dimethylbutanoyl]-4-azatricyclo[5.2.1.0^{2,6}]dec-8-en-3-yl]formamido}-3-[(3S)-2-oxopyrrolidin-3-yl]propanamide (81.0 mg, crude) as a yellow oil. LC-MS (ESI, m/z): 446 $[M+H]^+$.

Example 1

Compound 1

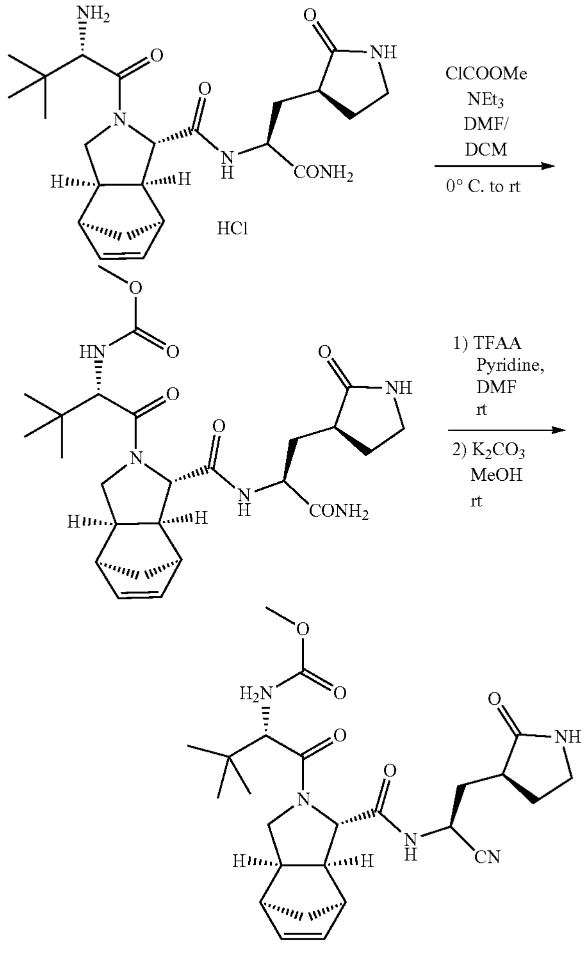

To a solution of (1S,3aR,4S,7R,7aS)—N—((S)-1-amino-1-oxo-3-((S)-2-oxopyrrolidin-3-yl)propan-2-yl)-2-((S)-2-amino-3,3-dimethylbutanoyl)-2,3,3a,4,7,7a-hexahydro-1H-4,7-methanoisoindole-1-carboxamide hydrochloride (80 mg, 0.166 mmol, 1.0 eq.) in DMF (1 mL) cooled at 0° C. were added $NEt_3$ (0.06 mL, 0.415 mmol, 2.5 eq.) and a solution of methyl chloroformate (0.02 mL, 0.249 mmol, 1.5 eq.) in DCM (0.5 mL). The mixture was slowly allowed to warm to rt and then stirred at rt for 4 h. Water (4 mL) was added. The mixture was extracted with EA (3×10 mL). The organic phases were combined, dried over $Na_2SO_4$, filtered and concentrated under reduced pressure. The residue was purified by flash chromatography on C18 using a gradient of ACN (40 to 50%) in 0.1% FA in water to afford methyl ((S)-1-((1S,3aR,4S,7R,7aS)-1-(((S)-1-amino-1-oxo-3-((S)-2-oxopyrrolidin-3-yl)propan-2-yl)carbamoyl)-1,3,3a,4,7,7a-hexahydro-2H-4,7-methanoisoindol-2-yl)-3,3-dimethyl-1-oxobutan-2-yl)carbamate (45 mg, 43%) as an off-white solid.

To a solution of methyl ((S)-1-((1S,3aR,4S,7R,7aS)-1-(((S)-1-amino-1-oxo-3-((S)-2-oxopyrrolidin-3-yl)propan-2-yl)carbamoyl)-1,3,3a,4,7,7a-hexahydro-2H-4,7-methanoisoindol-2-yl)-3,3-dimethyl-1-oxobutan-2-yl)carbamate (40 mg, 0.079 mmol, 1.0 eq.) in DMF (0.4 mL) were added pyridine (19 μL, 0.231 mmol, 2.9 eq.) and TFAA (23 μL, 0.163 mmol, 2.1 eq.). The mixture was stirred at rt for 30 min. The mixture was diluted with cold water (2 mL) and extracted with EA (5×5 mL). The organic phases were combined, dried over $Na_2SO_4$, filtered and concentrated under reduced pressure. The residue was dissolved in MeOH (1 mL). $K_2CO_3$ (19 mg, 0.137 mmol, 1.7 eq.) was added. The mixture was stirred at rt for 24 h. The mixture was diluted with EA (15 mL) and then filtered through celite. The filtrate was concentrated under reduced pressure. The residue was purified by prep-HPLC (Column: Gemini NX C18 Column, 10*250 mm, 5 μm; Mobile Phase A: 10 mM $NH_4HCO_3$ in water, Mobile Phase B: ACN; Flow rate: 8 mL/min; Gradient: 5% B to 55% B in 8 min) to afford methyl ((S)-1-((1S,3aR,4S,7R,7aS)-1-(((S)-1-cyano-2-((S)-2-oxopyrrolidin-3-yl)ethyl)carbamoyl)-1,3,3a,4,7,7a-hexahydro-2H-4,7-methanoisoindol-2-yl)-3,3-dimethyl-1-oxobutan-2-yl)carbamate (12 mg, 32%) as a white solid. $^1H$ NMR (500 MHz, 364K, DMSO-$d_6$) δ 8.45-8.75 (br. s., 1H), 7.26-7.74 (m, 1H), 6.33 (m, 1H), 5.97-6.19 (m, 2H), 4.76-4.94 (m, 1H), 4.10 (d, 1H), 3.98-4.07 (m, 1H), 3.60-3.87 (m, 1H), 3.57 (s, 3H), 3.36-3.53 (m, 1H), 3.00-3.26 (m, 3H), 2.79-2.94 (m, 2H), 2.73 (m, 1H), 2.36 (m, 1H), 2.08-2.31 (m, 2H), 1.64-1.92 (m, 2H), 1.34-1.47 (m, 2H), 0.82-0.94 (m, 9H). LCMS (ESI, m/z): 486 $[M+H]^+$.

Example 2

Compound 2

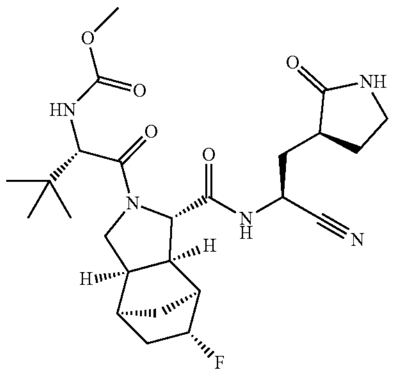 [SMILES: COC(=O)N[C@H](C(=O)N1C[C@@H]2[C@H]3C[C@@H]([C@@H]2[C@H]1C(=O)N[C@H](C#N)C[C@@H]1CCNC1=O)[C@H](F)C3)C(C)(C)C]

To a mixture of (1S,3aR,4S,6R,7S,7aR)—N—((S)-1-amino-1-oxo-3-((S)-2-oxopyrrolidin-3-yl)propan-2-yl)-2-((S)-2-amino-3,3-dimethylbutanoyl)-6-fluorooctahydro-1H-4,7-methanoisoindole-1-carboxamide hydrochloride (110 mg, 0.219 mmol, 1.0 eq.) in DCM (2 mL) were added triethylamine (133 mg, 1.31 mmol, 6.0 eq.) and methyl chloroformate (51.8 mg, 0.547 mmol, 2.5 eq.) at 0° C. The mixture was stirred for 30 min at 0° C. The reaction was quenched with water (20 mL). The mixture was extracted with DCM (3×60 mL). The organic layers were combined, washed with brine (2×30 mL), dried over anhydrous sodium sulfate, filtered and concentrated under reduced pressure to afford the crude product. The crude product was purified by C18 column with $CH_3CN$/Water (0.05% TFA), (32%). The desired fraction was concentrated under reduced pressure to provide methyl N-[(2S)-1-[(1S,2R,3S,6R,7S,9R)-3-{[(1S)-1-carbamoyl-2-[(3S)-2-oxopyrrolidin-3-yl]ethyl]carbamoyl}-9-fluoro-4-azatricyclo [5.2.1.0^{2,6}]decan-4-yl]-3,3- dimethyl-1-oxobutan-2-yl]carbamate (60 mg, crude) as a light yellow semi-solid. LCMS (ESI, m/z): 524 [M+H]$^+$.

To a mixture of methyl N-[(2S)-1-[(1S,2R,3S,6R,7S,9R)-3-{[(1S)-1-carbamoyl-2-[(3S)-2-oxopyrrolidin-3-yl]ethyl]carbamoyl}-9-fluoro-4-azatricyclo[5.2.1.0^{2,6}]decan-4-yl]-3,3-dimethyl-1-oxobutan-2-yl]carbamate (50.0 mg, 0.095 mmol, 1.0 eq.) in DCM (1 mL) were added pyridine (45.3 mg, 0.570 mmol, 6.0 eq.) and trifluoroacetic anhydride (50.1 mg, 0.237 mmol, 2.5 eq.). The mixture was stirred 1 h at rt. The reaction was quenched with water (20 mL). The mixture was extracted with DCM (3×50 mL). The organic layers were combined, washed with brine (2×30 mL), dried over anhydrous sodium sulfate, filtered and concentrated under reduced pressure to afford the crude product. The crude product was purified by prep-HPLC (Column: XSelect CSH Prep C18 OBD Column, 19*150 mm, 5 m; Mobile Phase A: Water (0.1% FA), Mobile Phase B: MeOH—HPLC; Flow rate: 25 mL/min; Gradient: 44% B to 74% B in 7 min, 74% B; Wave Length: 254 nm; RT1 (min): 5.2;) to provide methyl N-[(2S)-1-[(1S,2R,3S,6R,7S,9R)-3-{[(1S)-1-cyano-2-[(3S)-2-oxopyrrolidin-3-yl]ethyl]carbamoyl}-9-fluoro-4-azatricyclo[5.2.1.0^{2,6}]decan-4-yl]-3,3-dimethyl-1-oxobutan-2-yl]carbamate (5.0 mg, 10%) as a white solid. $^1$H NMR (400 MHz, 100° C., DMSO-$d_6$) δ 8.68-8.69 (m, 1H), 7.34 (br, 1H), 6.59-6.61 (m, 1H), 4.83-4.89 (m, 1H), 4.54-4.55 (m, 1H), 4.34-4.50 (m, 1H), 4.20-4.23 (m, 1H), 3.61-3.75 (m, 2H), 3.58 (s, 3H), 3.04-3.18 (m, 2H), 2.64-2.70 (m, 2H), 2.54-2.60 (m, 1H), 2.28-2.40 (m, 2H), 2.05-2.25 (m, 3H), 1.62-1.90 (m, 3H), 1.25-1.43 (m, 2H), 0.94-0.95 (m, 9H). LCMS (ESI, m/z): 506 [M+H]$^+$.

Example 3

Compound 3

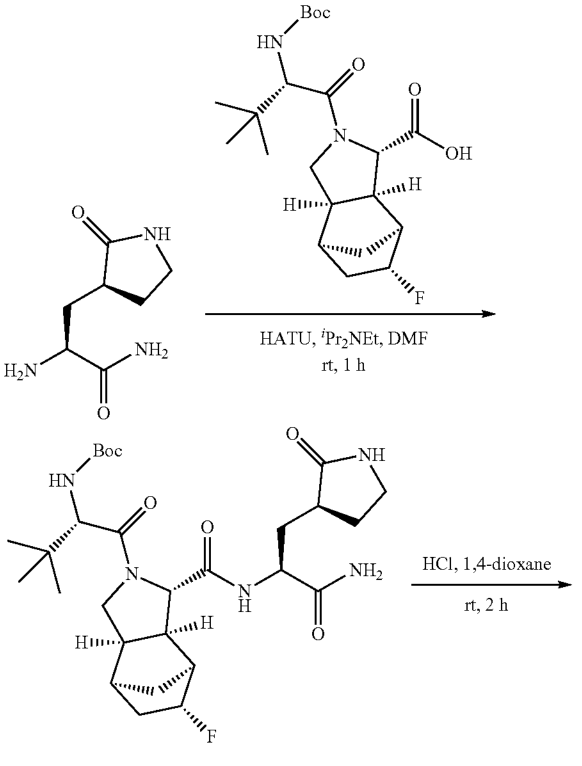

-continued

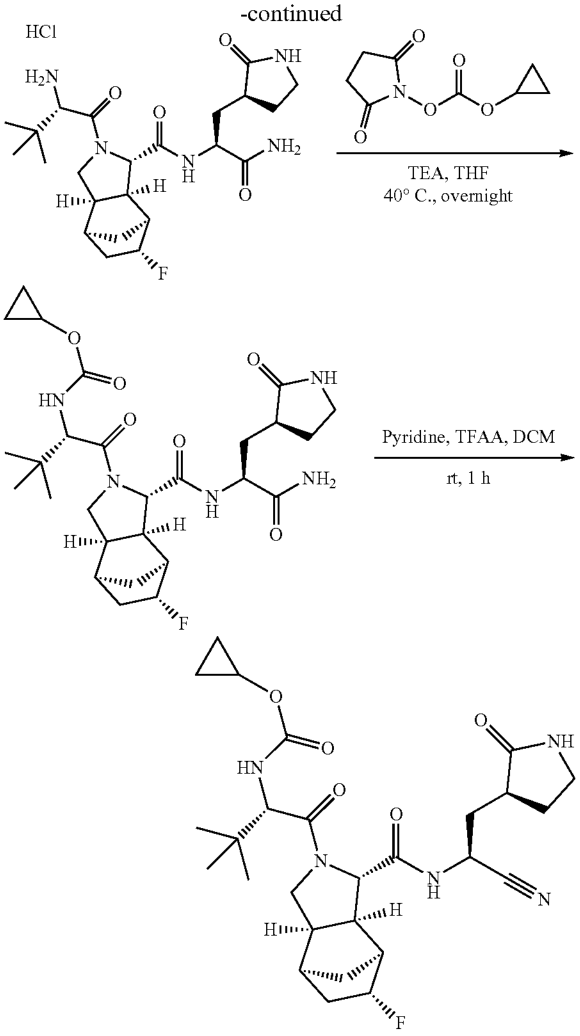

To a mixture of (1S,3aR,4S,6R,7S,7aR)-2-((S)-2-((tert-butoxycarbonyl)amino)-3,3-dimethylbutanoyl)-6-fluorooctahydro-1H-4,7-methanoisoindole-1-carboxylic acid (250 mg, 0.606 mmol, 1.0 eq.) in DMF (5 mL) were added o-(7-azabenzotriazol-1-yl)-N,N,N',N'-te-tramethyluronium hexafluorophosphate (277 mg, 0.727 mmol, 1.2 eq.) and N-ethyl-N-isopropylpropan-2-amine (392 mg, 3.03 mmol, 5.0 eq.) at 0° C. After stirring for 20 min, (S)-2-amino-3-((S)-2-oxopyrrolidin-3-yl)propanamide (109.57 mg, 0.640 mmol, 1.1 eq.) was added. The mixture was stirred for 1 h at rt and then purified by C18 column with $CH_3CN$/Water (0.05% TFA), (45%). The desired fraction was concentrated under reduced pressure to provide tert-butyl ((S)-1-((1S,3aR,4S,6R,7S,7aR)-1-(((S)-1-amino-1-oxo-3-((S)-2-oxopyrrolidin-3-yl)propan-2-yl)carbamoyl)-6-fluorooctahydro-2H-4,7-methanoisoindol-2-yl)-3,3-dimethyl-1-oxobutan-2-yl)carbamate (300 mg, 87%) as a yellow solid. LCMS (ESI, m/z): 566 [M+H]$^+$.

To a mixture of tert-butyl ((S)-1-((1S,3aR,4S,6R,7S,7aR)-1-(((S)-1-amino-1-oxo-3-((S)-2-oxopyrrolidin-3-yl)propan-2-yl)carbamoyl)-6-fluorooctahydro-2H-4,7-methanoisoindol-2-yl)-3,3-dimethyl-1-oxobutan-2-yl)carbamate (300 mg, 0.530 mmol, 1.0 eq.) in 1,4-dioxane (2 mL) was added hydrogen chloride (4 mL, 4 M in 1,4-dioxane) at rt. The mixture was stirred for 2 h and then concentrated under reduced pressure to afford (1S,3aR,4S,6R,7S,7aR)—

N—((S)-1-amino-1-oxo-3-((S)-2-oxopyrrolidin-3-yl)propan-2-yl)-2-((S)-2-amino-3,3-dimethylbutanoyl)-6-fluorooctahydro-1H-4,7-methanoisoindole-1-carboxamide hydrochloride (120 mg, crude) as a white solid. LCMS (ESI, m/z): 466 $[M+H]^+$.

To a mixture of (1S,3aR,4S,6R,7S,7aR)—N—((S)-1-amino-1-oxo-3-((S)-2-oxopyrrolidin-3-yl)propan-2-yl)-2-((S)-2-amino-3,3-dimethylbutanoyl)-6-fluorooctahydro-1H-4,7-methanoisoindole-1-carboxamide hydrochloride (120 mg, 0.239 mmol, 1.0 eq.) in THF (2 mL) were added cyclopropyl (2,5-dioxopyrrolidin-1-yl) carbonate (52.4 mg, 0.263 mmol, 1.1 eq.) and triethylamine (48.4 mg, 0.478 mmol, 2.0 eq.) at rt. The mixture was stirred overnight at 40° C. The reaction was quenched with water (20 mL). The mixture was extracted with EtOAc (3×50 mL). The organic layers were combined, washed with brine (2×30 mL), dried over anhydrous sodium sulfate, filtered and concentrated under reduced pressure to afford the crude product. The crude product was purified by C18 column with $CH_3CN$/Water (0.05% TFA), (31%). The desired fraction was concentrated under reduced pressure to provide cyclopropyl ((S)-1-((1S,3aR,4S,6R,7S,7aR)-1-(((S)-1-amino-1-oxo-3-((S)-2-oxopyrrolidin-3-yl)propan-2-yl)carbamoyl)-6-fluorooctahydro-2H-4,7-methanoisoindol-2-yl)-3,3-dimethyl-1-oxobutan-2-yl)carbamate (70 mg, crude) as an off-white solid. LCMS (ESI, m/z): 550 $[M+H]^+$.

To a mixture of cyclopropyl ((S)-1-((1S,3aR,4S,6R,7S,7aR)-1-(((S)-1-amino-1-oxo-3-((S)-2-oxopyrrolidin-3-yl)propan-2-yl)carbamoyl)-6-fluorooctahydro-2H-4,7-methanoisoindol-2-yl)-3,3-dimethyl-1-oxobutan-2-yl)carbamate (70.0 mg, 0.127 mmol, 1.0 eq.) in DCM (1 mL) were added pyridine (60.4 mg, 0.762 mmol, 6.0 eq.) and trifluoroacetic anhydride (66.9 mg, 0.318 mmol, 2.5 eq.). The mixture was stirred 1 h at rt. The reaction was quenched with water (30 mL). The mixture was extracted with DCM (3×50 mL). The organic layers were combined, washed with brine (2×30 mL), dried over anhydrous sodium sulfate, filtered and concentrated under reduced pressure to afford the crude product. The crude product was purified by prep-HPLC (Column: XSelect CSH Prep C18 OBD Column, 19*150 mm, 5 m; Mobile Phase A: Water (0.1% FA), Mobile Phase B: ACN; Flow rate: 25 mL/min; Gradient: 25% B to 52% B in 10 min, 52% B; Wave Length: 254 nm; RT1 (min): 8.07) to provide cyclopropyl ((S)-1-((1S,3aR,4S,6R,7S,7aR)-1-(((S)-1-cyano-2-((S)-2-oxopyrrolidin-3-yl)ethyl)carbamoyl)-6-fluorooctahydro-2H-4,7-methanoisoindol-2-yl)-3,3-dimethyl-1-oxobutan-2-yl)carbamate (11.9 mg, 17%) as a white solid. $^1H$ NMR (400 MHz, 100° C., DMSO-$d_6$) δ 8.64-8.65 (m, 1H), 7.31 (br, 1H), 6.55-6.57 (m, 1H), 4.82-4.89 (m, 1H), 4.54-4.55 (m, 1H), 4.34-4.49 (m, 1H), 4.19-4.23 (m, 1H), 3.90-3.98 (m, 1H), 3.71-3.74 (m, 1H), 3.55-3.60 (m, 1H), 3.07-3.15 (m, 2H), 2.56-2.64 (m, 2H), 2.49-2.53 (m, 1H), 2.27-2.33 (m, 2H), 2.04-2.16 (m, 3H), 1.62-1.80 (m, 3H), 1.24-1.50 (m, 2H), 0.89 (s, 9H), 0.49-0.62 (m, 4H). LCMS (ESI, m/z): 532 $[M+H]^+$.

Example 4

LC-MS Methods

| Compound No. | Rt (min) | $[M + H]^+$ or $[M - H]^-$ | LCMS Method |
|---|---|---|---|
| 1 | 2.001 | $[M + H]^+ = 486$ | A |
| 2 | 0.750 | $[M + H]^+ = 506$ | 11 |
| 3 | 0.800 | $[M + H]^+ = 532$ | 11 |

Final compounds can be obtained in some cases as a mixture with a corresponding stereoisomer. Retention times of the main isomers are depicted in the table above.

Description of LC-MS Methods

| LC Method | Instrument | Column | Mobile Phase | Gradient | Flow | Col T | Run Time |
|---|---|---|---|---|---|---|---|
| 11 | Shimadzu LCMS-2020 | HALO 2.0 μm C18 90A (2.0 μm, 3.0*30 mm) | A: Water/ 0.1% FA B: Acetonitrile/ 0.1% FA | From 95% A to 0% A in 1.09 min, held for 0.6 min, to 95% A in 0.05 min, held for 0.10 min | 1.5 mL/ min | 40 | 1.85 min |
| A | Agilent 6150 SQ Mass Spectrometer coupled to an Agilent 1290 Infinity LC System | Acquity UPLC BEH C18 (1.7 μm, 2.1*50 mm) | A: 0.1% FA in Water, B: 0.1% FA in Acetonitrile | 98% A held for 0.2 min, to 2% A in 1.3 min, held for 1.8 min, to 98% A in 0.1 min, held for 0.4 min | 0.6 mL/ min | 70 | 3.8 min |

EXAMPLE A

SARS-Cov-2 3CLpro and HRV3C Duplex Assay

Protease assays were performed in 384-well low volume polypropylene microtiter plates at ambient temperature. For the duplex assay, 3CLpro and HRV3C was added using a Multidrop Combi (Thermo Scientific; Waltham, MA) and preincubated for 30 mins with small molecules. The reactions were initiated by the addition of the two peptide substrates. The reactions were incubated for 30 mins and quenched by the addition of 0.5% formic acid (final) with subsequent neutralization using 1% sodium bicarbonate (final). Internal standard peptides were added in 20 mM Hepes pH 8.0 for quantitation of the protease products. For SAMDI-MS analysis, 2 μL of each reaction mixture was transferred using a 384-channel automated liquid handler to SAMDI biochip arrays functionalized with a neutravidin-presenting self-assembled monolayer. The SAMDI arrays were incubated for 1 h in a humidified chamber to allow the specific immobilization of the biotinylated peptide substrates, cleaved products and internal standards. The samples were purified by washing the SAMDI arrays with deionized ultrafiltered water and dried with compressed air. A matrix comprising alpha-cyano cinnamic acid in 80% acetonitrile: 20% aqueous ammonium citrate was applied in an automated format by dispensing 50 nL to each spot in the array. SAMDI-MS was performed using reflector-positive mode on an AB Sciex TOF-TOF 5800 System (AB Sciex, Framingham, MA) with 400 shots/spot analyzed in a random raster sampling. For data analysis, area under the curves (peaks) (AUCs) for the product and internal standard were calculated using the TOF/TOF Series Explorer (AB Sciex), and the amount of product formed was calculated using the equation (AUC product/AUC internal standard). The amount of product generated was calculated using the ratio of product area under the curve (AUC) divided by the AUC of the internal standard. Negative controls were pre-quenched with 0.5% formic acid final. Assay robustness was determined by Z-Factor. The $IC_{50}$s were determined by fitting the curves using a four-parameter equation in Graphpad Prism 8.

Table 1 indicates related $IC_{50}$ values for the tested compounds where 'A' indicates an $EC_{50}$<20 nM, 'B' indicates an $IC_{50}$ of ≥20 nM and <200 nM, 'C' indicates an $IC_{50}$≥200 nM and <2000 nM, 'D' indicates an $IC_{50}$≥2000 nM and <20000 nM and 'E' indicates an $IC_{50}$≥20000 nM and <100000 nM. As shown by the data in Table 1, compounds described herein (including pharmaceutically acceptable salts thereof) can effectively inhibit and be used to treat a coronavirus and rhinovirus.

TABLE 1

| Compound | SARS-Cov-2 | HRV |
|---|---|---|
| 1 | A | >0.5 μM |
| 2 | A | >0.5 μM |
| 3 | A | >0.5 μM |

Example B

Coronavirus Assay

OC43 Coronavirus Assay in HeLa Cells

The human beta-coronavirus OC43 was purchased from ATCC (Manassas, VA) and propagated using HCT-8 human colorectal epithelial cells (ATCC). HeLa human cervical epithelial cells (ATCC) were used as susceptible host cell lines and were cultured using EMEM media, supplemented with 10% fetal bovine serum (FBS), 1% (v/v) penicillin/streptomycin (P/S), 1% (v/v) HEPES and 1% (v/v) cellgro Glutagro™ supplement (all Corning, Manassas, VA) at 37° C. For the OC43 antiviral assay, $1.5\times10^4$ HeLa cells per well were plated in 100 μL complete media in white 96-well plates with clear bottoms at 37° C. for up to 24 h to facilitate attachment and allow cells to recover from seeding stresses. Next day, the cell culture medium was removed. Serially diluted compounds in 100 μL assay media (EMEM, 2% FBS, 1% P/S, 1% cellgro Glutagro™ supplement, 1% HEPES) were added to the cells and incubated for 4H at 37° C. in a humidified 5% $CO_2$ incubator. 100 μL of OC43 virus stock was diluted to a concentration known to produce optimal cytopathic effect, inducing 80-90% reduction in cell viability. 96-well plates were incubated for 6 (HeLa) days at 33° C.; each plate contains uninfected control wells as well as virus-infected wells that were not treated with compound. Cytotoxicity plates without the addition of OC43 virus were carried out in parallel. At the end of the incubation period, 100 μL cell culture supernatant was replaced with 100 μL cell-titer-glo reagent (Promega, Madison, WI) and incubated for at least 10 min at rt prior to measuring luminescence. Luminescence was measured on a Perkin Elmer (Waltham, MA) Envision plate reader. Antiviral % inhibition was calculated as follows: [(Compound treated cells infected sample)−(no compound infected control)]/[(Uninfected control)−(no compound infected control)]*100; Using GraphPad (San Diego, CA) prism software version 8.3.1, the antiviral dose-response plot was generated as a sigmoidal fit, log(inhibitor) vs response-variable slope (four parameters) model and the $EC_{50}$ was calculated which is the predicted compound concentration corresponding to a 50% inhibition of the viral cytopathic effect.

Table 2 indicates related $EC_{50}$ and $CC_{50}$ values for the tested compounds 'A' indicates an $EC_{50}$<100 nM, 'B' indicates an $EC_{50}$ of ≥100 nM and <1000 nM, 'C' indicates an $EC_{50}$≥1000 nM and <10000 nM and 'D' indicates an $EC_{50}$≥10000 nM and <100000 nM. For $CC_{50}$, the values are reported in micromolar (m), 'A' indicates a $CC_{50}$≥10000 nM and 'B' indicates a $CC_{50}$≥1 μM and <10 μM.

TABLE 2

| Compound | $EC_{50}$ | $CC_{50}$ |
|---|---|---|
| 1 | A | >100 |
| 2 | A | >100 |
| 3 | A | >100 |

B.1.1.7 Infection Model in A549-Dual_ACE2_TMPRSS2 Cells

The A549-dual_ACE2_TMPRSS2 cells (InvivoGen Cat #a549-cov2r) were propagated in the growth medium which was prepared by supplementing DMEM (gibco cat no 41965-039) with 10% v/v heat-inactivated FCS and 10 μg/mL blasticidin (InvivoGen ant-bl-05), 100 μg/mL hygromycin (InvivoGen ant-hg-1), 0.5 μg/mL puromycin (InvivoGen ant-pr-1) and 100 μg/mL zeocin (InvivoGen ant-zn-05) in a humidified 5% $CO_2$ incubator at 37° C. The assay medium was prepared by supplementing DMEM (gibco cat no 41965-039) with 2% v/v heat-inactivated FCS.

The virus isolate used is from the B.1.1.7 lineage (derived from hCoV-19/Belgium/rega-12211513/2020; EPI_ISL_791333,2020-12-21; see Abdelnabi et al., "Comparing infectivity and virulence of emerging SARS-CoV-2 variants in Syrian hamsters" EBioMedicine (2021) June;68: 103403. doi: 10.1016/j.ebiom.2021.103403).

For antiviral testing, cells were seeded in 96-well plates (Falcon) at a density of 15,000 cells per well in assay medium. After overnight growth, cells were treated with the indicated compound concentrations and infected with a MOI of 0.001 TCID50/cell (final volume 200 μL/well in assay medium). On day 4 p.i. differences in cell viability caused by virus-induced CPE or by compound-specific side effects are analyzed using MTS as described previously (PMID: 22575574).

For toxicity testing, the same experimental setup was used except that assay medium without virus was added to the cells and that an additional control of well without cells was added to the plate.

Table 3 indicates related $EC_{50}$ and $CC_{50}$ values for the tested compounds 'A' indicates an $EC_{50}$<100 nM, 'B' indicates an $EC_{50}$ of ≥100 nM and <1000 nM, 'C' indicates an $EC_{50}$≥1000 nM and <10000 nM. For $CC_{50}$, the values are reported in micromolar (M). 'A' indicates a $CC_{50}$≥10 μM. 'B' indicates a $CC_{50}$≥1 μM and <10 μM.

TABLE 3

| Compound | A549-dual_ACE2_TMPRSS2 ($EC_{50}$) | A549-dual_ACE2_TMPRSS2 ($CC_{50}$) |
|---|---|---|
| 1 | A | >1 |
| 2 | B | >1 |
| 3 | A | >1 |

Tables 2 and 3 demonstrate that compounds described herein (including pharmaceutically acceptable salts thereof) can effectively inhibit and treat a coronavirus.

Example C

Picornavirus & Norovirus Assays

Compounds of Formula (I), including pharmaceutically acceptable salts thereof, are tested following a protocol similar to the protocol described in one of the following articles: Kim et al., Journal of Virology (2012) 86(21): 11754-11762, Zhang et al, JACS (2020) (https://dx.doi.org/10.1021/acs.jmedchem.9b01828), and U.S. Pat. No. 9,603, 864.

The protocols of Kim et al., and Zhang et al., can be used to test for activity against a picornavirus and norovirus.

Example D

For the cathepsin L assay, 10 pM of human cathepsin L (R&D Systems; Minneapolis, MN) was preincubated for 30 mins with test compounds. Reactions were initiated by the addition of a peptide substrate Z-FR-AMC (final concentration 2 μM, Anaspec; Fremont, CA). Fluorescence was measured at 2-minute intervals for 30 mins using a 355/460 excitation/emission filter module on an Envision plate reader (Perkin Elmer; Waltham, MA). The $IC_{50}$ values were calculated for each assay by fitting the curves using a four-parameter equation in GraphPad Prism.

Table 4 indicates related $IC_{50}$ values for the tested compounds where 'A' indicates an $IC_{50}$≥10000 nM, 'B' indicates an $IC_{50}$ of ≥1000 nM and <10000 nM, 'C' indicates an $IC_{50}$≥100 nM and <1000 nM, 'D' indicates an $IC_{50}$<100 nM.

TABLE 4

| Compound | Cathepsin L $IC_{50}$ |
|---|---|
| 1 | A |
| 2 | A |
| 3 | A |

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the present disclosure.

What is claimed is:

1. A compound of Formula (I), or a pharmaceutically acceptable salt thereof, having the structure:

(I)

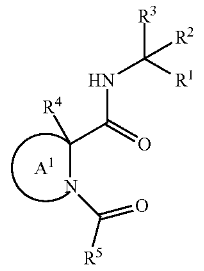

wherein:

Ring $A^1$ is selected from the group consisting of,

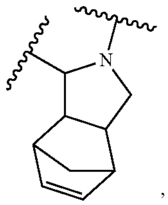 , 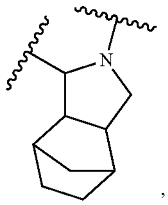 , 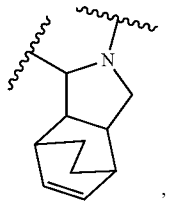 , 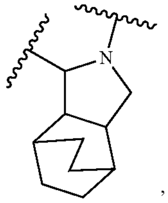 , 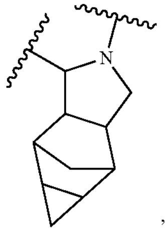 , 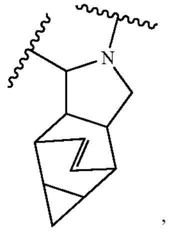 , 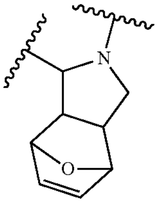 and, 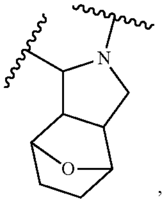 , and wherein Ring $A^1$ is optionally substituted with one or more moieties independently selected from the group consisting of =O, =$CH_2$, deuterium, halogen, hydroxy, an unsubstituted $C_{1-4}$ alkyl, an unsubstituted $C_{1-4}$ haloalkyl, an unsubstituted $C_{2-4}$ alkenyl and an unsubstituted or a substituted $C_{3-6}$ monocyclic cycloalkyl;

$R^1$ is selected from the group consisting of cyano, an unsubstituted or a substituted $C_{2-5}$ alkynyl, an unsubstituted or a substituted acyl, an unsubstituted or a substituted ketoamide, —CH(OH)—(S(=O)$_2$—O—), —CH(OH)((P=O)(OR$^6$)$_2$) and —C(=O) $CH_2$—O—((P=O)(OR$^7$)$_2$);

each $R^6$ and each $R^7$ are independently hydrogen, an unsubstituted $C_{1-6}$ alkyl, an unsubstituted $C_{2-6}$ alkenyl, an unsubstituted $C_{1-6}$ haloalkyl, an unsubstituted or a substituted aryl or an unsubstituted or a substituted aryl($C_{1-4}$ alkyl);

$R^2$ is hydrogen, deuterium or halogen;

$R^3$ is an unsubstituted or a substituted monocyclic nitrogen-containing heterocyclyl($C_{1-4}$ alkyl), an unsubstituted or a substituted bicyclic nitrogen-containing heterocyclyl($C_{1-4}$ alkyl) or an unsubstituted or a substituted monocyclic nitrogen-containing heteroaryl ($C_{1-4}$ alkyl);

$R^4$ is hydrogen, deuterium or halogen;

$R^5$ is;

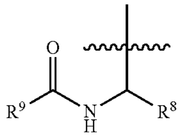

$R^8$ is selected from the group consisting of an unsubstituted or a substituted $C_{2-6}$ alkyl, an unsubstituted or a substituted $C_{2-6}$ alkenyl, an unsubstituted or a substituted $C_{2-6}$ alkynyl, an unsubstituted or a substituted monocyclic $C_{3-6}$ cycloalkyl, an unsubstituted or a substituted bicyclic $C_{5-8}$ cycloalkyl, an unsubstituted or a substituted monocyclic 4- to 6-membered heterocyclyl and an unsubstituted monocyclic $C_{3-6}$ cycloalkyl $(CH_2)$—, wherein when the $C_{2-6}$ alkyl is substituted, the $C_{2-6}$ alkyl is substituted 1, 2, 3 or 4 times with a substituent independently selected from the group consisting of halogen, cyano, an unsubstituted or a substituted monocyclic $C_{3-6}$ cycloalkyl, an unsubstituted $C_{1-4}$ alkoxy and an unsubstituted $C_{1-4}$ haloalkoxy, or the $C_{2-6}$ alkyl is substituted 1 to 13 times with deuterium;

wherein when the $C_{2-6}$ alkenyl, the $C_{2-6}$ alkynyl, the monocyclic $C_{3-6}$ cycloalkyl, the bicyclic $C_{5-8}$ cycloalkyl and the monocyclic 4- to 6-membered heterocyclyl are substituted, the $C_{2-6}$ alkenyl, the $C_{2-6}$ alkynyl, the monocyclic $C_{3-6}$ cycloalkyl, the bicyclic $C_{5-8}$ cycloalkyl and the monocyclic 4- to 6-membered heterocyclyl are substituted 1, 2, 3 or 4 times with a substituent independently selected from the group consisting of halogen, an unsubstituted $C_{1-4}$ alkyl, an unsubstituted $C_{2-4}$ alkenyl, an unsubstituted $C_{2-4}$ alkynyl, an unsubstituted $C_{1-4}$ haloalkyl, an unsubstituted or a substituted monocyclic $C_{3-6}$ cycloalkyl and an unsubstituted $C_{1-4}$ alkoxy; and $R^9$ is an unsubstituted or a substituted alkoxy.

2. The compound of claim 1, wherein $R^1$ is cyano.

3. The compound of claim 1, wherein Ring $A^1$ is an unsubstituted

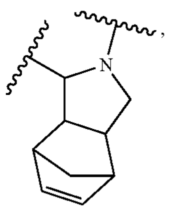 [SMILES: *C1C2C3C=CC(C3)C2CN1*]

a substituted

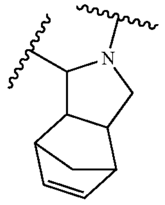 [SMILES: *C1C2C3C=CC(C3)C2CN1*]

substituted with one or more moieties independently selected from the group consisting of =O, $=CH_2$, deuterium, halogen, hydroxy, an unsubstituted $C_{1-4}$ alkyl, an unsubstituted $C_{1-4}$ haloalkyl, an unsubstituted $C_{2-4}$ alkenyl and an unsubstituted or a substituted $C_{3-6}$ monocyclic cycloalkyl, an unsubstituted

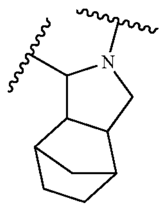 [SMILES: *C1C2C3CCC(C3)C2CN1*]

or a substituted

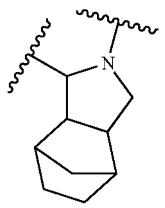 [SMILES: *C1C2C3CCC(C3)C2CN1*]

substituted with one or more moieties independently selected from the group consisting of =O, $=CH_2$, deuterium, halogen, hydroxy, an unsubstituted $C_{1-4}$ alkyl, an unsubstituted $C_{1-4}$ haloalkyl, an unsubstituted $C_{2-4}$ alkenyl and an unsubstituted or a substituted $C_{3-6}$ monocyclic cycloalkyl.

4. The compound of claim 1, wherein Ring $A^1$ is selected from the group consisting of

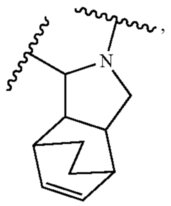
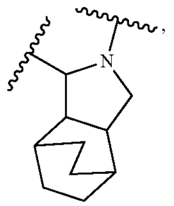
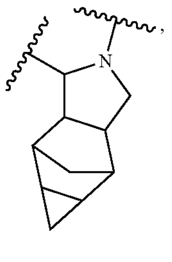

-continued

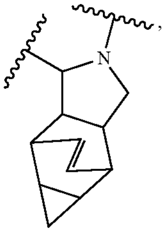 , 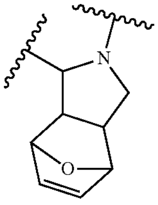 and 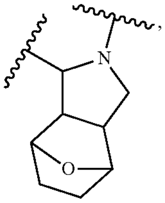 , and wherein Ring A[1] is optionally substituted with one or more moieties independently selected from the group consisting of =O, =$CH_2$, deuterium, halogen, hydroxy, an unsubstituted $C_{1-4}$ alkyl, an unsubstituted $C_{1-4}$ haloalkyl, an unsubstituted $C_{2-4}$ alkenyl and an unsubstituted or a substituted $C_{3-6}$ monocyclic cycloalkyl.

5. The compound of claim 1, wherein Ring A[1] is selected from the group consisting of:

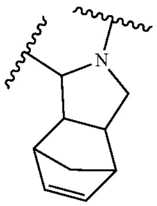 , 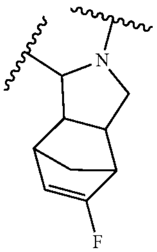 , 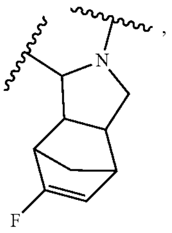 ,

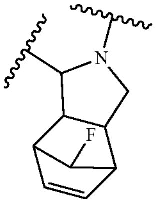 , 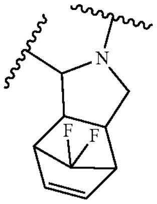 , 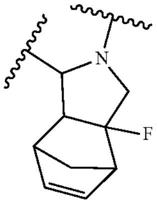 ,

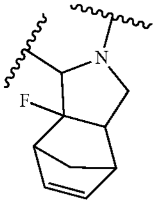 , 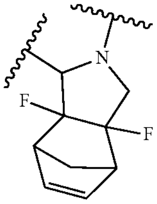 , 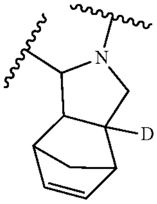 ,

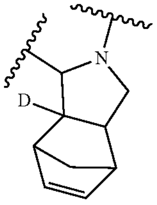 , 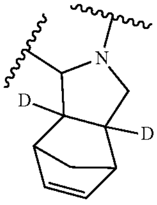 , 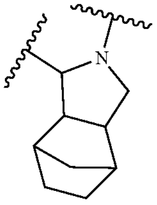 ,

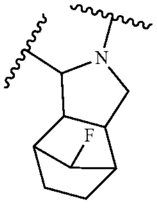 , 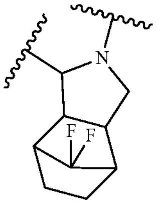 , 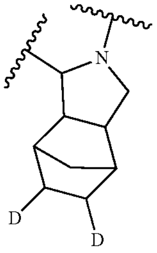 ,

-continued

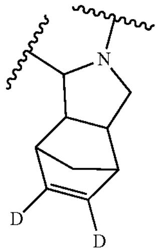 , 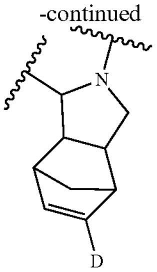 , 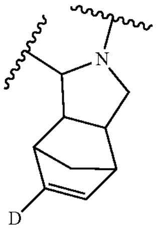 ,

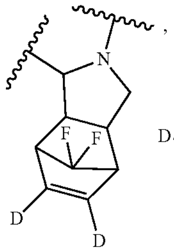 , 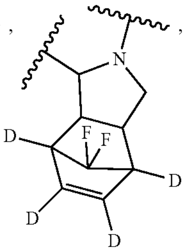 , 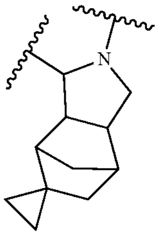 ,

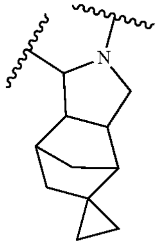 , 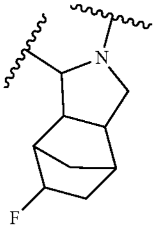 , 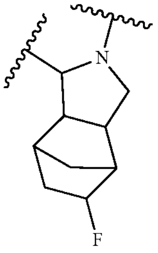 ,

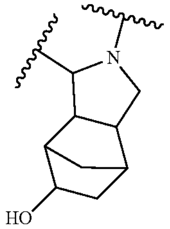 , 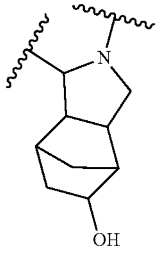 , 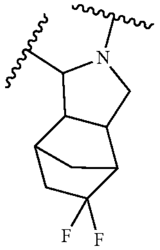 ,

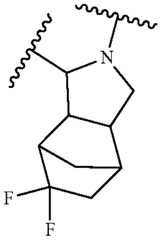 ,

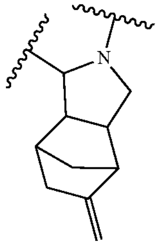 , 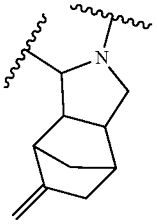 , 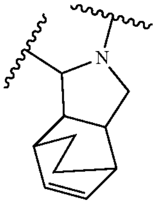 ,

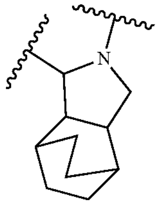 , 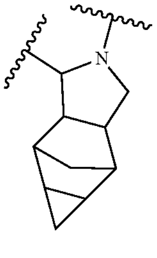 , 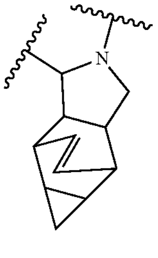 ,

-continued

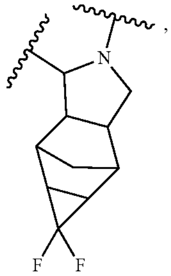,
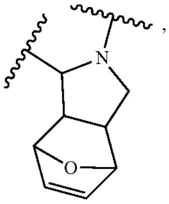,
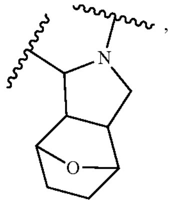,
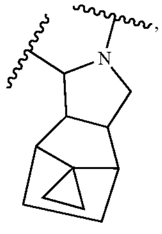,
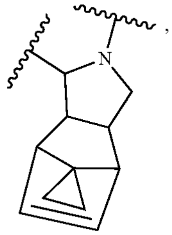,
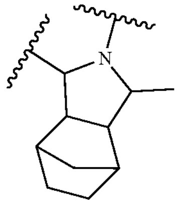,
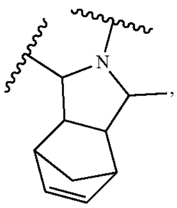,
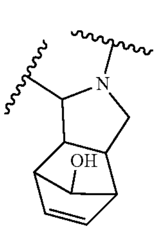 and
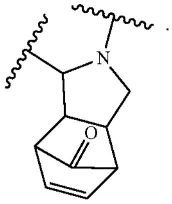.

6. The compound of claim 1, wherein $R^8$ is an unsubstituted $C_{2-6}$ alkyl.

7. The compound of claim 6, wherein $R^5$ is selected from the group consisting of:

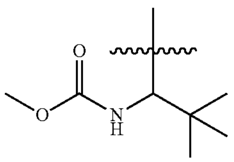 and
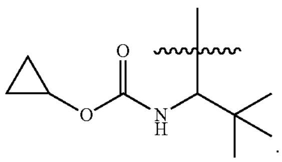.

8. The compound of claim 1, wherein $R^3$ is an unsubstituted or a substituted monocyclic nitrogen-containing heterocyclyl($C_{1-4}$ alkyl).

9. The compound of claim 8, wherein the monocyclic nitrogen-containing heterocyclyl($C_{1-4}$ alkyl) is azepan-2-one($C_{1-4}$ alkyl), imidazolidin-2-one($C_{1-4}$ alkyl), tetrahydropyrimidin-2-one($C_{1-4}$ alkyl), pyrrolidin-2-one($C_{1-4}$ alkyl), piperidin-2-one($C_{1-4}$ alkyl), pyrazolidin-3-one($C_{1-4}$ alkyl), oxazolidin-4-one($C_{1-4}$ alkyl), 1,4-oxazepan-3-one($C_{1-4}$ alkyl) or morpholin-3-one($C_{1-4}$ alkyl).

10. The compound of claim 1, wherein $R^3$ is

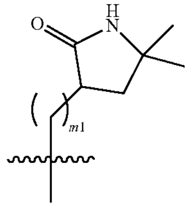,
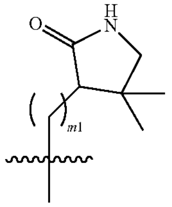,
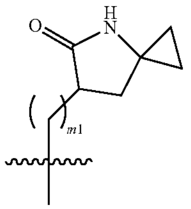,
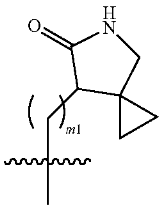,
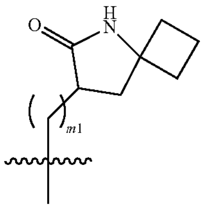,
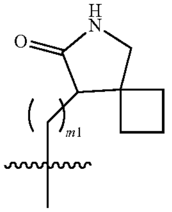,
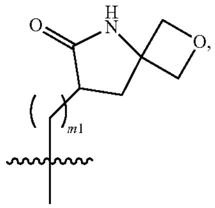
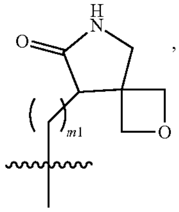,
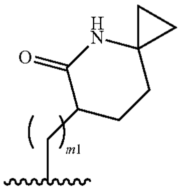,
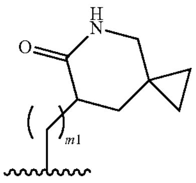,
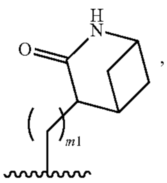,
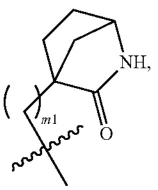
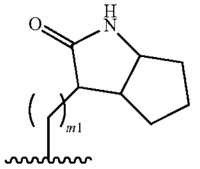,
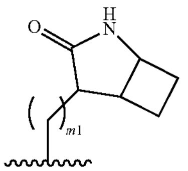,
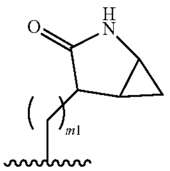,
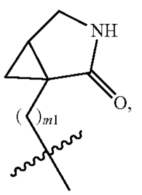
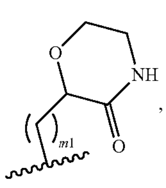,
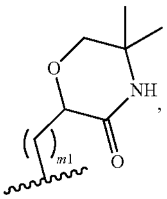, -continued
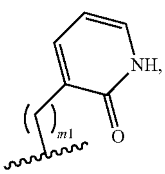
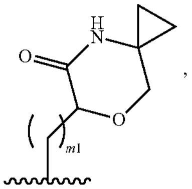
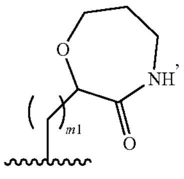
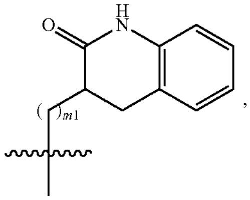
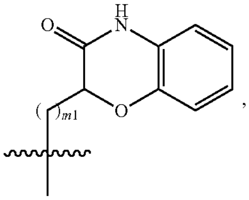
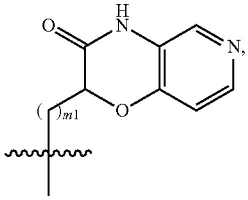
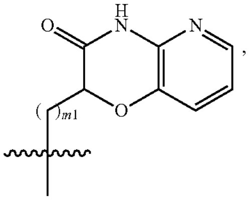
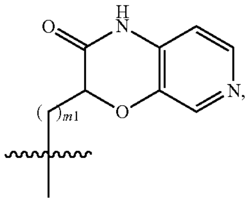
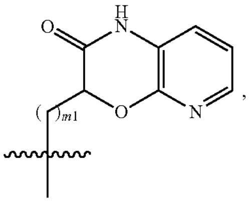
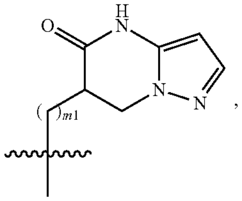
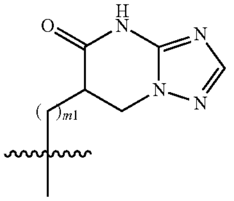
or
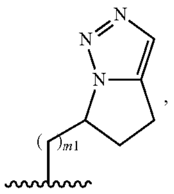
wherein each m1 is independently 1, 2, 3 or 4.
11. The compound of claim 1, wherein $R^3$ is selected from the group consisting of
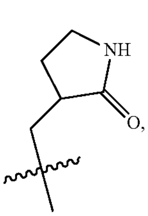
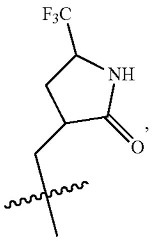
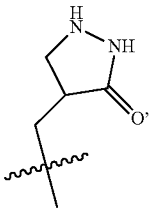
-continued
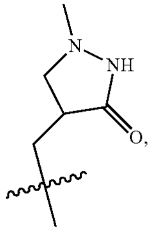
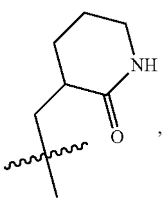
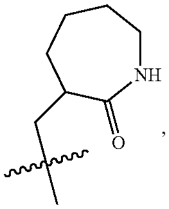
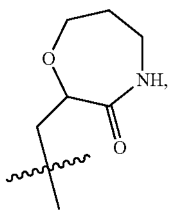
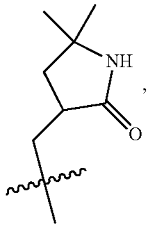
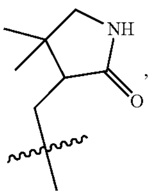
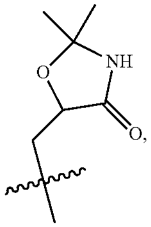
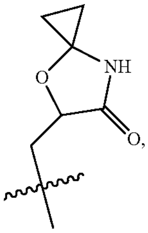
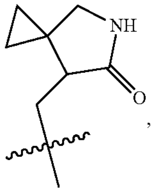
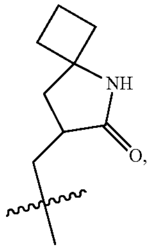
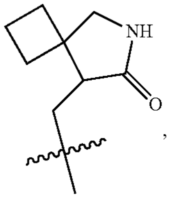
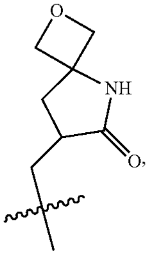
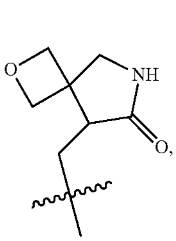
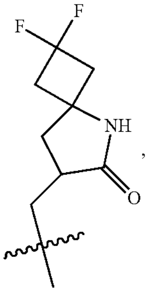
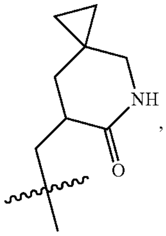
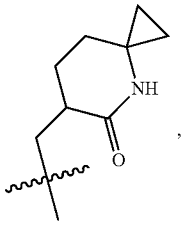
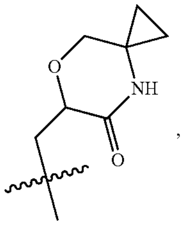
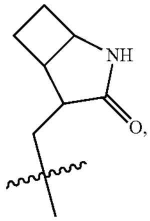
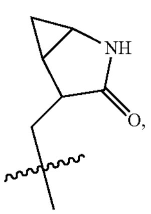
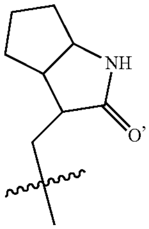
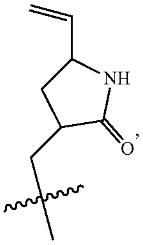

-continued
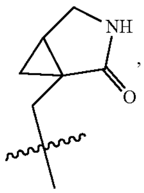,
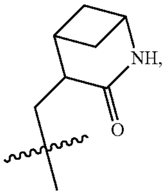
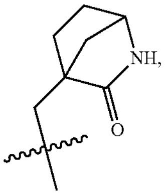
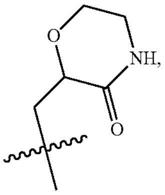
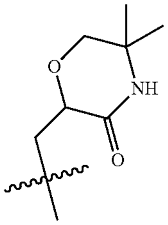,
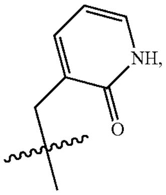
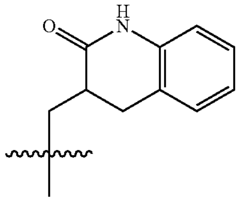,
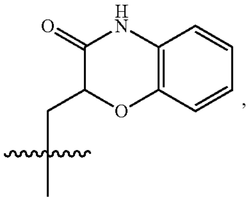,
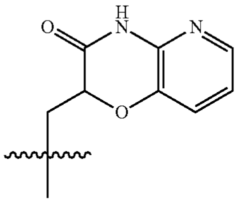,
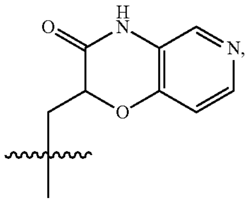
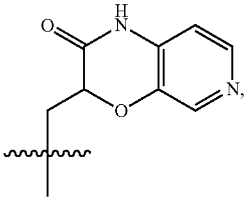
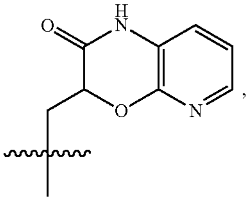,
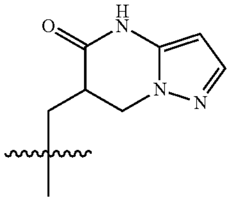,
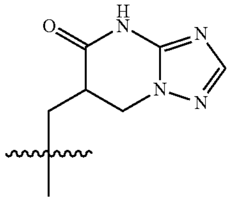
and
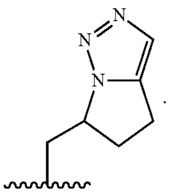.
12. The compound of claim 1, wherein $R^3$ is
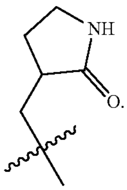 [SMILES: *CC1CCNC1=O]
13. The compound of claim 1, wherein $R^2$ is hydrogen; and $R^4$ is hydrogen.
14. The compound of claim 1, wherein the compound is selected from the group consisting of:
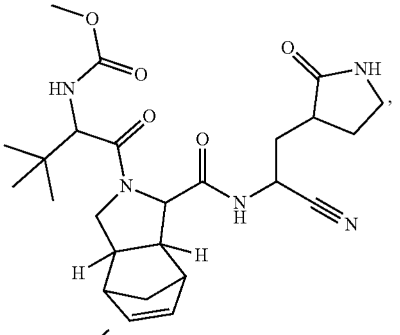,
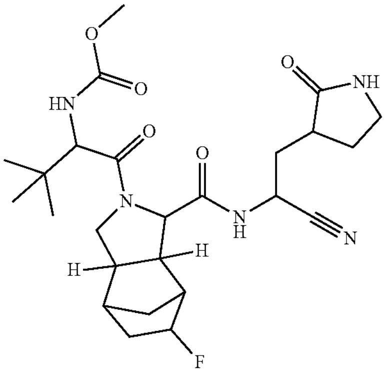
and
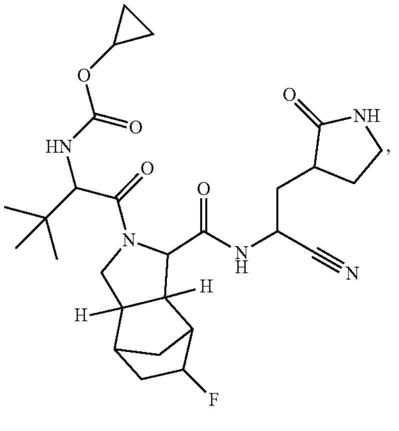,
or a pharmaceutically acceptable salt of any of the foregoing.

15. The compound of claim 1, wherein the compound is selected from the group consisting of:

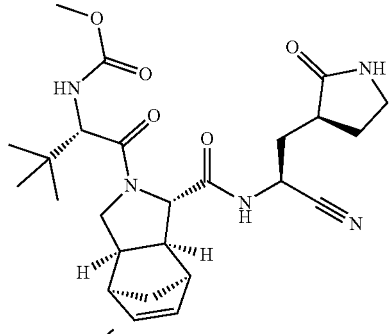

,

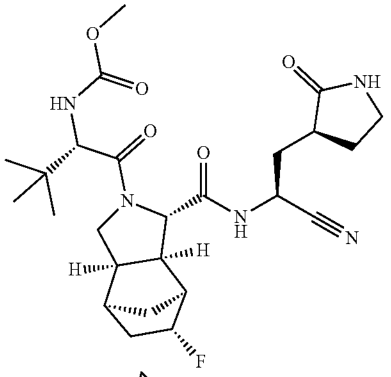

and

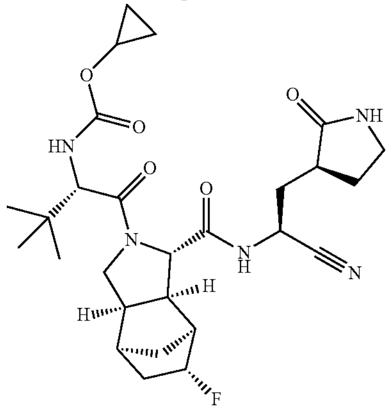

, or a pharmaceutically acceptable salt of any of the foregoing.

16. A pharmaceutical composition comprising an effective amount of a compound of claim 1, or a pharmaceutically acceptable salt thereof, and excipient.

17. A method for treating a coronavirus infection in a subject identified as suffering from the coronavirus infection comprising administering to the subject identified as suffering from the coronavirus infection an effective amount of a compound of claim 1, or a pharmaceutically acceptable salt thereof.

18. The method of claim 17, further comprising administering an additional agent selected from the group consisting of an ACE inhibitor, an anticoagulant, an anti-inflammatory, an ARB, an ASO, a Covid-19 convalescent plasma, an entry inhibitor, an $H_2$ pump antagonist, an H-conducting channel, an HIV protease inhibitor, an HMG-CoA reductase inhibitor, an immune globulin, an immunosuppressant, an immunotherapeutic agent, a neuraminidase inhibitor, a nucleoside inhibitor, a nucleoside analog inhibitor, a polymerase inhibitor, a protease inhibitor, an siRNA, a statin, a tissue plasminogen activator, an antibiotic, an antimicrobial and a vaccine.

19. A method for treating a picornavirus or a norovirus infection in a subject identified as suffering from the picornavirus infection or the norovirus infection comprising administering to the subject identified as suffering from the picornavirus infection or the norovirus infection an effective amount of a compound of claim 1, or a pharmaceutically acceptable salt thereof.

20. A method for inhibiting a coronavirus protease comprising contacting a cell infected with a coronavirus with an effective amount of a compound of claim 1, or a pharmaceutically acceptable salt thereof, wherein the compound of claim 1, or a pharmaceutically acceptable salt thereof, selectively inhibits the coronavirus protease compared to a host protease.

21. The method of claim 20, wherein the compound of formula (I) selectively inhibits the coronavirus protease over the host protease that is selected from the group consisting of Cathepsin L, Cathepsin B, Cathepsin D, Cathepsin K, Leukocyte Elastase, Chymotrypsin, Trypsin, Thrombin, Pepsin, Caspase 2, Elastase and Calpain.

* * * * *